(12) United States Patent
Vizcardo Sakoda et al.

(10) Patent No.: US 12,091,682 B2
(45) Date of Patent: Sep. 17, 2024

(54) METHODS FOR MAKING, COMPOSITIONS COMPRISING, AND METHODS OF USING REJUVENATED T CELLS

(71) Applicant: LYELL IMMUNOPHARMA, INC., South San Francisco, CA (US)

(72) Inventors: Raul E. Vizcardo Sakoda, Millbrae, CA (US); Nicholas Restifo, Burlingame, CA (US); Richard D. Klausner, Santa Clara, CA (US); Yin Huang, South San Francisco, CA (US); Takuya Maeda, Burlingame, CA (US); Naritaka Tamaoki, South San Francisco, CA (US); Yasuhiro Yamazaki, Burlingame, CA (US)

(73) Assignee: Lyell Immunopharma, Inc., South San Francisco, CA (US)

( * ) Notice: Subject to any disclaimer, the term of this patent is extended or adjusted under 35 U.S.C. 154(b) by 16 days.

(21) Appl. No.: 17/534,341

(22) Filed: Nov. 23, 2021

(65) Prior Publication Data
US 2022/0162551 A1 May 26, 2022

Related U.S. Application Data

(60) Provisional application No. 63/165,093, filed on Mar. 23, 2021, provisional application No. 63/153,881, filed on Feb. 25, 2021, provisional application No. 63/117,787, filed on Nov. 24, 2020.

(51) Int. Cl.
*C12N 5/0783* (2010.01)
*A61K 35/17* (2015.01)

(52) U.S. Cl.
CPC ............ *C12N 5/0636* (2013.01); *A61K 35/17* (2013.01); *C12N 2501/2302* (2013.01); *C12N 2501/51* (2013.01); *C12N 2501/515* (2013.01); *C12N 2501/602* (2013.01); *C12N 2501/603* (2013.01); *C12N 2501/604* (2013.01); *C12N 2501/606* (2013.01)

(58) Field of Classification Search
None
See application file for complete search history.

(56) References Cited

U.S. PATENT DOCUMENTS

| | | | |
|---|---|---|---|
| 5,827,642 A | 10/1998 | Riddell et al. |
| 5,830,462 A | 11/1998 | Crabtree et al. |
| 5,834,266 A | 11/1998 | Crabtree et al. |
| 5,858,358 A | 1/1999 | June et al. |
| 5,869,337 A | 2/1999 | Crabtree et al. |
| 5,883,223 A | 3/1999 | Gray |
| 6,040,177 A | 3/2000 | Riddell et al. |
| 6,165,787 A | 12/2000 | Crabtree et al. |
| 6,306,993 B1 | 10/2001 | Rothbard et al. |
| 6,352,694 B1 | 3/2002 | June et al. |
| 6,534,055 B1 | 3/2003 | June et al. |
| 6,624,189 B2 | 9/2003 | Wender et al. |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,067,698 B2 | 6/2006 | Wender et al. |
| 7,144,575 B2 | 12/2006 | June et al. |
| 7,151,116 B2 | 12/2006 | Wender et al. |
| 7,169,814 B2 | 1/2007 | Rothbard et al. |
| 7,172,869 B2 | 2/2007 | June et al. |
| 7,175,843 B2 | 2/2007 | June et al. |
| 7,232,566 B2 | 6/2007 | June et al. |
| 7,232,842 B2 | 6/2007 | Wender et al. |
| 7,572,631 B2 | 8/2009 | Berenson et al. |
| 7,585,834 B2 | 9/2009 | Wender et al. |
| 7,820,174 B2 | 10/2010 | Wang et al. |
| 8,216,565 B2 | 7/2012 | Restifo et al. |
| 8,246,995 B2 | 8/2012 | Dai et al. |

(Continued)

FOREIGN PATENT DOCUMENTS

| | | |
|---|---|---|
| WO | WO-9852614 A2 | 11/1998 |
| WO | WO-2002065986 A2 | 8/2002 |

(Continued)

OTHER PUBLICATIONS

Tan Q, et al. Isolation of T cell receptor specifically reactive with autologous tumour cells from tumour-infiltrating lymphocytes and construction of T cell receptor engineered T cells for esophageal squamous cell carcinoma. J Immunother Cancer. Aug. 28, 2019;7(1):232. doi: 10.1186/s40425-019-0709-7. (Year: 2019).*
Genomics-online. Lentiviral Particles. 2023. Available at https://www.genomics-online.com/plasmid/lentiviral-particles/#:~: text=Lentiviral%20particles%20are%20generated%20by,and%20used%20in%20later%20experiments. (Year: 2023).*
Karolinska Institutet. Lentiviral Vectors. Aug. 30, 2023. Available at https://ki.se/en/mbb/lentiviral-vectors. (Year: 2023).*
Miltenyi Biotec. T Cell TransAct Data Sheet. 2023. Available at https://static.miltenyibiotec.com/asset/150655405641/document_h4kco0qorl10r2cc8s69cnmm55?content-disposition=inline. (Year: 2023).*
Gianotti-Sommer, A., et al., "Generation of human induced pluripotent stem cells from peripheral blood using the STEMCCA lentiviral vector," J Vis Exp (68):4327, MYJoVE Corporation, United States (Oct. 2012).

(Continued)

*Primary Examiner* — Allison M Fox
*Assistant Examiner* — Alyssa G Weston
(74) *Attorney, Agent, or Firm* — Sterne, Kessler, Goldstein & Fox P.L.L.C.

(57) ABSTRACT

The present disclosure relates generally to methods of producing rejuvenated T cells, comprising, contacting T cells with at least one reprogramming factor and reactivating the contacted cells; and compositions and methods of using same. The present disclosure also describes cell populations prepared according to methods described herein. The disclosure also provides for methods of treating patients using cell populations prepared by the methods described herein.

32 Claims, 97 Drawing Sheets

(56) References Cited

U.S. PATENT DOCUMENTS

| | | | |
|---|---|---|---|
| 8,465,743 | B2 | 6/2013 | Rosenberg et al. |
| 8,486,693 | B2 | 7/2013 | Park et al. |
| 8,785,601 | B2 | 7/2014 | Rosenberg et al. |
| 9,102,919 | B2 | 8/2015 | Chevalier et al. |
| 10,457,917 | B2 | 10/2019 | Jaenisch et al. |
| 10,533,055 | B2 | 1/2020 | Chen et al. |
| 10,603,380 | B2 | 3/2020 | Wiltzius |
| 10,786,533 | B2 | 9/2020 | Mohler et al. |
| 2011/0286980 | A1 | 11/2011 | Brenner |
| 2012/0130076 | A1 | 5/2012 | Holt et al. |
| 2013/0078226 | A1 | 3/2013 | Nakauchi et al. |
| 2013/0274203 | A1 | 10/2013 | Morgan et al. |
| 2014/0037628 | A1 | 2/2014 | Morgan et al. |
| 2014/0162366 | A1 | 6/2014 | Izpisua Belmonte et al. |
| 2014/0171649 | A1 | 6/2014 | Li et al. |
| 2014/0274909 | A1 | 9/2014 | Orentas et al. |
| 2014/0286987 | A1 | 9/2014 | Spencer et al. |
| 2015/0266973 | A1 | 9/2015 | Jarjour et al. |
| 2016/0046700 | A1 | 2/2016 | Foster et al. |
| 2016/0215262 | A1 | 7/2016 | Powell |
| 2016/0376560 | A1* | 12/2016 | Prieur .................. A61P 21/00 435/366 |
| 2019/0271005 | A1 | 9/2019 | Valamehr et al. |
| 2020/0147210 | A1 | 5/2020 | Sade-Feldman et al. |

FOREIGN PATENT DOCUMENTS

| | | | |
|---|---|---|---|
| WO | WO-2003014076 | A2 | 2/2003 |
| WO | WO-2008069824 | A2 | 6/2008 |
| WO | WO-2009152529 | A2 | 12/2009 |
| WO | WO-2012079000 | A1 | 6/2012 |
| WO | WO-2012129514 | A1 | 9/2012 |
| WO | WO-2014127261 | A1 | 8/2014 |
| WO | WO-2015090229 | A1 | 6/2015 |
| WO | WO-2018067382 | A1 | 4/2018 |
| WO | WO-2019157597 | A1 | 8/2019 |
| WO | WO-2019178296 | A1 * | 9/2019 ........... A01N 1/0226 |

OTHER PUBLICATIONS

Good, M., et al., "Using Human Induced Pluripotent Stem Cells for the Generation of Tumor Antigen-specific T Cells," J Vis Exp (152), MYJoVE Corporation, United States (Oct. 2019).

Meraviglia, V., et al., "Generation of Induced Pluripotent Stem Cells from Frozen Buffy Coats using Non-integrating Episomal Plasmids," J Vis Exp (100):e52885, MYJoVE Corporation, United States (Jun. 2015).

Saito, H., et al., "Generation of Induced Pluripotent Stem Cells from Human Melanoma Tumor-Infiltrating Lymphocytes," J Vis Exp (117):54375, MYJoVE Corporation, United States (Nov. 2016).

Vizcardo, R., et al., "A Three-Dimensional Thymic Culture System to Generate Murine Induced Pluripotent Stem Cell-derived Tumor Antigen-specific Thymic Emigrants," J Vis Exp (150):10.3791/58672, MYJoVE Corporation, United States (Aug. 2019).

Alderton, G.K., "Pluripotency: partial reprogramming induces cancer," Nat Rev Cancer 14(4):216-217, Nature Portfolio, United Kingdom (Apr. 2014).

Abbott, A., "Trial hints at age-clock reversal," Nature 573(7773):173, Nature Publishing Group, United Kingdom (Sep. 2019).

Ando, M., et al., "Memory T cell, exhaustion, and tumor immunity," Immunol Med 43(1):1-9, Taylor & Francis, United Kingdom (Mar. 2020).

Ando, M., and Nakauchi, H., "Off-the-shelf immunotherapy with iPSC-derived rejuvenated cytotoxic T lymphocytes," Exp Hematol 47:2-12, Elsevier, Netherlands (Mar. 2017).

Ando, M., et al., "[iPSC-Derived Rejuvenated T-Cell Therapy for Epstein-Barr Virus-Associated Lymphomas]." [Rinsho Ketsueki] the Japanese Journal of Clinical Hematology 59 (7):932-38, The Japanese Society of Hematology, Japan (2018).

Ando, M., et al., "Long-term eradication of extranodal natural killer/T-cell lymphoma, nasal type, by induced pluripotent stem cell-derived Epstein-Barr virus-specific rejuvenated T cells in vivo," Haematologica 105(3):796-807, Ferrata Storti Foundation, Italy (Mar. 2020).

Ando, M., et al., "A Safeguard System for Induced Pluripotent Stem Cell-Derived Rejuvenated T Cell Therapy," Stem Cell Reports 5(4):597-608, Cell Press, United Kingdom (Oct. 2015).

Nagy, A., and Nagy, K., "The mysteries of induced pluripotency: where will they lead?," Nat Methods 7(1):22-24, Nature Publishing Group, United Kingdom (Jan. 2010).

Arnold, P.K., et al., "A non-canonical tricarboxylic acid cycle underlies cellular identity," Nature 603(7901):477-481, Nature Publishing Group, United Kingdom (Mar. 2022).

Minagawa, A., et al., "Enhancing T Cell Receptor Stability in Rejuvenated iPSC-Derived T Cells Improves Their Use in Cancer Immunotherapy," Cell Stem Cell 23(6):850-858, Cell Press, United Kingdom (Dec. 2018).

Audesse, A.J., and Webb, A.E., "Mechanisms of enhanced quiescence in neural stem cell aging," Mech Ageing Dev 191:111323, Elsevier, Netherlands (Oct. 2020).

Bell, C.G., et al., "DNA methylation aging clocks: challenges and recommendations," Genome Biol 20(1):249, BioMed Central Ltd., United Kingdom (Nov. 2019).

Bharathan, S.P., et al., "Systematic evaluation of markers used for the identification of human induced pluripotent stem cells," Biol Open 6(1):100-108, The Company of Biologists, United Kingdom (Jan. 2017).

Borgoni, S., et al., "Targeting immune dysfunction in aging," Ageing Res Rev 70:101410, Elsevier, Netherlands (Sep. 2021).

Breimer, M.E., et al., "Glycosphingolipids of human embryonic stem cells," Glycoconj J 34(6):713-723, Springer, Germany (Dec. 2017).

Browder, K.C., et al., "In vivo partial reprogramming alters age-associated molecular changes during physiological aging in mice," Nat Aging 2(3):243-253, Nature Portfolio, Germany (Mar. 2022).

Brown, M.E., et al., "Derivation of induced pluripotent stem cells from human peripheral blood T lymphocytes," PLoS One 5(6):e11373, PLOS, United States (Jun. 2010).

Brunet, A., et al., "Ageing and rejuvenation of tissue stem cells and their niches," Nat Rev Mol Cell Biol 24(1):45-62, Nature Publishing Group, United Kingdom (Jan. 2023).

Bueno, C., et al., "Reprogramming human B cells into induced pluripotent stem cells and its enhancement by C/EBPα," Leukemia 30(3):674-682, Nature Publishing Group, United Kingdom (Mar. 2016).

Ilce, B.Y., et al., "Cellular reprogramming: A new way to understand aging mechanisms," Wiley Interdiscip Rev Dev Biol 7(2), Wiley, United States (Mar. 2018).

Zebley, C.C., et al., "Rewriting History: Epigenetic Reprogramming of CD8+ T Cell Differentiation to Enhance Immunotherapy," Trends Immunol 41(8):665-675, Cell Press, United Kingdom (Aug. 2020).

Cao, S., et al., "Chromatin Accessibility Dynamics during Chemical Induction of Pluripotency," Cell Stem Cell 22(4):529-542, Cell Press, United Kingdom (Apr. 2018).

Cao, S., et al., "Generation of a Urine-Derived Ips Cell Line from a Patient with a Ventricular Septal Defect and Heart Failure and the Robust Differentiation of These Cells to Cardiomyocytes via Small Molecules," Cell Physiol Biochem 50(2):538-551, Cell Physiol Biochem Press, Germany (Oct. 2018).

Carey, B.W., et al., "Reprogramming of murine and human somatic cells using a single polycistronic vector," Proc Natl Acad Sci USA 106(1):157-162, National Academy of Sciences, United States (Jan. 2009).

Carrasco-Garcia, E., et al., "SOX2 expression diminishes with ageing in several tissues in mice and humans," Mech Ageing Dev 177:30-36, Elsevier, Netherlands (Jan. 2019).

Chan, J., et al., "Purging Exhausted Virus-Specific CD8 T Cell Phenotypes by Somatic Cell Reprogramming," AIDS Res Hum Retroviruses 33(S1):S59-S69, Mary Ann Liebert, United States (Nov. 2017).

Chan, E.M., et al., "Live cell imaging distinguishes bona fide human iPS cells from partially reprogrammed cells," Nat Biotechnol 27(11):1033-1037, Nature Publishing Group, United Kingdom (Nov. 2009).

(56) References Cited

OTHER PUBLICATIONS

Chang, C.J., et al., "Production of embryonic and fetal-like red blood cells from human induced pluripotent stem cells," PLoS One 6(10):e25761, PLOS, United States (2011).
Chen, F., et al., "High-efficiency generation of induced pluripotent mesenchymal stem cells from human dermal fibroblasts using recombinant proteins," Stem Cell Res Ther 7(1):99, BioMed Central Ltd., United Kingdom (Jul. 2016).
Chen, G., et al., "Chemically defined conditions for human iPSC derivation and culture," Nat Methods 8(5):424-429, Nature Publishing Group, United Kingdom (May 2011).
Chen, Q., et al., "Drug response to PD-1/PD-L1 blockade: based on biomarkers," Onco Targets Ther 11:4673-4683, Dove Medical Press, United Kingdom (Aug. 2018).
Chen, X., et al., "Insoluble Microenvironment Facilitating the Generation and Maintenance of Pluripotency," Tissue Eng Part B Rev 24(4):267-278, Mary Ann Liebert, United States (Aug. 2018).
Chen, Y., et al., "Reversible reprogramming of cardiomyocytes to a fetal state drives heart regeneration in mice," Science 373(6562):1537-1540, American Association for the Advancement of Science, United States (Sep. 2021).
Cheng, S., et al., "Characterization of Induced Pluripotent Stem Cells from Human Epidermal Melanocytes by Transduction with Two Combinations of Transcription Factors," Curr Gene Ther 19(6):395-403, Bentham Science, United Arab Emirates (2020).
Chiche, A., et al., "The crosstalk between cellular reprogramming and senescence in aging and regeneration," Exp Gerontol 138:111005, Elsevier, Netherlands (Sep. 2020).
Chondronasiou, D., et al., "Multi-omic rejuvenation of naturally aged tissues by a single cycle of transient reprogramming," Aging Cell 21(3):e13578, Wiley, United States (Mar. 2022).
Choong, P.F., et al., "Heterogeneity of osteosarcoma cell lines led to variable responses in reprogramming," Int J Med Sci 11(11):1154-1160, Ivyspring International Publisher, Australia (Aug. 2014).
Corominas-Faja, B., et al., "Nuclear reprogramming of luminal-like breast cancer cells generates Sox2-overexpressing cancer stem-like cellular states harboring transcriptional activation of the mTOR pathway," Cell Cycle 12(18):3109-3124, Landes Bioscience, United States (Sep. 2013).
Crompton, J.G., et al., "Memoirs of a reincarnated T cell," Cell Stem Cell 12(1):6-8, Cell Press, United Kingdom (Jan. 2013).
Crompton, J.G., et al., "Reprogramming antitumor immunity," Trends Immunol 35(4):178-185, Cell Press, United Kingdom (Apr. 2014).
Davenport, M.P., et al., "Building a T cell compartment: how immune cell development shapes function," Nat Rev Immunol 20(8):499-506, Nature Publishing Group, United Kingdom (Aug. 2020).
De Magalhaes, J.P., and Ocampo, A., "Cellular reprogramming and the rise of rejuvenation biotech," Trends Biotechnol 40(6):639-642, Elsevier, Netherlands (Jun. 2022).
Deng, F., et al., "Generation of induced pluripotent stem cells from human Tenon's capsule fibroblasts," Mol Vis 18:2871-2881, Molecular Vision, United States (Nov. 2012).
Gurusamy, D., et al., "Multi-phenotype CRISPR-Cas9 Screen Identifies p38 Kinase as a Target for Adoptive Immunotherapies," Cancer Cell 37(6):818-833, Cell Press, United Kingdom (Jun. 2020).
Di Stefano, B., et al., "C/EBPα creates elite cells for iPSC reprogramming by upregulating Klf4 and increasing the levels of Lsd1 and Brd4," Nat Cell Biol 18(4):371-381, Nature Publishing Group, United Kingdom (Apr. 2016).
Doeser, M.C., et al., "Reduction of Fibrosis and Scar Formation by Partial Reprogramming In Vivo," Stem Cells 36(8):1216-1225, Oxford Academic Press, United Kingdom (Aug. 2018).
Dong, Y., et al., "Poly(glycoamidoamine) Brushes Formulated Nanomaterials for Systemic siRNA and mRNA Delivery in Vivo," Nano Lett 16(2):842-848, American Chemical Society, United States (Feb. 2016).

Drews, K., et al., "Generation of iPSC lines from primary human amniotic fluid cells," Stem Cell Res 15(3):712-714, Elsevier, Netherlands (Nov. 2015).
Eisenstein, M., "Rejuvenation by controlled reprogramming is the latest gambit in anti-aging," Nat Biotechnol 40(2):144-146, Nature Publishing Group, United Kingdom (Feb. 2022).
Ema, H., and Nakauchi, H., "Self-renewal and lineage restriction of hematopoietic stem cells," Curr Opin Genet Dev 13(5):508-512, Elsevier, Netherlands (Oct. 2003).
Fahy, G.M., et al., "Reversal of epigenetic aging and immunosenescent trends in humans," Aging Cell 18(6):e13028, Wiley, United States (Dec. 2019).
Farber, D.L., et al., "Human memory T cells: generation, compartmentalization and homeostasis," Nat Rev Immunol 14(1):24-35, Nature Publishing Group, United Kingdom (Jan. 2014).
Feng, B., et al., "Molecules that promote or enhance reprogramming of somatic cells to induced pluripotent stem cells," Cell Stem Cell 4(4):301-312, Cell Press, United Kingdom (Apr. 2009).
Folmes, C.D.L., et al., "Somatic oxidative bioenergetics transitions into pluripotency-dependent glycolysis to facilitate nuclear reprogramming," Cell Metab 14(2):264-271, Cell Press, United Kingdom (Aug. 2011).
Frobel, J., et al., "Epigenetic rejuvenation of mesenchymal stromal cells derived from induced pluripotent stem cells," Stem Cell Reports 3(3):414-422, Cell Press, United Kingdom (Sep. 2014).
Fussner, E., et al., "Constitutive heterochromatin reorganization during somatic cell reprogramming," EMBO J 30(9):1778-1789, European Molecular Biology Organization, Germany (May 2011).
Galkin, F., et al., "Reversibility of irreversible aging," Ageing Res Rev 49:104-114, Elsevier, Netherlands (Jan. 2019).
Galluzzi, L., and Lugli, E., "Rejuvenated T cells attack old tumors," Oncoimmunology 2(2):e24103, Taylor & Francis, United States (Feb. 2013).
Gattinoni, L., et al., "A human memory T cell subset with stem cell-like properties," Nat Med 17(10):1290-1297, Nature Publishing Group, United Kingdom (Sep. 2011).
Gattinoni, L., et al., "Wnt/beta-catenin signaling in T-cell immunity and cancer immunotherapy," Clin Cancer Res 16(19):4695-4701, American Association for Cancer Research, United States (Oct. 2010).
Gattinoni, L., et al., "Wnt signaling arrests effector T cell differentiation and generates CD8+ memory stem cells," Nat Med 15(7):808-813, Nature Publishing Group, United Kingdom (Jul. 2009).
Ge, X., et al., "Human amniotic mesenchymal stem cell-derived induced pluripotent stem cells may generate a universal source of cardiac cells," Stem Cells Dev 21(15):2798-27808, Mary Ann Liebert, United States (Oct. 2012).
Ghassemi, S., et al., "Rapid manufacturing of non-activated potent CAR T cells," Nat Biomed Eng 6(2):118-128, Nature Publishing Group, United Kingdom (Feb. 2022).
Ghoneim, H.E., et al., "Cell-Intrinsic Barriers of T Cell-Based Immunotherapy," Trends Mol Med 22(12):1000-1011, Cell Press, United Kingdom (Dec. 2016).
Ghoneim, H.E., et al., "De Novo Epigenetic Programs Inhibit PD-1 Blockade-Mediated T Cell Rejuvenation," Cell 170(1):142-157.e19, Cell Press, United Kingdom (Jun. 2017).
Gibson, J., et al., "A meta-analysis of genome-wide association studies of epigenetic age acceleration," PLoS Genet 15(11):e1008104, PLOS, United States (Nov. 2019).
Gill, D., et al., "Multi-omic rejuvenation of human cells by maturation phase transient reprogramming," Elife 11:e71624, eLife Sciences Publications, United Kingdom (Apr. 2022).
Gong, L., et al., "p53 isoform Δ133p53 promotes efficiency of induced pluripotent stem cells and ensures genomic integrity during reprogramming," Sci Rep 6:37281, Nature Publishing Group, United Kingdom (Nov. 2016).
Gonzalez-Freire, M., et al., "The road ahead for health and lifespan interventions," Ageing Res Rev 59:101037, Elsevier, Netherlands (May 2020).
Goronzy, J.J., and Weyand, C.M., "Mechanisms underlying T cell ageing," Nat Rev Immunol 19(9):573-583, Nature Publishing Group, United Kingdom (Sep. 2019).

(56) References Cited

OTHER PUBLICATIONS

Goya, R.G., et al., "Rejuvenation by cell reprogramming: a new horizon in gerontology," Stem Cell Res Ther 9(1):349, BioMed Central Ltd., United Kingdom (Dec. 2018).
Hamanaka, S., et al., "Generation of germline-competent rat induced pluripotent stem cells," PLoS One 6(7):e22008, PLOS, United States (2011).
Hannum, G., et al., "Genome-wide methylation profiles reveal quantitative views of human aging rates," Mol Cell 49(2):359-367, Cell Press, United Kingdom (Jan. 2013).
Harland, K.L., et al., "Epigenetic plasticity of Cd8a locus during CD8(+) T-cell development and effector differentiation and reprogramming," Nat Commun 5:3547, Nature Publishing Group, United Kingdom (Mar. 2014).
Haynes, L., and Swain, S.L., "Aged-related shifts in T cell homeostasis lead to intrinsic T cell defects," Semin Immunol 24(5):350-355, Elsevier, Netherlands (Oct. 2012).
Hekmatimoghaddam, S., et al., "Sirt1 and Parp1 as epigenome safeguards and microRNAs as SASP-associated signals, in cellular senescence and aging," Ageing Res Rev 40:120-141, Elsevier, Netherlands (Nov. 2017).
Henzler, C.M., et al., "Staged miRNA re-regulation patterns during reprogramming," Genome Biol 14(12):R149, BioMed Central, United Kingdom (Dec. 2013).
Hiew, M.S.Y., et al., "Incomplete cellular reprogramming of colorectal cancer cells elicits an epithelial/mesenchymal hybrid phenotype," J Biomed Sci 25(1):57, BioMed Central, United Kingdom (Jul. 2018).
Hiramoto, T., et al., "Non-transmissible MV Vector with Segmented RNA Genome Establishes Different Types of iPSCs from Hematopoietic Cells," Mol Ther 28(1):129-141, Cell Press, United Kingdom (Jan. 2020).
Hishida, T., et al., "In vivo partial cellular reprogramming enhances liver plasticity and regeneration," Cell Rep 39(4):110730, Cell Press, United Kingdom (Apr. 2022).
Ho, P.C., et al., "Phosphoenolpyruvate Is a Metabolic Checkpoint of Anti-tumor T Cell Responses," Cell 162(6):1217-1228, Cell Press, United Kingdom (Sep. 2015).
Ho, R., et al., "Stage-specific regulation of reprogramming to induced pluripotent stem cells by Wnt signaling and T cell factor proteins," Cell Rep 3(6):2113-2126, Cell Press, United Kingdom (Jun. 2013).
Hogg, N., et al., "T-cell integrins: more than just sticking points," J Cell Sci 116(Pt 23):4695-4705, The Company of Biologists, United Kingdom (Dec. 2003).
Honda, T., et al., "Sustainable Tumor-Suppressive Effect of iPSC-Derived Rejuvenated T Cells Targeting Cervical Cancers," Mol Ther 28(11):2394-2405, Cell Press, United Kingdom (Nov. 2020).
Horvath, S., "DNA methylation age of human tissues and cell types," Genome Biol 14(10):R115, BioMed Central, United Kingdom (2013).
Horvath, S., "Erratum to: DNA methylation age of human tissues and cell types," Genome Biol 16(1):96, BioMed Central, United Kingdom (2015).
Horvath, S., et al., "Epigenetic clock for skin and blood cells applied to Hutchinson Gilford Progeria Syndrome and ex vivo studies," Aging (Albany NY) 10(7):1758-1775, Impact Journals, United States (Jul. 2018).
Horvath, S., and Raj, K., "DNA methylation-based biomarkers and the epigenetic clock theory of ageing," Nat Rev Genet 19(6):371-384, Nature Publishing Group, United Kingdom (Jun. 2018).
Hou, P., et al., "Pluripotent stem cells induced from mouse somatic cells by small-molecule compounds," Science 341(6146):651-654, American Association for the Advancement of Science, United States (Aug. 2013).
Hu, K., "A PIANO (Proper, Insufficient, Aberrant, and NO Reprogramming) Response to the Yamanaka Factors in the Initial Stages of Human iPSC Reprogramming," Int J Mol Sci 21(9):3229, MDPI, Switzerland (May 2020).

Huang, J., et al., "More synergetic cooperation of Yamanaka factors in induced pluripotent stem cells than in embryonic stem cells," Cell Res 19(10):1127-1138, Nature Publishing Group, United Kingdom (Oct. 2009).
Gai, H., et al., "Engineering Regenerative Thymic Tissues to Restore Long-Term T Cell Lymphopoiesis," Blood 132(Suppl 1):5092, Elsevier, Netherlands (Nov. 2018).
Hynes, K., et al., "Generation of functional mesenchymal stem cells from different induced pluripotent stem cell lines," Stem Cells Dev 23(10):1084-1096, Mary Ann Liebert, United States (May 2014).
Im, S.J., et al., "Defining CD8+ T cells that provide the proliferative burst after PD-1 therapy," Nature 537(7620):417-421, Nature Publishing Group, United Kingdom (Sep. 2016).
Iriguchi, S., and Kaneko, S., "Toward the development of true "off-the-shelf" synthetic T-cell immunotherapy," Cancer Sci 110(1):16-22, Wiley-Blackwell, United States (Jan. 2019).
Iriguchi, S., et al., "A clinically applicable and scalable method to regenerate T-cells from iPSCs for off-the-shelf T-cell immunotherapy," Nat Commun 12(1):430, Nature Publishing Group, United Kingdom (Jan. 2021).
Ishtiaq, M., et al., "MicroRNA Regulation Along the Course of Cellular Reprogramming to Pluripotency," Curr Mol Med 18(1):58-64, Bentham Science Publishers, United Arab Emirates (2018).
Itoh, M., et al., "Integration-free T cell-derived human induced pluripotent stem cells (iPSCs) from a healthy individual: WT-iPSC1," Stem Cell Res 17(1):22-24, Elsevier, Netherlands (Jul. 2016).
Itoh, M., et al., "Integration-free T cell-derived human induced pluripotent stem cells (iPSCs) from a patient with lymphedema-distichiasis syndrome (LDS) carrying an insertion-deletion complex mutation in the FOXC2 gene," Stem Cell Res 16(3):611-613, Elsevier, Netherlands (May 2016).
Jaffer, S., et al., "Mbd3 Promotes Reprogramming of Primary Human Fibroblasts," Int J Stem Cells 11(2):235-241, Wiley, United States (Nov. 2018).
Jiang, J., et al., "Zscan4 promotes genomic stability during reprogramming and dramatically improves the quality of iPS cells as demonstrated by tetraploid complementation," Cell Res 23(1):92-106, Nature Publishing Group, United Kingdom (Jan. 2013).
Jiang, Y., et al., "T-cell exhaustion in the tumor microenvironment," Cell Death Dis 6(6):e1792, Nature Publishing Group, United Kingdom (Jun. 2015).
Jiang, Y., et al., "Phosphatidic Acid Improves Reprogramming to Pluripotency by Reducing Apoptosis," Stem Cells Dev 25(1):43-54, Mary Ann Liebert, United States (Jan. 2016).
Sardina, J.L., et al., "Transcription Factors Drive Tet2-Mediated Enhancer Demethylation to Reprogram Cell Fate," Cell Stem Cell 23(5):727-741.e9, Cell Press, United Kingdom (Nov. 2018).
Kahler, D.J., et al., "Improved methods for reprogramming human dermal fibroblasts using fluorescence activated cell sorting," PLoS One 8(3):e59867, PLOS, United States (Mar. 2013).
Kahounova, Z., et al., "Generation of human iPSCs from fetal prostate fibroblasts HPrF," Stem Cell Res 35:101405, Elsevier, Netherlands (Mar. 2019).
Kane, A.E., and Sinclair, D.A., "Epigenetic changes during aging and their reprogramming potential," Crit Rev Biochem Mol Biol 54(1):61-83, Taylor & Francis, United Kingdom (Feb. 2019).
Kaneko, S., "In Vitro Generation of Antigen-Specific T Cells from Induced Pluripotent Stem Cells of Antigen-Specific T Cell Origin," Methods Mol Biol 1393:67-73, Humana Press, United States (2016).
Kaneko, S., et al., "Reprogramming adult hematopoietic cells," Curr Opin Hematol 17(4):271-275, Lippincott Williams and Wilkins Ltd, United States (Jul. 2010).
Kawai, Y., et al., "Generation of highly proliferative, rejuvenated cytotoxic T cell clones through pluripotency reprogramming for adoptive immunotherapy," Mol Ther 29(10):3027-3041, Cell Press, United Kingdom (Oct. 2021).
Kennedy, M., et al., "T lymphocyte potential marks the emergence of definitive hematopoietic progenitors in human pluripotent stem cell differentiation cultures," Cell Rep 2(6):1722-1735, Cell Press, United Kingdom (Dec. 2012).

(56) References Cited

OTHER PUBLICATIONS

Khan, M., et al., "Generation of two induced pluripotent stem cell lines NCCSi005A and NCCSi006A from CD4+T cells of healthy individuals of Indian origin," Stem Cell Res 39:101506, Elsevier, Netherlands (Aug. 2019).

Khodeer, S., and Era, T., "Identifying the Biphasic Role of Calcineurin/ NFAT Signaling Enables Replacement of Sox2 in Somatic Cell Reprogramming," Stem Cells 35(5):1162-1175, Oxford University Press, United Kingdom (May 2017).

Khoshchehreh, R., et al., "Epigenetic reprogramming of primary pancreatic cancer cells counteracts their in vivo tumourigenicity," Oncogene 38(34):6226-6239, Nature Publishing Group, United Kingdom (Aug. 2019).

Kisby, T., et al., "Transient Reprogramming of Neonatal Cardiomyocytes to a Proliferative Dedifferentiated State," BioRxiv, Cold Spring Harbor Laboratory, United States (2019).

Kitayama, S., et al., "Cellular Adjuvant Properties, Direct Cytotoxicity of Re-differentiated Vα24 Invariant NKT-like Cells from Human Induced Pluripotent Stem Cells," Stem Cell Reports 6(2):213-227, Cell Press, United Kingdom (Feb. 2016).

Kumano, K., et al., "Generation of induced pluripotent stem cells from primary chronic myelogenous leukemia patient samples," Blood 119(26):6234-6242, Elsevier, Netherlands (Jun. 2012).

Kurd, N., and Robey, E.A., "T-cell selection in the thymus: a spatial and temporal perspective," Immunol Rev 271(1):114-126, Wiley-Blackwell, United States (May 2016).

Lapasset, L., et al., "Rejuvenating senescent and centenarian human cells by reprogramming through the pluripotent state," Genes Dev 25(21):2248-2253, Cold Spring Harbor Laboratory Press, United States (Nov. 2011).

Lee, H.K., et al., "Peripheral blood mononuclear cell-converted induced pluripotent stem cells (iPSCs) from an early onset Alzheimer's patient," Stem Cell Res 16(2):213-125, Elsevier, Netherlands (Mar. 2016).

Lee, J., et al., "Induced pluripotency and spontaneous reversal of cellular aging in supercentenarian donor cells," Biochem Biophys Res Commun 525(3):563-569, Elsevier, Netherlands (May 2020).

Lee, T.H., et al., "Functional recapitulation of smooth muscle cells via induced pluripotent stem cells from human aortic smooth muscle cells," Circ res 106(1):120-128, Lippincott Williams & Wilkins, United States (Jan. 2010).

Lehmann, M., et al., "Partial Reprogramming As An Emerging Strategy for Safe Induced Cell Generation and Rejuvenation," Curr Gene Ther 19(4):248-254, Bentham Sciences, United Arab Emirates (2019).

Lehmann, M., et al., "Regulatable adenovector harboring the GFP and Yamanaka genes for implementing regenerative medicine in the brain," Gene Ther 26(10-11):432-440, Nature Publishing Group, United Kingdom (Nov. 2019).

Kurian, L., et al., "Conversion of human fibroblasts to angioblast-like progenitor cells," Nat Methods 10(1):77-83, Nature Publishing Group, United Kingdom (Jan. 2013).

Levine, M.E., et al., "An epigenetic biomarker of aging for lifespan and healthspan," Aging (Albany NY) 10(4):573-591, Impact Journals, United States (Apr. 2018).

Li, J.Q., et al., "[Retraction] Generation of induced pluripotent stem cells using skin fibroblasts from patients with myocardial infarction under feeder-free conditions," Mol Med Rep 10(2):1170, Spandidos Publications, Greece (Aug. 2014).

Lichtner, B., et al., "Generation of iPSC lines from primary human chorionic villi cells," Stem Cells Res 15(3):697-699, Elsevier, Netherlands (Nov. 2015).

Lim, R., et al., "Partial somatic to stem cell transformations induced by cell-permeable reprogramming factors," Sci Rep 4:4361, Nature Publishing Group, United Kingdom (Mar. 2014).

Liu, P., et al., "Low immunogenicity of neural progenitor cells differentiated from induced pluripotent stem cells derived from less immunogenic somatic cells," PLoS One 8(7):e69617, PLOS, United States (Jul. 2013).

Liu, Q., et al., "Generation and Characterization of Induced Pluripotent Stem Cells from Mononuclear Cells in Schizophrenic Patients," Cell J 21(2):161-168, Cell Press, United Kingdom (Jul. 2019).

Liu, Z., et al., "Characterization of iPSCs derived from low grade gliomas revealed early regional chromosomal amplifications during gliomagenesis," J Neurooncol 141(2):289-301, Springer Science + Business Media, Germany (Jan. 2019).

Lluis, F., et al., "T-cell factor 3 (Tcf3) deletion increases somatic cell reprogramming by inducing epigenome modifications," Proc Natl Acad Sci USA 108(29):11912-11917, National Academy of Sciences, United States (Jul. 2011).

Loh, Y.H., et al., "Reprogramming of T cells from human peripheral blood," Cell Stem Cell 7(1):15-19, Cell Press, United Kingdom (Jul. 2010).

Lopez-Otin, C., et al., "The hallmarks of aging," Cell 153(6):1194-1217, Cell Press, United Kingdom (Jun. 2013).

Lu, T.L., et al., "DNA methylation-based estimator of telomere length," Aging (Albany NY) 11(16):5895-5923, Impact Journals, United States (Aug. 2019).

Lu, Y., et al., "Reversal of ageing- and injury-induced vision loss by Tet-dependent epigenetic reprogramming," BioRxiv, Cold Springs Harbor Laboratory, United States (Jul. 2019).

Lu, Y., et al., "Reprogramming to recover youthful epigenetic information and restore vision," Nature 588(7836):124-129, Nature Publishing Group, United Kingdom (Dec. 2020).

Mack, A.A., et al., "Generation of induced pluripotent stem cells from CD34+ cells across blood drawn from multiple donors with non-integrating episomal vectors," PLoS One 6(11):e27956, PLOS, United States (2011).

Maeda, T., et al., "Regeneration of CD8αβ T Cells from T-cell-Derived iPSC Imparts Potent Tumor Antigen-Specific Cytotoxicity," Cancer Res 76(23):6839-6850, American Association for Cancer Research, United States (Dec. 2016).

Mai, T., et al., "NKX3-1 is required for induced pluripotent stem cell reprogramming and can replace OCT4 in mouse and human iPSC induction," Nat Cell Biol 20(8):900-908, Nature Publishing Group, United Kingdom (Aug. 2018).

Manukyan, M., and Singh, P.B., "Epigenetic rejuvenation," Genes Cells 17(5):337-343, Wiley-Blackwell, United States (May 2012).

Manukyan, M., and Singh, P.B., "Epigenome rejuvenation: HP1β mobility as a measure of pluripotent and senescent chromatin ground states," Sci Rep 4:4789, Nature Publishing Group, United Kingdom (Apr. 2014).

Mao, S.H., et al., "Osteogenic potential of induced pluripotent stem cells from human adipose-derived stem cells," Stem Cell Res Ther 10(1):303, BioMed Central, United Kingdom (Oct. 2019).

Mckinlay, C.J., et al., "Enhanced mRNA delivery into lymphocytes enabled by lipid-varied libraries of charge-altering releasable transporters," Proc Natl Acad Sci USA 115(26):E5859-5866, National Academy of Sciences, United States (Jun. 2018).

Mendelsohn, A.R., and Larrick, J.W., "Epigenetic Age Reversal by Cell-Extrinsic and Cell-Intrinsic Means," Rejuvenation Res 22(5):439-446, Mary Ann Liebert, United States (Oct. 2019).

Mendelsohn, A.R., et al., "Rejuvenation by Partial Reprogramming of the Epigenome," Rejuvenation Res 20(2):146-150, Mary Ann Liebert, United States (2017).

Mendelson, M.M., et al., "Epigenetic Age Acceleration: A Biological Doomsday Clock for Cardiovascular Disease?," Circ Genom Precis Med 11(3):e002089, Lippincott Williams and Wilkins Ltd., United States (Mar. 2018).

Mertens, J., et al., "Directly Reprogrammed Human Neurons Retain Aging-Associated Transcriptomic Signatures and Reveal Age-Related Nucleocytoplasmic Defects," Cell Stem Cell 17(6):705-718, Cell Press, United Kingdom (Dec. 2015).

Metzler, K.R.C. "Directing smooth muscle cell fate: a partial reprogramming approach to engineer vessels," Circ Res 112(11):1402-1404, Lippincott Williams & Wilkins, United States (May 2013).

Saetersmoen, M.L., et al., "Off-the-shelf cell therapy with induced pluripotent stem cell-derived natural killer cells," Semin Immunopathol 41(1):59-68, Springer Verlag, Germany (Jan. 2019).

Miller, J.D., et al., "Human iPSC-based modeling of late-onset disease via progerin-induced aging," Cell Stem Cell 13(6):691-705, Cell Press, United Kingdom (Dec. 2013).

(56) References Cited

OTHER PUBLICATIONS

Minagawa, A., and Kaneko, S., "Differentiating CD8αβ T Cells from TCR-Transduced iPSCs for Cancer Immunotherapy," Methods Mol Biol 2048:81-84, Humana Press, United States (2019).

Minato, N., et al., "Physiology and pathology of T-cell aging," Int Immunol 32(4):223-231, Oxford University Press, United Kingdom (Apr. 2020).

Mitchell, E., et al., "Clonal dynamics of haematopoiesis across the human lifespan," Nature 606(7913):343-350, Nature Publishing Group, United Kingdom (Jun. 2022).

Mittelbrunn, M., and Kroemer, G., "Hallmarks of T cell aging," Nat Immunol 22(6):687-698, Nature Publishing Group, United Kingdom (Jun. 2021).

Moffett, H.F., et al., "Hit-and-run programming of therapeutic cytoreagents using mRNA nanocarriers," Nat Commun 8(1):389, Nature Publishing Group, United Kingdom (Aug. 2017).

Kamal, N.S.M., et al., "Aging of the cells: Insight into cellular senescence and detection Methods," Eur J Cell Biol 99(6):151108, Elsevier, Netherlands (Aug. 2020).

Morris, B.J., et al., "Genetic and epigenetic regulation of human aging and longevity," Biochim Biophys Acta Mol Basis Dis 1865(7):1718-1744, Elsevier, Netherlands (Jul. 2019).

Morris, S.A., and Daley, G.Q., "A blueprint for engineering cell fate: current technologies to reprogram cell identity," Cell Res 23(1):33-48, Nature Publishing Group, United Kingdom (Jan. 2013).

Murayama, H., et al., "Successful reprogramming of epiblast stem cells by blocking nuclear localization of β-catenin," Stem Cell Reports 4(1):103-113, Cell Press, United Kingdom (Jan. 2015).

Nagano, S., et al., "High Frequency Production of T Cell-Derived iPSC Clones Capable of Generating Potent Cytotoxic T Cells," Mol Ther Methods Clin Dev 16:126-135, Cell Press, United Kingdom (Dec. 2019).

Nakagawa, M., et al., "Generation of induced pluripotent stem cells without Myc from mouse and human fibroblasts," Nat Biotechnol 26(1):101-106, Nature Publishing Group, United Kingdom (Jan. 2008).

Nakanishi, M., and Otsu, M., "Development of Sendai virus vectors and their potential applications in gene therapy and regenerative medicine," Curr Gene Ther 12(5):410-416, Bentham Sciences, United Arab Emirates (Oct. 2012).

Nakauchi, H., "Isolation and characterization of the hematopoietic stem cell," [Rinsho Ketsueki] the Japanese Journal of Clinical Hematology 36(5):400-405, The Japanese Society of Hematology, Japan (May 1995).

Nakauchi, H., "Isolation and clonal characterization of hematopoietic and liver stem cells," Cornea 23(8 Suppl):S2-7, Lippincott Williams and Wilkins Ltd., United States (Nov. 2004).

Negredo, P.N., et al., "Aging and Rejuvenation of Neural Stem Cells and Their Niches," Cell Stem Cell 27(2):202-223, Cell Press, United Kingdom (Aug. 2020).

Olova, N., et al., "Partial reprogramming induces a steady decline in epigenetic age before loss of somatic identity," Aging Cell 18(1):e12877, Wiley-Blackwell, United States (Feb. 2019).

Neri, S., et al., "Microsatellite instability and compromised mismatch repair gene expression during in vitro passaging of monoclonal human T lymphocytes," Rejuvenation Res 10(2):145-156, Mary Ann Liebert, United States (Jun. 2007).

Ni, A., et al., "Sphere formation permits Oct4 reprogramming of ciliary body epithelial cells into induced pluripotent stem cells," Stem Cells Dev 23(24):3065-3071, Mary Ann Liebert, United States (Dec. 2014).

Nikolich-Zugich, J., "Ageing and life-long maintenance of T-cell subsets in the face of latent persistent infections," Nat Rev Immunol 8(7):512-522, Nature Publishing Group, United Kingdom (Jul. 2008).

Nikolich-Zugich, J., "The twilight of immunity: emerging concepts in aging of the immune system," Nat Immunol 19(1):10-19, Nature Publishing Group, United Kingdom (Jan. 2018).

Nishimura, K., et al., "Mechanisms of the Metabolic Shift during Somatic Cell Reprogramming," Int J Mol Sci 20(9):2254, MDPI, Switzerland (May 2019).

Nishimura, K., et al., "Simple and effective generation of transgene-free induced pluripotent stem cells using an auto-erasable Sendai virus vector responding to microRNA-302," Stem Cell Res 23:13-19, Elsevier, Netherlands (Aug. 2017).

Nishimura, K., et al., "Development of defective and persistent Sendai virus vector: a unique gene delivery/expression system ideal for cell reprogramming," J Biol Chem 286(6):4760-4771, Elsevier, Netherlands (Feb. 2011).

Nishimura, T., and Nakauchi, H., "Generation of Antigen-Specific T Cells from Human Induced Pluripotent Stem Cells," Methods Mol Biol 1899:25-40, Humana Press, United States (2019).

Nishimura, T., et al., "Use of polyvinyl alcohol for chimeric antigen receptor T-cell expansion," Exp Hematol 80:16-20, Elsevier, Netherlands (Dec. 2019).

Nishimura, T., et al., "Generation of rejuvenated antigen-specific T cells by reprogramming to pluripotency and redifferentiation," Cell Stem Cell 12(1):114-126, Cell Press, United Kingdom (Jan. 2013).

Nishimura, T., et al., "Human iPSC Generation from Antigen-Specific T Cells," Methods Mol Biol 2048:53-57, Humana Press, United States (2019).

Ocampo, A., et al., "In Vivo Amelioration of Age-Associated Hallmarks by Partial Reprogramming," Cell 167(7):1719-1733.e12, Cell Press, United Kingdom (Dec. 2016).

Okabe, M., et al., "Definitive proof for direct reprogramming of hematopoietic cells to pluripotency," Blood 114(9):1764-1767, American Society of Hematology, United States (Aug. 2009).

Okita, K., et al., "An efficient nonviral method to generate integration-free human-induced pluripotent stem cells from cord blood and peripheral blood cells," Stem Cells 31(3):458-466, Oxford University Press, United Kingdom (Mar. 2013).

Okumura, T., et al., "Robust and highly efficient hiPSC generation from patient non-mobilized peripheral blood-derived CD34+ cells using the auto-erasable Sendai virus vector," Stem Cell Res Ther 10(1):185, BioMed Central, United Kingdom (Jun. 2019).

Osterloh, J.M., and Mullane, K., "Manipulating cell fate while confronting reproducibility concerns," Biochem Pharmacol 151:144-156, Elsevier, Netherlands (May 2018).

Palacio, L., et al., "Restored immune cell functions upon clearance of senescence in the irradiated splenic environment," Aging Cell 18(4):e12971, Wiley-Blackwell, United States (Aug. 2019).

Parras, A., et al., "In Vivo Reprogramming Leads to Premature Death due to Hepatic and Intestinal Failure," bioRxiv, Biochemistry, Cold Spring Harbor Laboratory, United States (May 2022).

Qin, Y., et al., "Generation of embryonic stem cells from mouse adipose-tissue derived cells via somatic cell nuclear transfer," Cell Cycle 14(8):1282-1290, Landes Bioscience, United States (2015).

Raab, S., et al., "A Comparative View on Human Somatic Cell Sources for iPSC Generation," Stem Cells 2014:768391, Oxford University Press, United Kingdom (2014).

Rando, T.A., and Chang, H.Y., "Aging, rejuvenation, and epigenetic reprogramming: resetting the aging clock," Cell 148(1-2):46-57, Cell Press, United Kingdom (Jan. 2012).

Ren, R., et al., "Regulation of Stem Cell Aging by Metabolism and Epigenetics," Cell Metab 26(3):460-474, Cell Press, United Kingdom (Sep. 2017).

Ren, Y., et al., "Generation of induced pluripotent stem cell-derived mice by reprogramming of a mature NKT cell," Int Immunol 26(10):551-561, Oxford University Press, United Kingdom (Oct. 2014).

Reyes, R., et al., "Tetraspanin CD9: A Key Regulator of Cell Adhesion in the Immune System," Front Immunol 9:863, Frontiers Media S.A., Switzerland (Apr. 2018).

Riley, J.L., and June, C.H., "The road to recovery: translating PD-1 biology into clinical benefit," Trends Immunol 28(2):48-50, Elsevier, Netherlands (Feb. 2007).

Rodriguez-Matellan, A., et al., "In Vivo Reprogramming Ameliorates Aging Features in Dentate Gyrus Cells and Improves Memory in Mice," Stem Cell Reports 15(5):1056-1066, Cell Press, United Kingdom (Nov. 2020).

(56) References Cited

OTHER PUBLICATIONS

Rosenberg, S.A., et al., "Durable complete responses in heavily pretreated patients with metastatic melanoma using T-cell transfer immunotherapy," Clin Cancer Res 17(13):4550-4557, American Association for Cancer Research, United States (Jul. 2011).

Roux, A., et a., "Partial Reprogramming Restores Youthful Gene Expression through Transient Suppression of Cell Identity." bioRxiv, Biochemistry, Cold Spring Harbor Laboratory, United States (May 2021).

Roux, A.E., et al., "Diverse partial reprogramming strategies restore youthful gene expression and transiently suppress cell identity," Cell Syst 13(7):574-587, Cell Press, United Kingdom (Jul. 2022).

Ruby, J.G., et al., "Estimates of the Heritability of Human Longevity Are Substantially Inflated due to Assortative Mating," Genetics 210(3):1109-1124, Oxford University Press, United Kingdom (Nov. 2018).

Ruetz, T., et al., "Constitutively Active SMAD2/3 Are Broad-Scope Potentiators of Transcription-Factor-Mediated Cellular Reprogramming," Cell Stem Cell 21(6):791-805, Cell Press, United Kingdom (Dec. 2017).

Saeidi, A., et al., "T-Cell Exhaustion in Chronic Infections: Reversing the State of Exhaustion and Reinvigorating Optimal Protective Immune Responses," Front Immunol 9:2569, Frontiers Media, Switzerland (Nov. 2018).

Saito, H., et al., "Adoptive Transfer of CD8+ T Cells Generated from Induced Pluripotent Stem Cells Triggers Regressions of Large Tumors Along with Immunological Memory," Cancer Res 76(12):3473-3483, American Association for Cancer Research, United States (Jun. 2016).

Saito, H., et al., "Reprogramming of Melanoma Tumor-Infiltrating Lymphocytes to Induced Pluripotent Stem Cells," Stem Cells Int 2016:8394960, Hindawi Publishing Corporation, United States (2016).

Sakuishi, K., et al., "Targeting Tim-3 and PD-1 pathways to reverse T cell exhaustion and restore anti-tumor immunity," J Exp Med 207(10):2187-2194, Rockefeller University Press, United States (Sep. 2010).

Salas, S., et al., "Induced Pluripotent Stem Cells from Ovarian Tissue," Curr Protoc Hum Genet 95:21, Wiley, United States (Oct. 2017).

Sarkar, T., and Sebastiano, V., "Rejuvenation on the Road to Pluripotency" Pluripotent Stem Cells—from the Bench to the Clinic (2016).

Sarkar, T., et al., "Transient Non-Integrative Nuclear Reprogramming Promotes Multifaceted Reversal of Aging in Human Cells," bioRxiv, Biochemistry, Cold Springs Harbor Laboratory, United States (2019).

Sartorelli, V., and Puri, P.L., "Shaping Gene Expression by Landscaping Chromatin Architecture: Lessons from a Master," Mol Cell 71(3):375-388, Cell Press, United Kingdom (Aug. 2018).

Schoenfeldt, L., et al., "Chemical Reprogramming Ameliorates Cellular Hallmarks Oflaging and Extends Lifespan," bioRxiv, Biochemistry, Cold Springs Harbor Press, United States (Aug. 2022).

Schultz, M.B., et al., "Age and life expectancy clocks based on machine learning analysis of mouse frailty," Nat Commun 11(1):4618, Nature Publishing Group, United Kingdom (Sep. 2020).

Seki, T., et al., "Generation of induced pluripotent stem cells from human terminally differentiated circulating T cells," Cell Stem Cell 7(1):11-14, Cell Press, United Kingdom (Jul. 2010).

Akunuru, S., and Geiger, H., "Aging, Clonality, and Rejuvenation of Hematopoietic Stem Cells," Trends Mol Med 22(8):701-712, Cell Press, United Kingdom (Aug. 2016).

Simpson, D.J., et al., "Cellular reprogramming and epigenetic rejuvenation," Clin Epigenetics 13(1):170, BioMed Central, United Kingdom (Sep. 2021).

Singh, P.B., et al., "Deconstructing age reprogramming," J Biosci 44(4):106, India Academy of Sciences, India (Sep. 2019).

Singh, P.B., and Zacouto, F., "Nuclear reprogramming and epigenetic rejuvenation," J Biosci 35(2):315-319, India Academy of Sciences, India (Jun. 2010).

Sochacki, J., et al., "Generation of urine iPS cell lines from patients with Attention Deficit Hyperactivity Disorder (ADHD) using a non-integrative method," Stem Cell Res 17(1):102-106, Elsevier, Netherlands (Jul. 2016).

Sousa-Victor, P., et al., "Muscle stem cell aging: identifying ways to induce tissue rejuvenation" Mech Ageing Dev 188:111246, Elsevier, Netherlands (Jun. 2020).

Staerk, J., et al., "Reprogramming of human peripheral blood cells to induced pluripotent stem cells," Cell Stem Cell 7(1):20-24, Cell Press, United Kingdom (Jul. 2010).

Su, R.J., et al., "Efficient generation of integration-free ips cells from human adult peripheral blood using BCL-XL together with Yamanaka factors," PLoS One 8(5):e64496, PLOS, United States (May 2013).

Vodnala, S.K., et al., "T cell stemness and dysfunction in tumors are triggered by a common mechanism," Science 363(6434):eaau0135, American Association for the Advancement of Science, United States (Mar. 2019).

Suzuki, Y.J., and Shults, N.V., "Antioxidant Regulation of Cell Reprogramming," Antioxidants (Basel) 8(8):323, MDPI, Switzerland (Aug. 2019).

Tabilas, C., et al., "Cutting Edge: Elevated Glycolytic Metabolism Limits the Formation of Memory CD8+ T Cells in Early Life," J Immunol 203(10):2571-2576, American Association of Immunologists, United States (Nov. 2019).

Taguchi, J., and Yamada, Y., "Unveiling the Role of Senescence-Induced Cellular Plasticity," Cell Stem Cell 20(3):293-294, Cell Press, United Kingdom (Mar. 2017).

Taheri, H., et al., "Reprogramming of Human Melanocytes and Melanoma Cells with Yamanaka Factors," Methods Mol Biol 1916:249-261, Humana Press, United States (2019).

Takahashi, K., et al., "Induction of pluripotency in human somatic cells via a transient state resembling primitive streak-like mesendoderm," Nat Commun 5:3678, Nature Publishing Group, United Kingdom (Apr. 2014).

Takahashi, K., et al., "Induction of pluripotent stem cells from adult human fibroblasts by defined factors," Cell 131(5):861-872, Cell Press, United Kingdom (Nov. 2007).

Takayama, N., et al., "Generation of functional platelets from human embryonic stem cells in vitro via ES-sacs, VEGF-promoted structures that concentrate hematopoietic progenitors," Blood 111(11):5298-5306, American Society of Hematology, United States (Jun. 2008).

Talkhabi, M., "Partial reprogramming as a therapeutic approach for heart disease: A state-of-the-art review," J Cell Biochem 120(9):14247-14261, Wiley, United States (Sep. 2019).

Tamanini, S., et al., "In Vivo Transient and Partial Cell Reprogramming to Pluripotency as a Therapeutic Tool for Neurodegenerative Diseases," Mol Neurobiol 55(8):6850-6862, Springer Science + Business Media, Germany (Aug. 2018).

Tanabe, K., et al., "Maturation, not initiation, is the major roadblock during reprogramming toward pluripotency from human fibroblasts," Proc Natl Acad Sci USA 110(30):12172-12179, National Academy of Sciences, United States (Jul. 2013).

Tanaka, N., et al., "Development of a High-Efficacy Reprogramming Method for Generating Human Induced Pluripotent Stem (iPS) Cells from Pathologic and Senescent Somatic Cells," Int J Mol Sci 21(18):6764, MDPI, Switzerland (Sep. 2020).

Tang, C., et al., "Generation of two induced pluripotent stem cell (iPSC) lines from human breast milk using episomal reprogramming system," Stem Cell Res 39:101511, Elsevier, Netherlands (Aug. 2019).

Sarkar, T.J., et al., "Transient non-integrative expression of nuclear reprogramming factors promotes multifaceted amelioration of aging in human cells," Nat Commun 11(1):1545, Nature Publishing Group, United Kingdom (Mar. 2020).

Themeli, M., et al., "Generation of tumor-targeted human T lymphocytes from induced pluripotent stem cells for cancer therapy," Nat Biotechnol 31(10):928-933, Nature Publishing Group, United Kingdom (Oct. 2013).

Themeli, M., et al., "New cell sources for T cell engineering and adoptive immunotherapy," Cell Stem Cell 16(4):357-366, Cell Press, United Kingdom (Apr. 2015).

(56) References Cited

OTHER PUBLICATIONS

Their, M., et al., "Direct conversion of fibroblasts into stably expandable neural stem cells," Cell Stem Cell 10(4):473-479, Cell Press, United Kingdom (Apr. 2012).

Tsai, P.H., et al., "Differentiation of blood T cells: Reprogramming human induced pluripotent stem cells into neuronal cells," J Chin Med Assoc 78(6):353-359, Elsevier Taiwan LLC, Taiwan (Jun. 2015).

Velychko, S., et al., "Excluding Oct4 from Yamanaka Cocktail Unleashes the Developmental Potential of iPSCs," Cell Stem Cell 25(6):737-753, Cell Press, United Kingdom (Dec. 2019).

Vizcardo, R., et al., "Generation of Tumor Antigen-Specific iPSC-Derived Thymic Emigrants Using a 3D Thymic Culture System," Cell Rep 22(12):3175-3190, Cell Press, United Kingdom (Mar. 2018).

Vizcardo, R., et al., "Regeneration of human tumor antigen-specific T cells from iPSCs derived from mature CD8(+) T cells," Cell Stem Cell 12(1):31-36, Cell Press, United Kingdom (Jan. 2013).

Wakao, H., "Reprogramming of MAIT Cells to Pluripotency and Redifferentiation," Methods Mol Biol 2098:237-257, Humana Press, United States (Dec. 2019).

Wakao, H., et al., "Expansion of functional human mucosal-associated invariant T cells via reprogramming to pluripotency and redifferentiation," Cell Stem Cell 12(5):546-558, Cell Press, United Kingdom (May 2013).

Wang, K., et al., "iTRAQ-based quantitative proteomic analysis of Yamanaka factors reprogrammed breast cancer cells," Oncotarget 8(21):34330-34339, Impact Journals LLC, United States (May 2017).

Wang, X., et al., "Reduced immunogenicity of induced pluripotent stem cells derived from Sertoli cells," PLoS One 9(8):e106110, PLOS, United States (Aug. 2014).

Watanabe, D., et al., "The Generation of Human γδT Cell-Derived Induced Pluripotent Stem Cells from Whole Peripheral Blood Mononuclear Cell Culture," Stem Cells Transl Med 7(1):34-44, Oxford University Press, United Kingdom (Jan. 2018).

Zhang, W., et al., "The ageing epigenome and its rejuvenation," Nat Rev Mol Cell Biol 21(3):137-150, Nature Publishing Group, United Kingdom (Mar. 2020).

Wen, Y., et al., "Reprogramming of fibroblasts from older women with pelvic floor disorders alters cellular behavior associated with donor age," Stem Cells Transl Med 2(2):118-128, Oxford University Press, United Kingdom (Feb. 2013).

Wherry, E.J., "T cell exhaustion," Nat Immunol 12(6):492-499, Nature Publishing Group, United Kingdom (Jun. 2011).

Wilkinson, A.C., et al., "Haematopoietic stem cell self-renewal in vivo and ex vivo," Nat Rev Genet 21(9):541-554, Nature Publishing Group, United Kingdom (Sep. 2020).

Xiao, X., et al., "Generation of Induced Pluripotent Stem Cells with Substitutes for Yamanaka's Four Transcription Factors," Cell Reprogram 18(5):281-297, Mary Ann Liebert, United States (Oct. 2016).

Xu, Y., et al., "Transcriptional Control of Somatic Cell Reprogramming," Trends Cell Biol 26(4):272-288, Cell Press, United Kingdom (Apr. 2016).

Xu, Y., et al., "Proliferation rate of somatic cells affects reprogramming efficiency," J Biol Chem 288(14):9767-9778, Elsevier, Netherlands (Apr. 2013).

Yamaguchi, T., et al., "Development of an all-in-one inducible lentiviral vector for gene specific analysis of reprogramming," PLoS One 7(7):e41007, PLOS, United States (2012).

Yamakawa, H., and Ieda, M., "Strategies for heart regeneration: approaches ranging from induced pluripotent stem cells to direct cardiac reprogramming," Int Heart J 56(1):1-5, International Heart Journal Association, Japan (2015).

Yamamoto, Ryo, et al., "Large-Scale Clonal Analysis Resolves Aging of the Mouse Hematopoietic Stem Cell Compartment," Cell Stem Cell 22(4):600-607, Cell Press, United Kingdom (Apr. 2018).

Yamamoto, R., and Nakauchi, H., "In vivo clonal analysis of aging hematopoietic stem cells," Mech Ageing Dev 192:111378, Elsevier, Netherlands (Dec. 2020).

Yamazaki, S., et al., "Insights into signaling and function of hematopoietic stem cells at the single-cell level," Curr Opin Hematol 16(4):255-258, Lippincott Williams and Wilkins Ltd., United States (Jul. 2009).

Yano, H., and Kaneko, S., "[Immune Cell Therapy Using iPS Cells]," [Rinsho Ketsueki] the Japanese Journal of Clinical Hematology 59 (2): 225-31, Japan Society of Clinical Hematology, Japan (2018).

Yashiro, Y., et al., "Transcriptional profiling of hematopoietic stem cells by high-throughput sequencing," Int J Hematol 89(1):24-33, Springer Science + Business Media, Germany (Jan. 2009).

Yi, J.S., et al., "T-cell exhaustion: characteristics, causes and conversion," Immunology 129(4):474-481, Wiley, United States (Apr. 2010).

Yue, F., et al., "Reprogramming of retinoblastoma cancer cells into cancer stem cells," Biochem Biophys Res Commun 482(4):549-555, Elsevier, Netherlands (Jan. 2017).

Zeng, J., et al., "Derivation of mimetic γδT cells endowed with cancer recognition receptors from reprogrammed γδT cell," PLoS One 14(5):e0216815, PLOS, United States (May 2019).

Zhang, C., et al., "NKG2A is a NK cell exhaustion checkpoint for HCV persistence," Nat Commun 10(1):1507, Nature Publishing Group, United Kingdom (Apr. 2019).

Zhao, H., et al., "Induced pluripotency of human prostatic epithelial cells," PLoS One 8(5):e64503, PLOS, United States (May 2013).

Zhou, H., et al., "Rapid and Efficient Generation of Transgene-Free iPSC from a Small Volume of Cryopreserved Blood," Stem Cell Rev Rep 11(4):652-665, Springer Science + Business Media, Germany (Aug. 2015).

Zhu, T., et al., "CancerClock: A DNA Methylation Age Predictor to Identify and Characterize Aging Clock in Pan-Cancer," Front Bioeng Biotechnol 7:388, Frontiers Media S.A., Switzerland (Dec. 2019).

Zhuang, Q., et al., "NCoR/SMRT co-repressors cooperate with c-MYC to create an epigenetic barrier to somatic cell reprogramming," Nat Cell Biol 20(4):400-412, Nature Publishing Group, United Kingdom (Apr. 2018).

"34th Annual Meeting & Pre-Conference Programs of the Society for Immunotherapy of Cancer (SITC 2019): Part 2." J Immunother Cancer 7(Suppl 1):283, BMJ Publishing Group, United Kingdom (Nov. 2019).

Singh, P.B., and Newman, A.G., "Age reprogramming and epigenetic rejuvenation," Epigenetics Chromatin 11(1):73, BMJ Publishing Group, United Kingdom (Dec. 2018).

International Search Report and Written Opinion for International Application No. PCT/US2021/060650, Commissioner for Patents, United States, mailed on Mar. 25, 2022, 19 pages.

Takada, K et al. "Generation of Peptides That Promote Positive Selection in the Thymus." Journal of immunology (Baltimore, Md. : 1950) vol. 198,6: 2215-2222. (Mar. 2017).

Yamagata, T., et al. "Self-reactivity in thymic double-positive cells commits cells to a CD8αα lineage with characteristics of innate immune cells." Nat Immunol 5, 597-605 (May 2004).

Fink, P. J. "The biology of recent thymic emigrants." Annual review of immunology vol. 31: 31-50. (Mar. 2013).

Kuderer, N. M., et al. "Mortality, morbidity, and cost associated with febrile neutropenia in adult cancer patients." Cancer vol. 106,1: 2258-66. (May 2006).

Graham, F. L., and Van Der Eb, A. J., "A new technique for the assay of infectivity of human adenovirus 5 DNA." Virology vol. 52,2 (1973): 456-67. (Apr. 1973).

Chu, G., and Sharp, P. A., "SV40 DNA transfection of cells in suspension: analysis of efficiency of transcription and translation of T-antigen." Gene vol. 13,2: 197-202. (Mar. 1981).

Devereux, J et al. "A comprehensive set of sequence analysis programs for the VAX." Nucleic acids research vol. 12,1 Pt 1 :387-95. (Jan. 1984).

Dayhoff, M. O., Schwartz, R. M., and Orcutt, B. C., "A model of evolutionary change in proteins." pp. 345-352 in M. O. Dayhoff, ed., Atlas of Protein Sequence and Structure vol. 5, suppl. 3. National Biomedical Research Foundation, Washington, D.C. (1978).

(56) References Cited

OTHER PUBLICATIONS

Henikoff, S., and Henikoff, J. G., "Amino acid substitution matrices from protein blocks." Proceedings of the National Academy of Sciences of the United States of America vol. 89,22 (1992): 10915-9. (Nov. 1992).
Gattinoni, L., et al., "Acquisition of full effector function in vitro paradoxically impairs the in vivo antitumor efficacy of adoptively transferred CD8+ T cells." The Journal of clinical investigation vol. 115,6 (2005): 1616-26. (Jun. 2005).
Lynn, R. C., et al., "c-Jun overexpression in CAR T cells induces exhaustion resistance." Nature vol. 576,7786 (2019): 293-300. (Dec. 2019).
Gattinoni, L., et al., "Paths to stemness: building the ultimate antitumour T cell." Nature reviews. Cancer vol. 12,10 (2012): 671-84. (Oct. 2012).
Klebanoff, C. A et al. "Sorting through subsets: which T-cell populations mediate highly effective adoptive immunotherapy ?." Journal of immunotherapy (Hagerstown, Md. : 1997) vol. 35,9 (2012): 651-60. (Nov. 2012).
Liu, B., et al., "Depleting the methyltransferase Suv39h1 improves DNA repair and extends lifespan in a progeria mouse model." Nature communications vol. 4 (2013): 1868. (May 2013).
Benayoun, B. A., et al., "Epigenetic regulation of ageing: linking environmental inputs to genomic stability." Nature reviews. Molecular cell biology vol. 16,10 (2015): 593-610. (Oct. 2015).
Xiao, D., et al., "Direct reprogramming of fibroblasts into neural stem cells by single non-neural progenitor transcription factor Ptf1a." Nature communications vol. 9,1 2865. (Jul. 2018).
Schmidt, R., and Plath, K., "The roles of the reprogramming factors Oct4, Sox2 and Klf4 in resetting the somatic cell epigenome during induced pluripotent stem cell generation." Genome biology vol. 13,10 251. (Oct. 2012).
Wu, C., et al. "Remote control of therapeutic T cells through a small molecule-gated chimeric receptor." Science (New York, N.Y.) vol. 350,6258 (2015): aab4077. (Apr. 2016).
Fegan, A., et al., "Chemically controlled protein assembly: techniques and applications." Chemical reviews vol. 110,6 (2010): 3315-36. (Jun. 2010).
Robbins, P. F., et al. "Single and dual amino acid substitutions in TCR CDRs can enhance antigen-specific T cell functions." Journal of immunology (Baltimore, Md. : 1950) vol. 180,9 (2008): 6116-31. (May 2008).
Thorvaldsdóttir, H., et al., "Integrative Genomics Viewer (IGV): high-performance genomics data visualization and exploration," Briefings in Bioinformatics, vol. 14, Issue 2, pp. 178-192. (Mar. 2013).
Dobin, A., et al., "STAR: ultrafast universal RNA-seq aligner." Bioinformatics (Oxford, England) vol. 29,1 (2013): 15-21. (Jan. 2013).
Li, B., Dewey, C.N., "RSEM: accurate transcript quantification from RNA-Seq data with or without a reference genome." BMC Bioinformatics 12, 323 (Aug. 2011).
Love, M.I., Huber, W. and Anders, S., "Moderated estimation of fold change and dispersion for RNA-seq data with DESeq2." Genome Biol 15, 550 (Dec. 2014).
Subramanian, A., et al. "Gene set enrichment analysis: a knowledge-based approach for interpreting genome-wide expression profiles." Proceedings of the National Academy of Sciences of the United States of America vol. 102,43 (2005): 15545-50. (Oct. 2005).
Yu, G., et al., "clusterProfiler: an R package for comparing biological themes among gene clusters." Omics : a journal of integrative biology vol. 16,5 (2012): 284-7. (May 2012).
Wong, G. K. et al. "Accelerated Loss of TCR Repertoire Diversity in Common Variable Immunodeficiency." Journal of immunology (Baltimore, Md. : 1950) vol. 197,5 (2016): 1642-9. (Sep. 2016).
Miyazaki, T., et al., Laminin E8 fragments support efficient adhesion and expansion of dissociated human pluripotent stem cells. Nat Commun 3, 1236 (Dec. 2012).
Feng, B., et al. "Reprogramming of fibroblasts into induced pluripotent stem cells with orphan nuclear receptor Esrrb." Nature cell biology vol. 11,2 (2009): 197-203. (Jan. 2009).
Hao, Y., et al., "Integrated analysis of multimodal single-cell data." Cell vol. 184,13 (2021): 3573-3587.e29. (Jun. 2021).
Kochenderfer, J. N., et al., "Chemotherapy-refractory diffuse large B-cell lymphoma and indolent B-cell malignancies can be effectively treated with autologous T cells expressing an anti-CD19 chimeric antigen receptor." Journal of clinical oncology : official journal of the American Society of Clinical Oncology vol. 33,6 (2015): 540-9. (Aug. 2014).

* cited by examiner

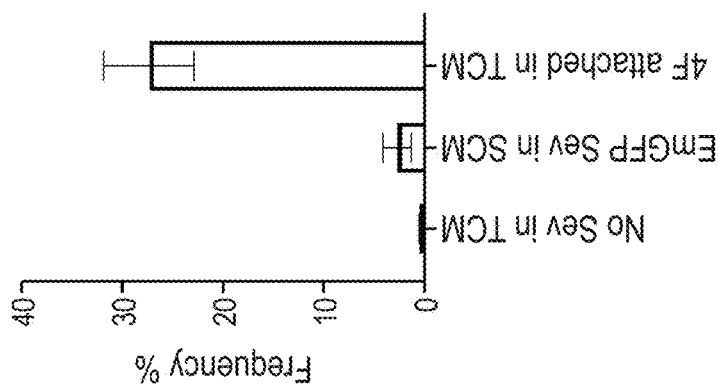
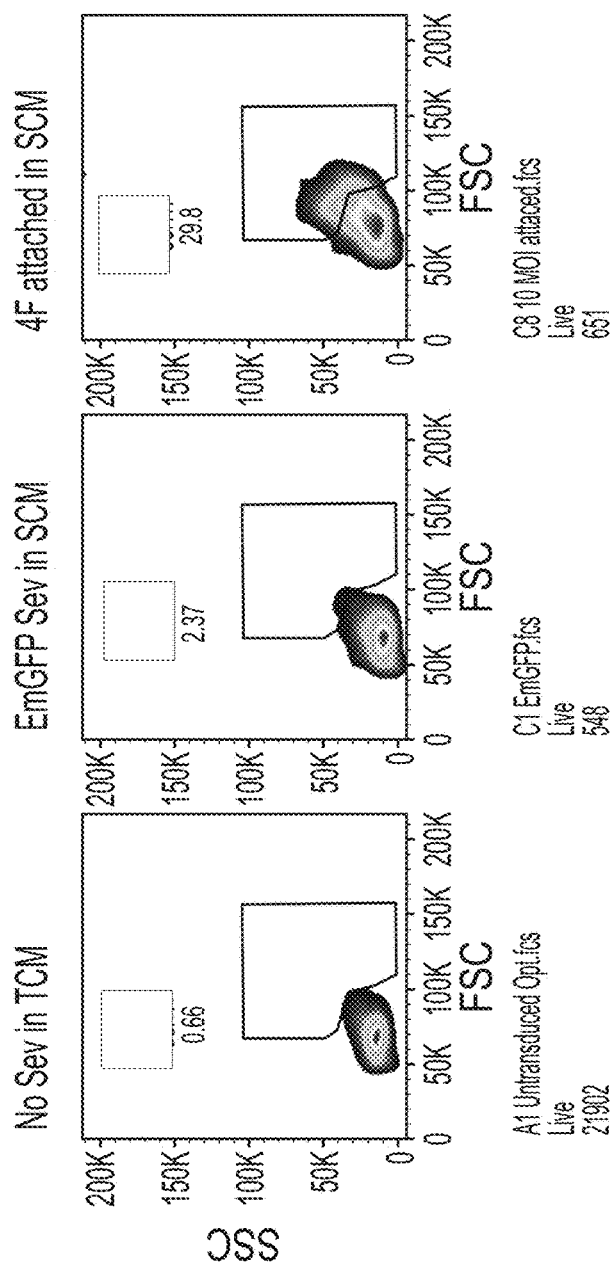
FIG. 6

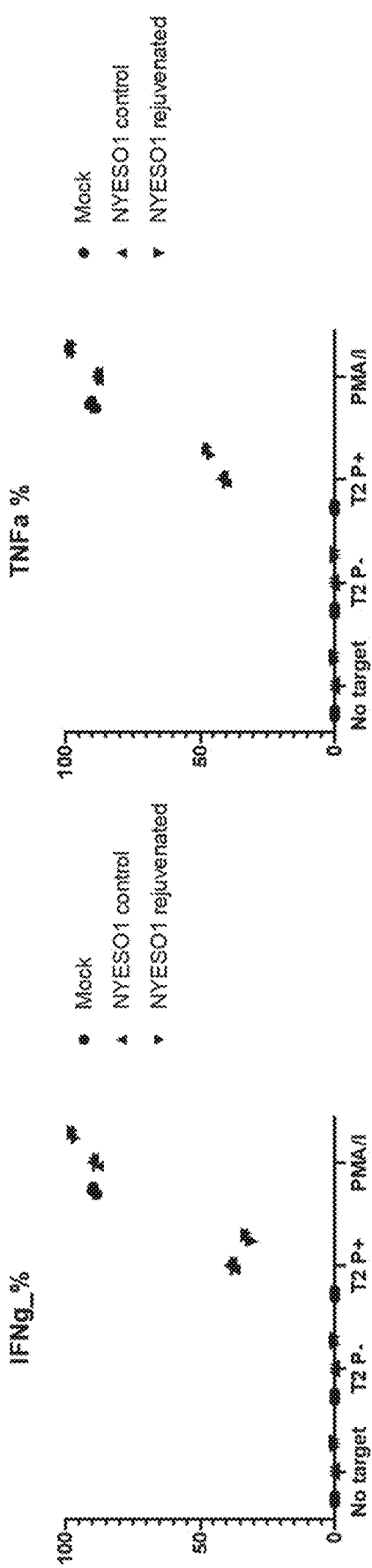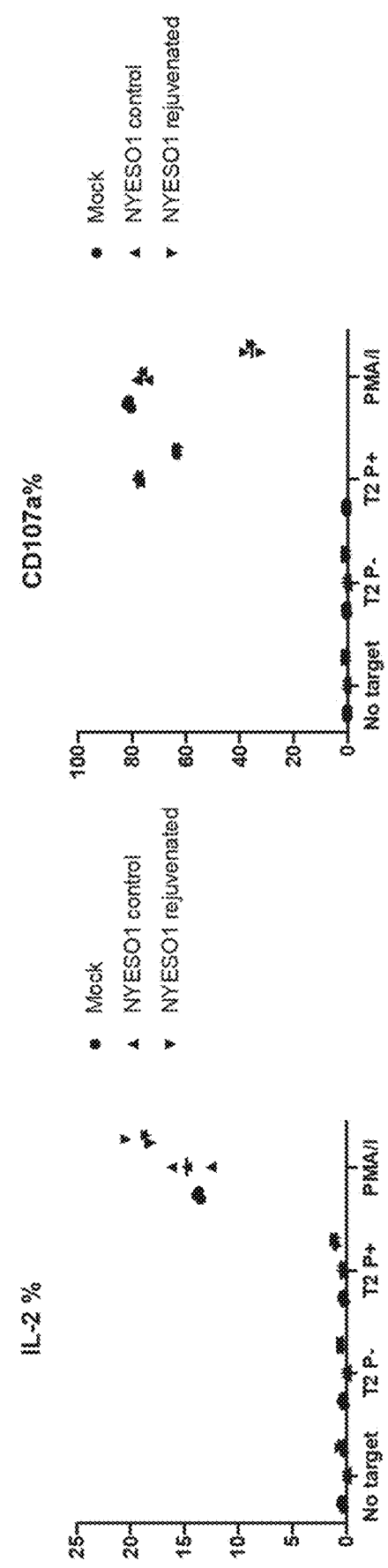
FIG. 14A  FIG. 14B  FIG. 14C  FIG. 14D

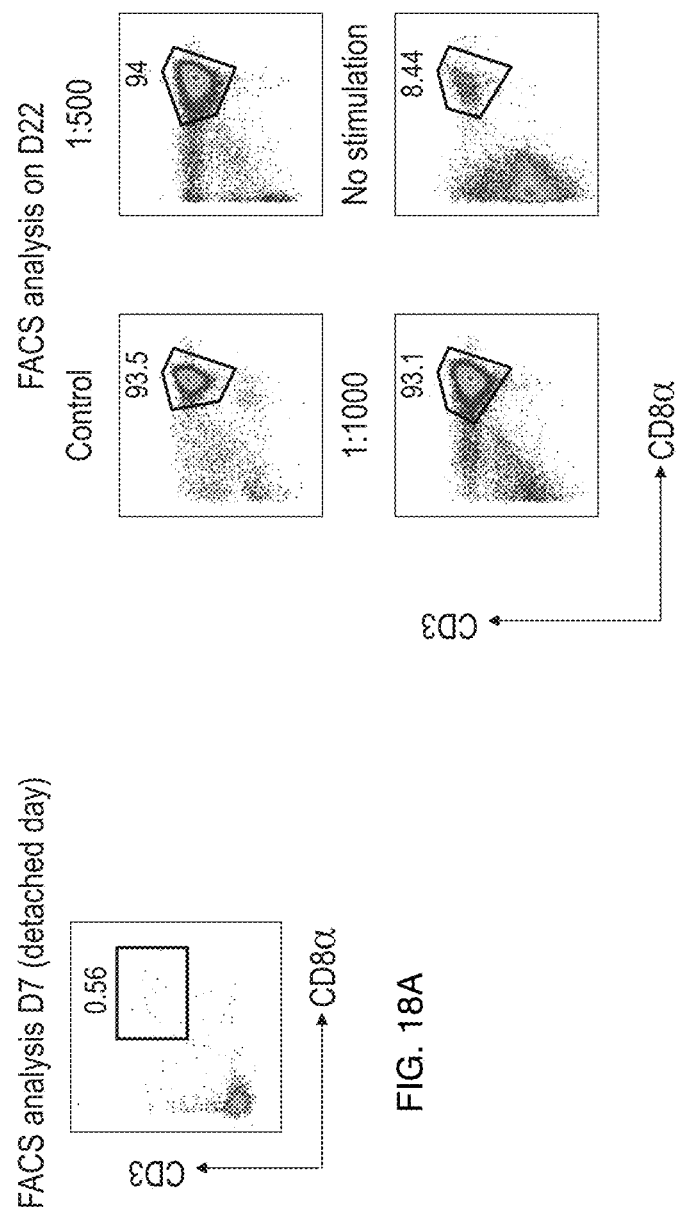

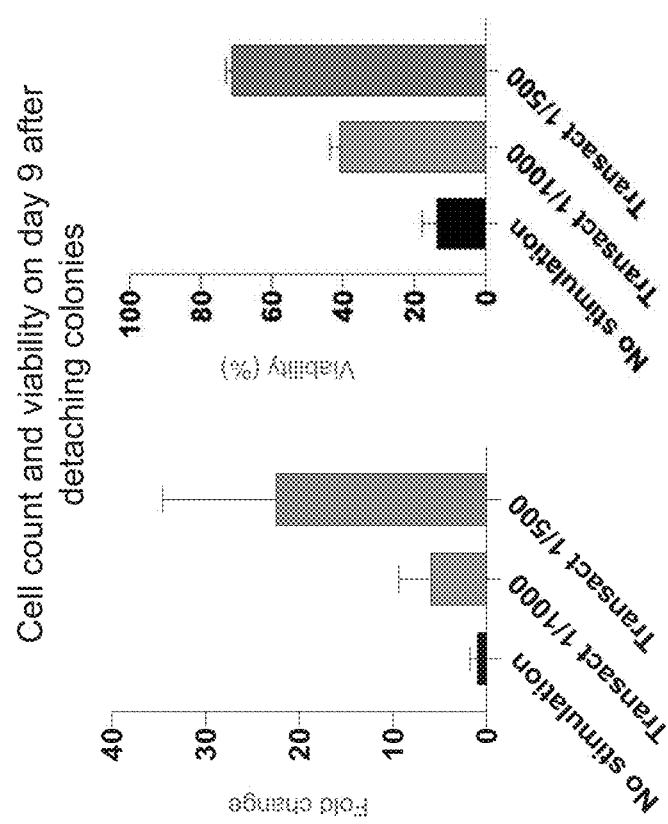

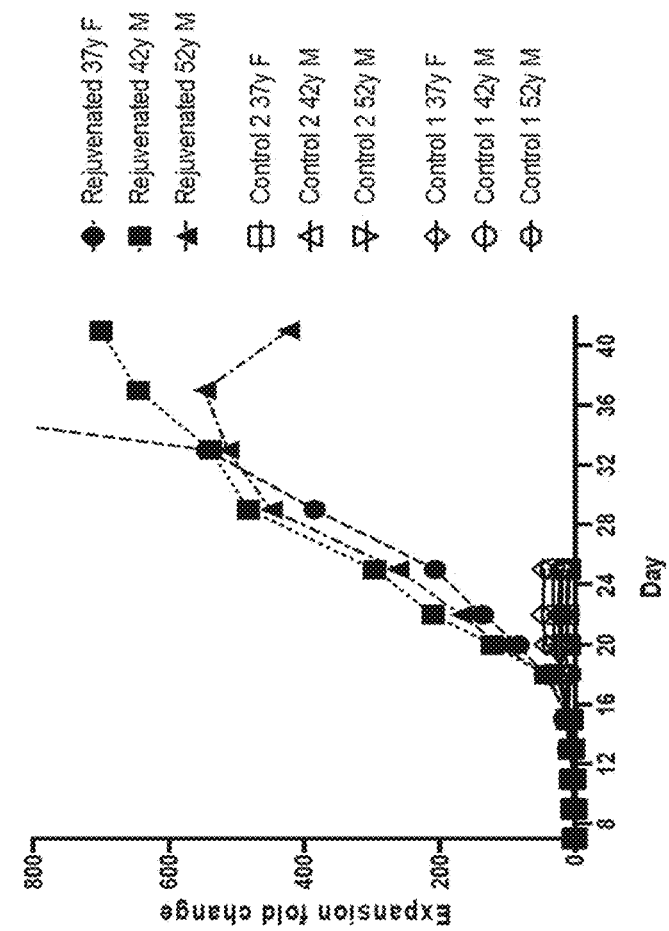
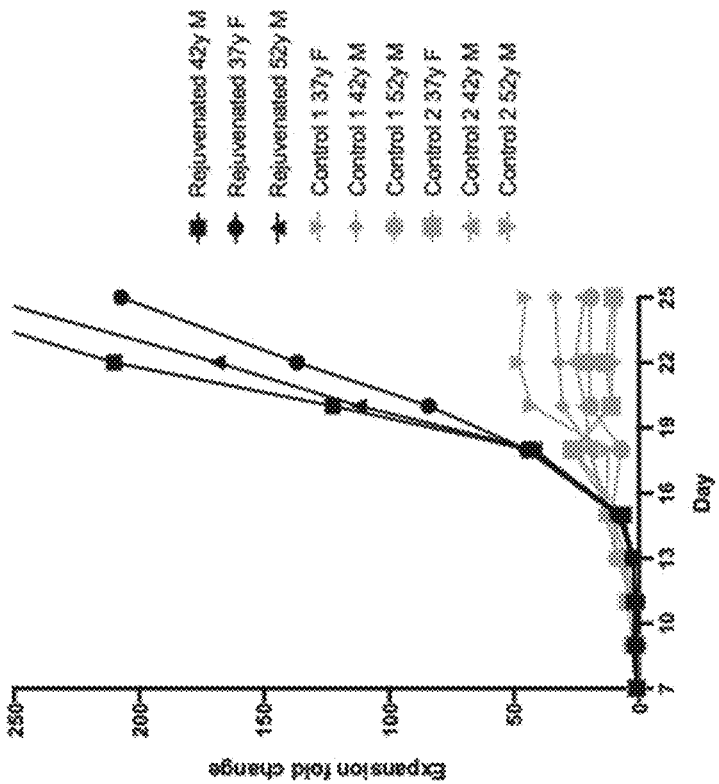
FIG. 19B
FIG. 19A

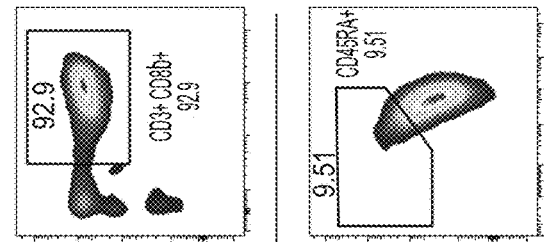
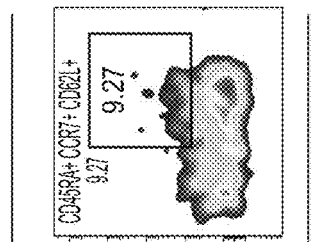
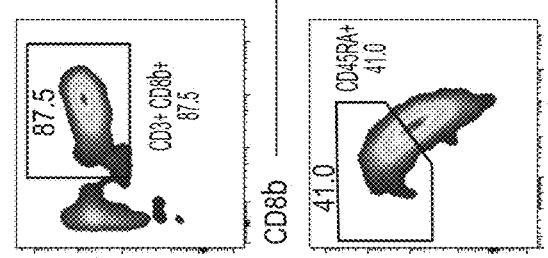
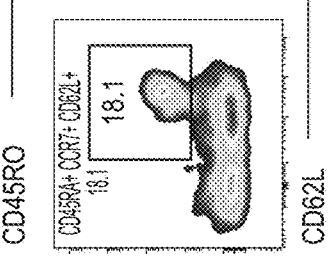
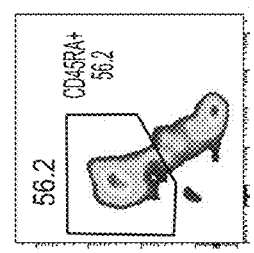
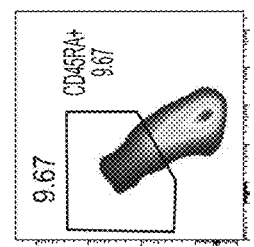
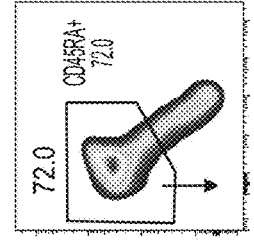
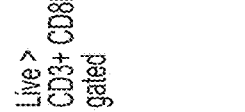
FIG. 23

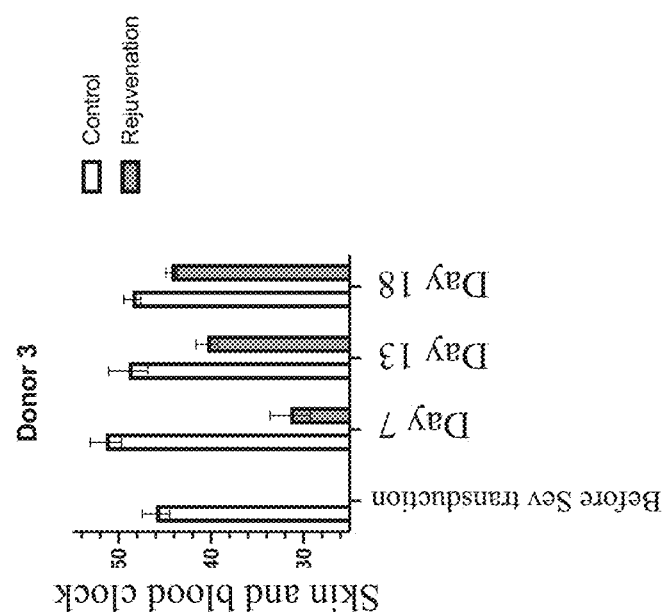
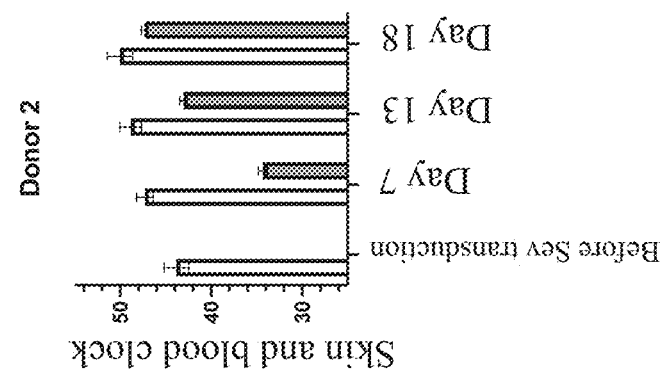
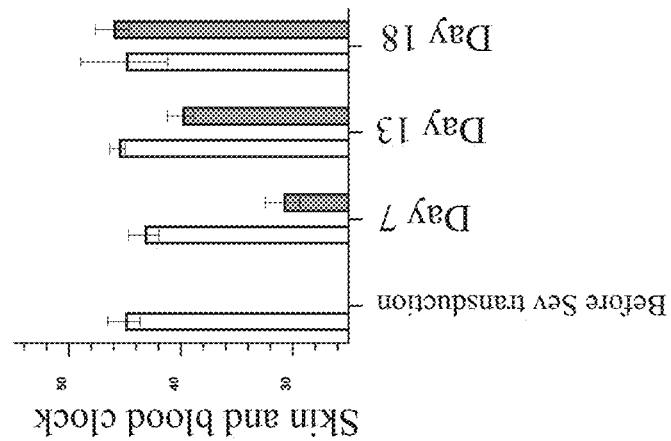

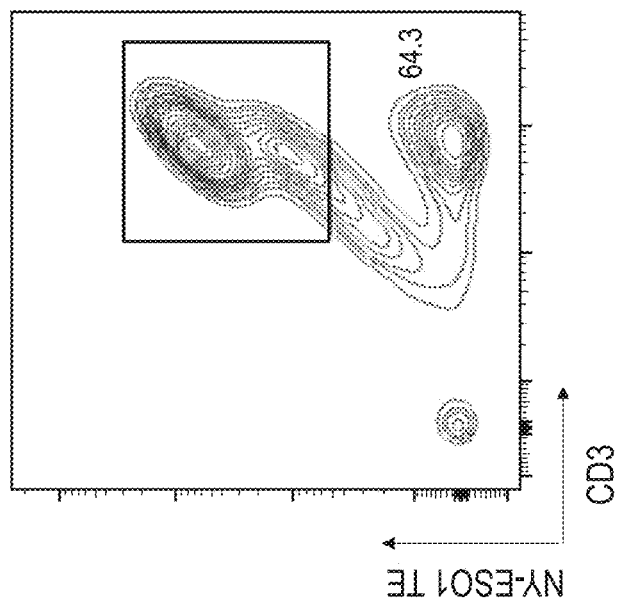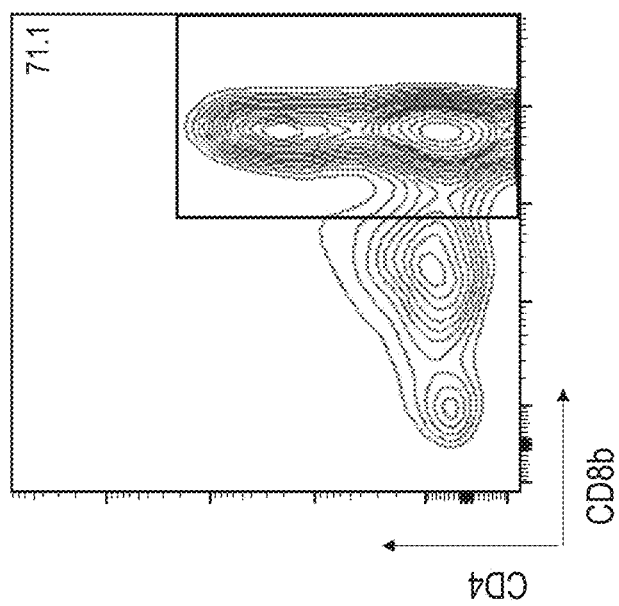
FIG. 40

Day 11 detach

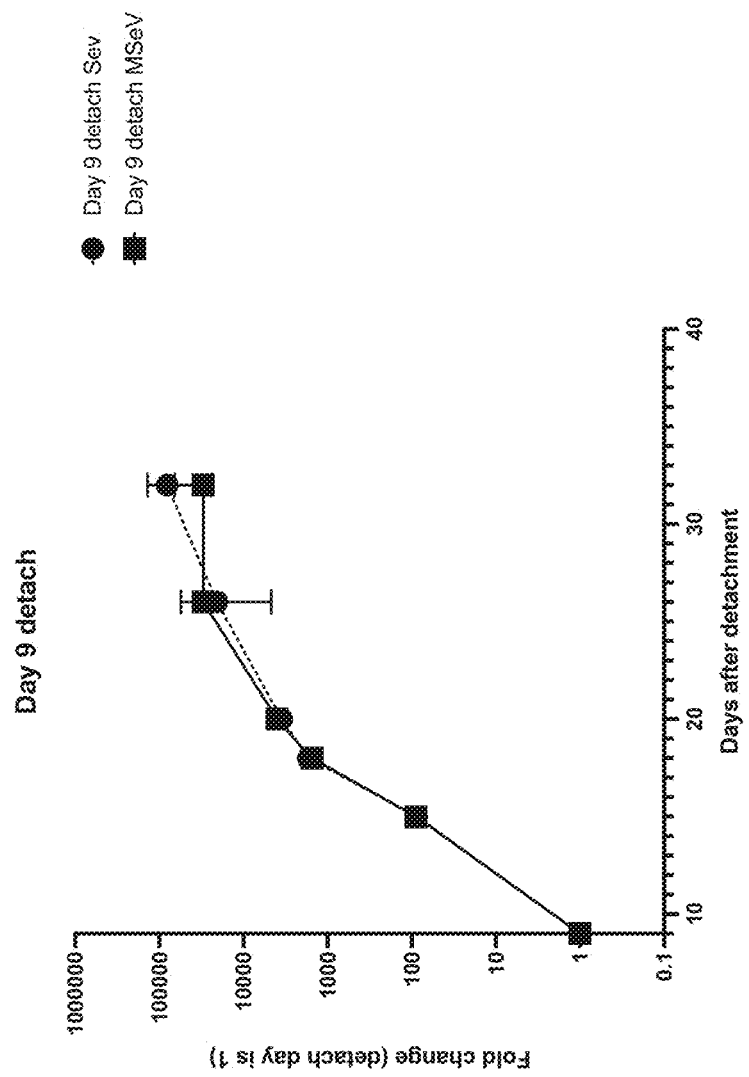

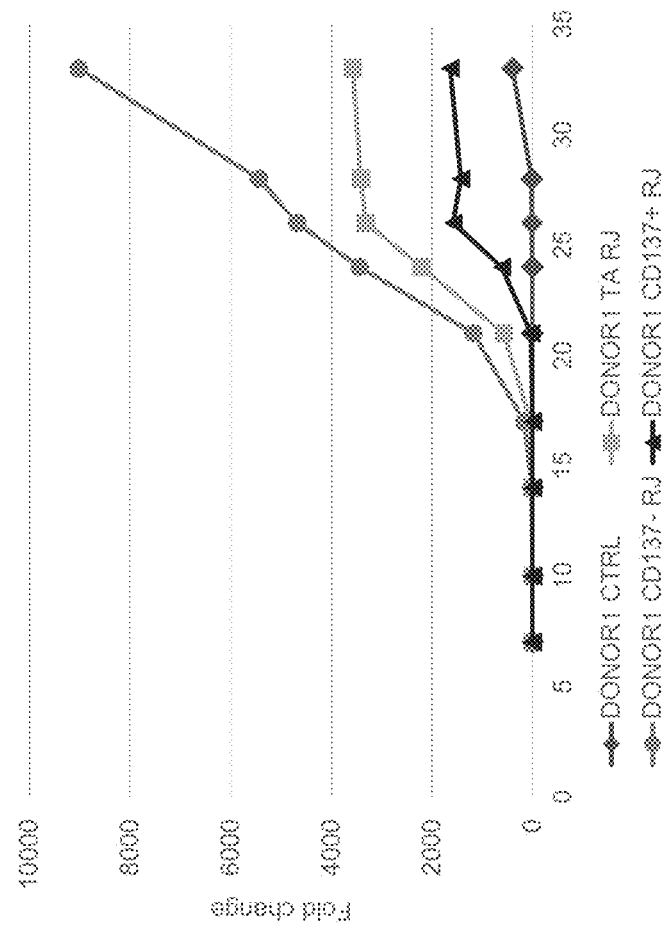

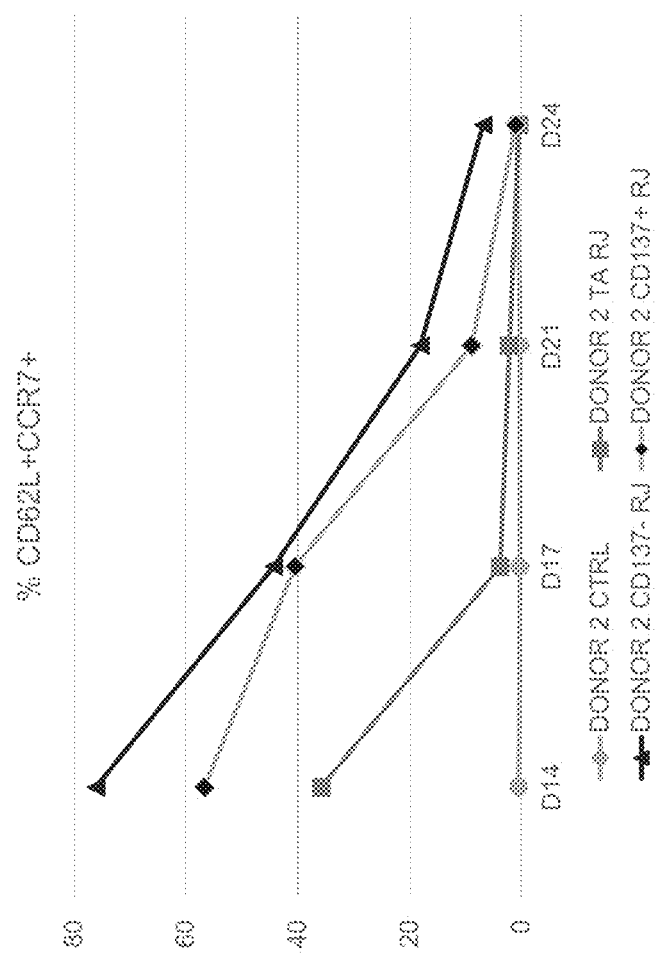

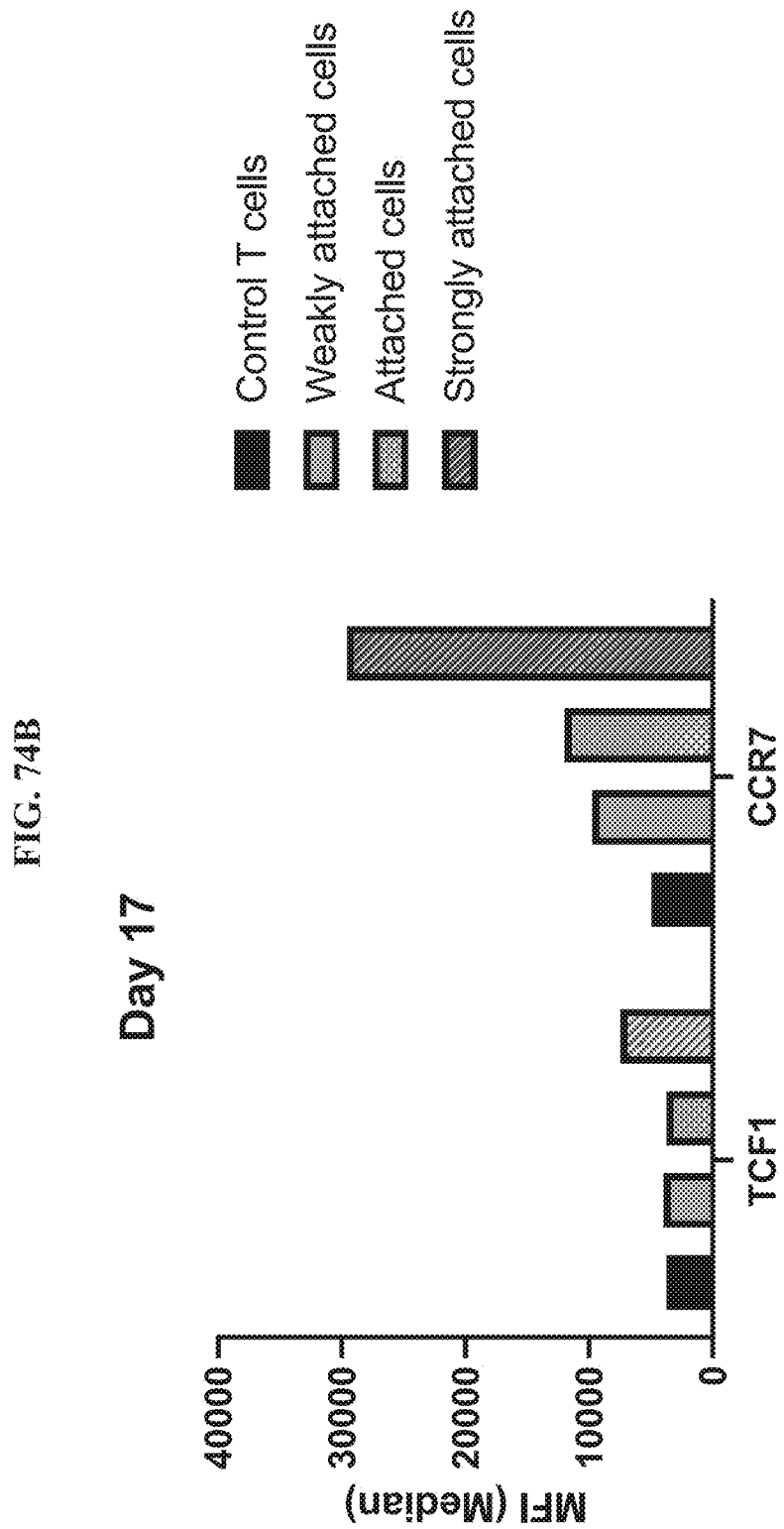

METHODS FOR MAKING, COMPOSITIONS COMPRISING, AND METHODS OF USING REJUVENATED T CELLS

CROSS REFERENCE TO RELATED APPLICATIONS

This Non-Provisional Patent Application claims priority to U.S. Provisional Patent Application No. 63/117,787, filed on Nov. 24, 2020, U.S. Provisional Patent Application No. 63/153,881, filed on Feb. 25, 2021, and U.S. Provisional Patent Application No. 63/165,093, filed on Mar. 23, 2021, the contents of each of which are incorporated herein in their entireties.

BACKGROUND OF THE INVENTION

Tumor Infiltrating Lymphocytes ("TILs") are immune cells (e.g., T cells) found within tumors that can recognize and kill cancer cells. Adoptive transfer of autologous TILs have been extensively studied, but one disadvantage of TIL-based therapies is that these cells often exhibit cellular markers of extensive differentiation and aging along with loss of functionality. See, e.g., Gurusamy, et al., 2020, Cancer Cell 37, 818-833; Jiang, et al., 2015, Cell Death Dis 6, e1792. Typically, TILs are largely composed of TEM or TEMRA cells and have characteristics of exhaustion. Sakuishi et al., 2010, J Exp Med 207, 2187-2194. Additionally, preclinical evidence strongly suggests that impaired T cell function in the tumor site can drive poor clinical efficacy of T cell products.

T cells (also termed T lymphocytes) are a type of blood cell with unique properties that develop from stem cells found in bone marrow; T cells protect against infection and fight cancer. T cells are structurally and functionally different from other cell types such as fibroblasts and undergo a complex development that requires positive and negative selection in the thymus and involves somatic gene rearrangement at the T cell receptor gene loci (see e.g., Kurd and Robey, Immunol Rev. 2016 May; 271(1): 114-126). Although fibroblasts are also involved in the body's immune response, fibroblasts are cells that synthesize extracellular matrix and collagen, thereby producing the structural framework for animal tissues. Fibroblasts are primarily involved in the process of wound healing.

Tumor reactive T cells, in addition to exhibiting characteristics of exhaustion and increased differentiation, are subject to the induction of cell senescence pathways. Senescence is a process of progressive loss of potency and functionality that results from aging and repeated cycles of cell divisions. Several characteristics related to cell senescence, including epigenetic changes (Vodnala et al., 2019, Cancer Cell 37, 818-833 e819), reduced length of telomeres (Rosenberg et al., 2011, Clin Cancer Res 17, 4550-4557) and the loss of functionality, proliferative potential and cell viability (Im et al., 2016, Nature 537, 417-421), are associated with poor T cell function. Although TIL-based cell therapy can mediate responses in some patients, clinical evidence has demonstrated that TIL products with elevated expression of CCR7 and increased telomere length are associated with improved therapeutic outcome. Rosenberg et al., 2011, Clin Cancer Res 17, 4550-4557. Accordingly, many groups have pursued methods of cellular dedifferentiation or reprogramming as a method of reversing T cell exhaustion, differentiation and senescence.

Cellular dedifferentiation (reprogramming) has been accomplished in the past by utilizing iPS cell technology to revert somatic cells into pluripotent stem cells, followed by redifferentiation into desired cellular lineages. Takahashi et al., 2007, Cell 131, 861-872. iPS cell technology has been shown to be able to reprogram tumor antigen specific tumor infiltrated lymphocytes into iPS cells with the ability to generate T lineage cells in vitro. Vizcardo et al., 2013, Cell Stem Cell 12, 31-36. Driving cells to iPS cells has the advantage of totally resetting the biological and epigenetic clock of the cell.

However, the iPS cells derived from T cells often have abnormal biology—for example, immature phenotype, non MHC dependent killing, improper CD8αβ dimerization, dysregulation of gene expression and failure to produce a developmentally homogeneous population of T cells. (see e.g., Vizcardo et al., 2018, Cell Rep 22, 3175-3190; Takada, K., Kondo, K., and Takahama, Y. 2017 J. Immunol. 198, 2215-2222; Yamagata, T., et al., (2004). Nat. Immunol. 5, 597-605; Fink, P. J. (2013). Annu. Rev. Immunol. 31, 31-50; Kuderer, N. M., et al., 2006 Cancer 106, 2258-2266). While these limitations may be overcome by differentiating iPS cells on 3D thymic organoid cultures (see, e.g., Vizcardo et al., 2018, Cell Rep 22, 3175-3190), these methods are both time and resource intensive. More scalable methods for reversing T cell exhaustion, differentiation and senescence are desirable for achieving commercially feasible adoptive cell therapy with T cells.

SUMMARY OF THE INVENTION

Given that the improvement of T cell anti-tumor function would be beneficial for all modalities of cellular immunotherapy, the present disclosure relates to methods for improving therapeutic T cell product quality and anti-tumor potential, compositions comprising such improved T cells and methods of treatment and other uses of the improved T cell compositions. Consequently, this system can be applicable to many other therapeutic processes for cancer, such as TCR and CAR transduced T cells, along with cells genetically modified with anti-exhaustion or pro-functionality genes for improved function of T cells in the tumor microenvironment.

This system will also be amenable to new methods of T cell expansion in future iterations of media and innovations devised by artificial neoproteins. Taken together, the rejuvenated T cells of the present disclosure can enhance the efficiency of all modalities of cellular immunotherapy by generating T cells that have enhanced capacity for expansion, improved metabolic qualities, and augmented ability to persist and eliminate established solid tumors.

In various embodiments, the present disclosure relates to a method of producing a rejuvenated T cell, comprising, contacting a population of T cells with at least one reprogramming factor selected from the group consisting of KLF4, OCT3/4, SOX2 and C-MYC; and optionally SV40 for at least a period of time sufficient for T cell derived adherent cells to form and wherein said T cells are not transformed into iPS or totipotent cells; and contacting the T cell derived adherent cells with at least one T cell activating agent.

In various embodiments, the present disclosure provides a method of producing a rejuvenated T cell, comprising contacting a T cell with (i) at least one reprogramming factor selected from the group consisting of KLF4, OCT3/4, SOX2 and C-MYC, and (ii) optionally SV40, for a period of time sufficient for a T cell derived adherent cell to form and wherein said T cell is not transformed into an iPS or totipotent cell; and contacting the T cell derived adherent cell with at least one T cell activating agent.

In various embodiments, the present disclosure relates to a method of producing a T cell, comprising contacting a population of T cells in a first culture medium in a culture vessel with at least one reprogramming factor selected from the group consisting of KLF4, OCT3/4, SOX2 and C-MYC; and optionally SV40 for at least a period of time sufficient for the T cells to form at least one colony attached to the culture vessel surface and wherein said T cells are not transformed into iPS cells; and contacting the at least one attached colony with at least one T cell activating agent.

In various embodiments, the present disclosure relates to a method of producing a T cell, comprising contacting a population of isolated T cells in a first culture medium with at least one reprogramming factor selected from the group consisting of KLF4, OCT3/4, SOX2 and C-MYC; and SV40 for a period of at least about 5 days to about 10 days and wherein said T cells are not transformed into iPS cells or totipotent cells; contacting said contacted T cells with at least one T cell activating agent.

In various embodiments, the present disclosure relates to a method of producing at least one T cell, comprising contacting a population of isolated T cells with at least one reprogramming factor selected from the group consisting of KLF4, OCT3/4, SOX2 and C-MYC; and SV40 for at least a period of time sufficient for the T cells to express at least one marker selected from the group consisting of SSEA4, CD9, and CD90 and wherein said T cells are not transformed into iPS cells or totipotent cells; and contacting said contacted T cells with at least one T cell activating agent.

In various embodiments, the isolated T cells are contacted with the at least one reprogramming factor for at least a period of time sufficient for at least a portion of the T cells to express CD3 and at least one marker selected from the group consisting of SSEA4, CD9, and CD90. In various embodiments, the T cells are transiently contacted with the at least one reprogramming factor for at least a period of time sufficient for at least a portion of said contacted T cells to express SSEA4 and CD3. In various embodiments, the T cells are transiently contacted with the at least one reprogramming factor for at least a period of time sufficient for at least a portion of said contacted T cells to express CD3, CD9 and CD90. In various embodiments, the T cells are contacted with the at least one reprogramming factor for at least a period of time sufficient for at least a portion of said contacted T cells to express CD3, SSEA4, CD9 and CD90.

In various embodiments, prior to contacting said isolated T cells with the at least one reprogramming factor, said transiently contacted T cells are contacted with IL-2 and at least one compound capable of activating said isolated T cells. In various embodiments, the T cell is a TCRαβ T cell; a TCRgd T cell; a CD4+CD8αβ+ double positive cell, CD4+ single positive cell (such as Th1, Th2, Th17, Treg), a naïve T cell, a central memory T cell, or effector memory T cell. In various embodiments, the T cell is a TIL. In various embodiments, said isolated T cells are isolated from a mammal.

In various embodiments, the isolated T cells are transiently contacted with KLF4, OCT3/4, SOX2 and C-MYC. In various embodiments, the isolated T cells are transiently contacted with KLF4, OCT3/4, SOX2 and C-MYC for at least about 4 to 10 days.

In various embodiments, the isolated T cells are contacted with KLF4, OCT3/4, SOX2 and C-MYC for at least about 4 to 7 days. In various embodiments, the isolated T cells are contacted with KLF4, OCT3/4, SOX2 and C-MYC for about 5 days.

In various embodiments, KLF4, OCT3/4, SOX2 and C-MYC are transiently expressed in the T cell. In various embodiments, KLF4, OCT3/4, SOX2 and C-MYC are transiently expressed using a non-integrating viral vector. In this regard, the T cells may be transduced with one or more viral vectors encoding the reprogramming factors. In various embodiments, KLF4, OCT3/4, SOX2 and C-MYC are transiently expressed using a Sendai virus. In various embodiments, KLF4, OCT3/4, SOX2 and C-MYC are constitutively expressed, wherein expression is later inhibited by the addition of a compound that inhibits expression of KLF4, OCT3/4, SOX2 AND C-MYC. In various embodiments, said compound is a small molecule inhibitor that specifically inhibits the expression of one or more of KLF4, OCT3/4, SOX2 and C-MYC expression. In various embodiments, said compound is an siRNA or shRNA molecule that specifically inhibits the expression of one or more of KLF4, OCT3/4, SOX2 and C-MYC. In various embodiments, KLF4, OCT3/4, SOX2 and C-MYC are transiently expressed following delivery using a nanoparticle.

In various embodiments, the disclosure provides further contacting the contacted T cells (i.e., the partially reprogrammed T cells) with at least one T cell activating compound, and optionally at least one cytokine selected from the group consisting of IL-2, IL-7, IL-15, and IL-12. In various embodiments the partially reprogrammed cells are T cell derived adherent cells. In various embodiments, said at least one T cell activating compound comprises an antibody that binds CD3 or an antibody that binds CD28 or both; or wherein the at least one T cell activating compound is a tumor antigen. In various embodiments, the disclosure provides further engineering the T cell to express a cell surface receptor, wherein said T cell is engineered prior to contacting said T cell with said at least one reprogramming factor. In various embodiments, the disclosure provides further engineering the T cell to express a cell surface receptor, wherein said T cell is engineered after transiently contacting said T cell with said at least one reprogramming factor.

In various embodiments, said cell surface receptor is either a chimeric antigen receptor or an engineered T cell receptor or a hybrid receptor thereof. In various embodiments, said cell surface receptor recognizes a specific antigenic moiety on the surface of a target cell. In various embodiments, the antigenic moiety is MHC class I dependent. In various embodiments, the antigenic moiety is MHC class I independent.

In various embodiments, the resulting T cells comprise an incomplete set of V, D, and J segments of T cell receptor genes. In various embodiments, the disclosure provides further measuring the epigenetic age of the resulting T cells. In various embodiments, the epigenetic age of the resulting T cells is at least 5% younger than the population of T cells prior to reprogramming. In various embodiments, the partially reprogrammed T cells are capable of expanding at least 25-fold greater than the initially isolated cells. In various embodiments, the disclosure provides further contacting said isolated T cells with at least one factor selected from the group consisting of KLF4, OCT3/4, SOX2 and C-MYC; and SV40 results in a reduction in CD3 and CD8 expression.

In various embodiments, the present disclosure provides for a method of producing a T cell, comprising, obtaining a plurality of isolated T cells from a source; culturing said isolated T cells in a first medium comprising IL-2 and activating said isolated T cells with at least one T cell activating compound or agent and a costimulatory agent, such as an antibody specific for CD3 and/or for CD28; transiently contacting said activated T cells with KLF4, OCT3/4, SOX2 and C-MYC, for a period of about 5 days to about 10 days in a second culture medium that does not comprise IL-2, or antibody specific for CD3 or CD28; wherein said isolated T cells are not completely reprogrammed into iPS cells; replacing said second culture medium with a third culture medium comprising IL-2 and at least one antibody specific for CD3 and/or CD28; wherein said transiently contacted T cells are cultured in said third culture medium for at least about 5 days.

In various embodiments, the disclosure provides further expanding said partially reprogrammed, reactivated T cells. In various embodiments, said T cell is a TCRαβ cell; a TCRgd cell; a CD4+CD8αβ+ double positive cell, CD4+ single positive cell (Th1, Th2, Th17, Treg), a naïve T cell, a central memory T cell, or effector memory T cell. In various embodiments, said T cell is a tumor infiltrating lymphocyte (TIL).

In various embodiments, the present disclosure provides for a population of T cells whose epigenetic age is at least 5% younger than its chronological age. In various embodiments, the present disclosure provides for a population of T cells, wherein the epigenetic age is at least 25% younger than its chronological age. In various embodiments, the present disclosure provides for a population of T cell derived adherent cells, wherein at least 70% of the cells express both CD3 and SSEA4. In various embodiments, the present disclosure provides for a population of T cell derived adherent cells, wherein at least 30% of the cells express CD9 or CD90 or both CD9 and CD90.

In various embodiments, the invention provides for a population of tumor infiltrating lymphocytes, wherein at least 35%, 40%, 45%, 50%, 55%, 60%, 65%, 70%, 75%, 80%, 85%, 90%, or 95% of the tumor infiltrating lymphocytes express both CCR7 and CD62L. In various embodiment, the invention provides, for a population of tumor infiltrating lymphocytes, wherein at least 35%, 40%, 45%, 50%, 55%, 60%, 65%, 70%, 75%, 80%, 85%, 90%, or 95% of the tumor infiltrating lymphocytes express both CCR7 and TCF7.

In various embodiments, the present disclosure provides for a population of T cells produced by a method comprising transiently contacting a population of T cells with at least one reprogramming factor selected from the group consisting of KLF4, OCT3/4, SOX2 AND C-MYC; and optionally SV40 for a period of time sufficient for T cell derived adherent cells to form and wherein said isolated T cells are not transformed into iPS or totipotent cells; and contacting the T cell derived adherent cells with at least one T cell activating compound.

In various embodiments, the present disclosure provides for a population of T cells produced by a method comprising transiently contacting a population of isolated T cells in a first culture medium in a culture vessel with at least one reprogramming factor selected from the group consisting of KLF4, OCT3/4, SOX2 and C-MYC; and optionally SV40 for a period of time sufficient for the isolated T cells to form at least one colony attached to the culture vessel surface and wherein said isolated T cells are not transformed into iPS cells; and contacting the at least one attached colony with at least one T cell activating compound.

In various embodiments, the present disclosure provides for a population of T cells produced by a method comprising transiently contacting a population of isolated T cells in a first culture medium with at least one reprogramming factor selected from the group consisting of KLF4, OCT3/4, SOX2 and C-MYC; and SV40 for a period of at least about 5 days and no more than about 10 days and wherein said isolated T cells are not transformed into iPS cells; contacting said transiently contacted T cells with at least one T cell activating compound.

In various embodiments, the present disclosure provides for a population of T cells produced by a method comprising transiently contacting a population of isolated T cells with at least one reprogramming factor selected from the group consisting of KLF4, OCT3/4, SOX2 and C-MYC; and SV40 for a period of time sufficient for the isolated T cells to express at least one marker selected from the group consisting of SSEA4, CD9, and CD90 and wherein said isolated T cells are not transformed into iPS cells; and contacting said transiently contacted T cells with at least one T cell activating compound.

In various embodiments, the isolated T cells are transiently contacted with the at least one reprogramming factor for a period of time sufficient for at least a portion of the isolated T cells to express CD3 and at least one marker selected from the group consisting of SSEA4, CD9, and CD90. In various embodiments, the isolated T cells are transiently contacted with the at least one reprogramming factor for a period of time sufficient for at least a portion of said transiently contacted T cells to express SSEA4 and CD3. In various embodiments, the isolated T cells are transiently contacted with the at least one reprogramming factor for a period of time sufficient for at least a portion of said transiently contacted T cells to express CD3, CD9 and CD90. In various embodiments, the isolated T cells are transiently contacted with the at least one reprogramming factor for a period of time sufficient for at least a portion of said transiently contacted T cells to express CD3, SSEA4, CD9 and CD90.

In various embodiments, prior to contacting said isolated T cells with the at least one reprogramming factor, said transiently contacted T cells are contacted with IL-2 and at least one compound capable of activating said isolated T cells.

In various embodiments, the T cell is a TCRαβ cell; a TCRγδ cell; a CD4+CD8αβ+ double positive cell, CD4+ single positive cell (such as Th1, Th2, Th17, Treg), a naïve T cell, a central memory T cell, or effector memory T cell. In various embodiments, the T cell is a TIL. In various embodiments, said isolated T cells are isolated from a mammal. In various embodiments, the isolated T cells are transiently contacted with KLF4, OCT3/4, SOX2 and C-MYC.

In various embodiments, the isolated T cells are transiently contacted with KLF4, OCT3/4, SOX2 and C-MYC for at least about 4 to 10 days. In various embodiments, the isolated T cells are transiently contacted with KLF4, OCT3/4, SOX2 and C-MYC for at least about 4 to 7 days.

In various embodiments, the isolated T cells are transiently contacted with KLF4, OCT3/4, SOX2 and C-MYC for about 5 days. In various embodiments, KLF4, OCT3/4, SOX2 and C-MYC are transiently expressed in the T cell. In various embodiments, KLF4, OCT3/4, SOX2 and C-MYC are transiently expressed using a non-integrating viral vector. In various embodiments, KLF4, OCT3/4, SOX2 and C-MYC are transiently expressed using a Sendai virus. In various embodiments, KLF4, OCT3/4, SOX2 and C-MYC are constitutively expressed, wherein expression is later inhibited by the addition of a compound that inhibits expression of KLF4, OCT3/4, SOX2 AND C-MYC. In various embodiments, said compound is a small molecule inhibitor that specifically inhibits the expression of one or more of KLF4, OCT3/4, SOX2 and C-MYC expression. In various embodiments, said compound is an siRNA or shRNA molecule that specifically inhibits the expression of one or more of KLF4, OCT3/4, SOX2 and C-MYC. In various embodiments, KLF4, OCT3/4, SOX2 and C-MYC are transiently expressed using a nanoparticle.

In various embodiments, the present disclosure provides for further contacting the transiently contacted T cells (e.g., the partially reprogrammed T cells) with at least one cytokine selected from the group consisting of IL-2, IL-7, IL-15, and IL-12; and/or with at least one T cell activating agent and/or at least one T cell costimulatory agent (e.g., anti-CD3 and/or anti-CD28 antibodies). In various embodiments, at least one T cell activating compound comprises an antibody that binds CD3 or an antibody that binds CD28 or both; or wherein the at least one T cell activating compound is a tumor antigen.

In various embodiments, the present disclosure provides for further engineering the T cell to express a cell surface receptor, wherein said T cell is engineered prior to transiently contacting said T cell with said at least one reprogramming factor. In various embodiments, the present disclosure provides for further engineering the T cell to express a cell surface receptor, wherein said T cell is engineered after transiently contacting said T cell with said at least one reprogramming factor.

In various embodiments, said cell surface receptor is either a chimeric antigen receptor or a T cell receptor or a hybrid receptor thereof. In various embodiments, said cell surface receptor recognizes a specific antigenic moiety on the surface of a target cell. In various embodiments, the antigenic moiety is MHC class I dependent. In various embodiments, the antigenic moiety is MHC class I independent. In various embodiments, the resulting T cells comprise an incomplete set of V, D, and J segments of T cell receptor genes. In various embodiments, the present disclosure provides for further measuring the epigenetic age of the resulting T cells. In various embodiments, the epigenetic age of the resulting T cells is at least 5% younger than the population of T cells prior to reprogramming. In various embodiments, the partially reprogrammed T cells are capable of expanding at least 25-fold greater than the initially isolated cells. In various embodiments, the present disclosure provides for further contacting said isolated T cells with at least one factor selected from the group consisting of KLF4, OCT3/4, SOX2 and C-MYC; and SV40 results in a reduction in CD3 and CD8 expression.

In various embodiments, the present disclosure relates to a population of T cells produced by a method comprising obtaining a plurality of isolated T cells from a source; culturing said isolated T cells in a first medium comprising IL-2 and activating said isolated T cells with at least one antibody specific for CD3 and/or for CD28; transiently contacting said activated T cells with KLF4, OCT3/4, SOX2 and C-MYC, for a period of about 5 days to about 10 days in a second culture medium that does not comprise IL-2, or antibody specific for CD3 and/or CD28; wherein said isolated T cells are not completely reprogrammed into iPS cells; replacing said second culture medium with a third culture medium comprising IL-2 and at least one antibody specific for CD3 and/or CD28; wherein said transiently contacted T cells are cultured in said third culture medium for at least about 5 days.

In various embodiments, the present disclosure relates to further expanding said transiently contacted T cells. In various embodiments, said T cell is a TCRαβ cell; a TCRγδ cell; a CD4+CD8αβ+ double positive cell, CD4+ single positive cell (Th1, Th2, Th17, Treg), a naïve T cell, a central memory T cell, or effector memory T cell. In various embodiments, said T cell is a tumor infiltrating lymphocyte (TIL).

In various embodiments, the present disclosure relates to a method of treating a patient in need thereof with a population of T cells produced by a method disclosed herein or by the population of T cells disclosed herein. In various embodiments, the method of treatment is a method for treating a cancer, a viral condition or an autoimmune disorder.

In various embodiments, the cancer is acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, head and neck cancers (e.g., cancer of the nose, nasal cavity, or middle ear, cancer of the oral cavity), cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, or urinary bladder cancer.

In various embodiments, the invention relates to a method of producing at least one rejuvenated T cell, comprising: a. isolating a T cell from a tumor, wherein the T cell is a tumor infiltrating lymphocyte; wherein the tumor infiltrating lymphocyte expresses CD137; b. activating said tumor infiltrating lymphocyte with at least one T cell activating compound, wherein the T cell activating compound is a tumor antigen; c. transiently contacting a population of isolated T cells with at least one reprogramming factor selected from the group consisting of KLF4, OCT3/4, SOX2 and C-MYC; and optionally SV40 for a period of time sufficient for T cell derived adherent cells to form and wherein said isolated T cells are not transformed into iPS or totipotent cells; and d. contacting the T cell derived adherent cells with at least one T cell activating compound.

In various embodiments, the invention relates to a method of producing at least one rejuvenated tumor infiltrating lymphocyte (TIL), the method comprising (a) isolating a TIL from a tumor, wherein the TIL expresses CD137, (b) activating said TIL with at least one first tumor antigen, and (c) transiently contacting a population of isolated TILs with (i) at least one reprogramming factor selected from the group consisting of KLF4, OCT3/4, SOX2 and C-MYC, and (ii) optionally SV40, for a period of time sufficient for TIL-derived adherent cells to form and wherein said isolated TILs are not transformed into iPS or totipotent cells.

In various embodiments, the invention relates to a method of producing rejuvenated T cells, comprising contacting a population of T cells (i) at least one reprogramming factor selected from the group consisting of KLF4, OCT3/4, SOX2 and C-MYC, and (ii) optionally SV40, for at least a period of time sufficient for at least 20% of the contacted T cells to express α6β1 integrin and wherein said contacted T cells are not transformed into iPS cells; isolating said at least 20% of the contacted T cells with a binding molecule that specifically binds to α6β1 integrin; contacting the isolated cells of (b) with a T cell activating and/or a T cell costimulatory agent; thereby producing rejuvenated T cells.

In various embodiments, the invention relates to a method of producing at least one rejuvenated T cell, comprising transiently contacting the population of T cells with (i) at least one reprogramming factor selected from the group consisting of KLF4, OCT3/4, SOX2 AND C-MYC, and (ii) optionally SV40, for a period of time sufficient for T cell derived adherent cells to form; wherein said T cells are not transformed into iPS or totipotent cells; isolating a subpopulation of T cell derived adherent cells that express either a6 (CD49f) or b1 (CD29) integrin or both; and contacting the isolated subpopulation with at least one T cell activating compound.

In various embodiments, the invention relates to a population of rejuvenated T cells produced by a method comprising contacting the population of T cells with (i) at least one reprogramming factor selected from the group consisting of KLF4, OCT3/4, SOX2 AND C-MYC, and (ii) SV40, for a period of time sufficient for T cell derived adherent cells to form; wherein said T cells are not transformed into iPS or totipotent cells; isolating a subpopulation of T cell derived adherent cells that express either a6 integrin, b1 integrin or both; and contacting the subpopulation of T cell derived adherent cells with at least one T cell activating compound.

In various embodiments, the invention relates to a population of T cell derived adherent cells, wherein at least 70% of the cells express integrin α6 or integrin β1.

In various embodiments, the invention relates to a population of T cell derived adherent cells, wherein at least 50% of the cells express both integrin α6 and integrin β1.

In various embodiments, the invention relates to a population of T cell derived adherent cells, wherein at least 70% of the cells express both integrin α6 and integrin β1.

Additional features and aspects of the present invention will be understood by persons of ordinary skill in the art in view of the following disclosure and the accompanying claims and figures.

BRIEF DESCRIPTION OF THE FIGURES

FIG. 3A shows the attached cells colony formation from Group #4, FIG. 3B shows the T cells in Group #3 which do not show attachment and colony formation; FIG. 3C shows the same panel as FIG. 3A for comparison to FIG. 3D. FIG. 3D shows T cells after 3 days in standard T cell culture medium with anti-CD3 antibody (100 ng/ml) and anti-CD28 antibody (2 μg/ml) stimulation; FIG. 3E is the same panel as FIG. 3A for comparison to FIG. 3F. FIG. 3F shows a normal iPS cell colony. The attached cells shown in FIGS. 3A, 3C, and 3E are referred to herein as T cell derived adherent cells.

FIG. 6 is a SSC/FSC FACS contour plot showing that day 5 attached cells become bigger with a complex structure.

FIG. 12A show FACS plots for expression of CD8a and CD8b days 7, 9 and 10 and FIG. 12B is a graph plotting the percentage of cells positive for CD8a and CD3CD8ab on days 6-10. See Example 4. The CD4-CD8a+ population was gated for further analysis of CD8B and CD3. No Sendai infection means CD8 T cells received the first and the second stimulation but were not infected by Sendai virus (no reprogramming factors).

FIGS. 14A-14D are graphs showing the results from cytokine production and degranulation assays of rejuvenated NY-ESO-1 TCR transduced T cells. The FACS results were analyzed by FlowJo software. Single cells>Live cells>CD3+>CD8+CD4–>NY-ESO-1 tetramer+ cells were gated for NY-ESO-1 Tg T cells and Single cells>Live cells>CD3+>CD8+CD4–>NY-ESO-1 tetramer– cells were gated for mock control T cells. The frequency of IFNg+(A), TNFa+(B), IL-2+(C), and CD107a+(D) were calculated and plotted as shown.

FIGS. 18A-18D show that stimulation signaling is critical for partially reprogrammed T cells to reacquire expression of conventional T cell markers CD3 and CD8a, and to survive and proliferate. FIG. 18A is a FACS contour plot showing the percentage of partially reprogrammed cells expressing CD3 and CD8a at day 7 (day of detachment). FIG. 18B is a FACS contour plot showing percentage of cells expressing CD3 and CD8a at day 20 after either activation with 1:500 or 1:1000 dilution TRANSACT or in T cell culture media (TCM+IL2 60 IU/ml) only. FIGS. 18C and 18D show proliferation and viability of the different groups.

FIGS. 19A-19B show that rejuvenated T cells exhibit dramatically enhanced and sustained proliferation in vitro. T cells were obtained from a 37-year-old Female, a 42-year-old male and a 52-year-old male donor.

FIG. 23 is a FACS contour plot analysis of cell markers used to define differentiation state of T cells (CD3, CD45RA, CD45RO, CD62L and CCR7).

FIG. 27A is a graph plotting the cell expansion and comparing the fold change of rejuvenated TIL to the control cells. FIG. 27B shows FACS plots for expression of CCR7-CD62L and CCR7-TCF7 and shows the rejuvenated TIL exhibited a high expression of stemness related markers.

FIG. 29A shows representative FACS plots of Donor 1, showing the frequency of CD3+CD8b+ (gated on singlets, dead stain negative, and lymphocyte SSC/FSC). FIG. 29B is a bar graph of CD3+CD8b+ frequencies gated as in FIG. 29A; each bar shows the average of Donors 1-3. The error bar indicates +/–1SD FIGS. 30A-30C show the skin and blood clock results before Sev transduction, and days 7, 13, 18 after the transduction in Donors 1-3 of Example 12. "Before Sev transduction" indicates the sample before the activation for Sendai virus transduction. The error bar shows ☐1SD.FIG

T cells produced more cytokines (IFNg (A), IL-2 (B) and TNFa (C)) upon co-culture with T2 cells with NY-ESO-1 peptide. t-test p-value statistical significance: *<0.05, <0.005, *<0.0005, ****<0.0001.

Figure 36:
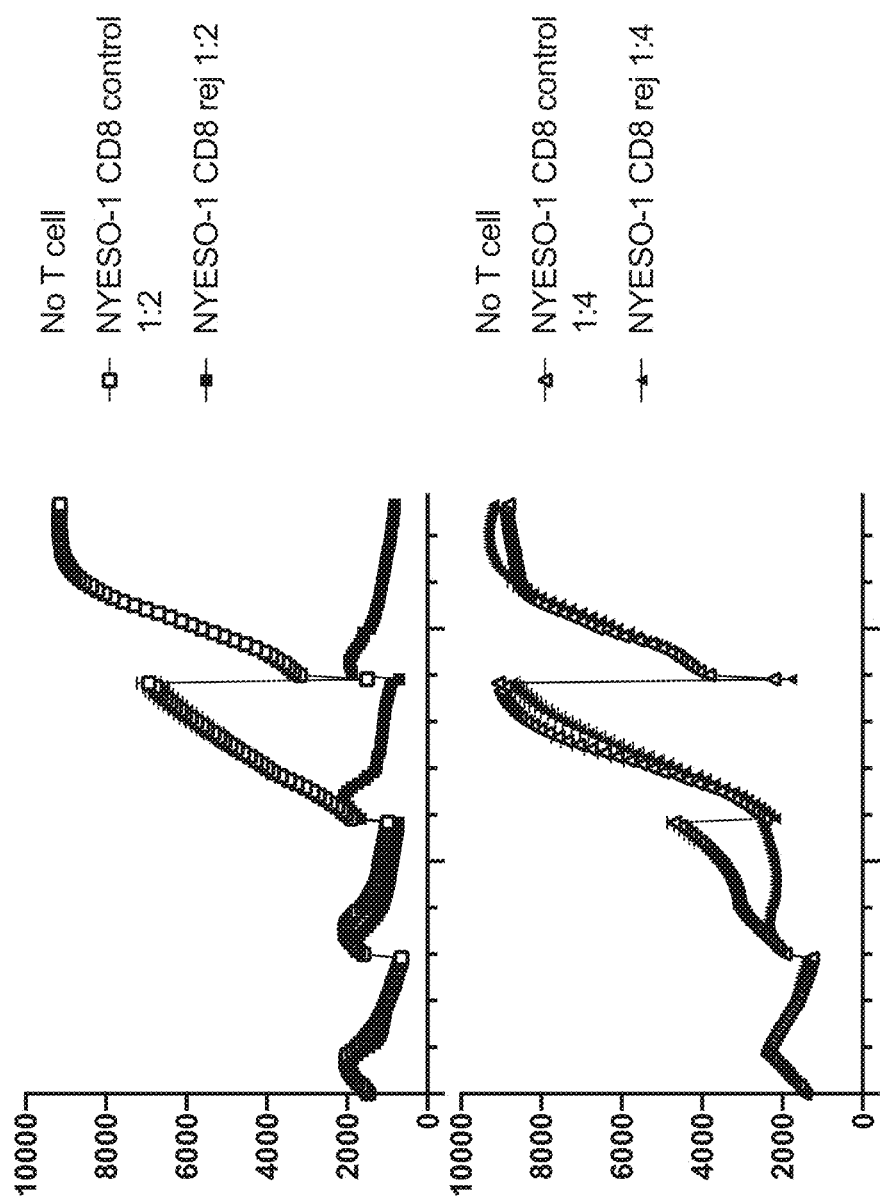

FIG. 36 illustrates the results of rejuvenation NY-ESO-1 Tg CD8 T cells persisted and kept their cytotoxic activity longer upon repeated co-culture with NY-ESO-1 expressing target cells (A375-NLR).

Figure 37:
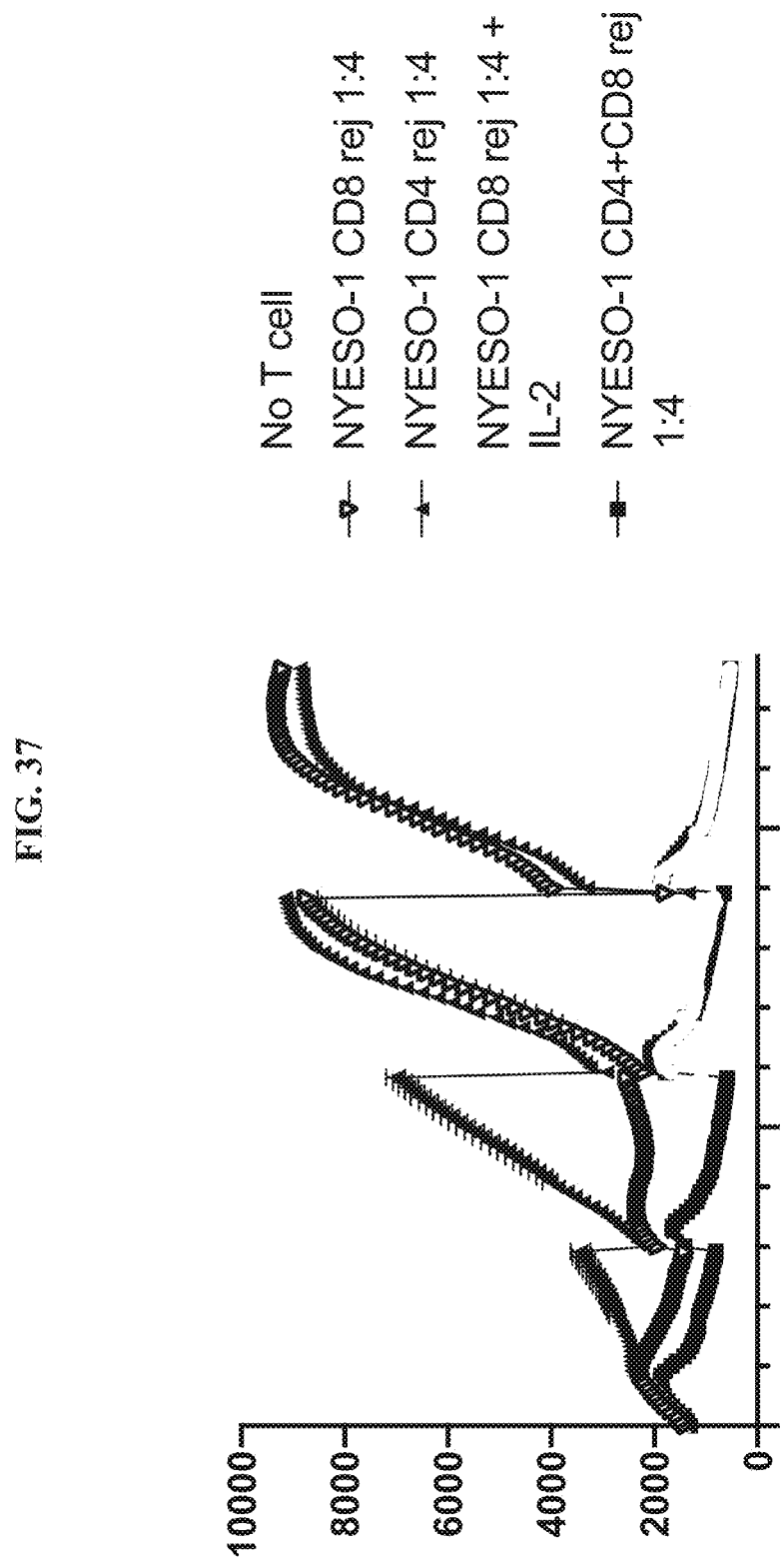

FIG. 37 describes the enhanced cytotoxicity of rejuvenated NY-ESO-1 Tg CD8 T cells resulting from addition of rejuvenated NY-ESO-1 Tg CD4 T cells.

Figure 38A:
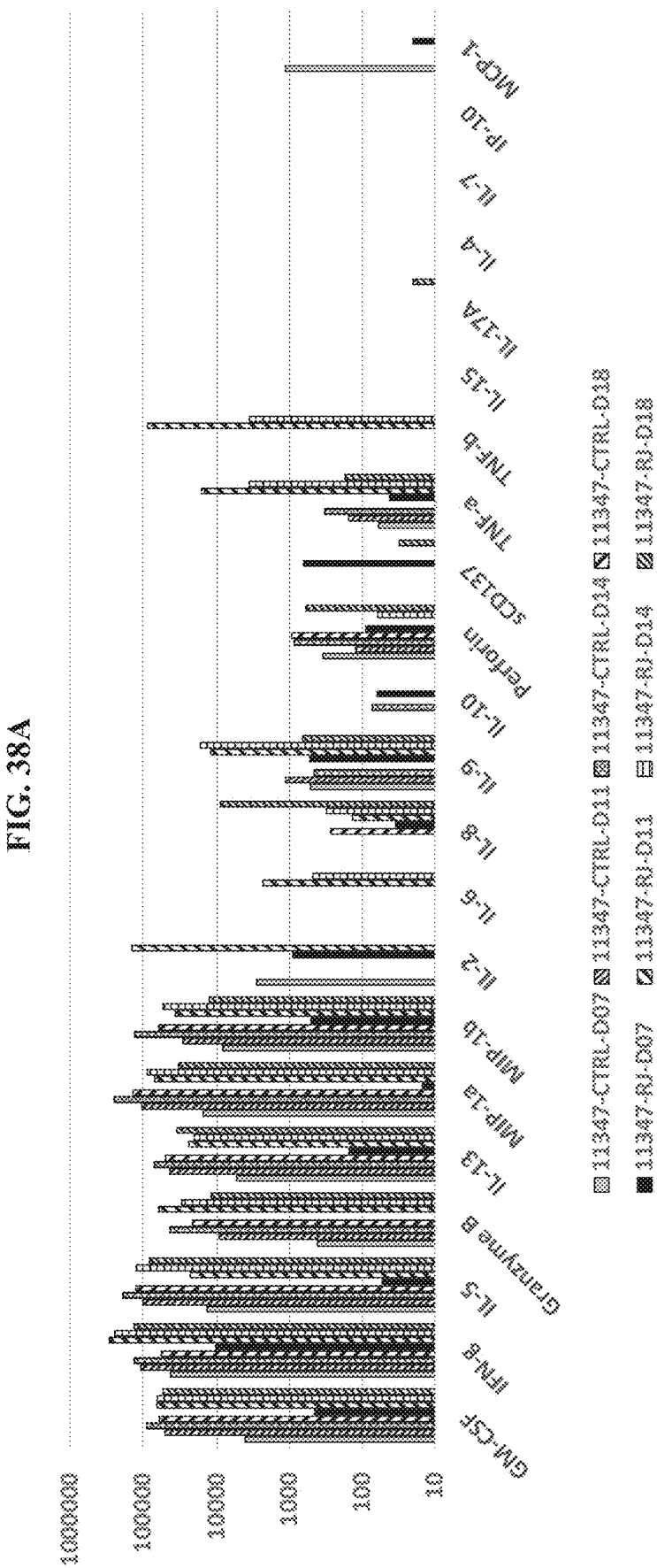
Figure 38B:
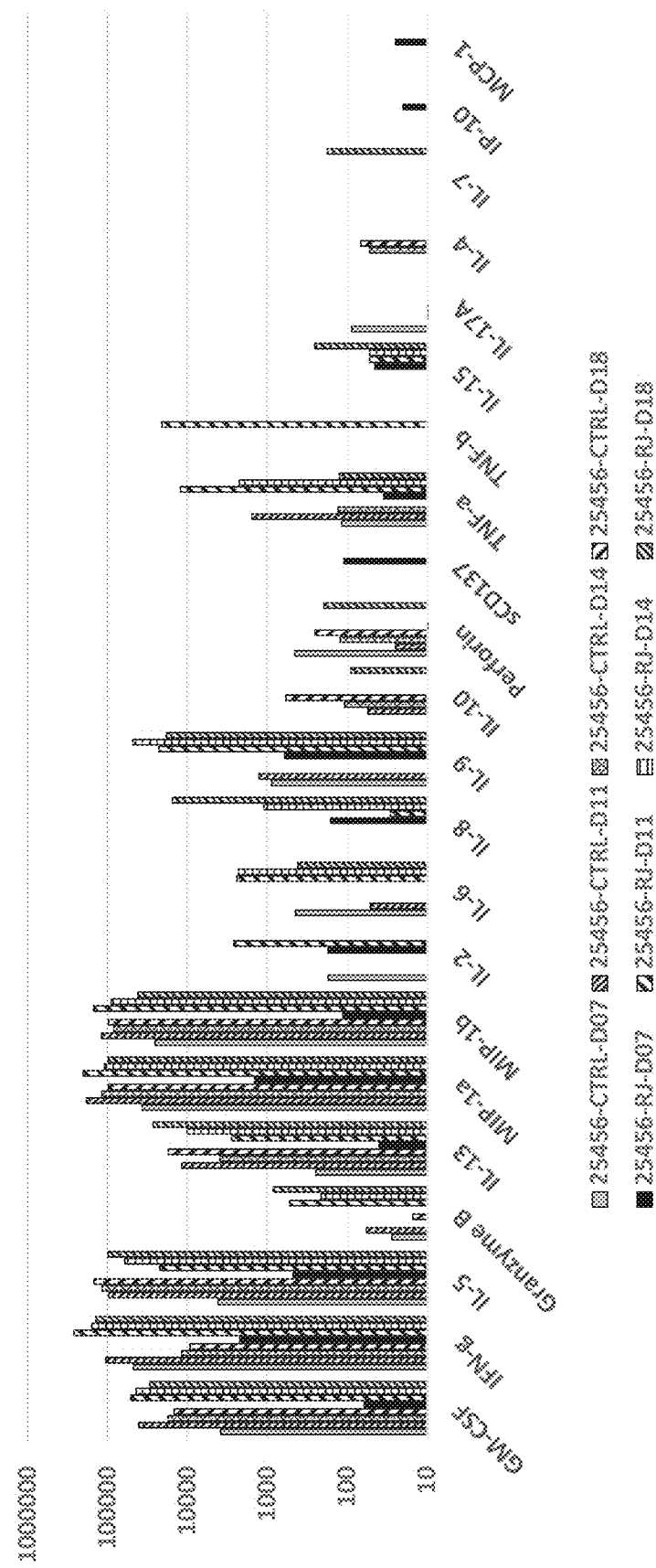

FIGS. 38A and 38B show the expression levels of adaptive immune related cytokines of rejuvenated cells and control cells from two different donors at the indicated time points. The y-axis denotes concentration of cytokine in pg/mL.

Figure 39A:
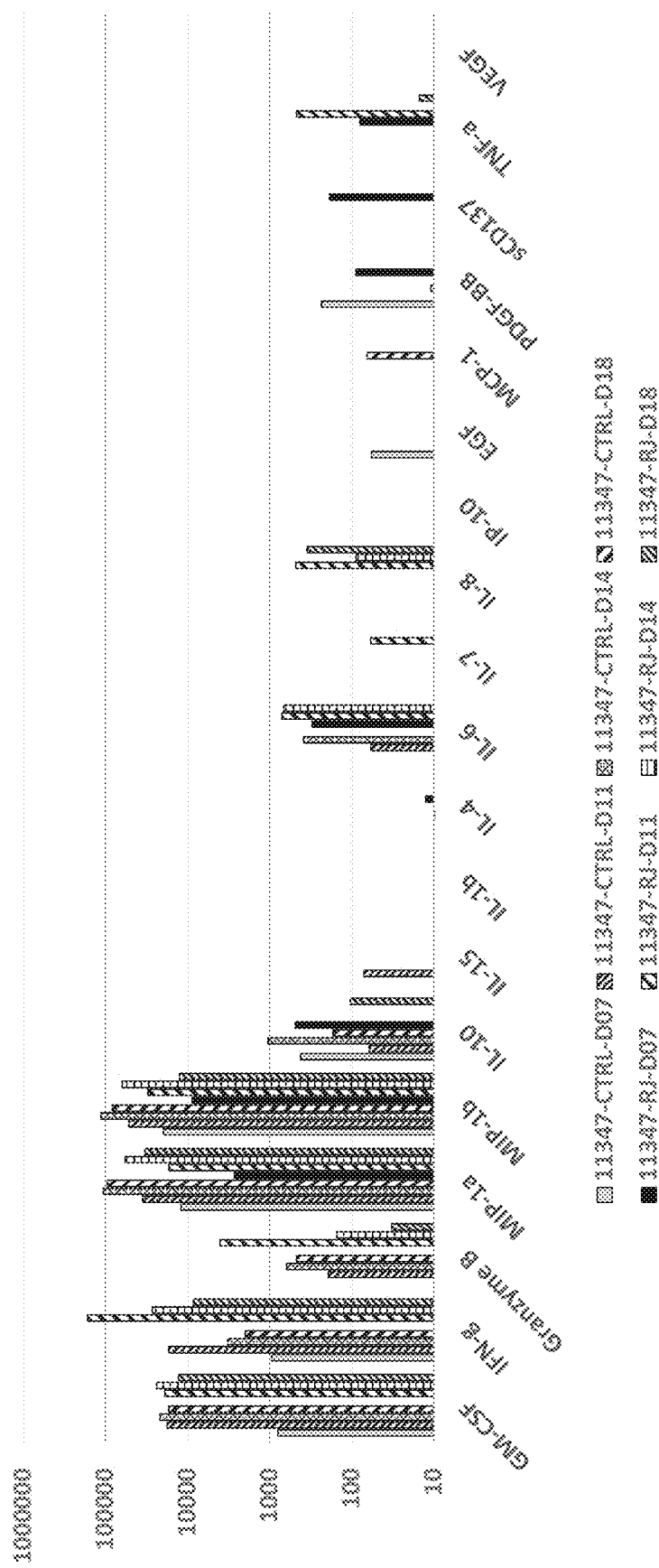
Figure 39B:
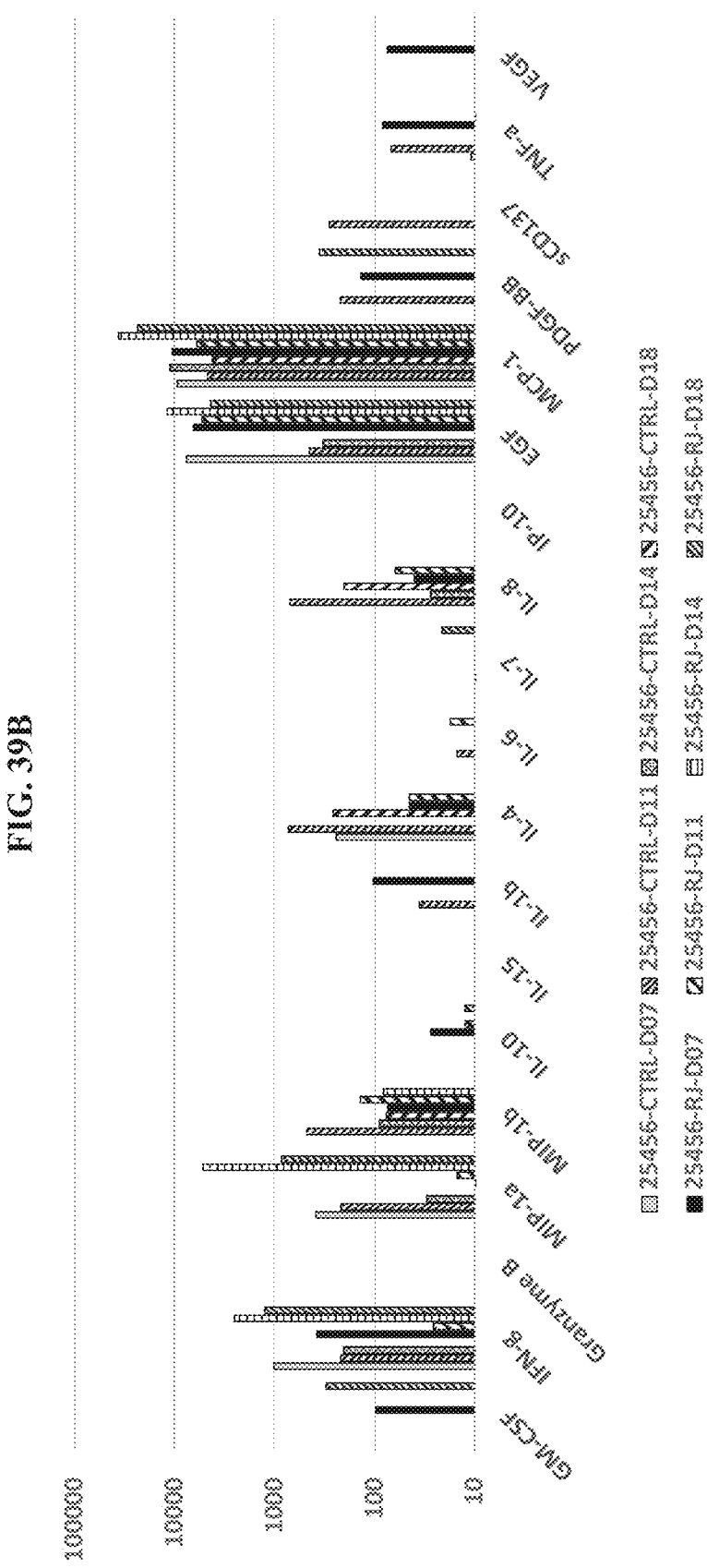

FIGS. 39A and 39B show the expression levels of innate immune related cytokines of rejuvenated cells and control cells from two different donors at indicated times. The y-axis denotes concentration of cytokine in pg/mL.

FIG. 40 describes NY-ESO-1 TCR transduction efficiency in CD8 T cells using representative FACS plots of NY-ESO-1 TCR transduced T cells: (Left) CD4×CD8b, (Right) CD3×NY-ESO-1 TCR TE. See Example 15.

Figures 41, 42:
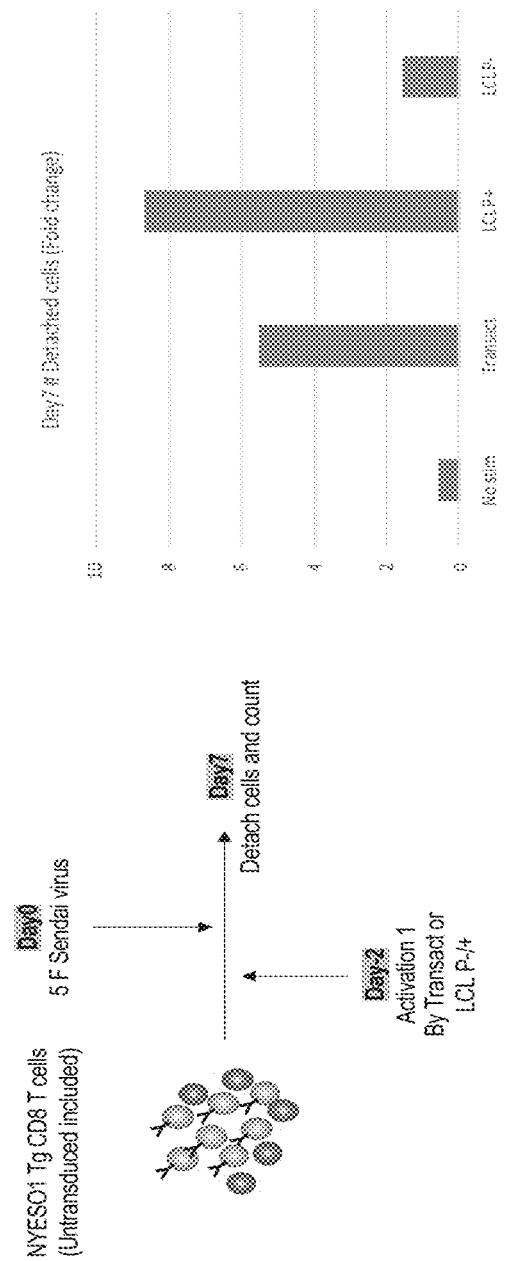

FIG. 41 provides a schematic representation of the procedure of Example 15.

FIG. 42 provides bar graphs showing the fold change of the detached cell numbers collected from each condition on day 7 as compared to day 0. See Example 15.

Figure 43:
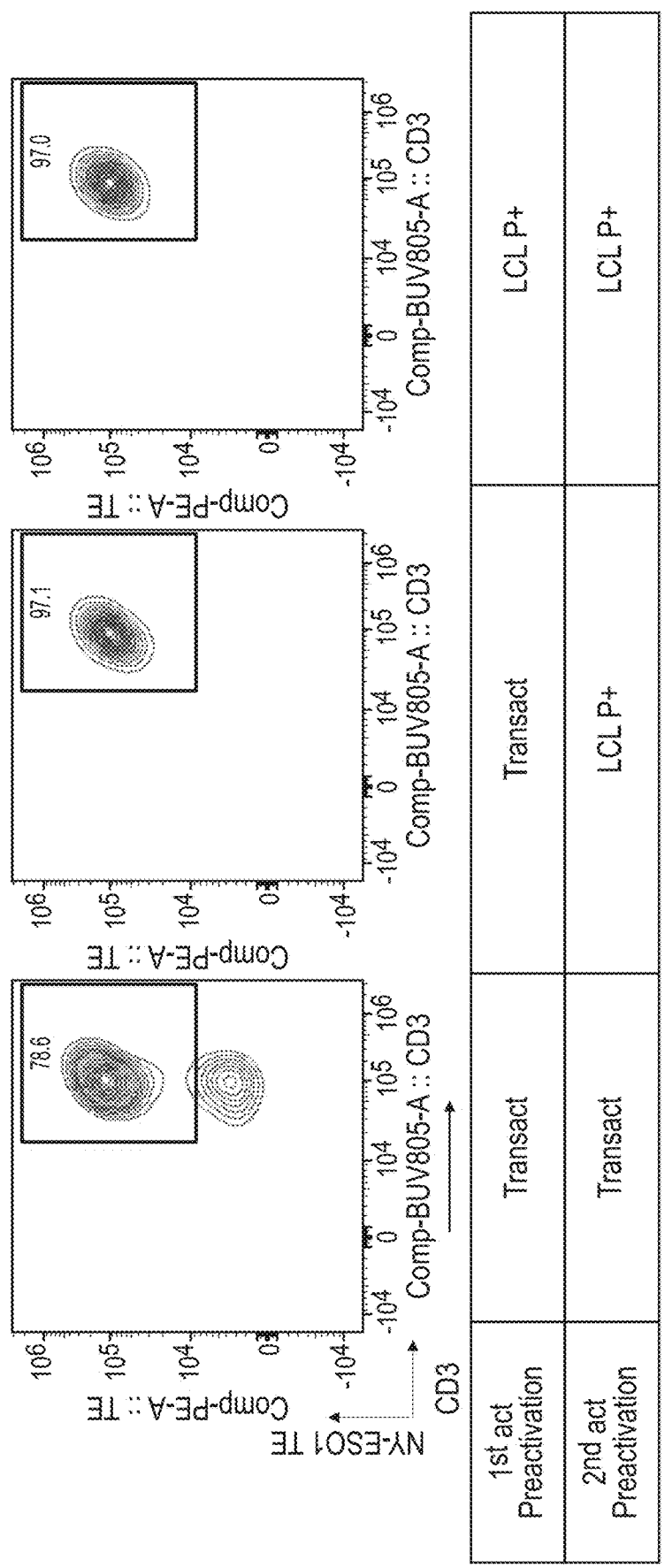

FIG. 43 describes the re-stimulation of partially reprogrammed NY-ESO-1 TCR Tg T cells. FIG. 43 provides representative FACS plots of the day 14. Frequency of NY-ESO-1 TCR TE+ cells are provided. See Example 15.

Figure 44:
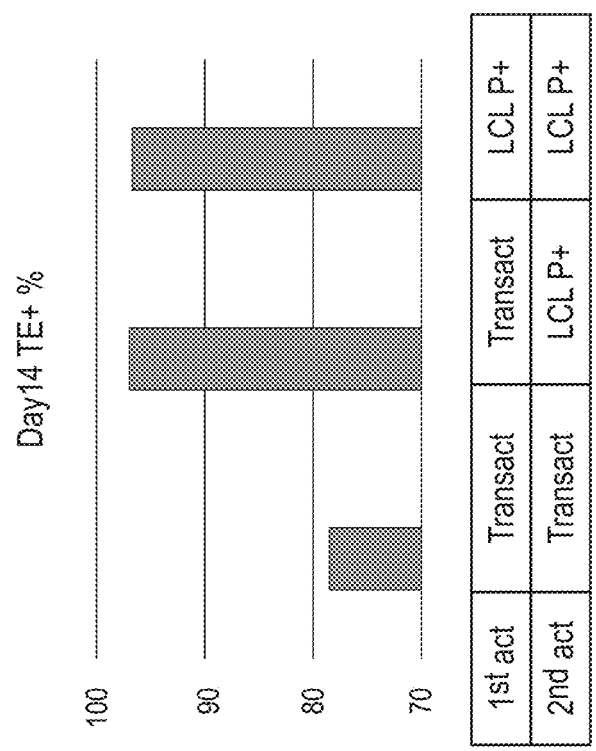

FIG. 44 describes the re-stimulation of partially reprogrammed NY-ESO-1 TCR Tg T cells. FIG. 44 provides representative bar graphs of the day 14 frequency of NY-ESO-1 TCR TE+ cells. See Example 15.

Figure 45:
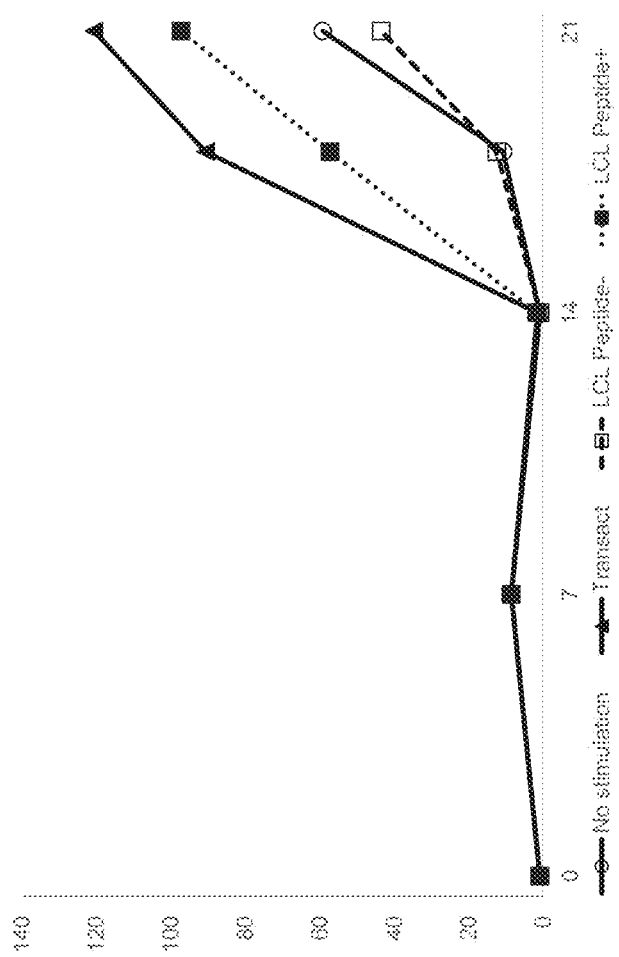

FIG. 45 is a proliferation curve showing that rejuvenated NY-ESO-1 Tg T cells have higher proliferative capacity than non-rejuvenated controls (see Example 15).

Figure 46:
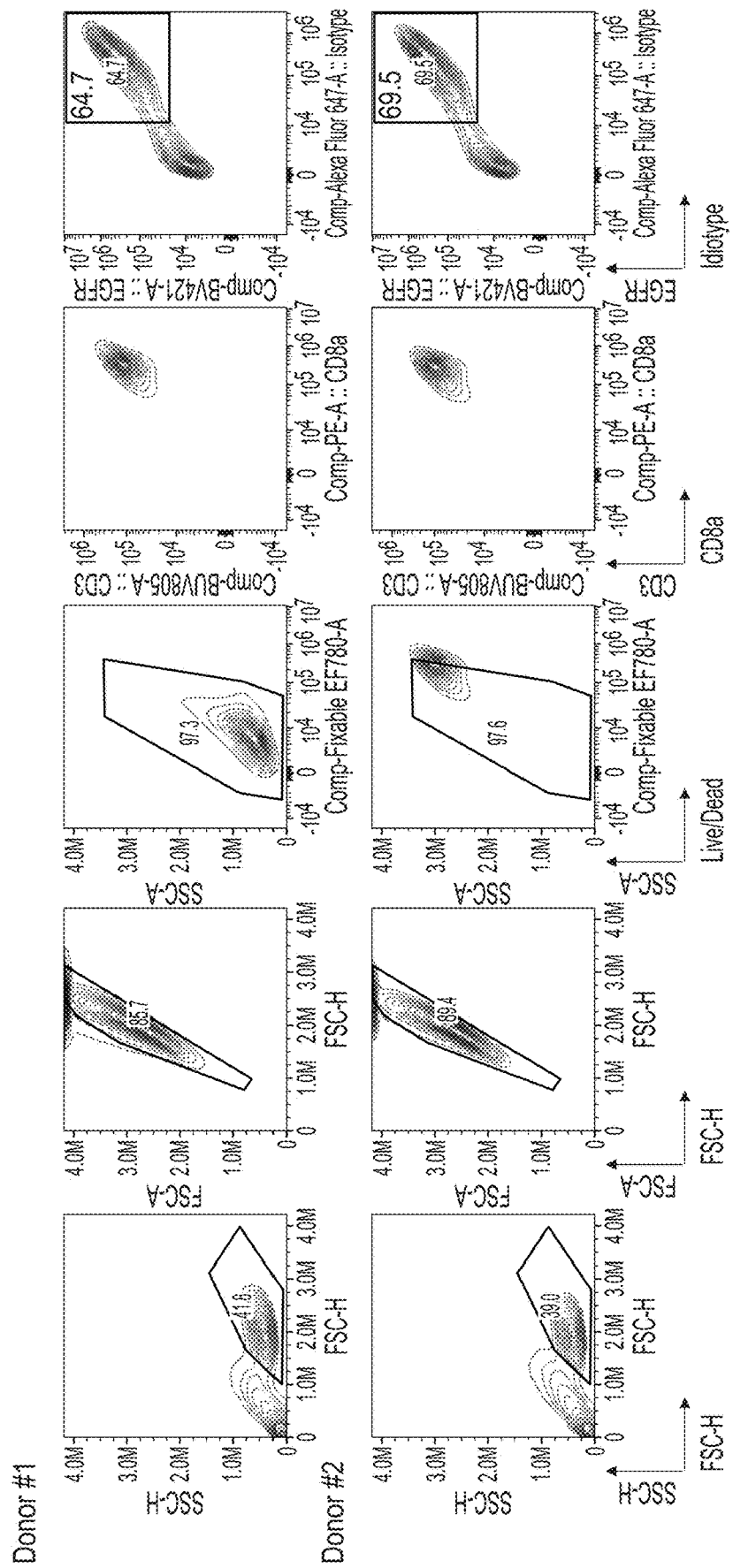

FIG. 46 illustrates the CD19 CAR transduction efficiency in CD8 T cells. See Example 16. Cells were gated as Lymphocytes>Single cells>Live/Dead−, and plotted as CD3×CD8a (second from right), CAR idiotype×EGFR (far right). tEGFR was expressed as a marker of successful transduction.

Figure 47:
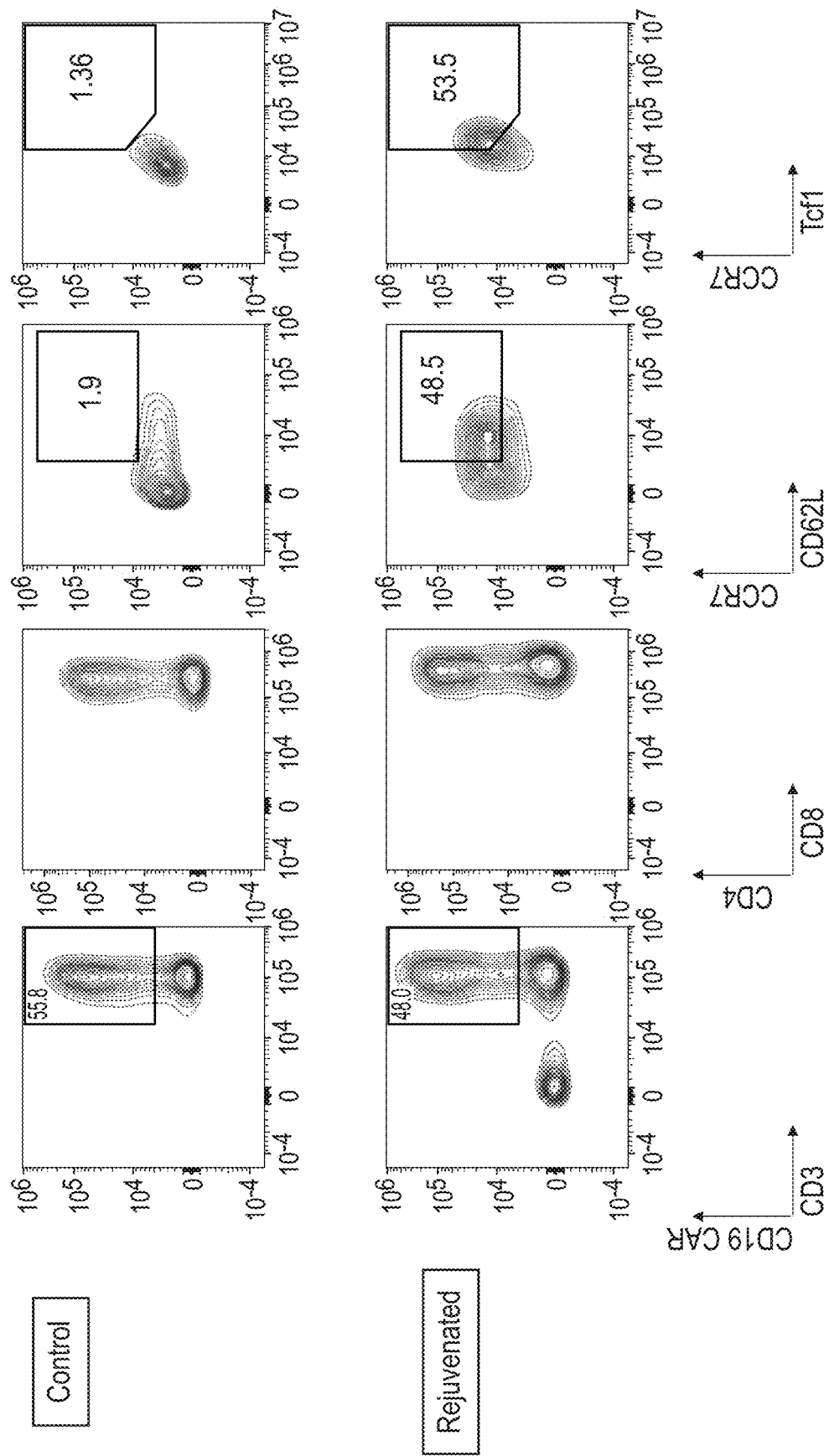

FIG. 47 illustrates that rejuvenated CD19 CAR T cells showed less differentiated phenotype. On day 13 control and rejuvenated CD19 CAR Tg T cells were analyzed for surface markers and Tcf1 expression by FACS. Cells were gated as Lymphocytes>Single cells>Live/Dead−>CD19 CAR+, and plotted as CD4×CD8a (second from left), CCR7×CD62L (second from right) and CCR7×Tcf1 (far right)

Figure 48:

FIG. 48 shows that rejuvenated CD19 CAR T cells proliferated more than control CD19 CAR T cells. See Example 16. CD19 CAR Tg T cells were rejuvenated and cultured as described in section 3, and cell number was counted every 3-4 days. The Graph depicts the fold changes compared to day 7 after transduction of the reprogramming factors in two healthy donors and their corresponding control cells over time.

Figure 49:
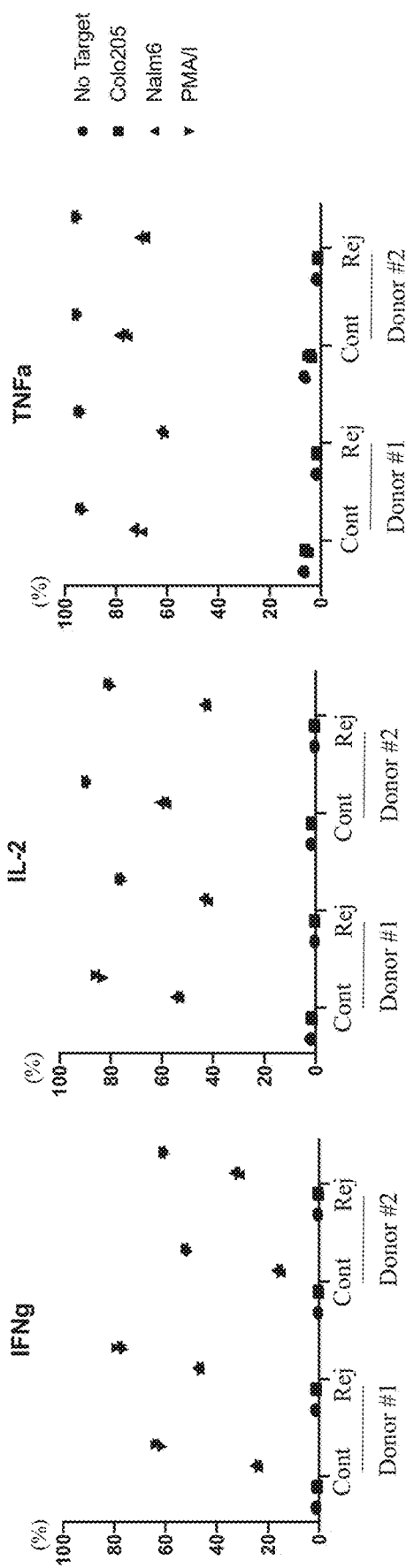

FIG. 49 illustrates that rejuvenated CD19 CAR T cells produced comparable level of cytokines upon co-culture with CD19 expressing target cells. See Example 16. On day 20 control or rejuvenated CD19 CAR Tg T cells were cultured alone, or with PMA/Ionomycin, Colo205 (CD19−) or Nalm6 (CD19+) in the presence of Golgi transporter inhibitors. After staining surface antigens, cells were fixed, permeabilized and stained by intracellular Abs. Frequency of each cytokine positive CAR+ cells were depicted.

Figure 50A:
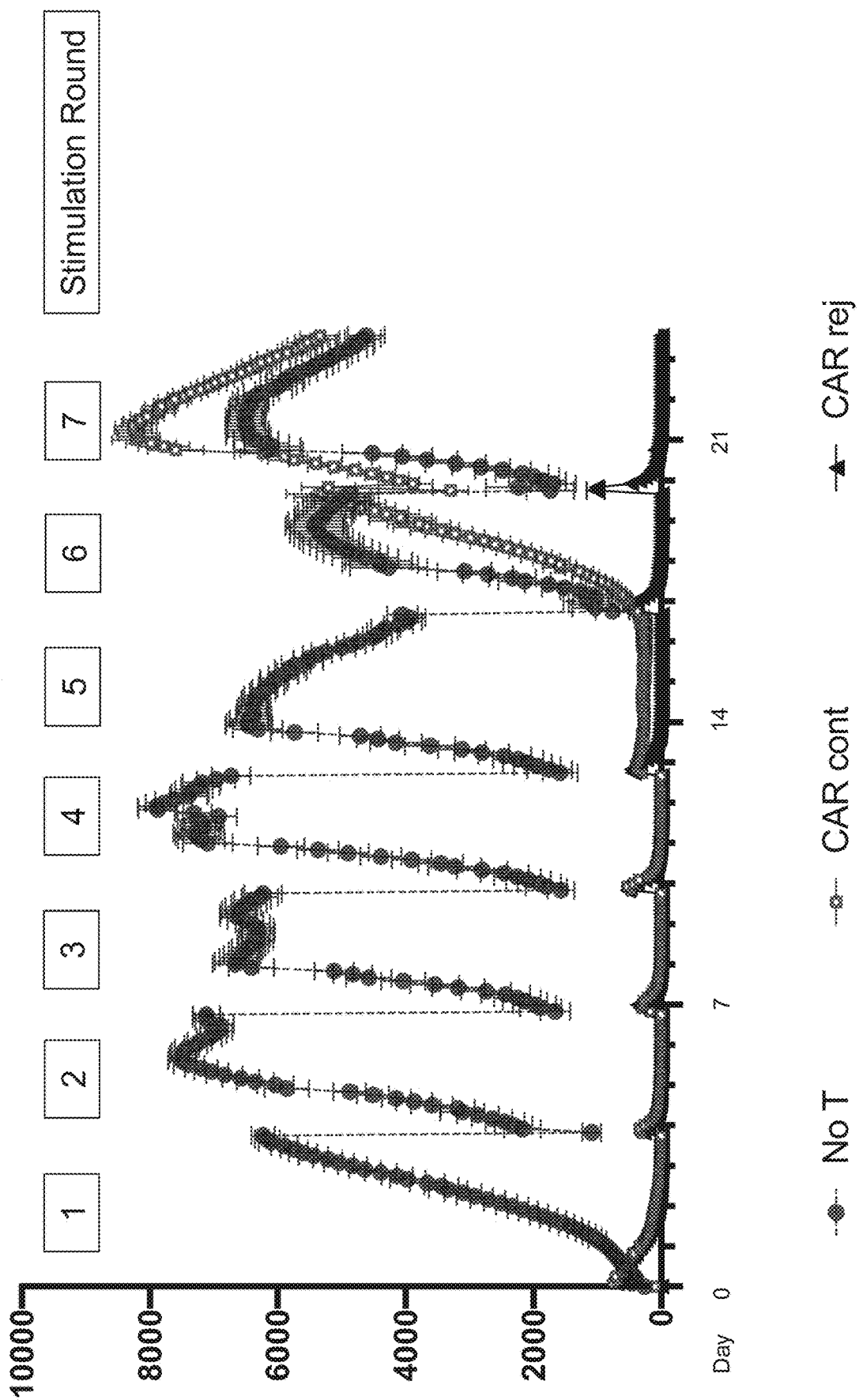
Figure 50B:
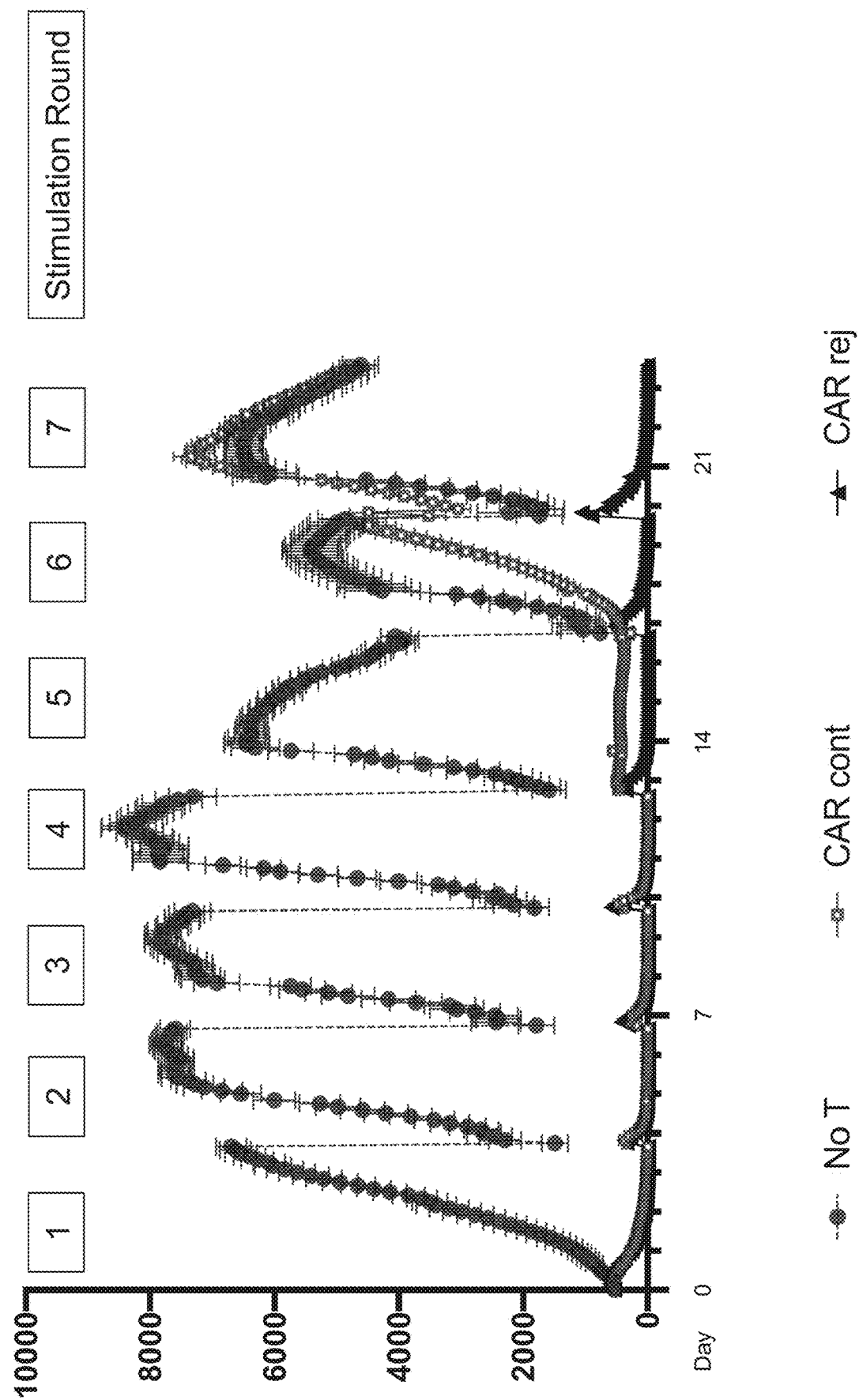

FIGS. 50A and 50B show that rejuvenated CD19 CAR T cells persisted and retained their cytotoxic activity longer upon repeated co-culture with CD19 expressing target cells. See Example 16. FIGS. 50A and 50B show the results of co-culturing control or rejuvenated CD19 CAR Tg T cells with Nalm6-NLR cell line. Every 3-4 days, 25% (10% for 4th and 5th co-culture) of the previous culture was transferred into a new plate with fresh targets. Growth of the target was monitored using the Incucyte® live-cell analysis system and analyzed with the Base Software Analysis Module. Graphs show the numbers of Nalm6-NLR/image of each condition of Donor #1 (FIG. 50A) and #2 (FIG. 50B).

Figure 51:
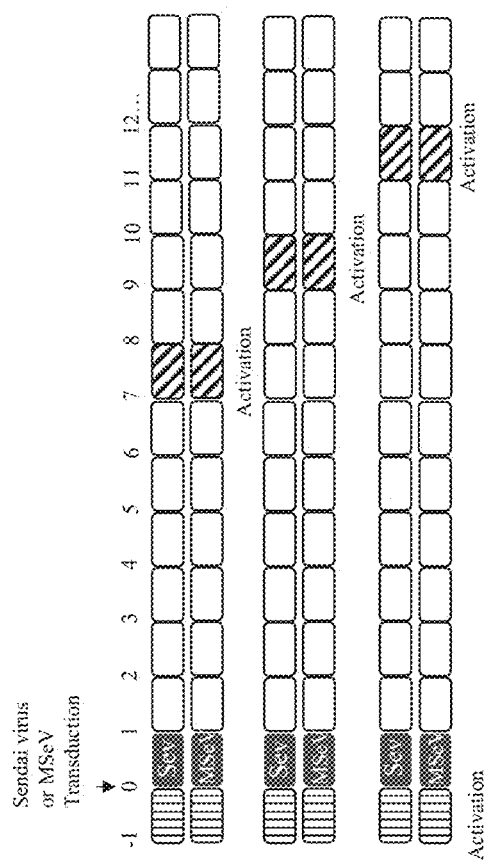

FIG. 51 is an exemplary, non-limiting experimental design of the rejuvenation protocol described in Example 17 for purposes of illustration.

Figure 52A:
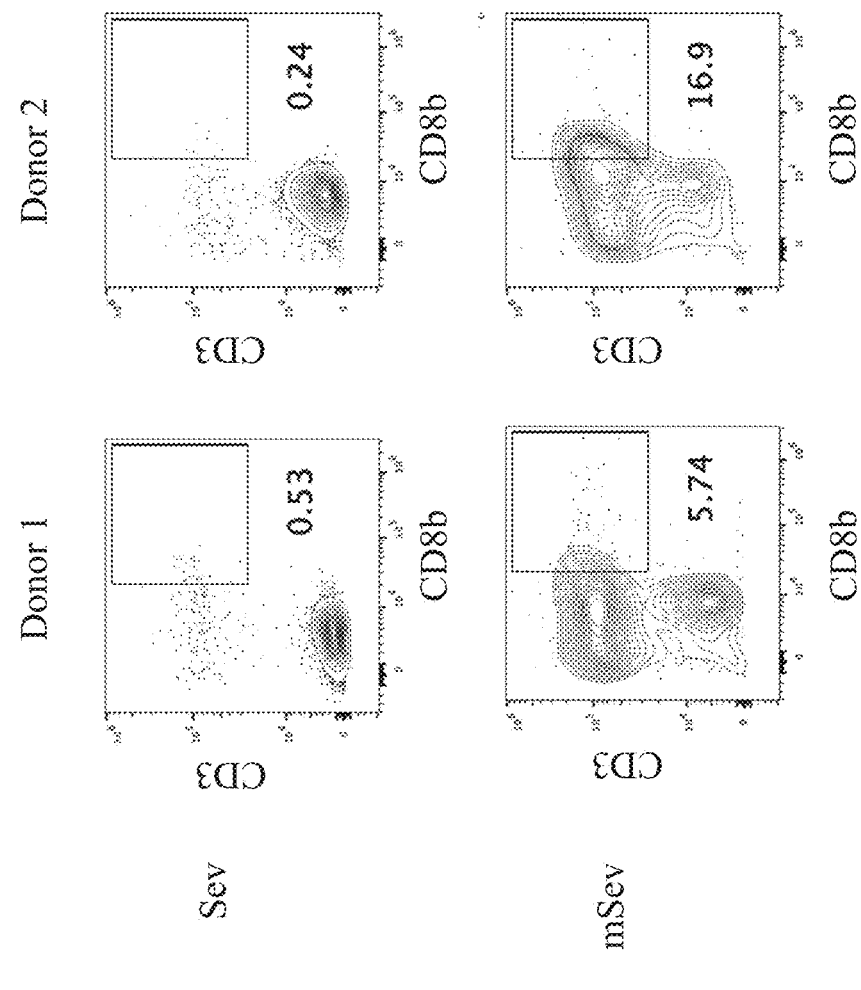
Figure 52B:
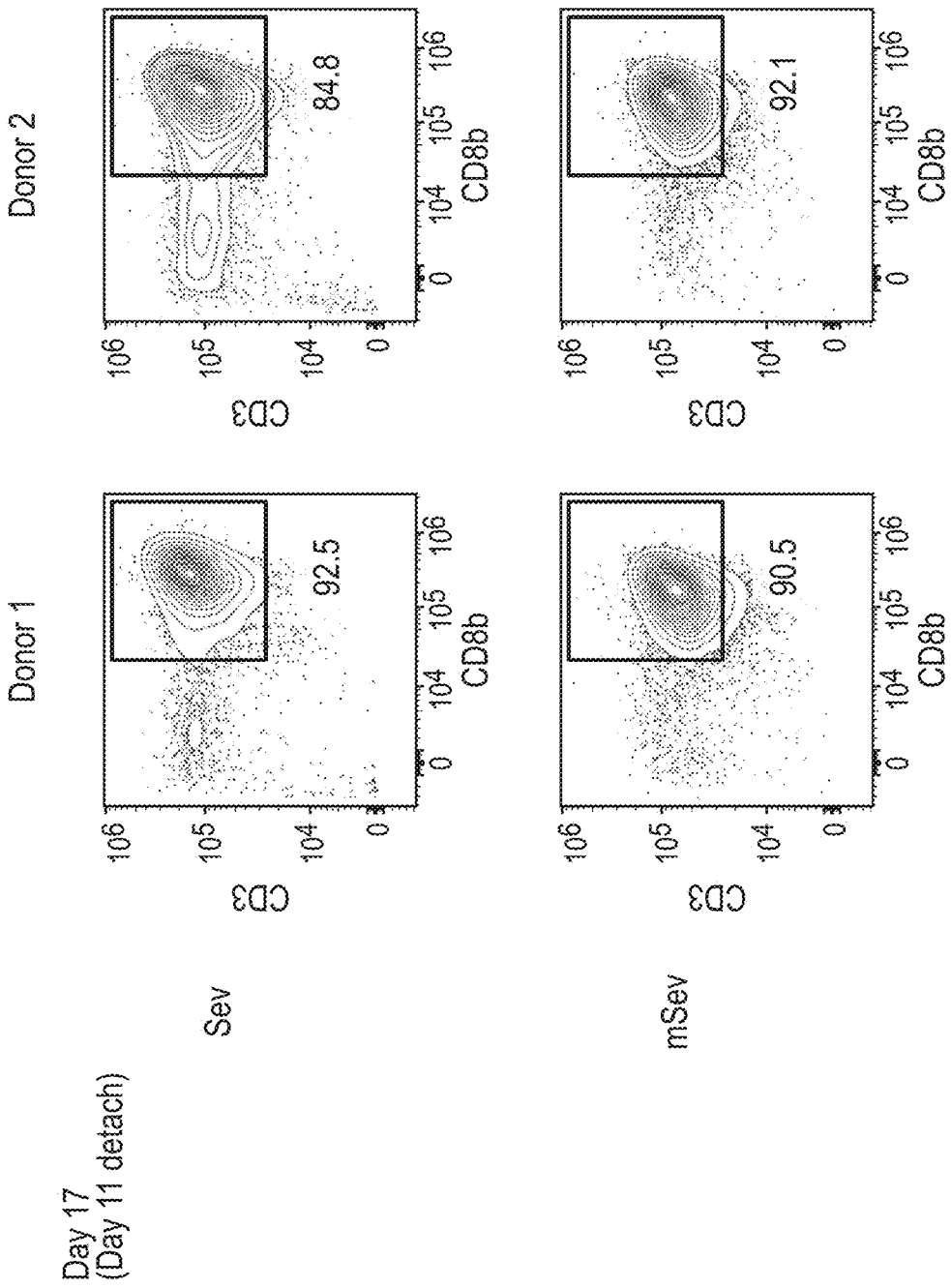

FIGS. 52A and 52B are the results of phenotypic analyses of cells detached on Day 11 (FIG. 52A) and the same cells (i.e., having detached on Day 11) on Day 17 (FIG. 52B) in each of the Sev and mSev groups discussed in Example 17. The provided FACS plots show the frequency of CD3+ CD8b+ (gated on singlets, dead stain negative, and lymphocyte SSC/FSC).

Figure 53A:
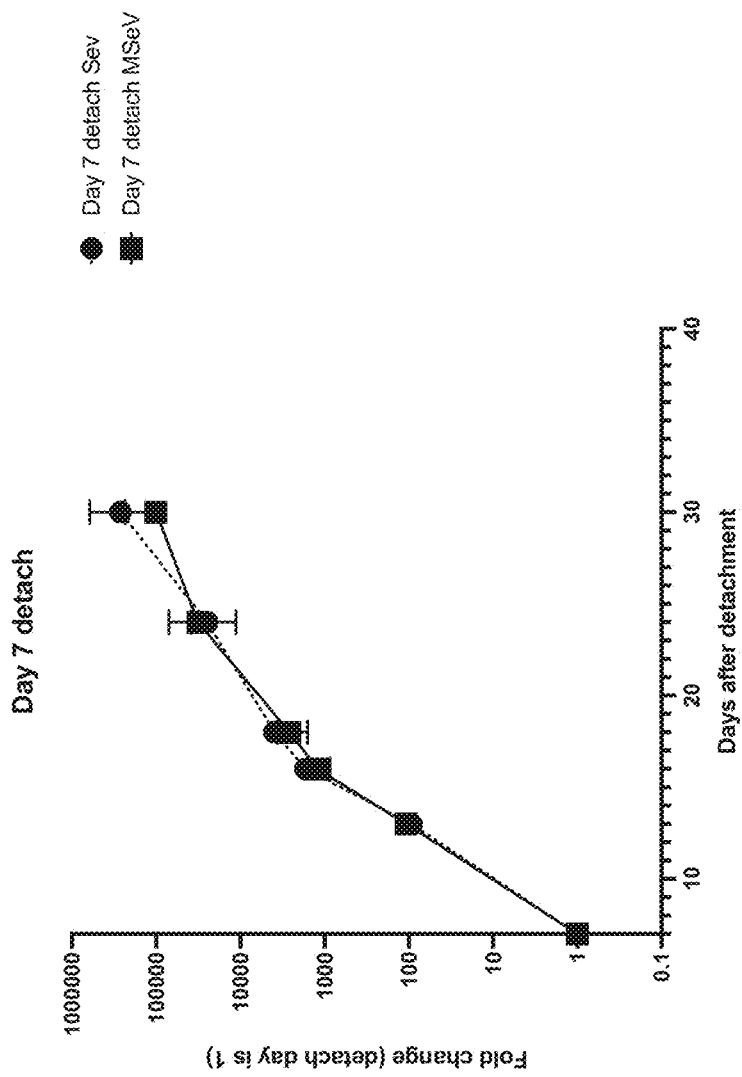
Figure 53C:
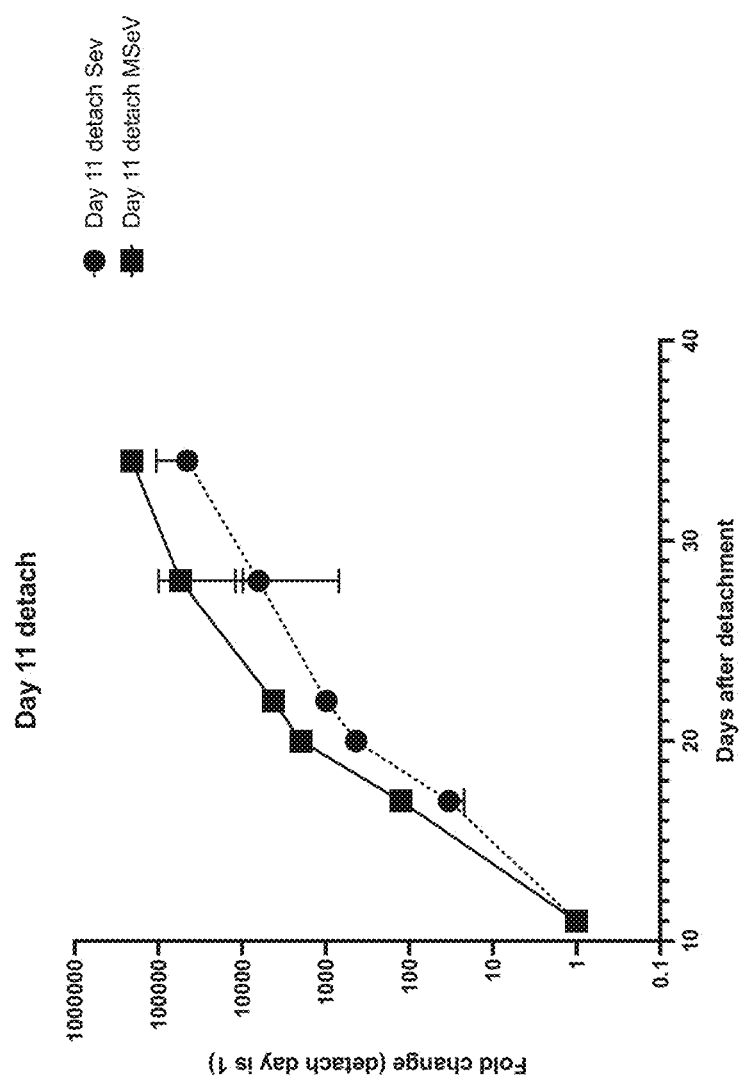

FIGS. 53A-53C are proliferation curves showing the fold change after various numbers of days following detachment (see Example 17). FIG. 53A shows fold change in cell count following detachment occurring on Day 7. FIG. 53B shows fold change in cell count following detachment occurring on Day 9. FIG. 53C shows fold change in cell count following detachment occurring on Day 11. Each dot in each of FIGS. 53A-53C indicates the average of the 2 donors. Error bars indicate ±1 SD.

Figure 54A:
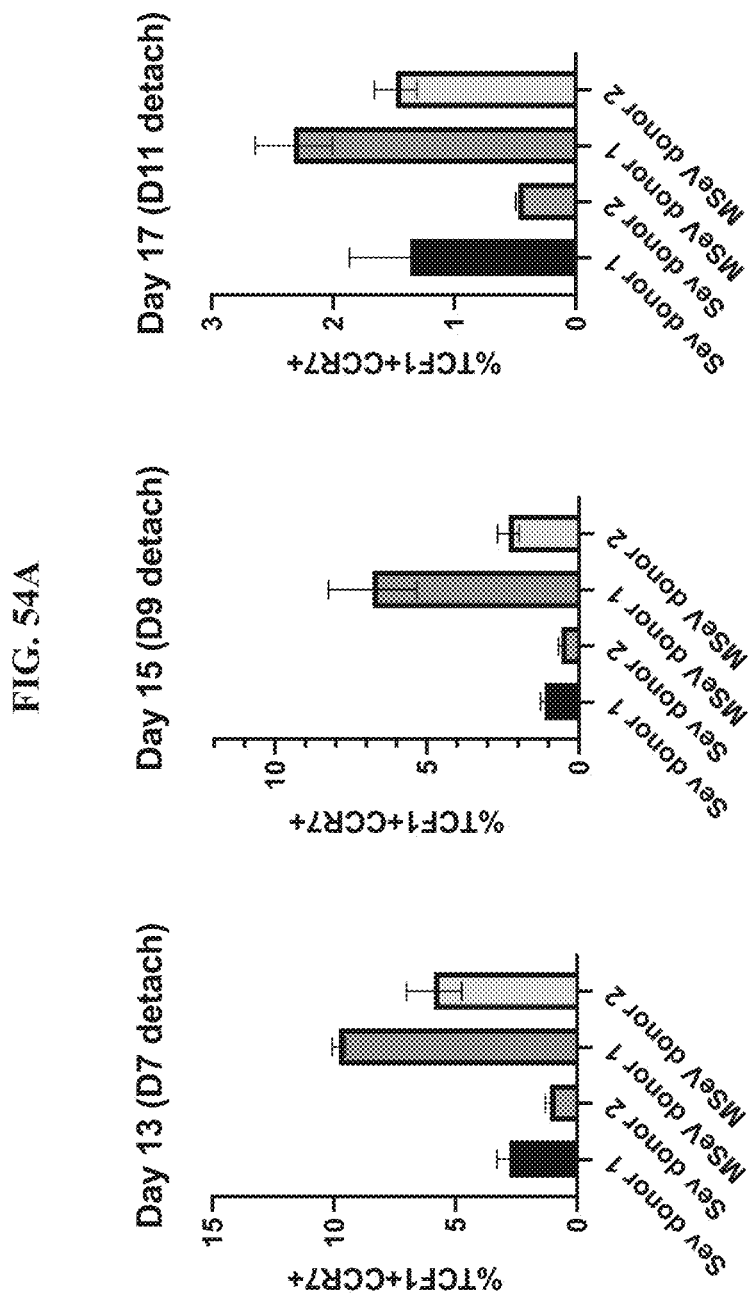

FIG. 54A shows the stemness phenotype exhibited 6 days after detachment of the reprogrammed T cells of Example 17. Bar graphs show the average TCF1+CCR7+ frequency (gated on singlets, dead stain negative, lymphocyte SSC/FSC, and CD3+CD8b+) in technical duplicates. Error bars indicate ±1SD.

Figure 54B:
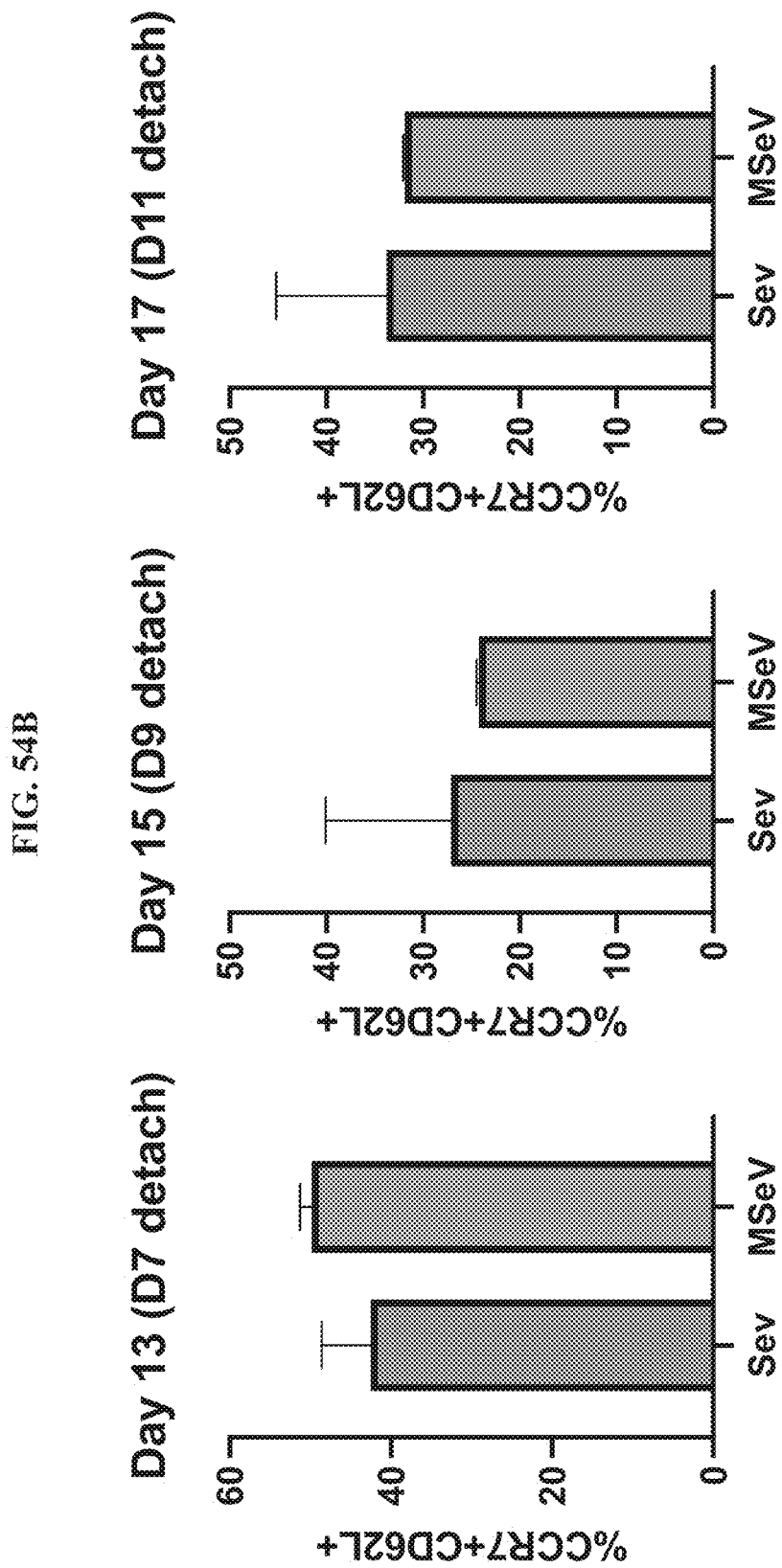

FIG. 54B shows the stemness phenotype six days after detachment of the reprogrammed T cells of Example 17. Bar graphs show the average CCR7+CD62L+ frequency (gated on singlets, dead stain negative, lymphocyte SSC/FSC, and CD3+CD8b+) in technical duplicates. Error bars indicate ±1SD.

Figure 55:
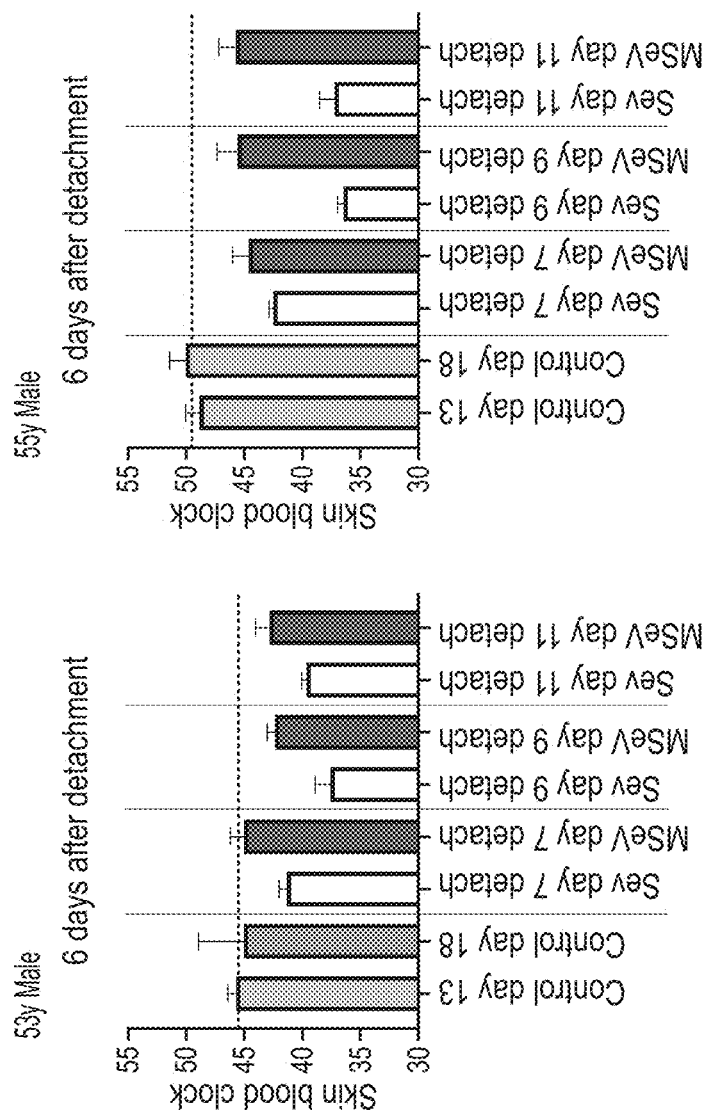

FIG. 55 shows the epigenetic age of T cells transiently reprogrammed with either Sev or mSev and detached at Days 7, 9, and 11, as described in Example 17. Epigenetic age was measured using the Horvath skin blood clock.

Figure 56:
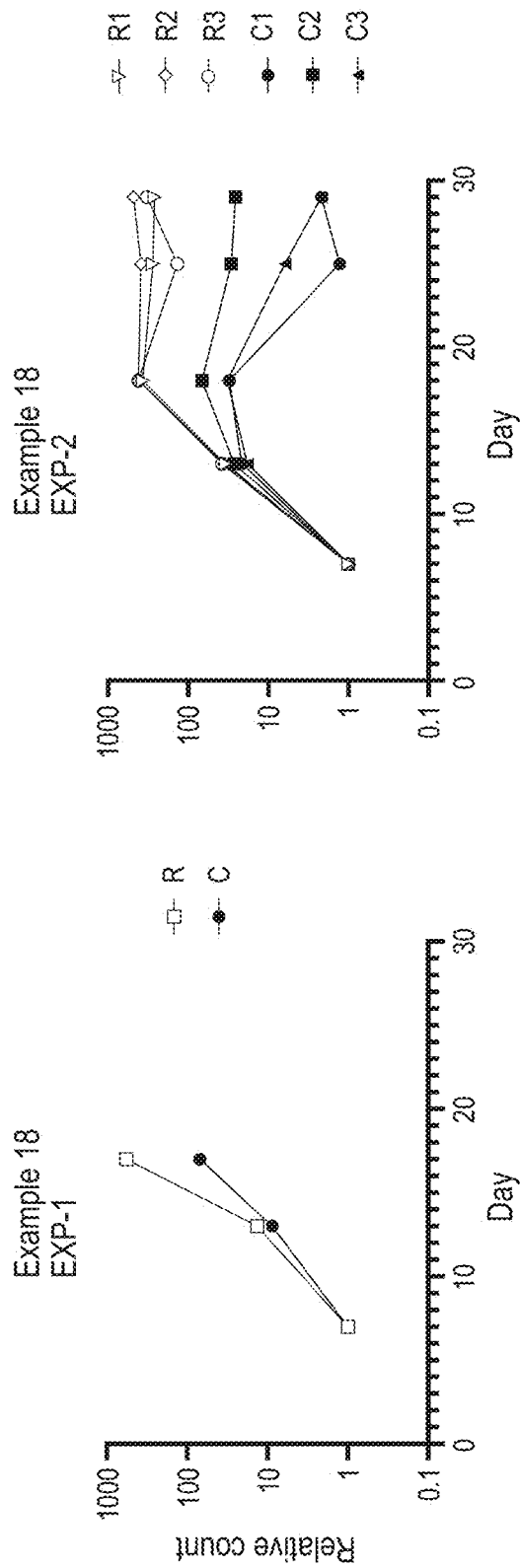

FIG. 56 shows proliferation curves for rejuvenated and control cells of Example 18.

Figure 57A:
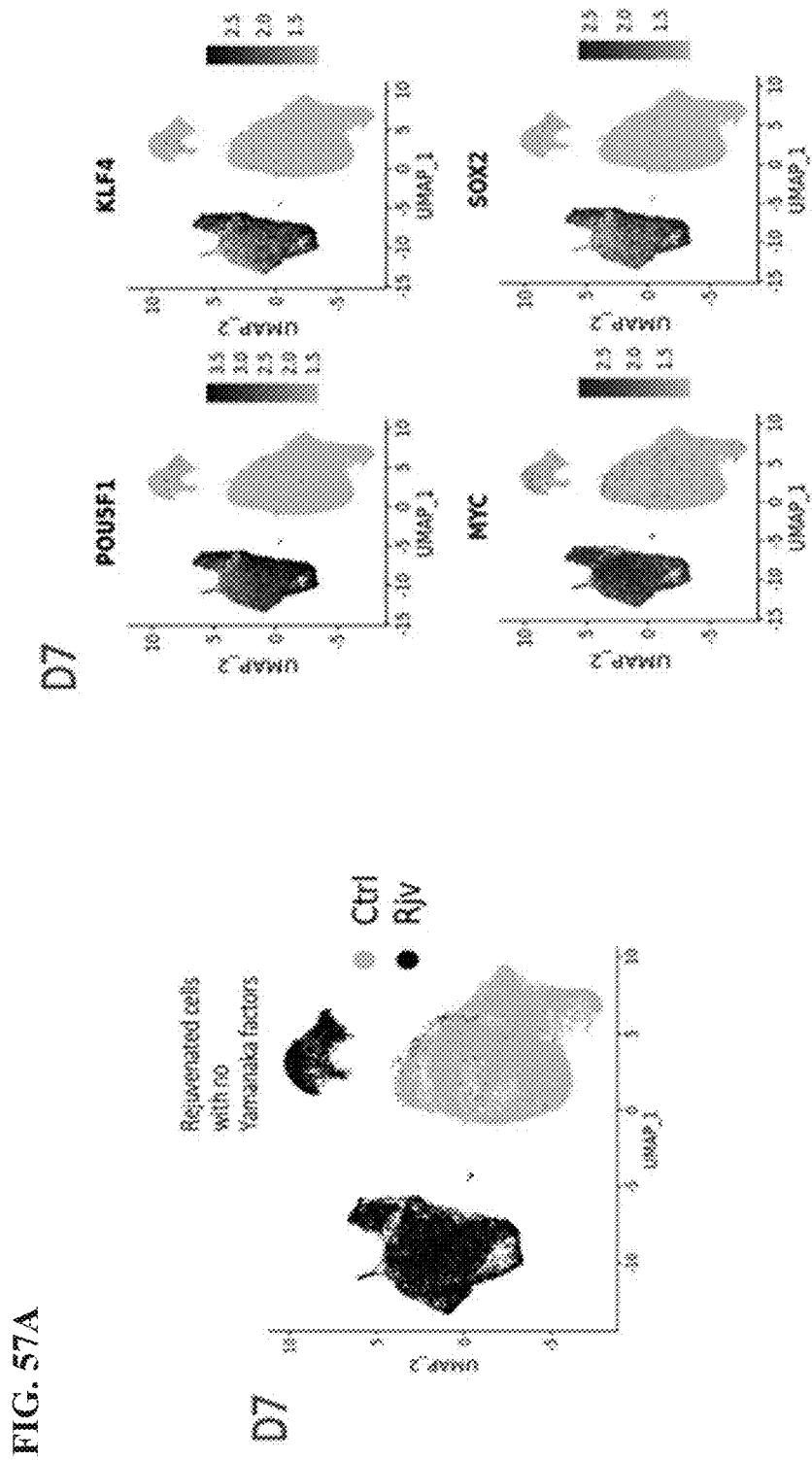
Figure 57B:
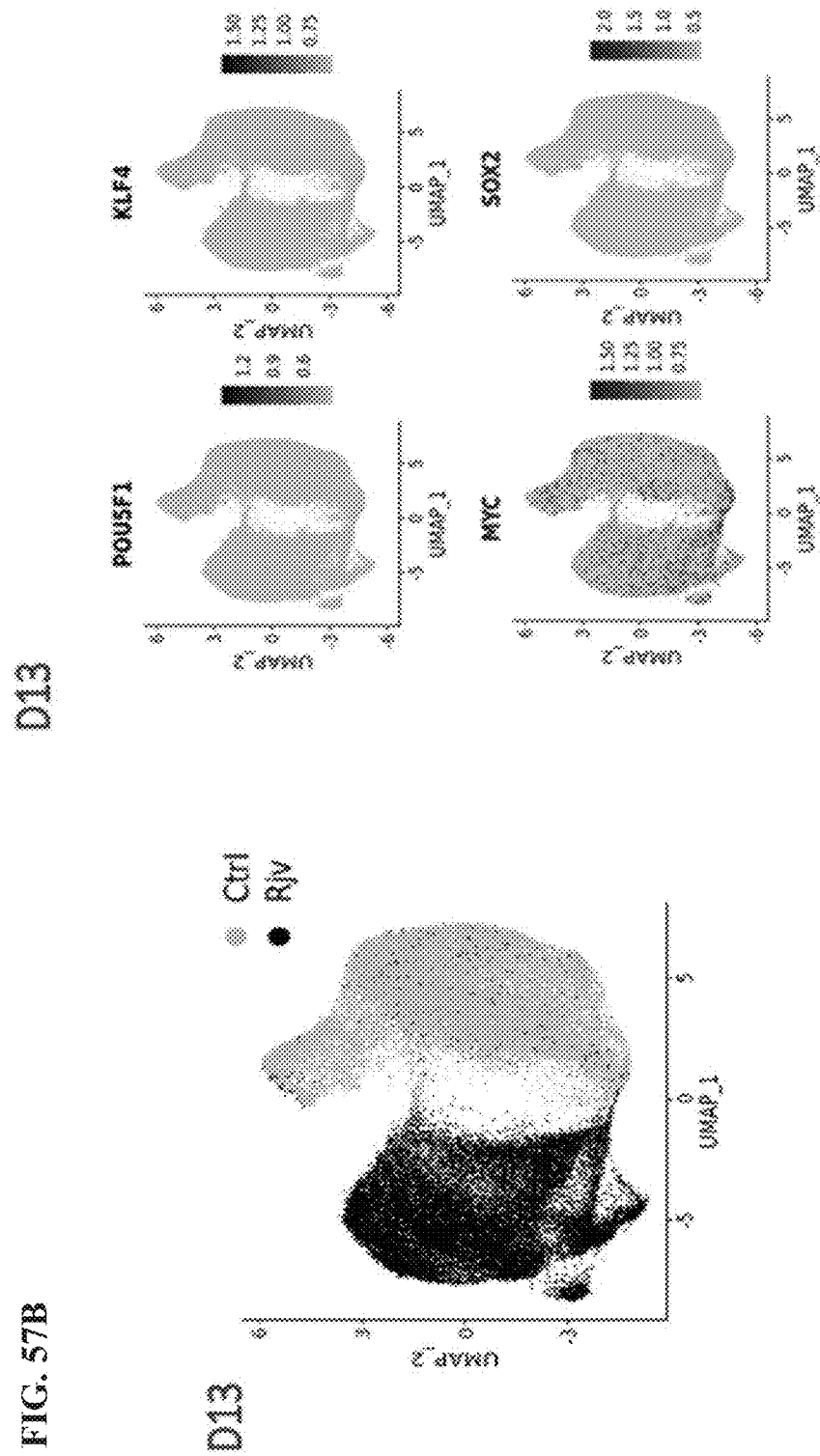
Figure 57C:
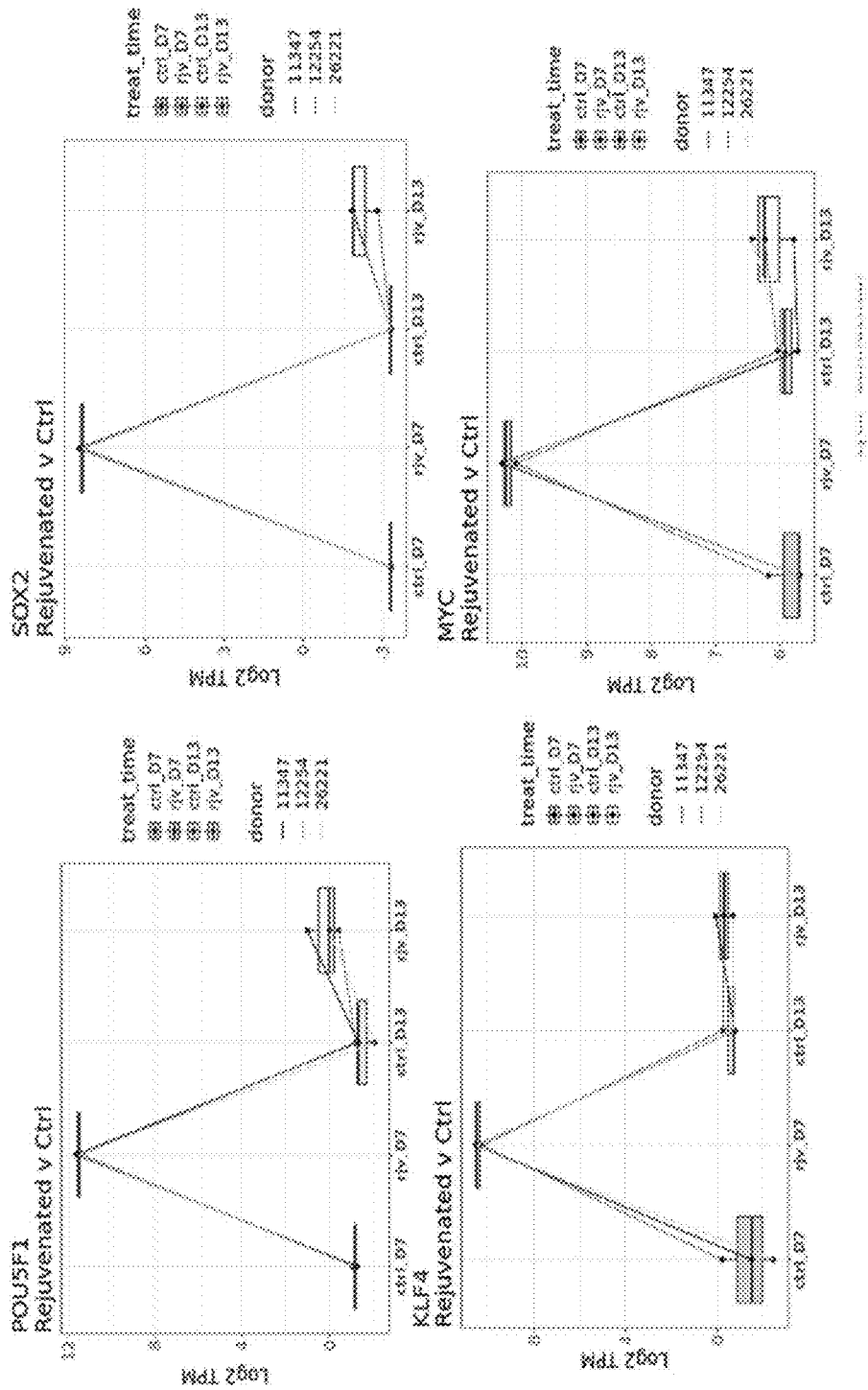
Figure 57D:
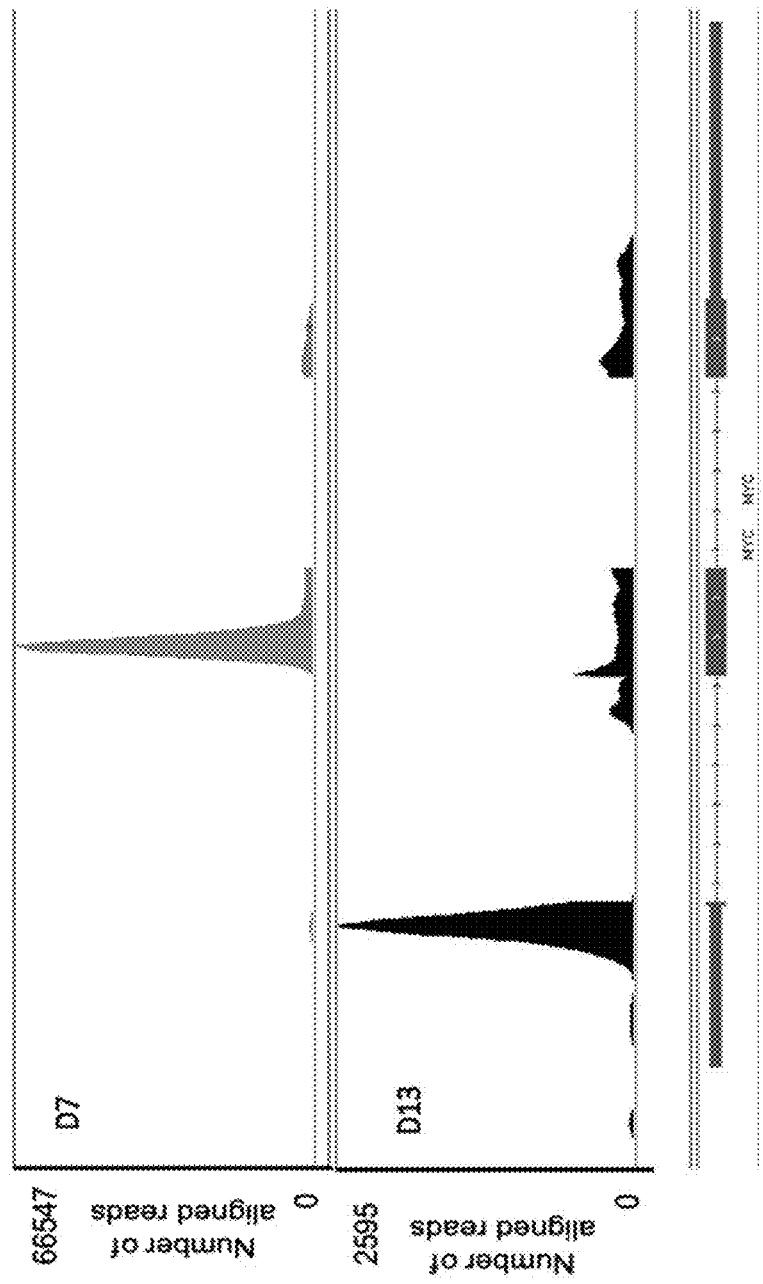

FIGS. 57A-57D shows the transcriptome profiling of healthy donor CD8+ T-cells from control and rejuvenated cells on Day 7 and Day 13 of Example 18. FIG. 57A shows single-cell RNA-seq data of CD8+ T-cells from control and rejuvenated cells from all four donors visualized by UMAP. FIG. 57B shows expression levels of transcripts encoding for the Yamanaka factors in the rejuvenated cells in single-cell RNA-seq data of CD8+ T-cells from control and rejuvenated cells. FIG. 57C shows expression levels of transcripts encoding for the Yamanaka factors in bulk RNA-seq data of CD8+ T-cells from control and rejuvenated cells. FIG. 57D shows the genome alignment visualization of reads that align to the endogenous cMYC gene in healthy donor CD8+ T-cells from control and rejuvenated cells on Days 7 and 13.

Figure 58A:
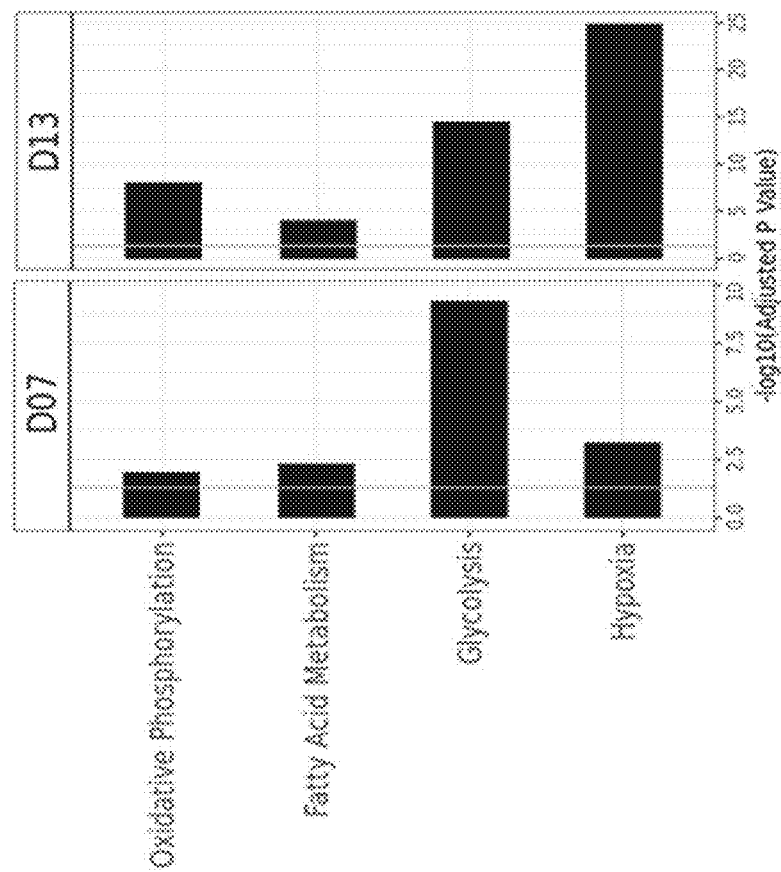

FIG. 58A depicts Enrichment of metabolic gene sets in rejuvenated cells compared to control cells on Days 7 and 13 in the 3 donors of the bulk RNA-seq data of Example 18 (i.e., Donor Nos. 11347, 12254 and 26221). The difference in the scale of x-axis shows the adjusted p values for Days 7 and 13. The solid gray line shows the threshold of significance (Adjusted P value<0.05).

Figure 58B:
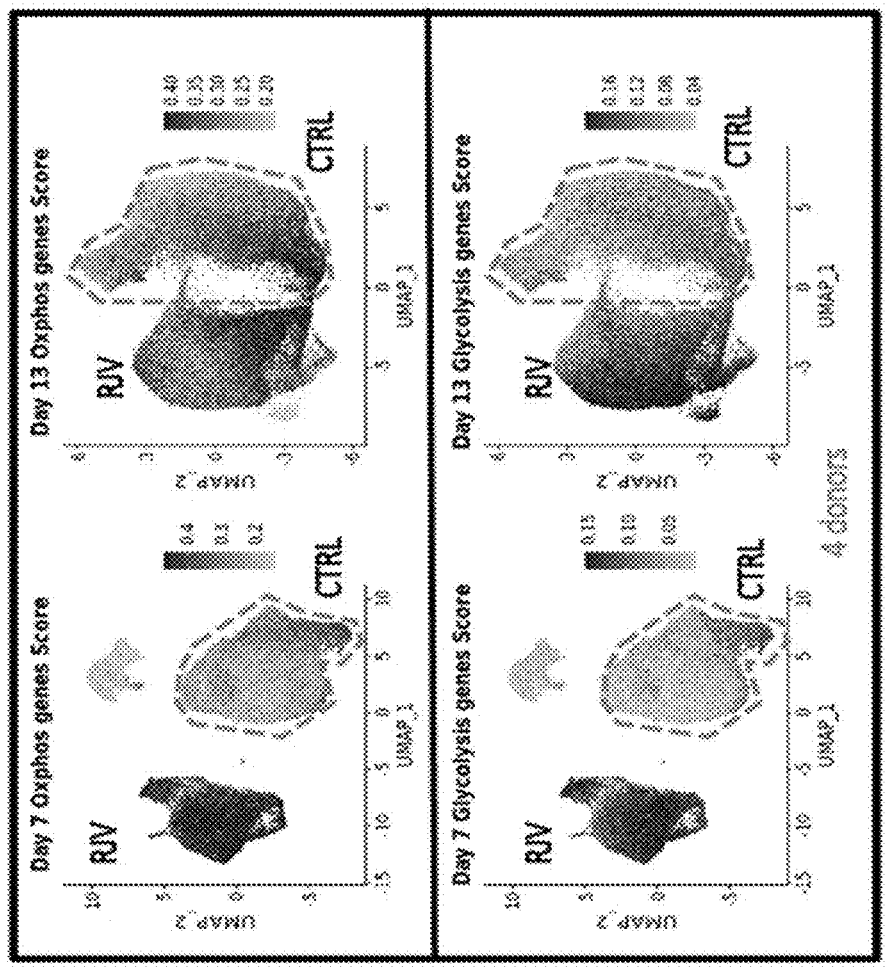
Figure 59A:
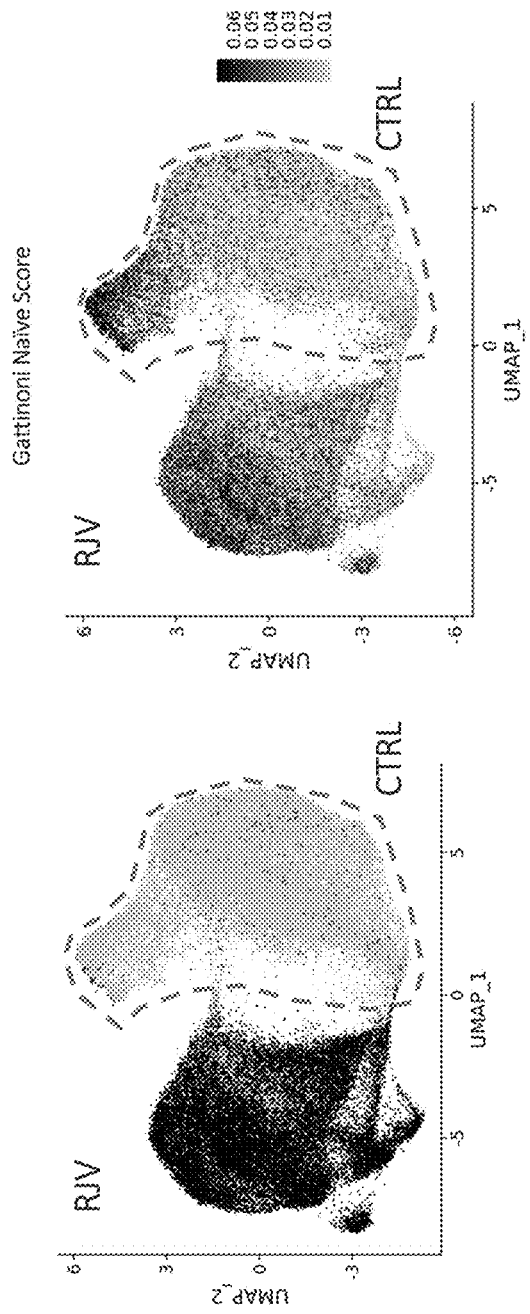

FIG. 58B shows the AddModule scores of glycolysis and oxidative phosphorylation gene sets on the same UMAP representation shown in FIG. 59A (see Example 18).

FIG. 59A is a UMAP illustrating that rejuvenated cells are enriched for naïve gene sets (Gattinoni) on Day 13 as compared to control cells (see Example 18).

Figure 59B:
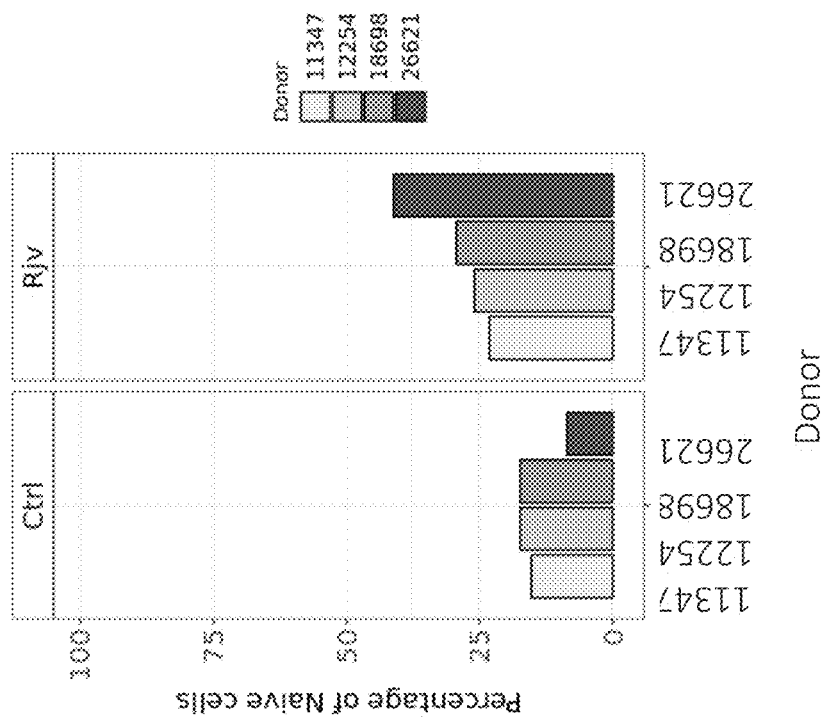

FIG. 59B is a bar graph illustrating that rejuvenated cells are enriched for naïve gene sets (Gattinoni) on Day 13 as compared to control cells (see Example 18).

Figure 60B:
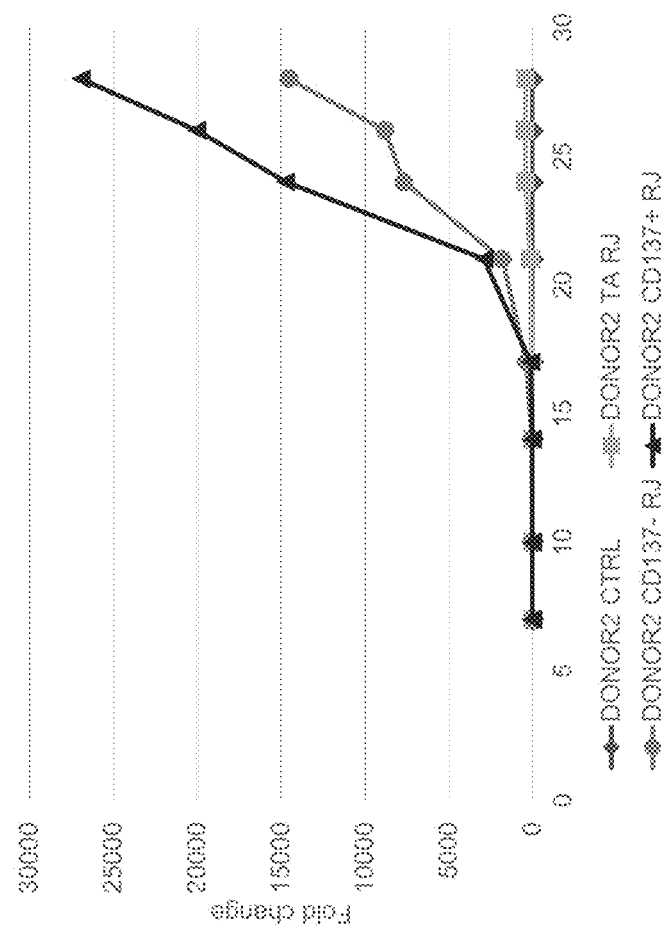

FIGS. 60A and 60B are graphs showing proliferation curves of Donors 1 and 2 following rejuvenation. All rejuvenated cells showed much higher fold of expansion than control group. In one donor, TransAct stimulated group showed higher expansion than CD137+ selected group while in the other donor it is lower. This suggested a differing affinity of tumor-reactive populations to stimulation. Expansion after 33 days showed a decrease, which can be due to seeding cell density of that culture is suboptimal for the culture plate causing insufficient nutrient and oxygen supply. See Example 19.

Figure 61A:
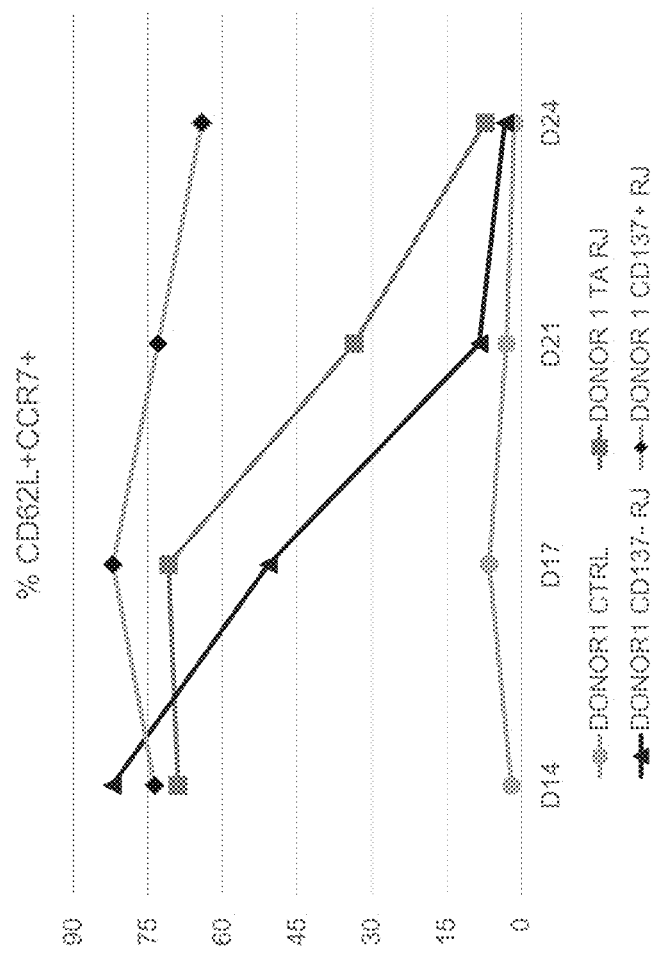

FIGS. 61A and 61B are graphs showing expression of CD62L and CCR7 in rejuvenated and control cells over time. CD62L+CCR7+ was preserved in the early stage of rejuvenation. Cells were harvested at indicated day and stained with fluorescent labeled antibodies, followed by analysis on flow cytometry. Results showed that rejuvenated cells were highly expressing CD62L+CCR7+ at D14 and D17 in these two donors. See Example 19.

Figure 62:
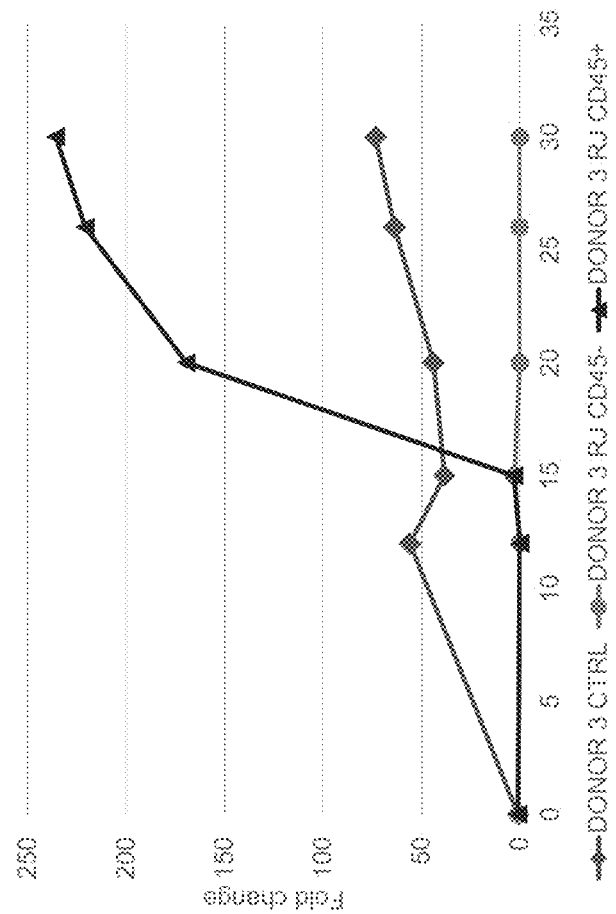

FIG. 62 is a graph showing proliferation curves of Donor 3 following rejuvenation. TILs were enriched with CD45+, and then stimulated with TransAct, followed by rejuvenation. Cells were counted at indicated days. Rejuvenated CD45+ showed a much-enhanced proliferation as compared to control cells, while CD45− group showed very limited expansion. See Example 19.

Figure 63:
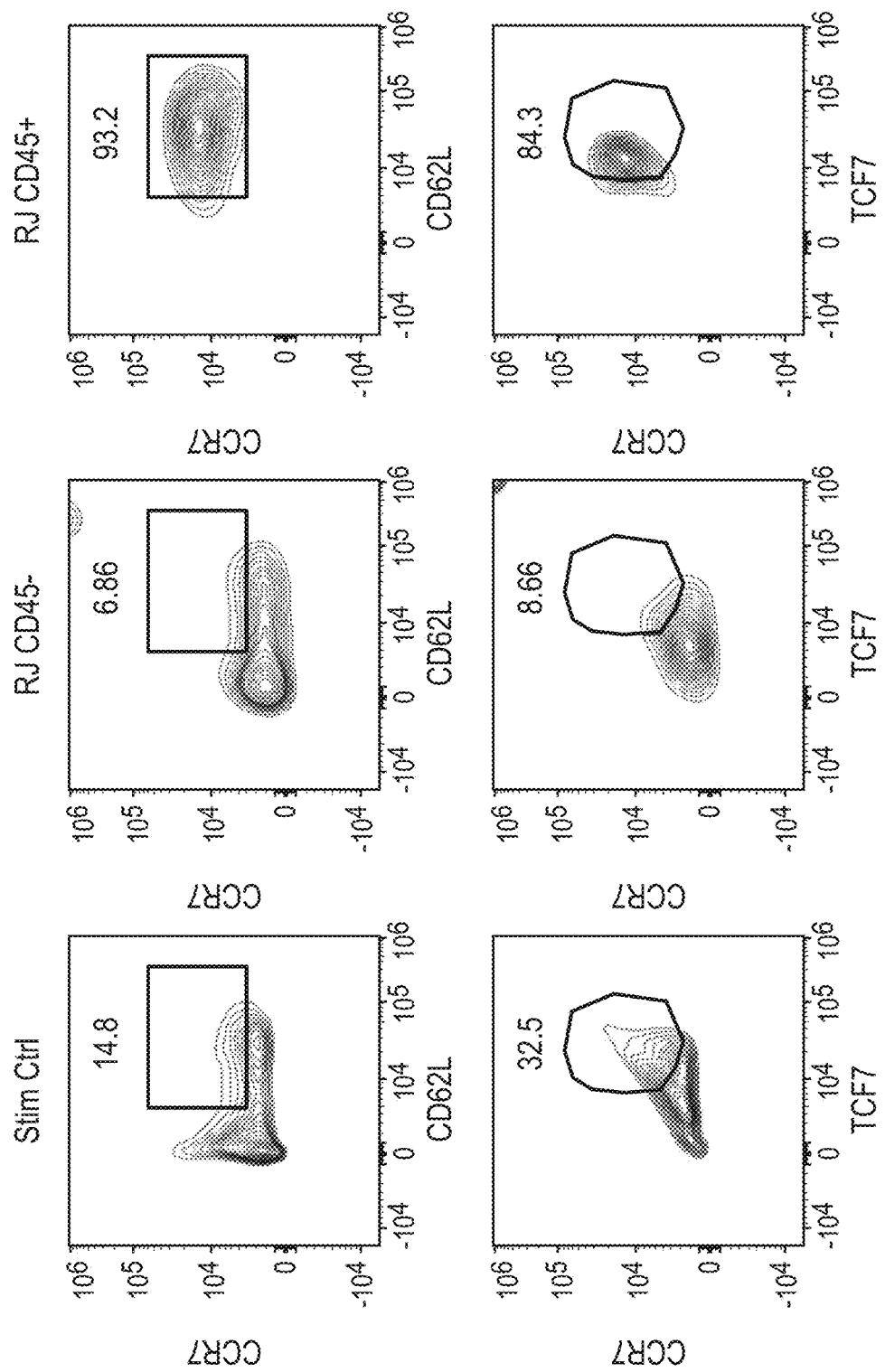

FIG. 63 shows FACS contour plots measuring expression of markers associated with stemness in control and Donor 3 at day 15. Rejuvenated CD45+ TILs but not CD45− cells showed much higher expression of CD62L+CCR7+ and TCF7+CCR7+. See Example 19.

Figure 64:
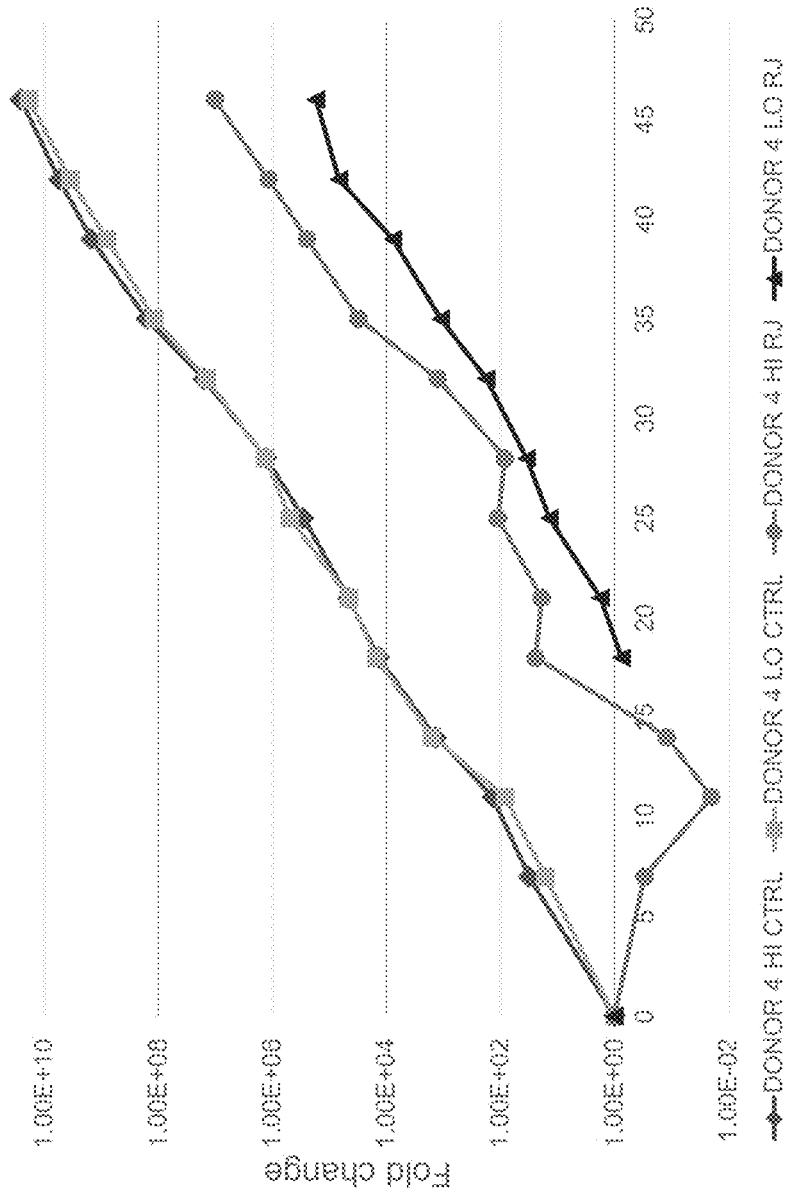

FIG. 64 is a graph showing proliferation curves of controls and Donor 4 following rejuvenation. Cells were stimulated with TransAct either 1:500 (HI) or 1:2000 (LO). Rejuvenated cells (both HI and LO group) showed similar expansion rate as controls after redirection to T cells.

Figure 65:
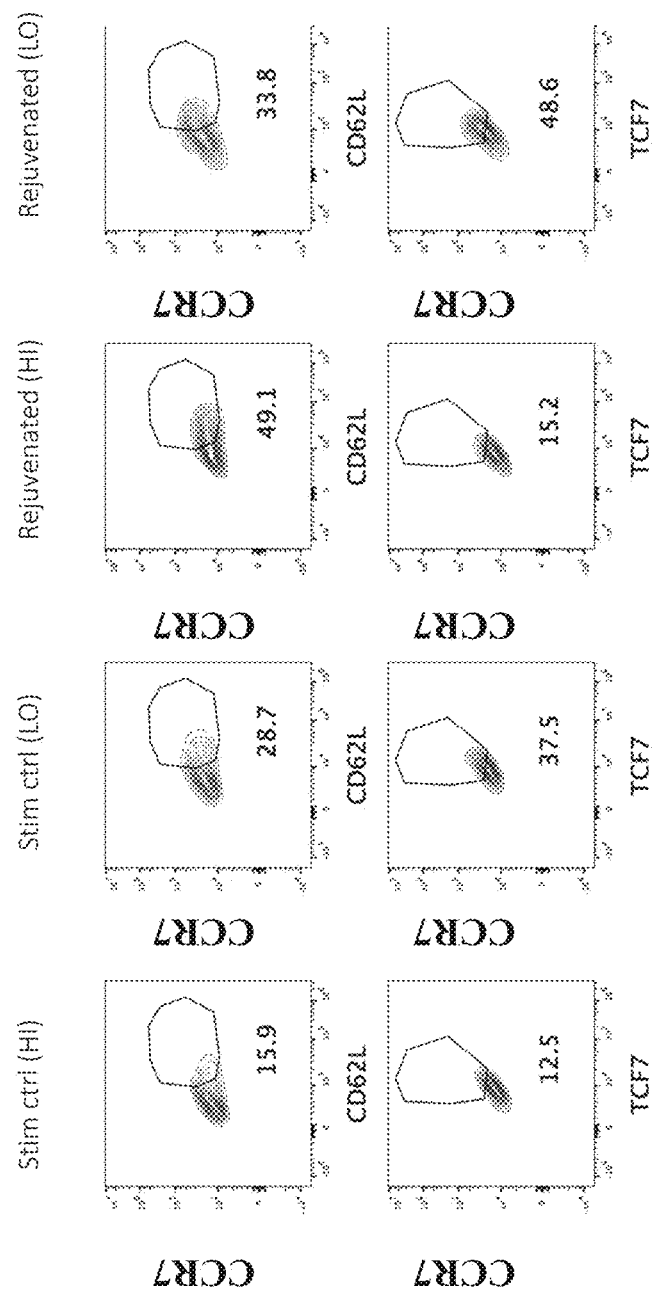

FIG. 65 shows FACS contour plots measuring expression of markers associated with stemness in control cells and Donor 4 and day 21 following rejuvenation. Rejuvenated cells (both HI and LO group) showed higher expression of CD62L+CCR7+ and TCF7+CCR7+ than control cells. See Example 19.

Figure 66:
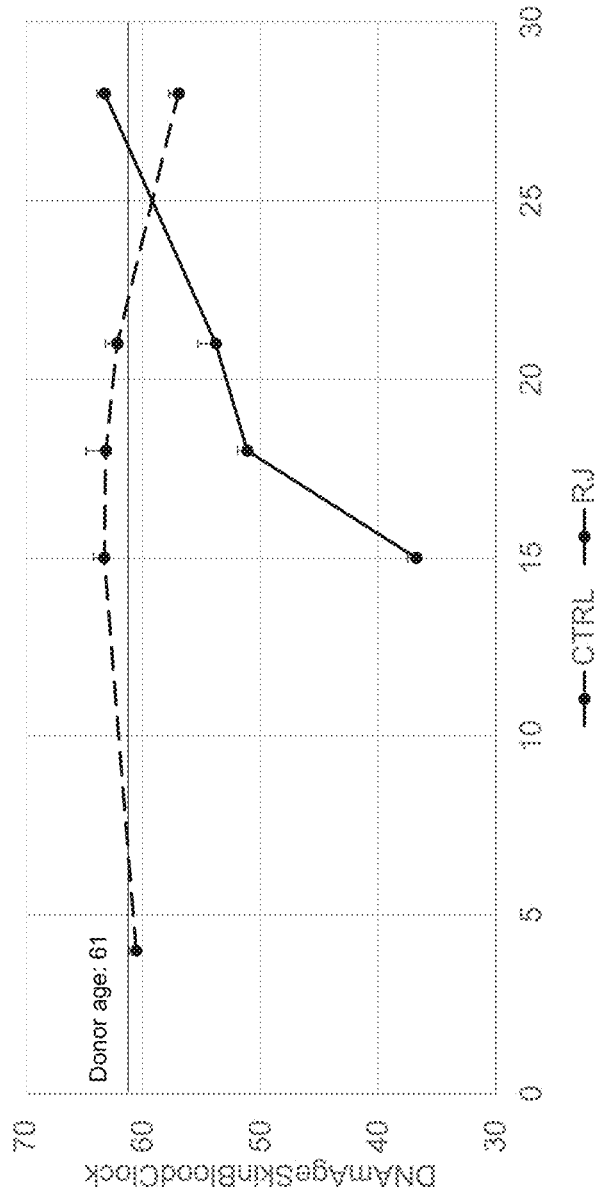

FIG. 66 is a graph showing epigenetic age (eAge) of control or rejuvenated cells from Donor 7 at indicated times. The epigenetic age of the control cells was similar to the donor chronological age, while rejuvenated cells showed a much lower age at day 15, which gradually increased with expansion time. See Example 19.

Figure 67:
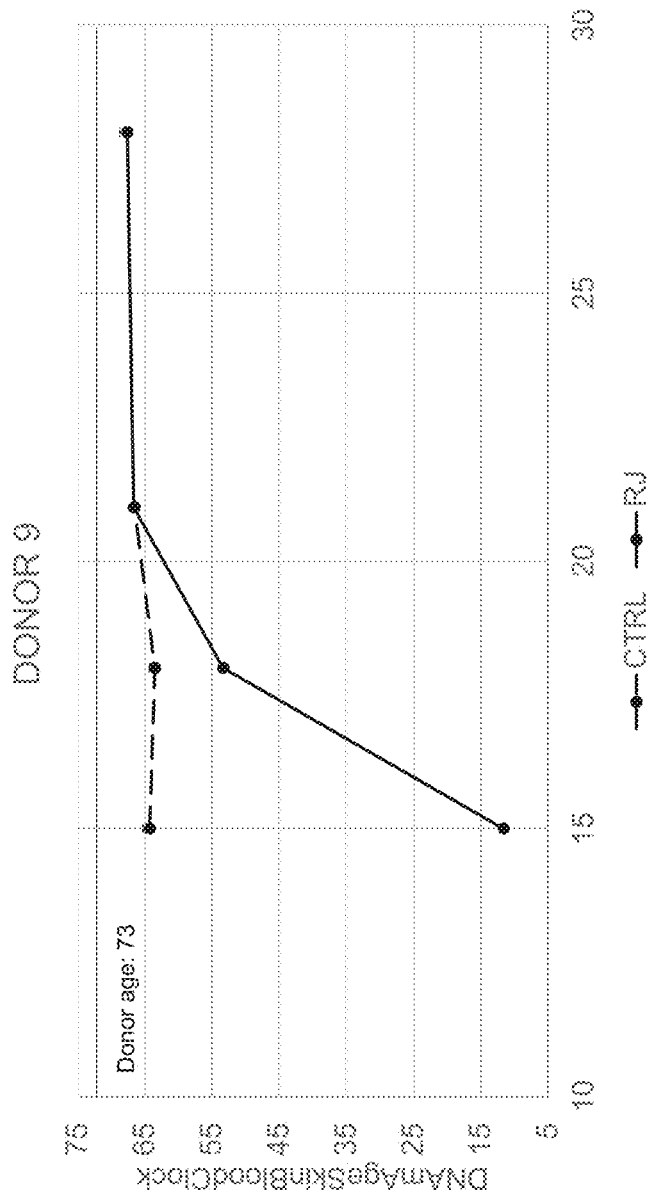

FIG. 67 is a graph showing epigenetic age (eAge) of control or rejuvenated cells from Donor 9 at indicated times. The epigenetic age of the control group is similar to the chronological donor age, while rejuvenated cells showed a much lower epigenetic age at day 15, which gradually returned to control level over time of proliferation in culture. See Example 19.

Figure 68:
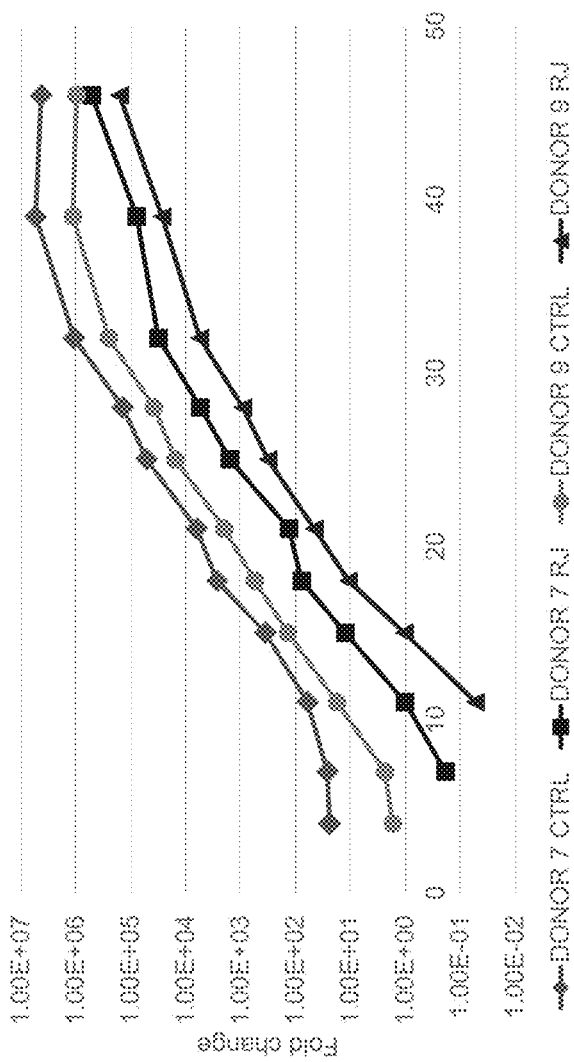

FIG. 68 is a graph showing the proliferation of control and rejuvenated cells from Donor 7 and Donor 9. Rejuvenated cells showed similar expansion rate as controls after redirection to T cells. See Example 19.

Figure 69A:
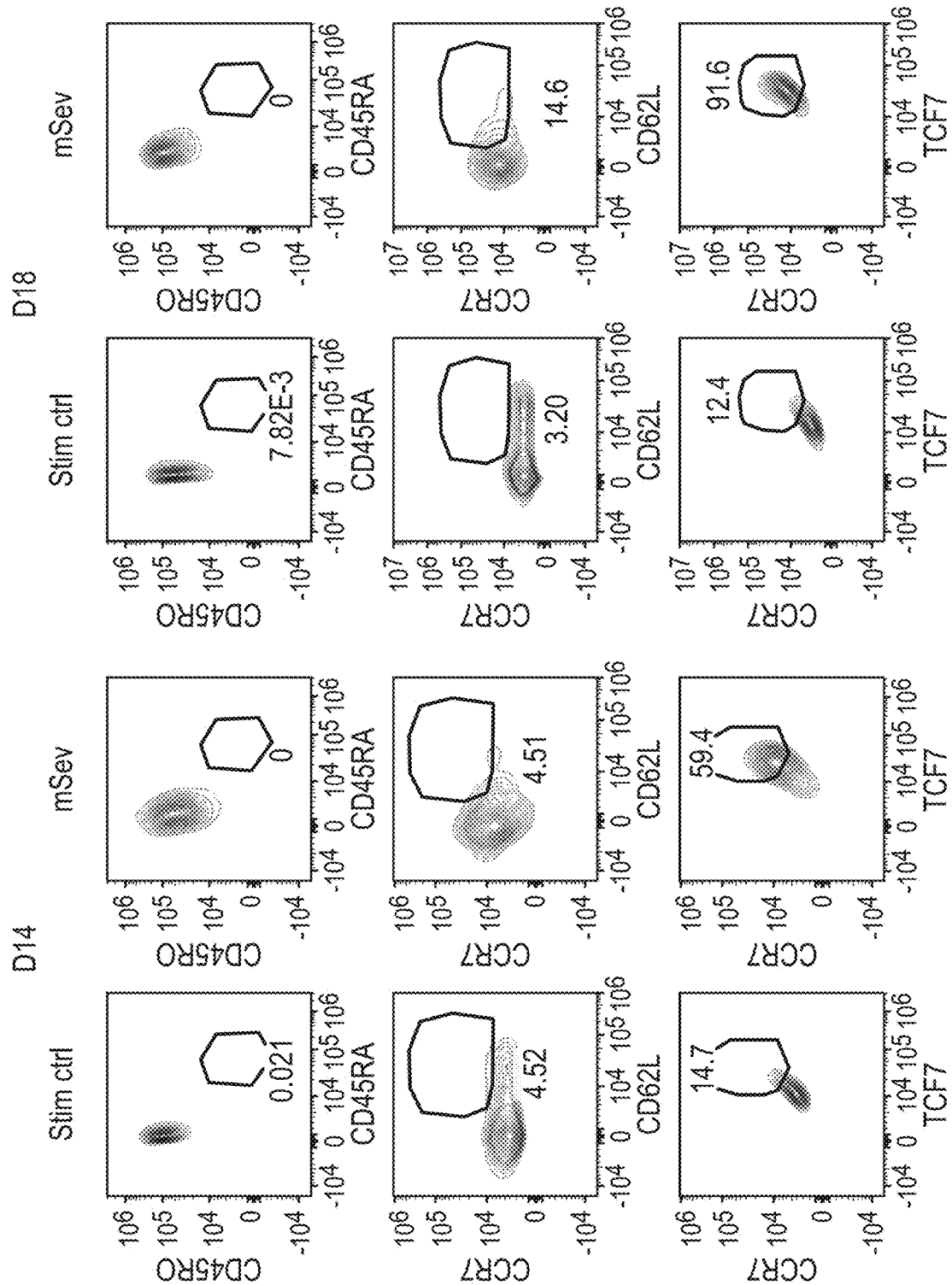

FIG. 69A shows the phenotypic analysis of Day 11 detached cells on Days 14 and 18 from Donor 6 of Example 20. The FACS plots show the frequency of CD3+ (gated on singlets, dead stain negative, and CD3+ cells). Rejuvenated cells showed higher TCF7+CCR7+ on Days 14 and 18. See Example 20 and Table 10.

Figure 69B:
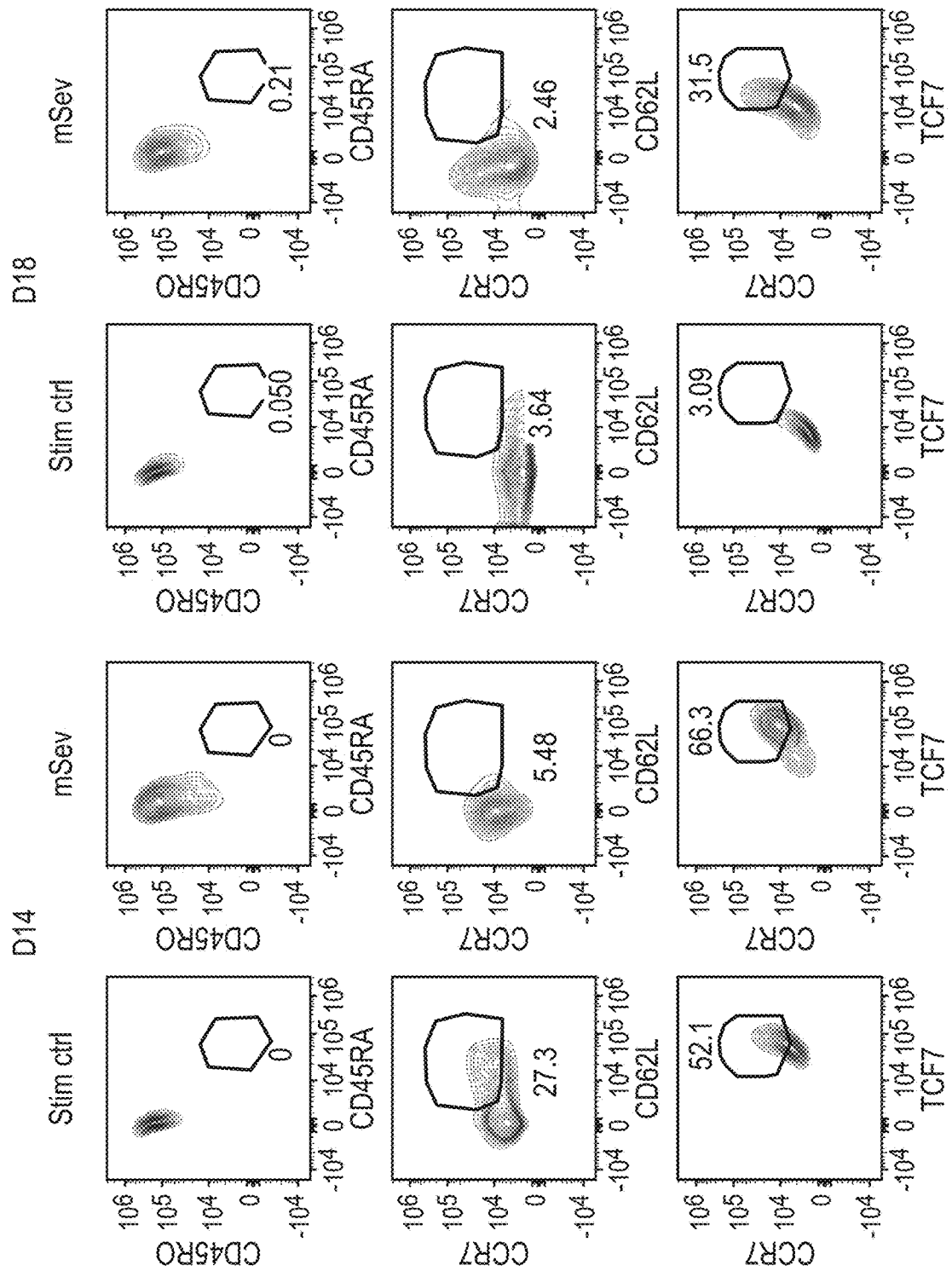

FIG. 69B shows the phenotypic analysis of Day 11 detached cells on Days 14 and 18 from Donor 8 of Example 20. The FACS plots show the frequency of CD3+ (gated on singlets, dead stain negative, and CD3+ cells). Rejuvenated cells showed higher TCF7+CCR7+ on Days 14 and 18. See Example 20 and Table 10.

Figure 70:
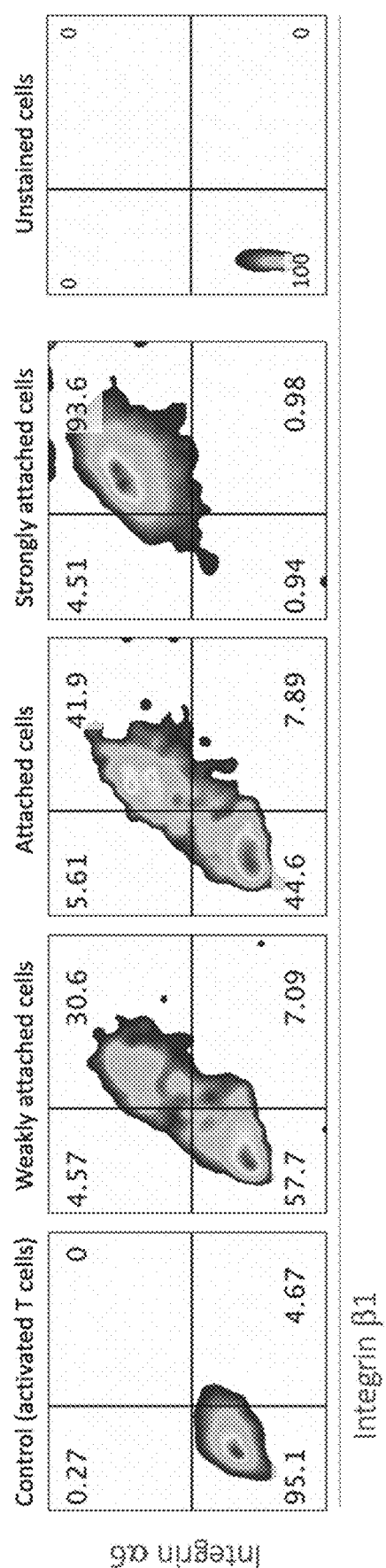

FIG. 70 shows that attached cells (weakly attached cells, attached cells, strongly attached cells) show higher integrin a6 and integrin b1 expression than activated T cell control on Day 10. Strongly attached cells show higher expression of integrin a6 and integrin b1 than weakly attached cells and attached cells. The plots were acquired after singlet and live gating.

Figure 71:
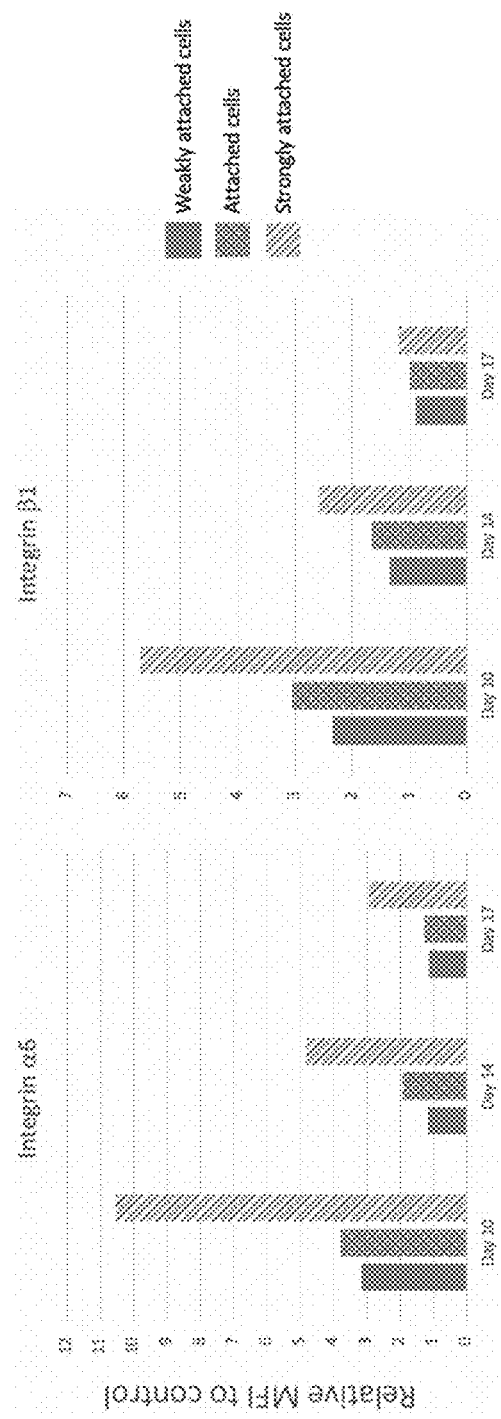

FIG. 71 shows integrin a6 and integrin b1 expression was reduced after T cell activation on day 10. The bar graph shows MFI (mean fluorescent intensity) of the plots of FIG. 70. The values were normalized by the MFI of activated T cell control of each time point. The control values were 1.

Figure 72:
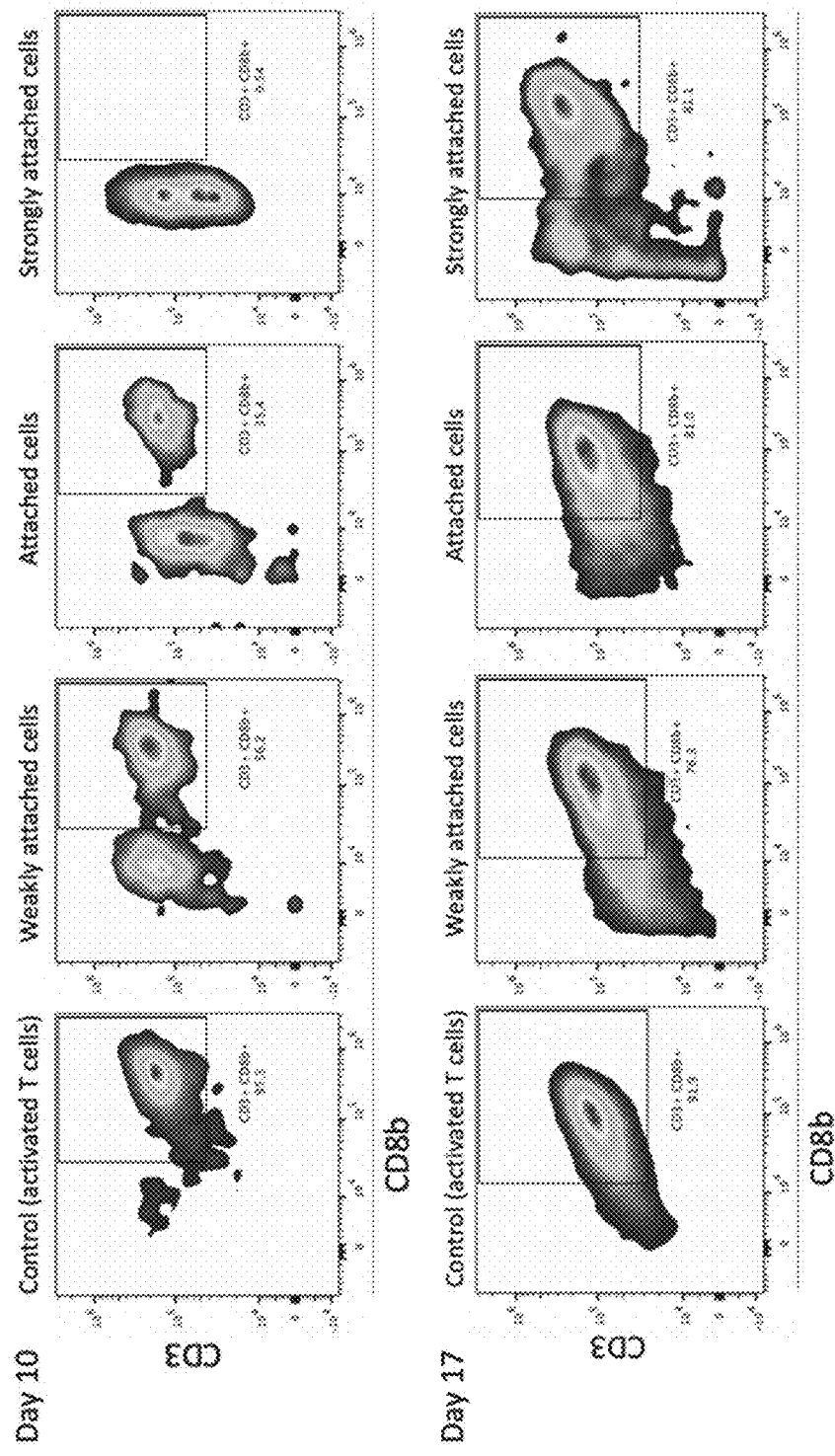

FIG. 72 shows that attached cells lost CD3 expression on day 10 but acquired CD3 expression on Day 17.

Figure 73:
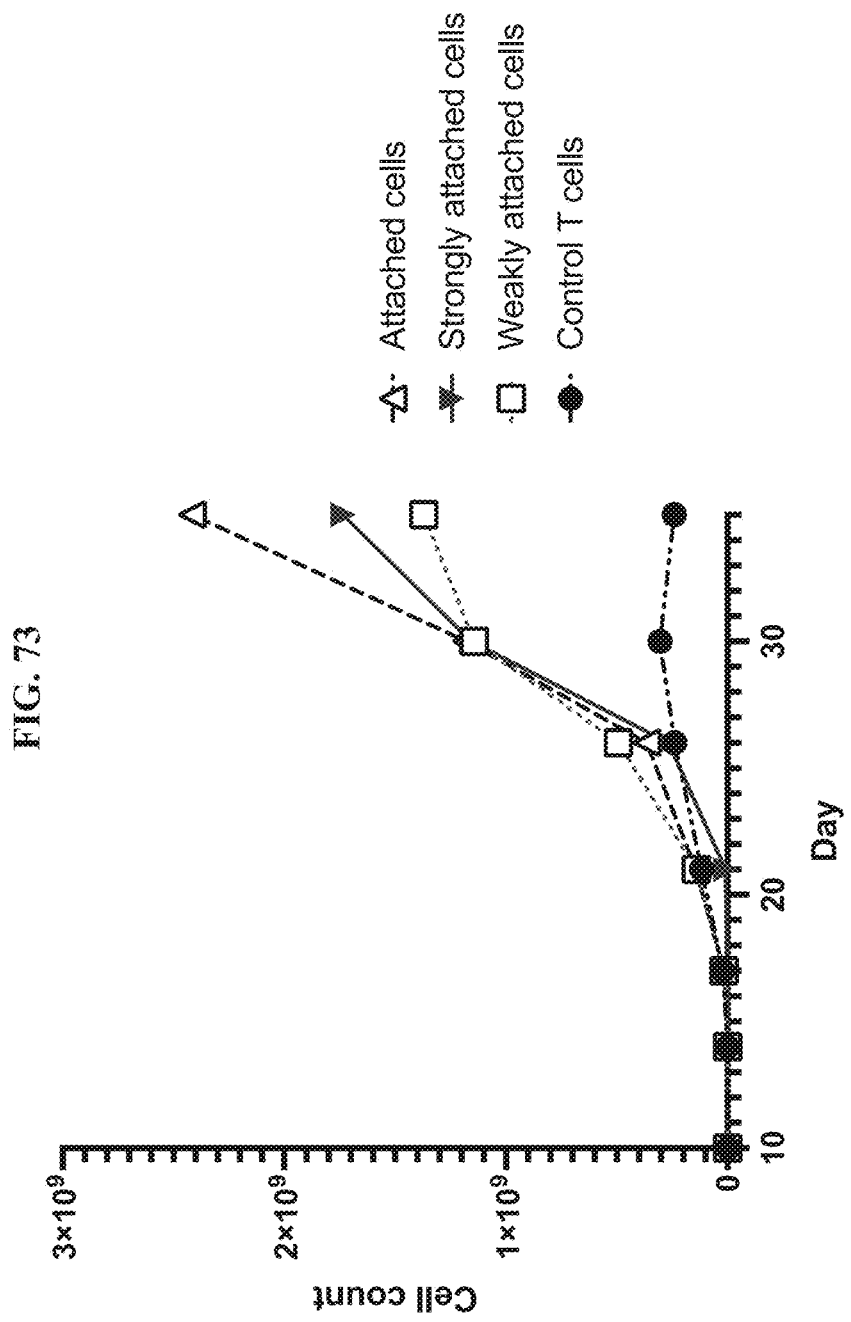

FIG. 73 shows high proliferation exhibited by weakly attached cells, attached cells, and strongly attached cells. The strongly attached cells showed late start of cell expansion.

Figure 74A:
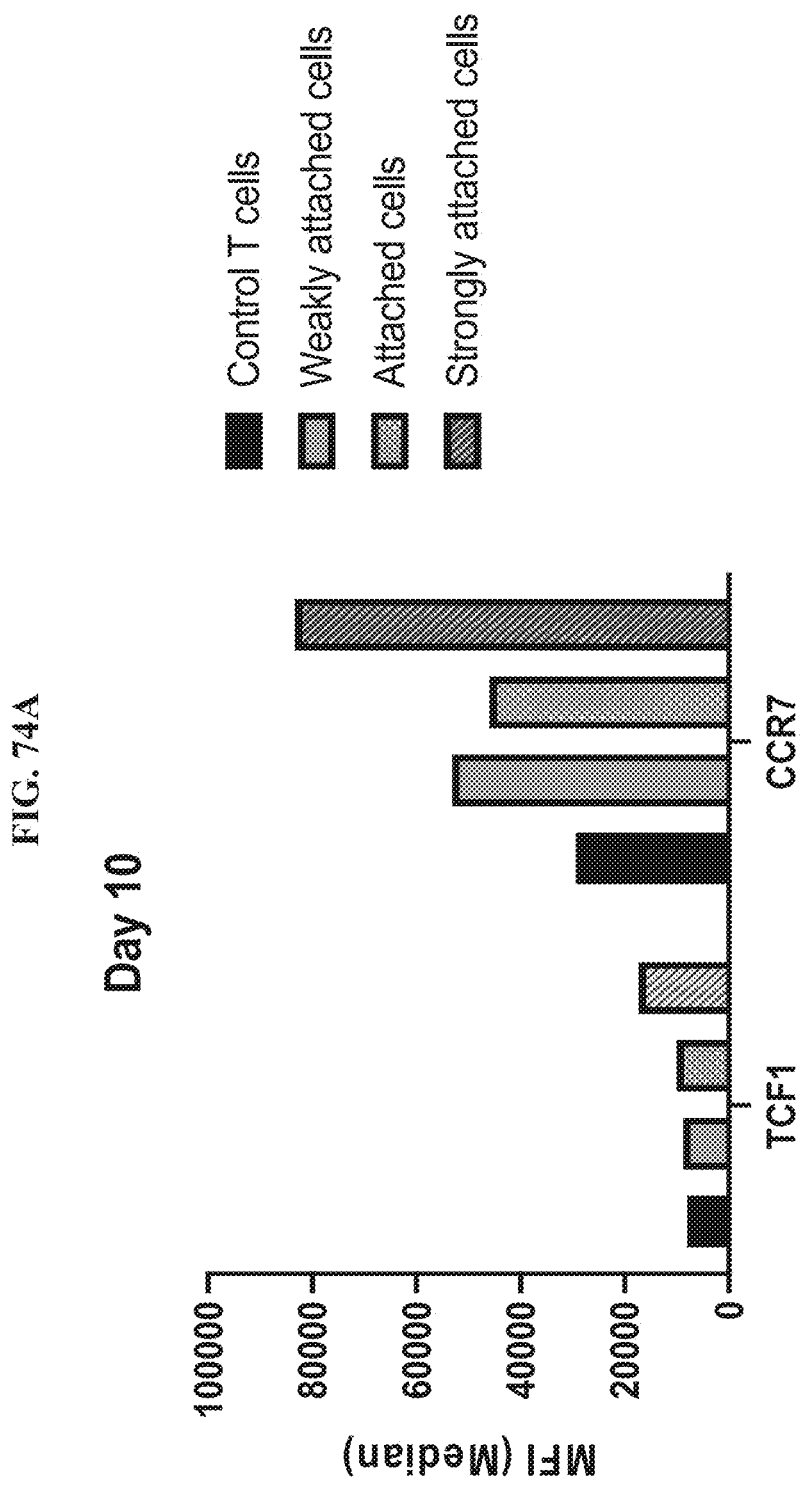

FIGS. 74A and 74B show that attached cells (especially strongly attached) exhibited high TCF1 and CCR7 expression on Days 10 (FIG. 74A) and 17 (FIG. 74B). The MFI was acquired from the data after singlet and live gating.

Figure 75:
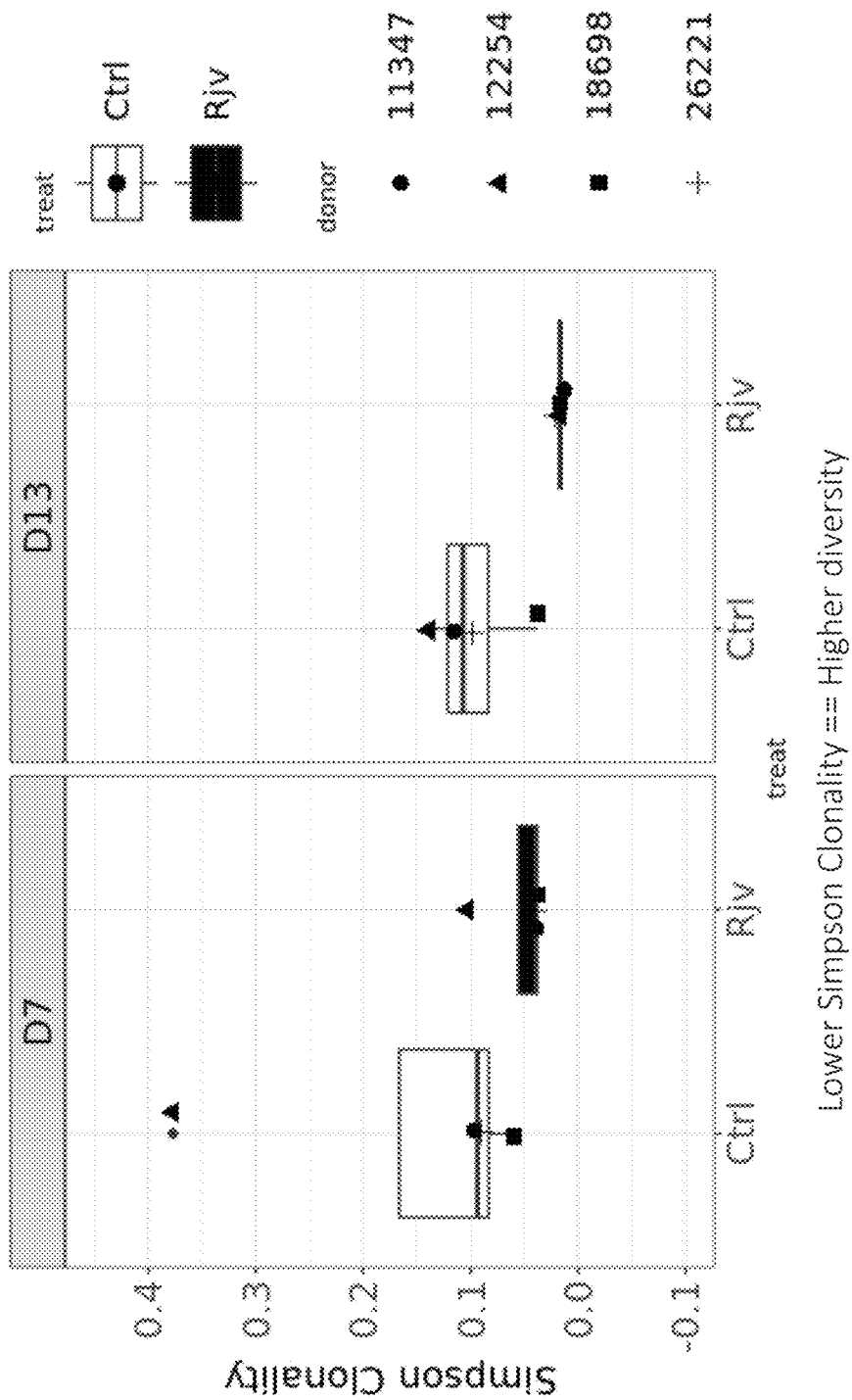

FIG. 75 shows Simpson clonality distribution of single cell TCR sequences from control and rejuvenated cells at day 7 and day 13 (see Example 18).

DETAILED DESCRIPTION

It will be understood that descriptions herein are exemplary and explanatory only and are not restrictive of the disclosure as claimed. In this application, the use of the singular includes the plural unless specifically stated otherwise.

The section headings used herein are for organizational purposes only and are not to be construed as limiting the subject matter described.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs. As utilized in accordance with the present disclosure, the following terms, unless otherwise indicated, shall be understood to have the following meanings:

In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

The present disclosure relates in part to methods of generating rejuvenated T cells by a process of partial reprogramming and reactivation to return the partially reprogrammed cells to a rejuvenated and functioning T cell. In certain embodiments, partial reprogramming comprises the transient expression in the T cells of reprogramming factors. The partial reprogramming process results in the formation of "T cell derived adherent" cells that express one or more markers of de-differentiated cells but that retain phenotypic markers of the T cell lineage. Thus, a T cell derived adherent cell is a partially dedifferentiated T cell that, when contacted with a T cell activating compound agent, returns to a functioning T cell. T cells generated by this process show characteristics of cellular rejuvenation while retaining lineage stability and retaining antigen-specificity, as described in further detail herein.

As used herein, the term "immune cell(s)" denotes any type of immune cell, including for example T cells, B cells, monocytes, macrophages, dendritic cells, and the like. In certain exemplary embodiments, immune cells disclosed herein are T cells.

The term "polynucleotide", "nucleotide", or "nucleic acid" includes both single-stranded and double-stranded nucleotide polymers. The nucleotides comprising the polynucleotide can be ribonucleotides or deoxyribonucleotides or a modified form of either type of nucleotide. Said modifications include base modifications such as bromouridine and inosine derivatives, ribose modifications such as 2', 3'-dideoxyribose, and internucleotide linkage modifications such as phosphorothioate, phosphorodithioate, phosphoroselenoate, phosphoro-diselenoate, phosphoro-anilothioate, phoshoraniladate and phosphoroamidate.

The term "oligonucleotide" refers to a polynucleotide comprising 200 or fewer nucleotides. Oligonucleotides can be single stranded or double stranded, e.g., for use in the construction of a mutant gene. Oligonucleotides can be sense or antisense oligonucleotides. An oligonucleotide can include a label, including a radiolabel, a fluorescent label, a hapten or an antigenic label, for detection assays. Oligonucleotides can be used, for example, as PCR primers, cloning primers or hybridization probes.

The term "control sequence" refers to a polynucleotide sequence that can affect the expression and processing of coding sequences to which it is ligated. The nature of such control sequences can depend upon the host organism. In particular embodiments, control sequences for prokaryotes can include a promoter, a ribosomal binding site, and a transcription termination sequence. For example, control sequences for eukaryotes can include promoters comprising one or a plurality of recognition sites for transcription factors, transcription enhancer sequences, and transcription termination sequence. "Control sequences" can include leader sequences (signal peptides) and/or fusion partner sequences.

As used herein, "operably linked" means that the components to which the term is applied are in a relationship that allows them to carry out their inherent functions under suitable conditions.

The term "vector" means any molecule or entity (e.g., nucleic acid, plasmid, bacteriophage or virus) used to transfer protein coding information into a host cell. The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct can include, but is not limited to, sequences that affect or control transcription, translation, and, if introns are present, affect RNA splicing of a coding region operably linked thereto.

The term "host cell" refers to a cell that has been transformed, or is capable of being transformed, with a nucleic acid sequence and thereby expresses a gene of interest. The term includes the progeny of the parent cell, whether or not the progeny is identical in morphology or in genetic make-up to the original parent cell, so long as the gene of interest is present.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, delivery using nanoparticles (e.g., lipid nanoparticles), or other techniques. Following transfection or transduction, the transforming DNA can recombine with that of the cell by physically integrating into a chromosome of the cell, or can be maintained transiently as an episomal element without being replicated, or can replicate independently as a plasmid. A cell is considered to have been "stably transformed" when the transforming DNA is replicated with the division of the cell.

The term "transfection" refers to the uptake of foreign or exogenous genetic material (DNA or RNA) by a cell. A number of transfection techniques are well known in the art and are disclosed herein. See, e.g., Graham et al., 1973, Virology, 1973, 52:456; Sambrook et al., Molecular Cloning: A Laboratory Manual, 2001, supra; Davis et al., Basic Methods in Molecular Biology, 1986, Elsevier; Chu et al., 1981, Gene, 13:197.

The term "transduction" refers to the process whereby foreign DNA or RNA is introduced into a cell via viral vector. See, e.g., Jones et al., Genetics: Principles and Analysis, 1998, Boston: Jones & Bartlett Publ.

The terms "polypeptide" or "protein" refer to a macromolecule having the amino acid sequence of a protein, including deletions from, additions to, and/or substitutions of one or more amino acids of the native sequence. The terms "polypeptide" and "protein" specifically encompass antigen-binding molecules, antibodies, or sequences that have deletions from, additions to, and/or substitutions of one or more amino acid of antigen-binding protein. The term "polypeptide fragment" refers to a polypeptide that has an amino-terminal deletion, a carboxyl-terminal deletion, and/or an internal deletion as compared with the full-length native protein. Such fragments can also contain modified amino acids as compared with the native protein. Useful polypeptide fragments include immunologically functional fragments of antigen-binding molecules.

The term "isolated" means (i) free of at least some other proteins with which it would normally be found, (ii) is essentially free of other proteins from the same source, e.g., from the same species, (iii) separated from at least about 50 percent of polynucleotides, lipids, carbohydrates, or other materials with which it is associated in nature, (iv) operably associated (by covalent or noncovalent interaction) with a polypeptide with which it is not associated in nature, or (v) does not occur in nature.

A "variant" of a polypeptide (e.g., an antigen-binding molecule) comprises an amino acid sequence wherein one or more amino acid residues are inserted into, deleted from and/or substituted into the amino acid sequence relative to another polypeptide sequence. Variants include fusion proteins.

The term "identity" refers to a relationship between the sequences of two or more polypeptide molecules or two or more nucleic acid molecules, as determined by aligning and comparing the sequences. "Percent identity" means the percent of identical residues between the amino acids or nucleotides in the compared molecules and is calculated based on the size of the smallest of the molecules being compared. For these calculations, gaps in alignments (if any) are preferably addressed by a particular mathematical model or computer program (i.e., an "algorithm").

To calculate percent identity, the sequences being compared are typically aligned in a way that gives the largest match between the sequences. One example of a computer program that can be used to determine percent identity is the GCG program package, which includes GAP (Devereux et al., Nucl. Acid Res., 1984, 12, 387; Genetics Computer Group, University of Wisconsin, Madison, Wis.). The computer algorithm GAP is used to align the two polypeptides or polynucleotides for which the percent sequence identity is to be determined. The sequences are aligned for optimal matching of their respective amino acid or nucleotide (the "matched span", as determined by the algorithm). In certain embodiments, a standard comparison matrix (see, e.g., Dayhoff et al., 1978, Atlas of Protein Sequence and Structure, 5:345-352 for the PAM 250 comparison matrix; Henikoff et al., 1992, Proc. Natl. Acad. Sci. U.S.A., 89, 10915-10919 for the BLO-SUM 62 comparison matrix) is also used by the algorithm.

As used herein, the twenty conventional (e.g., naturally occurring) amino acids and their abbreviations follow conventional usage. See, e.g., Immunology A Synthesis (2nd Edition, Golub and Green, Eds., Sinauer Assoc., Sunderland, Mass. (1991)), which is incorporated herein by reference for any purpose. Stereoisomers (e.g., D-amino acids) of the twenty conventional amino acids, unnatural amino acids such as alpha-, alpha-disubstituted amino acids, N-alkyl amino acids, lactic acid, and other unconventional amino acids can also be suitable components for polypeptides of the present disclosure. Examples of unconventional amino acids include: 4-hydroxyproline, γcarboxy-glutamate, epsilon-N,N,N-trimethyllysine, e-N-acetyllysine, 0-phosphoserine, N-acetylserine, N-formylmethionine, 3-methylhistidine, 5-hydroxylysine, .sigma.-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Conservative amino acid substitutions can encompass non-naturally occurring amino acid residues, which are typically incorporated by chemical peptide synthesis rather than by synthesis in biological systems. These include peptidomimetics and other reversed or inverted forms of amino acid moieties. Naturally occurring residues can be divided into classes based on common side chain properties:
 a) hydrophobic: norleucine, Met, Ala, Val, Leu, Ile;
 b) neutral hydrophilic: Cys, Ser, Thr, Asn, Gln;
 c) acidic: Asp, Glu;
 d) basic: His, Lys, Arg;
 e) residues that influence chain orientation: Gly, Pro; and
 f) aromatic: Trp, Tyr, Phe.

For example, non-conservative substitutions can involve the exchange of a member of one of these classes for a member from another class.

In making changes to the antigen-binding molecule, the costimulatory or activating domains of the engineered T cell, according to certain embodiments, the hydropathic index of amino acids can be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (3.5); lysine (−3.9); and arginine (−4.5). See, e.g., Kyte et al., 1982, J. Mol. Biol., 157, 105-131. It is known that certain amino acids can be substituted for other amino acids having a similar hydropathic index or score and still retain a similar biological activity. It is also understood in the art that the substitution of like amino acids can be made effectively on the basis of hydrophilicity, particularly where the biologically functional protein or peptide thereby created is intended for use in immunological embodiments, as in the present case. Exemplary amino acid substitutions are set forth in Table 1.

TABLE 1

| Original Residues | Exemplary Substitutions | Preferred Substitutions |
| --- | --- | --- |
| Ala | Val, Leu, Ile | Val |
| Arg | Lys, Gin, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Va, Met, Ala, Phe | Ile |
| Lys | Arg, 1, 4 Diamino-butyric Acid, Gin, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

The term "derivative" refers to a molecule that includes a chemical modification other than an insertion, deletion, or substitution of amino acids (or nucleic acids). In certain embodiments, derivatives comprise covalent modifications, including, but not limited to, chemical bonding with polymers, lipids, or other organic or inorganic moieties. In certain embodiments, a chemically modified antigen-binding molecule can have a greater circulating half-life than an antigen-binding molecule that is not chemically modified. In some embodiments, a derivative antigen-binding molecule is covalently modified to include one or more water soluble polymer attachments, including, but not limited to, polyethylene glycol, polyoxyethylene glycol, or polypropylene glycol.

Peptide analogs are commonly used in the pharmaceutical industry as non-peptide drugs with properties analogous to those of the template peptide. These types of non-peptide compound are termed "peptide mimetics" or "peptidomimetics." Fauchere, J. L., 1986, Adv. Drug Res., 1986, 15, 29; Veber, D. F. & Freidinger, R. M., 1985, Trends in Neuroscience, 8, 392-396; and Evans, B. E., et al., 1987, J. Med. Chem., 30, 1229-1239, which are incorporated herein by reference for any purpose.

The term "therapeutically effective amount" refers to the amount of immune cells (e.g., T cells) or other therapeutic agent determined to produce a therapeutic response in a mammal. Such therapeutically effective amounts are readily ascertained by one of ordinary skill in the art.

The terms "patient" and "subject" are used interchangeably and include human and non-human animal subjects as well as those with formally diagnosed disorders, those without formally recognized disorders, those receiving medical attention, those at risk of developing the disorders, etc.

The term "treat" and "treatment" includes therapeutic treatments, prophylactic treatments, and applications in which one reduces the risk that a subject will develop a disorder or other risk factor. Treatment does not require the complete curing of a disorder and encompasses embodiments in which one reduces symptoms or underlying risk factors. The term "prevent" does not require the 100% elimination of the possibility of an event. Rather, it denotes that the likelihood of the occurrence of the event has been reduced in the presence of the compound or method.

Standard techniques can be used for recombinant DNA, oligonucleotide synthesis, and tissue culture and transformation (e.g., electroporation, lipofection). Enzymatic reactions and purification techniques can be performed according to manufacturer's specifications or as commonly accomplished in the art or as described herein. The foregoing techniques and procedures can be generally performed according to conventional methods well known in the art and as described in various general and more specific references that are cited and discussed throughout the present specification. See, e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

As used herein, the term "substantially" or "essentially" refers to a quantity, level, value, number, frequency, percentage, dimension, size, amount, weight or length that is about 90%, 91%, 92%, 93%, 94%, 95%, 96%, 97%, 98%, or 99% higher compared to a reference quantity, level, value, number, frequency, percentage, dimension, size, amount, weight or length. In certain embodiments, the terms "essentially the same" or "substantially the same" refer to a range of quantity, level, value, number, frequency, percentage, dimension, size, amount, weight or length that is about the same as a reference quantity, level, value, number, frequency, percentage, dimension, size, amount, weight or length.

As used herein, the terms "substantially free of" and "essentially free of" are used interchangeably, and when used to describe a composition, such as a cell population or culture media, refer to a composition that is free of a specified substance, such as, 95% free, 96% free, 97% free, 98% free, 99% free of the specified substance, or is undetectable as measured by conventional means. Similar meaning can be applied to the term "absence of," where referring to the absence of a particular substance or component of a composition.

As used herein, the term "appreciable" refers to a range of quantity, level, value, number, frequency, percentage, dimension, size, amount, weight or length or an event that is readily detectable by one or more standard methods. The terms "not-appreciable" and "not appreciable" and equivalents refer to a range of quantity, level, value, number, frequency, percentage, dimension, size, amount, weight or length or an event that is not readily detectable or undetectable by standard methods. In certain embodiments, an event is not appreciable if it occurs less than 5%, 4%, 3%, 2%, 1%, 0.1%, 0.001%, or less of the time.

Throughout this specification, unless the context requires otherwise, the words "comprise," "comprises" and "comprising" will be understood to imply the inclusion of stated step or element or group of steps or elements but not the exclusion of any other step or element or group of steps or elements. In particular embodiments, the terms "include," "has," "contains," and "comprise" are used synonymously.

As used herein, "consisting of" is meant including, and limited to, whatever follows the phrase "consisting of". Thus, the phrase "consisting of" indicates that the listed elements are required or mandatory, and that no other elements may be present.

By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

By reserving the right to proviso out or exclude any individual members of any such group, including any subranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" or "approximately" refers to a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5% or 1%, or any intervening ranges thereof.

As used herein, "associated with" denotes a relationship between two events, entities and/or phenomena. Two events, entities and/or phenomena are "associated" with one another, as that term is used herein, if the presence, level and/or form of one is correlated with that of the other.

As used herein, the term "memory" T cells refers to T cells that have previously encountered and responded to their cognate antigen (e.g., in vivo, in vitro, or ex vivo) or which have been stimulated, e.g., with an anti-CD3 antibody (e.g., in vitro or ex vivo) Immune cells having a "memory-like" phenotype upon secondary exposure, such memory T cells can reproduce to mount a faster and stronger immune response than during the primary exposure. In some aspects, memory T cells comprise central memory T cells (TCM cells), effector memory T cells (TEM cells), tissue resident memory T cells (TRM cells), stem cell-like memory T cells (TSCM cells), or any combination thereof.

As used herein, the term "stem cell-like memory T cells," "T memory stem cells," or "TSCM cells" refers to memory T cells that express CD95, CD45RA, CCR7, and CD62L and are endowed with the stem cell-like ability to self-renew and the multipotent capacity to reconstitute the entire spectrum of memory and effector T cell subsets.

As used herein, the term "central memory T cells" or "TCM cells" refers to memory T cells that express CD45RO, CCR7, and CD62L. Central memory T cells are generally found within the lymph nodes and in peripheral circulation.

As used herein, the term "effector memory T cells" or "TEM cells" refers to memory T cells that express CD45RO but lack expression of CCR7 and CD62L. Because effector memory T cells lack lymph node-homing receptors (e.g., CCR7 and CD62L), these cells are typically found in peripheral circulation and in non-lymphoid tissues.

As used herein, the term "tissue resident memory T cells" or "TRM cells" refers to memory T cells that do not circulate and remain resident in peripheral tissues, such as skin, lung, and gastrointestinal tract. In some aspects, tissue resident memory T cells are also effector memory T cells.

As used herein, the term "naïve T cells" or "TN cells" refers to T cells that express CD45RA, CCR7, and CD62L, but which do not express CD95. TN cells represent the most undifferentiated cell in the T cell lineage. The interaction between a TN cell and an antigen presenting cell (APC) induces differentiation of the TN cell towards an activated TEFF cell and an immune response.

As used herein, the term "stemness," "stem cell-like," "stem-like," or "less-differentiated" refers to an immune cell (e.g., a T cell or a TIL), that expresses markers consistent with a more naïve phenotype. For example, a less differentiated T cell can express one or more marker characteristic of a TN or a TSCM cell. In some aspects, a "less-differentiated" or "stem-like" T cell expresses CD45RA, CCR7, and CD62L. In some aspects, a "less-differentiated" or "stem-like" T cell expresses CD45RA, CCR7, CD62L, and TCF7. In some aspect, a "less-differentiated" or "stem-like" T cell does not express CD45RO or is CD45ROlow. In some aspects, the methods disclosed herein promote immune cells (e.g., T cells) having a less-differentiated phenotype. Without being bound by any particular mechanism, in some aspects, the methods disclosed herein block, inhibit, or limit differentiation of less-differentiated immune cells (e.g., T cells), resulting in an increased number of stem-like cells in culture. For example, it is generally thought that to effectively control tumors, adoptive transfer of less-differentiated immune cells, e.g., T cells, with a stem cell-like memory or central memory phenotype are preferred. See Gattinoni, L., et al., J. Clin. Invest. 115:1616-1626 (2005), Gattinoni, L., et al. Nat Med 15(7):808-814 (2009), Lynn, R. C., et al., Nature 576(7786): 293-300 (2019); Gattinoni, L., et al. Nat Rev 12:671-684 (2012), Klebanoff, C., et al., J. Immunother 35(9):651-670 (2012) and Gattinoni, L., et al., Nat Med 17(10): 1290-1297 (2011).

Stemness is characterized by the capacity to self-renew, the multipotency, and the persistence of proliferative potential. In some aspects, stemness is characterized by a particular gene signature, e.g., a combined pattern of expression across a multitude of genes. In some aspects, the stem-like cells can be identified by a transcriptome analysis, e.g., using stemness gene signatures disclosed herein. In some aspects, the gene signature comprises one or more genes selected from ACTN1, DSC1, TSHZ2, MYB, LEF1, TIMD4, MAL, KRT73, SESN3, CDCA7L, LOC283174, TCF7, SLC16A10, LASS6, UBE2E2, IL7R, GCNT4, TAF4B, SULT1B1, SELP, KRT72, STXBP1, TCEA3, FCGBP, CXCRS, GPA33, NELL2, APBA2, SELL, VIPR1, FAM153B, PPFIBP2, FCER1G, GJB6, OCM2, GCET2, LRRN1, IL6ST, LRRC16A, IGSF9B, EFHA2, LOC129293, APP, PKIA, ZC3H12D, CHMP7, KIAA0748, SLC22A17, FLJ13197, NRCAM, C5orf13, GIPC3, WNT7A, FAM117B, BENDS, LGMN, FAM63A, FAM153B, ARHGEF11, RBM11, RIC3, LDLRAP1, *PELI*1, PTK2, KCTD12, LMO7, CEP68, SDK2, MCOLN3, ZNF238, EDAR, FAM153C, FAAH2, BCL9, C17orf48, MAP1D, ZSWIM1, SORBS3, IL4R, SERPINF1, C16orf45, SPTBN1, KCNQ1, LDHB, BZW2, NBEA, GAL3ST4, CRTC3, MAP3K1, HLA-DOA, RAB43, SGTB, CNN3, CWH43, KLHL3, PIM2, RGMB, C16orf74, AEBP1, SNORD115-11, SNORD115-11, GRAP, and any combination thereof (see, e.g., Gattinoni et al., Nature Medicine 17(10):1290-97 (2011)). In some aspects, the gene signature comprises one or more gene selected from NOG, TIMD4, MYB, UBE2E2, FCER1G, HAVCR1, FCGBP, PPFIBP2, TPST1, ACTN1, IGF1R, KRT72, SLC16A10, GJB6, LRRN1, PRAGMIN, GIPC3, FLNB, ARRB1, SLC7A8, NUCB2, LRRC7, MYO15B, MAL, AEBP1, SDK2, BZW2, GAL3ST4, PITPNM2, ZNF496, FAM117B, C16orf74, TDRD6, TSPAN32, C18orf22, C3orf44, LOC129293, ZC3H12D, MLXIP, C7orf10, STXBP1, KCNQ1, FLJ13197, LDLRAP1, RAB43, RIN3, SLC22A17, AGBL3, TCEA3, NCRNA00185, FAM153B, FAM153C, VIPR1, MMP19, HBS1L, EEF2K, SNORASC, UBASH3A, FLJ43390, RP6-213H19.1, INPPSA, PIM2, TNFRSF10D, SNRK, LOC100128288, PIGV, LOC100129858, SPTBN1, PROS1, MMP28, HES1, CACHD1, NSUNSC, LEF1, TTTY14, SNORA54, HSF2, C16orf67, NSUNSB, KIAA1257, NRG2, CAD, TARBP1, STRADB, MT1F, TMEM41B, PDHX, KDM6B, LOC100288322, UXS1, LGMN, NANOS2, PYGB, RASGRP2, C14orf80, XPO6, SLC24A6, FAM113A, MRM1, FBXW8, NDUFS2, KCTD12, and any combination thereof (see, e.g., Gattinoni, L., et al., Nat Med 17(10): 1290-1297 (2011)).

As used herein, the term "mononuclear cell" refers to a cell found in blood that has a single, round nucleus.

As used herein, the term "totipotent" refers to the ability of a cell to give rise to any cell type found in an embryo as well as extra-embryonic (placenta) cells.

As used herein, the term "pluripotent" refers to the ability of a cell to form all lineages of the body or soma (i.e., the embryo proper but not the placenta). For example, an embryonic stem cell is a type of pluripotent stem cell that is available to form cells from each of the three germ layers: the ectoderm, the mesoderm and the endoderm. Pluripotency can be determined in part, by assessing the pluripotency characteristics of the cells. Pluripotency characteristics may include, but are not limited to: (i) pluripotent stem cell morphology; (ii) the potential for unlimited self-renewal; (iii) ability to differentiate to all three somatic lineages (ectoderm, mesoderm and endoderm); (iv) teratoma formation consisting of the three somatic lineages; and (v) formation of embryoid bodies consisting of cells from the three somatic lineages; (vi) expression of one or more pluripotent stem cell markers including, but not limited to SSEA1 (mouse only), SSEA3/4, SSEA5, TRA1-60/81, TRA2-54 (ALP), TRA1-85, GCTM-2, TG343, TRA2-49, CD340, CD326, Podoplanin, and TG30 (CD9); (vii) expression of certain other markers associated with somatic stem cells or early differentiated cells from embryonic stem cells, including, but not limited to, integrin α6β1, CD29, CD133/prominin, CD140a, CD56, CD73, CD90, CD105, CD30 and/or LD50; (viii) expression of certain pluripotent genes including OCT4, NANOG, SOX2.

As used herein, the term "multipotent" refers to the ability of a cell to develop into a limited number of cell types in a particular lineage.

As used herein, the term "non-pluripotent cell" refers to any cell that does not possess full pluripotency, such as incompletely or partially pluripotent stem cells, multipotent cells, oligopotent cells, unipotent cells (e.g. progenitor cells), and terminally differentiated cells.

As used herein, the term "introducing" refers to a process that comprises contacting a cell with a polynucleotide, polypeptide, or small molecule. An introducing step may also comprise microinjection of polynucleotides or polypeptides into the cell, use of liposomes to deliver polynucleotides or polypeptides into the cell, or fusion of polynucleotides or polypeptides to cell permeable moieties to introduce them into a cell.

An embodiment of the disclosure provides a method of preparing an isolated or purified population of immune cells (e.g., T cells) in vitro. The isolated or purified population of immune cells (e.g., T cells) may be included in a pharmaceutical composition useful for the treatment or prevention of a variety of different conditions as described herein.

"Differentiation" is the process by which a cell loses its potency and capacity for self-renewal and ultimately becomes a mature and discrete cell type within a discrete lineage (see e.g., Crompton 2014, Trends in Immunol. 35:178-185).

"Dedifferentiation" refers to a process by which cells become less specialized. In certain embodiments, dedifferentiation is the loss of specialization characteristics that are within the normal development path or within the same cell lineage. In certain embodiments, dedifferentiation is dedifferentiation within the same cell lineage (hierarchical dedifferentiation). However, as described herein, in another embodiment, dedifferentiation may not be within the same cell lineage. For example, in certain embodiments, partial reprogramming of T cells as described herein results in cells that dedifferentiate by gaining expression of CD9 and/or CD90 and/or SSEA4, markers not usually associated with the conventional T cell lineage in humans, and which cells begin to lose expression of T cell markers CD3 and/or CD4 and/or CD8. Such dedifferentiation is not along the standard T cell hierarchical lineage. These cells can return to conventional T cells following stimulation with T cell activation agents. CD90 expression is only associated with rare populations of human T cells such as cortical thymocytes and a subset of Th17.

Rejuvenation is a process in which cellular function lost by cell aging is restored. Cell age can be described as the sum of the chronological age of the donor plus an alpha factor determined by the combination of several factors inducing stress in the cell microenvironment. These factors can be observed in vivo (e.g. heavy smoking, chronic illness including autoimmune disease, infection, obesity, metabolic problems and possibly depression) and might be artificially induced in vitro (e.g. long exposure to tumor antigens or other stimulation, high levels of cytokines, hypoxia etc.). Cells that become older due to chronological age or as a product of continual strong stress stimuli are known as senescent cells. Several cellular processes have been identified as compromised by cell age such as chronological age, tumor antigen specificity, killer cell properties, proliferation ability, metabolism, DNA repair system abrogation, telomere length and loss of stemness potential.

"Rejuvenated T cell" as used herein refers to a T cell that has been contacted with one or more reprogramming factors for a period of time sufficient for the T cells to begin to attach to the culture vessel surface to form T cell derived adherent cells that return to a functioning T cell after stimulation with a T cell activation agent and optionally, an immunomodulatory molecule.

For example, the methods described herein produce rejuvenated T cells that provide any one or more of increased in vivo proliferation, survival, persistence, and/or cytotoxicity; reduced epigenetic age, increased telomere length, improved metabolism, decreased apoptosis and other markers associated with cell senescence and improved anti-tumor activity as compared to terminally differentiated T cells. In certain embodiments, rejuvenated T cells exhibit a polyclonal TCR repertoire and the capacity for long term in vivo engraftment. Rejuvenated T cells may exhibit biological and phenotypic characteristics of younger T cells in terms of epigenetic signature, telomere length, metabolic activity and functionality. In various embodiments, the partial reprogramming process as described herein may cause the T cell to partially dedifferentiate, e.g., to lose certain aspects of the T cell phenotype, which are regained through T cell activation through TCR signaling and/or culturing in an appropriate media.

In various embodiments, the rejuvenated T cells can be used to target cancers, viruses, or autoimmune diseases. In various embodiments, the partially reprogrammed T cells can be used to reconstitute the whole adaptive immune system or alleviate immunocompromised patients.

In certain embodiments, the T cells are partially reprogrammed and rejuvenated through transient expression of reprogramming factors. In various embodiments, the morphology and cell surface expression profile of the T cells begins to change. In particular, in certain embodiments, the cell begins to express certain cell surface markers and the expression of T cell markers decreases. In certain embodiments, the cell begins to express certain cell surface markers and the expression of T cell markers decreases from about day 5 of partial reprogramming, indicating that the dedifferentiation process has initiated. In various embodiments, the dedifferentiated T cells (also referred to herein as "T cell derived adherent" cells) are stimulated with one or more T cell activating molecules, such as anti-CD3 antibodies or other CD3 agonist, and cultured in a T cell culture condition. In certain embodiments, this T cell stimulation, also referred to herein as "reactivation", can drive the dedifferentiated cells to return to the T lineage cell. Remarkably, the reactivated T cells have characteristics of much younger cells based on the epigenetic clock analysis, have a more stem-like phenotype and have acquired high proliferating potential.

As used herein, "transient" means for a period of time sufficient to achieve partial reprogramming of one or more T cells, (e.g., a period of time sufficient for T cell derived adherent cells to form, but not long enough to transform the one or more T cells into iPS cells or totipotent cells).

For example, "transiently contacting" with one or more reprogramming factors means contacting with one or more reprogramming factors for a period of time which is sufficient for T cell derived adherent cells to form, or for the one or more T cells to form at least one colony attached to a culture vessel surface, but not a period of time long enough to permit the one or more T cells to transform into iPS cells or totipotent cells. In various embodiments, "transiently contacting" can mean contacting for a period of time of up to 1 day, or up to 2 days, or up to 3 days, or up to 4 days, or up to 5 days, or up to 6 days, or up to 7 days, or up to 8 days, or up to 9 days, or up to 10 days, or up to 11 days, or up to 12 days, or up to 13 days, or up to 14 days.

For example, "transiently expressing" or "transient expression" or the like means expression or causing expression of one or more of the Yamanaka factors so as to achieve partial reprogramming of one or more T cells (i.e., where transformation to an iPS cell or totipotent cell is not achieved).

As used herein, "epigenetic age" (or "eAge") means the age of a cell as determined using known epigenetic clocks, e.g., the Horvath Clock, the Hannum Clock or the Levine Clock (see, e.g., Horvath et al., 2018, Aging 10, 1758-1775; Hannum et al., 2013, Mol. Cell. 49(2), 359-367; Levine et al., 2018, Aging, 10(4):573-592). In certain embodiments, the eAge is the age of a cell as determined using the Horvath Clock method of measuring methylation status at 353 CpGs (Horvath and Raj, 2018 Nature Reviews Genetics, 19:371-385). These results indicated that the partial reprogramming and reactivation methods described herein can generate rejuvenated T cells without going through an iPS cell stage, which is time-consuming and requires complex differentiation steps. Moreover, T cells that are differentiated from iPS cells, in absence of an autologous thymic education, lack true T cell function and possess abnormalities including immature phenotype, non MHC dependent killing, improper CD8αβ dimerization, dysregulation of gene expression and failure to produce a developmentally homogeneous population of T cells. Vizcardo et al., 2018, Cell Rep 22, 3175-3190. Thus, the rejuvenated T cells generated using the partial reprogramming methods described herein provide unexpected and advantageous properties over T cells generated using methods known in the art.

I. Methods of Producing Rejuvenated T Cells

Described below are non-limiting exemplary embodiments of the present invention. Additional aspects of the compositions and methods of the present invention will become apparent to persons of ordinary skill in the art based on the disclosure provided herein.

In various embodiments, the present disclosure relates to a method of producing rejuvenated T cells. In various embodiments, the method comprises (i) transiently contacting a population of T cells with at least one reprogramming factor for a period of time sufficient to achieve partial reprogramming and wherein said T cells are not transformed into iPS cells; and (ii) contacting the partially reprogrammed T cell with at least one T cell activating compound or agent and, optionally, one or more immunomodulating agent.

In various embodiments, the present disclosure relates to a method of producing rejuvenated T cells. In various embodiments, the method comprises (i) transiently contacting a population of T cells with at least one reprogramming factor selected from the group consisting of KLF4, OCT3/4, SOX2, NANOG, LIN28, L-MYC and C-MYC; and optionally SV40 for a period of time sufficient to achieve partial reprogramming, wherein said T cells are not transformed into iPS cells; and (ii) contacting the partially reprogrammed T cell with at least one T cell activating compound or agent and, optionally, one or more immunomodulating agent.

In various embodiments, the present disclosure relates to a method of producing rejuvenated T cells. In various embodiments, the method comprises (i) contacting a population of T cells with at least one reprogramming factor selected from the group consisting of KLF4, OCT3/4, SOX2, NANOG, LIN28, L-MYC and C-MYC; and optionally SV40 for a period of time sufficient for formation of T cell derived adherent cells and wherein said T cells are not transformed into iPS cells; and (ii) contacting the T cell derived adherent cells with at least one T cell activating compound or agent and/or a T cell costimulatory agent, and optionally, one or more immunomodulating agent.

As used herein, "reprogramming" refers to the process of erasing and/or re-establishing epigenetic modifications acquired during mammalian cell development or in cell culture. For example, muscle cells can be reprogrammed to a neuron. Reprogramming is not intrinsically related to aging and rejuvenation. (see e.g., Takahashi et al., Cell (2007) 131, 861-872)

"Complete reprogramming" refers to reprogramming of a somatic cell to a pluripotent stem (iPS) cell or a totipotent stem cell.

"Partial reprogramming" refers to a process of reprogramming without reaching a totipotent stem cell state or a pluripotent stem cell state (iPS cell). Thus, partial preprogramming is any reprogramming that is not complete reprogramming "Partial" or "incomplete" or "transient" reprogramming is reprogramming that is not complete reprogramming, e.g., as compared to a cell that has been completely reprogrammed to an iPS cell. In certain embodiments, partial reprogramming is reprogramming carried out from about 1 to about 20 days. In certain embodiments, partial reprogramming is reprogramming carried out for about 1, 2, 3, 4, 5, 6, 7, 8, 9, 10, 11, 12, 13, 14, 15, 16, 17, 18, 19, 20, 21, 22, 23, 24, or about 25 days.

In certain embodiments, partial T cell reprogramming is a reprogramming process carried out until T cell reactivation is initiated. In another embodiment, partial T cell reprogramming is a reprogramming process that is carried out at least until the T cells begin to lose expression of one or more T cell markers and/or begin to express markers associated with a non-T cell lineage. In certain embodiments, partial T cell reprogramming is a process of reprogramming carried out for a period of time up to the time that the T cells can no longer be returned to a cell expressing CD3, CD4 and/or CD8 by reactivation with a T cell activation agent.

"Partially reprogrammed T cell" refers to a T cell that has been reprogrammed without reaching a totipotent stem cell state or a pluripotent stem cell state (iPS cells). In a further embodiment, partial reprogramming of a T cell is incomplete and/or partial and/or transient reprogramming compared to an iPS cell. A partially reprogrammed T cell refers to a T cell that has been reprogrammed by contacting the T cells with one or more reprogramming factors for a period of time such that the T cells form T cell derived adherent cells. In certain embodiments, the T cell derived adherent cells are loosely attached to the culture vessel surface. T cell derived adherent cells as described herein retain lineage stability e.g., return to the T cell lineage after stimulation (reactivation) with a T cell activation agent and optionally an immunomodulatory molecule (e.g. cytokines). In certain embodiments, the T cell derived adherent cells are semi-adherent, loosely adherent, adherent, or strongly adherent (strongly attached).

1. Source of and Isolating T Cells

The cells useful in the methods of partial reprogramming described herein in some embodiments are derived from primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells for use in the partial reprogramming methods are derived from cell lines, e.g., T cell lines. The cells in some embodiments are obtained from a xenogeneic source, for example, from mouse, rat, non-human primate, and pig.

In various embodiments, the present disclosure relates to isolating T cells from a source and partially reprogramming said T cells to ameliorate aging and improving the function of the T cells. Examples of suitable source cells include, but are not limited to, peripheral blood mononuclear cells (PBMCs). T cells for use in the methods herein may include, but are not limited to, cultured T cells, e.g., primary T cells or T cells from a cultured T cell line, e.g., Jurkat, SupT1, etc., or T cells obtained from a mammal. If obtained from a mammal, the source cells can be obtained from numerous sources, including but not limited to blood, bone marrow, lymph node, tumor, thymus, spleen, or other tissues or fluids. Source cells can also be enriched for or purified. The T cells can be any type of T cells and can be of any developmental stage, including but not limited to CD4+ CD8αβ+ double positive T cells, CD4+ helper T cells, e.g., Th1 and Th2 cells, CD4+ T cells, CD8+ T cells (e.g., cytotoxic T cells), peripheral blood mononuclear cells (PBMCs), peripheral blood leukocytes (PBLs), tumor infiltrating cells (TILs), memory T cells, naïve T cells, and the like.

In various embodiments, the T cells are isolated from tumors, in particular the T cells for use in the partial reprogramming methods described herein are TILs. As used herein, "tumor infiltrating lymphocytes" or "TILs" means a population of cells originally obtained as cells that have left the bloodstream of a subject and migrated into a tumor. TILs include, but are not limited to, CD8+ cytotoxic T cells (lymphocytes), Th1 and Th17 CD4+ T cells, natural killer cells, dendritic cells and M1 macrophages. TILs include both primary and secondary TILs. "Primary TILs" are those that are obtained from patient tissue samples as outlined herein (sometimes referred to as "freshly harvested"). In some embodiments, TILs can be categorized by expressing one or more of the following biomarkers: CD4, CD8, TCRαβ, CD27, CD28, CD56, CCR7, CD45Ra, CD95, PD-1, and CD25.

In various embodiments of the disclosure, the source cells may have a naïve T cell ((TN) phenotype, central memory T cell (TCM) phenotype, or effector memory T cell (TEM) phenotype, stem-like T cell (Tscm). The phenotypes of TN, TCM and TEM cells are known in the art and are described elsewhere herein. For example, CCR7 and CD62L are expressed by TN and TCM cells, but are not expressed by TEM cells. The transcription factors LEF1, FOXP1 and KLF7 are expressed by TN and TCM cells, but are not expressed by TEM cells. CD45RO and KLRG1 are not expressed by TN cells, but are expressed by TEM cells. Gattinoni et al., 2012, Nat. Rev. Cancer, 12:671-84. Alternatively or additionally, TN and TCM cells may be characterized by longer telomeres as compared to those of TEM cells.

A specific subpopulation of T cells, such as CD3+, CD45+, CD137+, CD25+, CD28+, CD4+, CD8+, CD45RA+, GITR+, and/or CD45RO+ T cells, can be isolated by positive or negative selection techniques (e.g., using fluorescence-based or magnetic-based cell sorting). For example, T cells can be isolated by incubation with any of a variety of commercially available antibody-conjugated beads, such as Dynabeads®, CELLection™, DETACHa-BEAD™ (Thermo Fisher) or MACS® cell separation products (Miltenyi Biotec), for a time period sufficient for positive selection of the desired T cells or negative selection for removal of unwanted cells.

In the various embodiments herein, the T cells, either for the isolation, the preactivation phase, the reactivation or the expansion phase, are cultured in an appropriate culture media. T cell culture conditions are known in the art. The media for culturing the T cells here in certain embodiments may be carried out from a starting media, referred to as a "basal" media. Basal media refers to any starting media that is supplemented with one or more of the additional elements disclosed herein, e.g., glucose, one of a variety of salts, one or more cytokines, such as IL-2, IL-7, IL-15, IL-21, or any combination thereof. The basal media can be any media for culturing immune cells, e.g., T cells. In some aspects, the basal media comprises a balanced salt solution (e.g., PBS, DPBS, HBSS, EBSS), Dulbecco's Modified Eagle's Medium (DMEM), Click's medium, Minimal Essential Medium (MEM), Basal Medium Eagle (BME), F-10, F-12, RPMI 1640, Glasgow Minimal Essential Medium (GMEM), alpha Minimal Essential Medium (alpha MEM), Iscove's Modified Dulbecco's Medium (IMDM), M199, OPT-MIZER™ Pro, OPTMIZER™ CTS™ T-Cell Expansion Basal Medium (ThermoFisher), OPTMIZER™, OPT-MIZER™ Complete, IMMUNOCULT™ XF (STEM-CELL™ Technologies), AIM V™, TEXMACS™ medium, PRIME-XV® T cell CDM, X-VIVO™ 15 (Lonza), TRANSACT™ TIL expansion medium, or any combination thereof. In some aspects, the basal medium is serum free. In some aspects, the basal media comprises PRIME-XV® T cell CDM. In some aspects, the basal media comprises OPTMIZER™. In some aspects, the basal media comprises OPTMIZER™ Pro. In some aspects, the basal medium further comprises immune cell serum replacement (ICSR).

As used herein, the term "cytokine" refers to small, secreted proteins released by cells that have a specific effect on the interactions and communications between cells. Non-limiting examples of cytokines include interleukins (e.g., interleukin (IL)-1, IL-2, IL-4, IL-7, IL-9, IL-13, IL-15, IL-3, IL-5, IL-6, IL-11, IL-10, IL-20, IL-14, IL-16, IL-17, IL-21 and IL-23), interferons (IFN; e.g., IFN-α, IFN-β, and IFN-γ), tumor necrosis factor (TNF) family members, and transforming growth factor (TGF) family members. Some aspects of the present disclosure are directed to methods of culturing and/or expanding immune cells, e.g., T cells or one or more engineered immune cell disclosed herein, in a medium comprising a cytokine. In some aspects, the cytokine is an interleukin. In some aspects, the cytokine comprises IL-2, IL-7, IL-15, IL-21 or any combination thereof.

In various embodiments of the disclosure, the T cells for use in the partial reprogramming methods herein are TCRαβ cells. In this regard, the TCRαβ cells may express a functional, antigen-specific T cell receptor (TCR) including both an alpha (a) chain and a beta (β) chain. The TCR alpha and beta chains are known in the art. The TCR can comprise any amino acid sequence, provided that the TCR can specifically bind to and immunologically recognize an antigen. The TCR may have antigenic specificity for any desired antigen. The phrases "antigen-specific" and "antigenic specificity," as used herein, mean that the TCR can specifically bind to and immunologically recognize an antigen, e.g., a condition-specific antigen, or an epitope thereof, such that biding of the TCR to an antigen, or the epitope thereof, elicits an immune response.

In various embodiments, the mammal from which a T cell is isolated is immunized with an antigen of, or specific for, a condition. Desirably, the mammal is immunized prior to obtaining the T cell from the mammal. In this way, the isolated T cell can include T cells induced to have specificity for the condition to be treated, or include a higher proportion of cells specific for the condition.

Alternatively, a T cell comprising an endogenous antigen-specific TCR can be a T cell within a mixed population of cells isolated from a mammal. In certain embodiments, the mixed population can be exposed to the antigen which is recognized by the endogenous TCR while being cultured in vitro. In this manner, the T cell which comprises the TCR that recognizes the condition-specific antigen, expands or proliferates in vitro, thereby increasing the number of T cells having the endogenous antigen-specific receptor.

The antigen-specific TCR can be an exogenous TCR, i.e., an antigen-specific TCR that is not native to (not naturally-occurring on) the T cell. A recombinant TCR is a TCR which has been generated through recombinant expression of one or more exogenous TCR α-, β-, γ-, and/or δ-chain encoding genes. A recombinant TCR can comprise polypeptide chains derived entirely from a single mammalian species, or the antigen-specific TCR can be a chimeric or hybrid TCR comprised of amino acid sequences derived from TCRs from two-different mammalian species. For example, the antigen-specific TCR can comprise a variable region derived from a murine TCR, and a constant region of a human TCR such that the TCR is "humanized" Methods of making recombinant TCRs are known in the art. See, e.g., U.S. Pat. Nos. 7,820,174; 8,785,601; 8,216,565; and U.S. Patent Application Publication No. 2013/0274203.

A T cell comprising an endogenous antigen-specific TCR can also be transformed, e.g., transduced or transfected, with one or more nucleic acids encoding an exogenous (e.g., recombinant) TCR or other recombinant chimeric receptor. Such exogenous chimeric receptors, e.g., chimeric CRs, can confer specificity for additional antigens to the transformed T cell beyond the antigens for which the endogenous TCR is naturally specific. This can, but need not, result in the production of T cells having dual antigen specificities.

A T cell comprising an endogenous antigen-specific TCR can also be transformed, e.g., transduced or transfected, with one or more nucleic acids encoding a "chimeric antigen receptor" (CAR). Typically, a CAR comprises the antigen binding domain of an antibody, e.g., a single-chain variable fragment (scFv), fused to the transmembrane and intracellular domains of a TCR; and in some embodiments, one or more costimulatory domains such as an intracellular signaling region of a T cell costimulatory molecule. Thus, the antigenic specificity of a TCR can be encoded by a scFv which specifically binds to the antigen, or an epitope thereof. Methods of making such CARs are known in the art. See, e.g., U.S. Pat. Nos. 8,465,743, 10,533,055, 10,603,380 and U.S. Patent Application Publication Nos. 2014/0037628 and 2014/0274909.

Any suitable nucleic acid encoding a CAR, engineered TCR, or TCR-like protein or polypeptide can be used. In these embodiments, the partial reprogramming process, as discussed further below, can occur before, after or simultaneously with, genetic modification of a T cell with a CAR, engineered TCR or TCR-like protein or polypeptide. The CAR or engineered TCR encoded by the nucleic acids can be of any suitable form including for example, a single-chain CAR or TCR or a fusion with other proteins or polypeptides (e.g., without limitation co-stimulatory molecules).

The antigen which is recognized by the T cells herein, whether by the endogenous antigen-specific TCR, an engineered TCR or CAR, can be any antigen which is associated with a condition. For example, the antigen may be, but is not limited to, a cancer antigen (also termed a tumor antigen or a tumor-associated antigen) or an infectious condition antigen (e.g., a viral antigen. Viral antigens are known in the art and include, for example, any viral protein, e.g., env, gag, pol, gp120, thymidine kinase, and the like).

In certain embodiments, the antigen is or is derived from CD19, TRAC, TCRβ, BCMA, CLL-1, CS1, CD38, CD19, TSHR, CD123, CD22, CD30, CD70, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp1OO, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3c, CD4, CD5, CD7, the extracellular portion of the APRIL protein, or any combinations thereof.

In certain embodiments, the CAR or engineered TCR targets AFP, CD19, TRAC, TCRβ, BCMA, CLL-1, CS1, CD38, CD19, TSHR, CD123, CD22, CD30, CD171, CD33, EGFRvIII, GD2, GD3, Tn Ag, PSMA, ROR1, ROR2, GPC1, GPC2, FLT3, FAP, TAG72, CD44v6, CEA, EPCAM, B7H3, KIT, IL-13Ra2, mesothelin, IL-11Ra, PSCA, PRSS21, VEGFR2, LewisY, CD24, PDGFR-beta, SSEA-4, CD20, folate receptor alpha, ERBB2 (Her2/neu), MUC1, MUC16, EGFR, NCAM, prostase, PAP, ELF2M, Ephrin B2, IGF-I receptor, CAIX, LMP2, gp1OO, bcr-abl, tyrosinase, EphA2, fucosyl GM1, sLe, GM3, TGS5, HMWMAA, o-acetyl-GD2, folate receptor beta, TEM1/CD248, TEM7R, CLDN6, GPRC5D, CXORF61, CD97, CD179a, ALK, Polysialic acid, PLAC1, GloboH, NY-BR-1, UPK2, HAVCR1, ADRB3, PANX3, GPR20, LY6K, OR51E2, TARP, WT1, NY-ESO-1, LAGE-1a, MAGE-A1, legumain, HPV E6, E7, MAGE A1, ETV6-AML, sperm protein 17, XAGE1, Tie 2, MAD-CT-1, MAD-CT-2, Fos-related antigen 1, p53, p53 mutant, prostein, surviving, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3c, CD4, CD5, CD7, the extracellular portion of the APRIL protein, or any combinations thereof.

The term "cancer antigen," or "tumor-associated antigen" as used herein, refers to any molecule (e.g., protein, polypeptide, peptide, lipid, carbohydrate, etc.) solely or predominantly expressed by or over-expressed by a tumor cell or cancer cell, such that the antigen is associated with the tumor or cancer. The cancer antigen can be, for example, a mutated tumor antigen or neoantigen. The cancer antigen can additionally be expressed by normal, non-tumor, or non-cancerous cells. However, in such cases the expression of the cancer antigen by normal, non-tumor, or non-cancerous cells is not as robust as the expression by tumor or cancer cells. In this regard, the tumor or cancer cells can over-express the antigen or express the antigen at a significantly higher level, as compared to the expression of the antigen by normal, non-tumor or non-cancerous cells. Also, the cancer antigen can additionally be expressed by cells of a different state of development or maturation. For instance, the cancer antigen can be additionally expressed by cells of the embryonic or fetal stage, which cells are not normally found in an adult mammal. Alternatively, the cancer antigen can be additionally expressed by stem cells or precursor cells, which cells are not normally found in an adult mammal. Cancer antigens are known in the art and include, for instance, the cancer antigens listed above, shared tumor antigens such as, e.g., mesothelin, CD19, CD22, CD276 (B7H3), gp100, MART-1, Epidermal Growth Factor Receptor Variant III (EGFRVIII), TRP-1, KRAS, TRP-2, tyrosinase, NY-ESO-1 (also known as CAG-3), MAGE-1, MAGE-3, etc. In an embodiment of the disclosure, the cancer antigen is a patient-specific neoantigen. A patient-specific neoantigen may arise as a consequence of a tumor-specific mutation.

The cancer antigen can be an antigen expressed by any cell of any cancer or tumor, including the cancers and tumors described herein. The cancer antigen may be a cancer antigen of only one type of cancer or tumor, such that the cancer antigen is associated with or characteristic of only one type of cancer or tumor. Alternatively, the cancer antigen may be a cancer antigen (e.g., may be characteristic) of more than one type of cancer or tumor. For example, the cancer antigen may be expressed by both breast and prostate cancer cells and not expressed at all by normal, non-tumor, or non-cancer cells.

The condition which is associated with or is characterized by the antigen recognized by the TCR or CAR can be any condition. For instance, the condition can be a cancer or an infectious condition, e.g., a viral condition, as discussed herein.

The cancer may be any cancer, including any of sarcoma, carcinoma, acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, head and neck cancers (e.g., cancer of the nose, nasal cavity, or middle ear, cancer of the oral cavity), cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, and urinary bladder cancer.

For purposes herein, "viral condition" means a condition that can be transmitted from person to person or from organism to organism, and is caused by a virus. In an embodiment of the disclosure, the viral condition is caused by a virus selected from the group consisting of herpes viruses, pox viruses, hepadnaviruses, papilloma viruses, adenoviruses, coronaviruses, orthomyxoviruses, paramyxoviruses, flaviviruses, and caliciviruses. For example, the viral condition may be caused by a virus selected from the group consisting of respiratory syncytial virus (RSV), influenza virus, herpes simplex virus, Epstein-Barr virus, varicella virus, cytomegalovirus, hepatitis A virus, hepatitis B virus, hepatitis C virus, human immunodeficiency virus (HIV), human T-lymphotropic virus, calicivirus, adenovirus, and Arena virus.

The viral condition may be, for example, influenza, pneumonia, herpes, hepatitis, hepatitis A, hepatitis B, hepatitis C, chronic fatigue syndrome, sudden acute respiratory syndrome (SARS), gastroenteritis, enteritis, carditis, encephalitis, bronchiolitis, respiratory papillomatosis, meningitis, HIV/AIDS, and mononucleosis.

T cells for use in the partial reprogramming methods of the present disclosure can be isolated or purified from a source using any suitable technique known in the art. For example, the immune cells (e.g., T cells) may be obtained from a subject. Immune cells (e.g., T cells) can be obtained from a number of sources, including peripheral blood mononuclear cells (PBMCs), bone marrow, lymph nodes tissue, cord blood, thymus tissue, tissue from a site of infection, ascites, pleural effusion, spleen tissue, and tumors. In certain embodiments, immune cells (e.g., T cells) can be obtained from a unit of blood collected from the subject using any number of techniques known to the skilled person, such as FICOLL™ separation. Cells may preferably be obtained from the circulating blood of an individual by apheresis. The apheresis product typically contains lymphocytes, including T cells, monocytes, granulocytes, B cells, other nucleated white blood cells, red blood cells, and platelets. In certain embodiments, the cells collected by apheresis may be washed to remove the plasma fraction, and placed in an appropriate buffer or media for subsequent processing. The cells may be washed with PBS. As will be appreciated, a washing step may be used, such as by using a semiautomated flowthrough centrifuge for example, the Cobe™ 2991 cell processor, the Baxter Cyto-Mate™ or the like. After washing, the cells may be resuspended in a variety of biocompatible buffers, or other saline solution with or without buffer. In certain embodiments, the undesired components of the apheresis sample may be removed.

2. Partial Reprogramming of T Cells

The present disclosure relates in part to methods for partially reprogramming T cells. In certain embodiments, the T cells are partially reprogrammed by contacting the T cells with one or more reprogramming factors for a period of days such that one or more of the T cells form colonies attached (or partially attached) to the culture vessel surface (form T cell derived adherent cell colonies) where such adherent cells return to a functioning T cell after stimulation (reactivation) with a T cell activation agent and optionally an immunomodulatory molecule (e.g. cytokines)

As used herein, the term "reprogramming factors" refers to any protein, polypeptide, amino acid, mRNA, DNA or small molecule capable of erasing and/or reestablishing epigenetic modifications acquired during mammalian cell development or in cell culture. Reprogramming factors can alter the differentiational state of a cell. Such reprogramming factors can include, but are not limited to the transcription factors, OCT4 (or OCT3/4), SOX3, KLF4 and C-MYC, discovered by Yamanaka and colleagues (see, e.g., Takahashi and Yamanaka, 2006, Cell, 136, 364-377) which are referred to herein as "OSKM" or the "Yamanaka factors." Reprogramming factors refers to other factors that might alter the differentiation state of a cell, or that might enhance or alter the efficiency of cell reprogramming Such factors are known in the art. Exemplary reprogramming factors are described in Feng et al. 2009, Cell Stem Cell Review, 4:301-313.

In various embodiments, the reprogramming factor is at least one of the groups consisting of KLF4, OCT3/4, SOX2, C-MYC and SV40. In various embodiments, not all of the four Yamanaka Factors are stringently necessary (see e.g., Genome Biol. 2012; 13(10): 251; Cell Stem Cell, 2019, 25(6):737-753; Nature Communications (2018) 9:2865). In various embodiments, the isolated immune cells (e.g., T cells) are contacted with OCT3/4 and SOX2. In various embodiments, the isolated immune cells (e.g., T cells) are contacted with OCT3/4, SOX2 and C-MYC. In various embodiments, the isolated cells are contacted with OCT3/4, SOX2 and KLF4. in certain embodiments, the T cells are contacted with OCT3/4, SOX2 and KLF4, and either C-MYC or SV40.

Additional reprogramming factors may be used in various embodiments to partially reprogram the isolated immune cells (e.g., T cells). Such factors include, but are not limited to, LIN28, NANOG, Esrrb, Pax5 shRNA, C/EBPa, p53 siRNA, UTF1, DNMT shRNA, Wnt3a, GLIS1, DLX4, CDH1, SV40 LT(T) and hTERT. In various embodiments, reprogramming factors may upregulate or downregulate certain miRNAs involved in reprogramming. In certain embodiments, a reprogramming factor may upregulate or downregulate expression of one or more of the genes upstream or downstream of one or more of the Yamanaka Factors. In various embodiments, the one or more reprogramming factors may include, but are not limited to, histone methyltransferase inhibitors, L-type calcium channel agonists, G9a methyltransferase inhibitors, DNA methyltransferase inhibitors, histone deacetylase inhibitors, MEK inhibitors, GSK3 inhibitors or TGF-B inhibitors. Any factor that modulates the upstream or downstream molecular pathway of the reprogramming transcription factors is contemplated for use in the partial reprogramming methods herein. Illustrative inhibitors include, but are not limited to BIX01294, BayK 8644, CHIR 99021, Forskolin, and RepSox. In certain embodiments, serine/threonine-protein kinase B-Raf (BRAF) inhibitors, epidermal growth factor receptor (EGFR) inhibitors, vascular endothelial growth factor 1 (VEGFR1) inhibitors, and/or fibroblast growth factor receptor 1 (FGFR1) inhibitors may be used in the reprogramming methods herein (see, e.g., US2017114323).

In various embodiments, the present disclosure relates to a method of producing a rejuvenated T cell, wherein the T cell is transiently contacted with at least one reprogramming factor selected from the group selected from KLF4, OCT3/4, SOX2 and C-MYC. In various embodiments of the present disclosure, the isolated immune cells (e.g., T cells) are transiently contacted with KLF4, OCT3/4, SOX2 and C-MYC and optionally SV40.

There are many strategies known in the art for delivering reprogramming factors to a cell. These strategies include the utilization of single-stranded negative sense RNA virus (Vizcardo et al., 2013), episomal plasmid systems for example, as described in Nat. Methods 2011, 8(5):409-412, mRNA transfection by nanoparticles (Moffett et al., 2017), and the use of small molecules known to induce gene expression of factors conferring pluripotency (Feng et al., 2009; Hou et al., 2013).

In various embodiments, one or more reprogramming factors is transiently expressed in the isolated immune cells (e.g., T cells). In various embodiments, the one or more reprogramming factors may include one or more or all of KLF4, OCT3/4, SOX2 and C-MYC; or may additionally include one or more other reprogramming factors. In various embodiments, the reprogramming factors may be expressed in the isolated T cells using a gene editing technology (e.g. TALENS, CRISPR/cas) known in the art. In various embodiments, the gene editing technology delivers an inducible set of reprogramming factors to be expressed in the isolated T cells. In various embodiments, the nucleic acid(s) encoding the stem cell-associated gene/s is/are carried in one or more recombinant expression vectors. The recombinant expression vector(s) can comprise any type of nucleotides, including, but not limited to DNA and RNA, which can be single-stranded or double-stranded, synthesized or obtained in part from natural sources, and which can contain natural, non-natural or altered nucleotides. The recombinant expression vector(s) can comprise naturally-occurring or non-naturally-occurring internucleotide linkages, or both types of linkages. The vector(s) may contain regulatory nucleic acid sequences which provide for expression of the stem cell-associated genes.

In some embodiments, the recombinant expression vector is a viral vector. Suitable viral vectors include, without limitation, Sendai virus vectors, retroviral vectors, lentiviral vectors, alphaviral, vaccinia, adenoviral, adeno-associated viral, herpes viral, and fowl pox viral vectors, and preferably have a native or engineered capacity to transform immune cells (e.g., T cells). In certain embodiments, the viral vectors are pseudotyped with a heterologous viral envelope protein. In certain embodiments, the viral vector is a lentivirus or Sendai virus vector pseudotyped with a suitable envelope, e.g., a virus envelope (see e.g., Blood Adv 2017 Oct. 24; 1(23):2088-2104; Mol Ther 2012 September; 20(9):1699-712). In certain embodiments, the viral vector is an integration deficient lentiviral vector. Suitable viral vectors are known in the art and described, for example, in J. Biol. Chem. (2011) 286:4760-4771; Stem Cell Research & Therapy (2019) 10:185.

In various embodiments, the recombinant expression vector is delivered in a nanoparticle. In various embodiments, the reprogramming factors are delivered using a nanoparticle. Such nanoparticles can be designed to deliver specific mRNA or other macromolecules to lymphocytes in a transient and dose-controlled manner. These nanoparticles can be designed to target specific cell subtypes and, upon binding to them, stimulate receptor mediated endocytosis, thereby introducing the synthetic mRNA they carry which the cells can now express. Because nuclear transport and transcription of the transgene are not required, this process is fast and efficient.

In various embodiments, one or more reprogramming vectors are delivered to the immune cells (e.g., T cells) in separate vectors. In various embodiments, KLF4, OCT3/4, SOX2 (KOS) are delivered in a single vector. In various embodiments, the vector expressing KOS is a viral vector and is delivered at a titer of 1, 2, 3, 4, 5, 6, 7, 8, 9, 10, 15, 20, 25, or 30 MOIs (Multiplicity of Infection). In various embodiments, KLF4 is delivered in a viral vector at a titer of 1, 2, 3, 4, 5, 6, 7, 8, 9, 10, 15, 20, 25, or 30 MOIs. In various embodiments, cMyc is delivered in a viral vector at a titer of 1, 2, 3, 4, 5, 6, 7, 8, 9, 10, 15, 20, 25, or 30 MOIs. In various embodiments a vector expressing SV40 is further delivered to the cell and is a viral vector delivered at a titer of 1, 2, 3, 4, 5, 6, 7, 8, 9, 10, 15, 20, 25, or 30 MOIs. In various embodiments, the immune cells (e.g., T cells) is contacted with a Sendai vector expressing KOS at 10 MOI, a Sendai vector expressing KLF4 at 10 MOI, a Sendai vector expressing C-MYC at 3 MOI, and a Sendai vector expressing SV40 at 5 MOI. In certain embodiments, the T cell is contacted with a multicistronic vector, such as a lentiviral vector, a Sendai virus vector or a non-viral vector, expressing KOSM.

In certain embodiments, prior to being contacted with the one or more reprogramming factors the T cells are stimulated with a T cell activating agent and optionally one or more immunomodulatory molecules, for a time sufficient to stimulate and activate the T cells. In certain embodiments, the T cells are stimulated with tumor antigen or with autologous tumor cells or tumor cell line. In some embodiments, the T cells are TILs and the TILs are stimulated with tumor target cells or tumor antigen derived therefrom, from the cancer patient, or one or more tumor-associated antigen.

Non-limiting examples of tumor-associated antigens include: AFP (alpha-fetoprotein), αvβ6 or another integrin, BCMA, BRAF, B7-H3, B7-H6, CA9 (carbonic anhydrase 9), (carcinoembryonic antigen), Claudin 18.2, Claudin 6, c-MET, DLL3 (delta-like protein 3), DLL4, ENPP3 (ectonucleotide pyrophosphatase/phosphodiesterase family member 3), EpCAM, EPG-2 (epithelial glycoprotein 2), EPG-40, ephrinB2, EPHa2 (ephrine receptor A2), ERBB dimers, estrogen receptor, ETBR (endothelin B receptor), FAP-α (fibroblast activation protein α), fetal AchR (fetal acetylcholine receptor), FBP (a folate binding protein), FCRL5, FR-α (folate receptor alpha), GCC (guanyl cyclase C), GD2, GD3, GPC2 (glypican-2), GPC3, gp100 (glycoprotein 100), GPNMB (glycoprotein NMB), GPRC5D (G Protein Coupled Receptor 5D), HER2, HER3, HER4, hepatitis B surface antigen, melanoma-associated antigen (MAGE)-A1, MAGE-A3, MAGE-A6, MART-1 (melan A), mesothelin, mucin 1 (MUC1), MUC16, MHC/peptide complexes (e.g., HLA-A complexed with peptides derived from AFP, KRAS, NY-ESO, MAGE-A, and WT1), NCAM (neural cell adhesion molecule), Nectin-4, NY-ESO, oncofetal antigen, PRAME (preferentially expressed antigen of melanoma), progesterone receptor, PSA (prostate specific antigen), PSCA (prostate stem cell antigen), PSMA (prostate specific membrane antigen), ROR1, ROR2, SIRPα (signal-regulatory protein alpha), SLIT, SLITRK6 (NTRK-like protein 6), survivin, TAG72 (tumor-associated glycoprotein 72), TPBG (trophoblast glycoprotein), Trop-2, VEGFR1 (vascular endothelial growth factor receptor 1), p53, p53 mutant, prostein, survivin, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3c, CD4, CD5, CD7, the extracellular portion of the APRIL protein, neoantigen, or any combinations thereof.

In this manner, polyclonal antigen-specific (e.g., tumor-specific) T cells from cancer patients can be partially reprogrammed and rejuvenated. In certain embodiments, the T cells are selected, sorted, or otherwise enriched for following stimulation with an antigen, such as tumor antigen, tumor organoid, autologous tumor cells or tumor cell line. In certain embodiments, the T cells are enriched, selected for or sorted by selecting for cells expressing one or more cell surface markers, such as 4-1BB (CD137), PD1, LAG3, CD45, CD39, TIGIT, TIM3, CD69, OX40, CD28, CD25, CD49d, and CTLA4. In certain embodiments, the T cells are enriched, selected for or sorted before activation with any of the T cell activating agents described herein. In certain embodiments, CD45+ T cells are selected for or enriched prior to activation with any of the activation agents described herein.

In some embodiments, the methods include activating the cells prior to, during and/or subsequent to the incubation of cells with the viral vector particles. In some embodiments, the stimulating conditions may include incubation of cells in the presence of an agent capable of activating one or more intracellular signaling domains of one or more components of a TCR complex, such as a primary agent that specifically binds to a member of a TCR complex, e.g., CD3, and a secondary agent that specifically binds to a T cell costimulatory molecule, e.g., CD28, CD27, CD137 (4-1BB), OX40, or ICOS, including antibodies such as those present on the surface of a solid support, such as a bead (for example, TRANSACT, Miltenyi). Without being bound by theory, stimulating the T cells in this manner (preactivation phase) increases the efficiency of viral transduction and delivery of the reprogramming factors. Similarly, if transfection of nucleic acid is used for delivery of the reprogramming factors, prior stimulation of the T cells increases efficiency of the gene delivery.

In certain embodiments, the T cells are preactivated, reactivated and/or expanded with one or more T cell activating and/or costimulatory and/or immunomodulatory compounds.

In certain embodiments, the T cells are contacted with the one or more reprogramming factors for a period of about 4, 5, 6, 7, 8, 9, 10, 11, 12, 13, 14, 15, 16, 17, 18, 19, 20, or about 21 days. In certain embodiments, the T cells are contacted with the one or more reprogramming factors for a period of about 7 days. In certain embodiments, the T cells are contacted with the one or more reprogramming factors for a period of about 8 days. In certain embodiments, the T cells are contacted with the one or more reprogramming factors for a period of about 9 days. In certain embodiments, the T cells are contacted with the one or more reprogramming factors for a period of about 10 days. In certain embodiments, the T cells are contacted with the one or more reprogramming factors for a period of about 11 days. In certain embodiments, the T cells are contacted with the one or more reprogramming factors for a period of about 12 days. In certain embodiments, the T cells are contacted with the one or more reprogramming factors for a period of about 13 days. In certain embodiments, the T cells are contacted with the one or more reprogramming factors for a period of about 14 days.

In certain embodiments, the T cells are contacted with the one or more reprogramming factors for a period of at least about 5 days and not more than about 10 days. In certain embodiments, the T cells are contacted with the one or more reprogramming factors for a period of at least about 5 days and not more than about 11 days. In certain embodiments, the T cells are contacted with the one or more reprogramming factors for a period of at least about 5 days and not more than about 12 days. In certain embodiments, the T cells are contacted with the one or more reprogramming factors for a period of at least about 5 days and not more than about 12 days. In certain embodiments, the T cells are contacted with the one or more reprogramming factors for a period of at least about 5 days and not more than about 13 days.

In certain embodiments, the T cells are contacted with the one or more reprogramming factors for a period of at least about 6 days and not more than about 10 days. In certain embodiments, the T cells are contacted with the one or more reprogramming factors for a period of at least about 6 days and not more than about 11 days. In certain embodiments, the T cells are contacted with the one or more reprogramming factors for a period of at least about 6 days and not more than about 12 days. In certain embodiments, the T cells are contacted with the one or more reprogramming factors for a period of at least about 6 days and not more than about 12 days. In certain embodiments, the T cells are contacted with the one or more reprogramming factors for a period of at least about 6 days and not more than about 13 days.

The period of time that T cells are contacted with the one or more reprogramming factors may vary depending on the amount or level of expression of the reprogramming factors. For example, in an embodiment where T cells are transduced with a viral vector expressing high levels of one or more of the reprogramming factors, a shorter time period may be required to achieve the desired partial reprogramming (formation of T cell derived adherent cells). In another embodiment, T cells are transduced with a viral vector expressing low levels of one or more of the reprogramming factors and a longer time period may be required to achieve the desired partial reprogramming (formation of T cell derived adherent cells). In this regard, in certain embodiments, an expression vector, such as viral vector, encoding the one or more reprogramming factors may comprise an inducible promoter where the expression of the partial reprogramming factors can be tuned to a desired expression level.

In certain embodiments, the T cells are contacted with the one or more reprogramming factors for a period of about 5-30 days. In certain embodiments, the T cells are contacted with the one or more reprogramming factors for a period of about 5-25 days. In certain embodiments, the T cells are contacted with the one or more reprogramming factors for a period of about 5-20 days. In certain embodiments, the T cells are contacted with the one or more reprogramming factors for a period of about 5-15 days. In certain embodiments, the T cells are contacted with the one or more reprogramming factors for a period of about 5-13 days. In certain embodiments, the T cells are contacted with the one or more reprogramming factors for a period of about 5-12 days. In certain embodiments, the T cells are contacted with the one or more reprogramming factors for a period of about 6-12 days. In certain embodiments, the T cells are contacted with the one or more reprogramming factors for a period of about 6-13 days. In certain embodiments, the T cells are contacted with the one or more reprogramming factors for a period of about 7-12 days. In certain embodiments, the T cells are contacted with the one or more reprogramming factors for a period of about 7-13 days. In certain embodiments, the T cells are contacted with the one or more reprogramming factors for a period of about 7-14 days. In certain embodiments, the T cells are contacted with the one or more reprogramming factors for a period of about 6-20, 7-20, 8-20, 9-20, 10-20, 5-18, 6-18, 7-18, 8-18, 9-18, or 10-18 days.

During the somatic cell reprogramming toward totipotent or pluripotent stem cells (TSCs or PSCs), somatic cells will start to dedifferentiate and lose their lineage specific epigenetic status, while they also start to acquire PSC phenotypes. These changes proceed gradually, so the longer somatic cells stay in the reprogramming process, the more PSC phenotypes they will acquire. In various embodiments of the present disclosure, the reprogramming process is stopped before the somatic cells dedifferentiate so much as to prevent them from losing their source cell functions. In various embodiments, the partial reprogramming will be sufficient for the immune cell (e.g., a T cell) to form at least one cell that is attached to the culture vessel surface and to transform into an intermediate cell type referred to herein as a "T cell derived adherent cells".

"T cell derived adherent cells" as used herein refers to an intermediate cell in the T cell partial reprogramming process. The T cell derived adherent cell attaches (at least in part) to the culture vessel surface and forms a colony during the partial reprogramming process. In certain embodiments, the T cell derived adherent cell is loosely attached to the culture vessel surface. T cell derived adherent cells differ from iPS cells (and iTSCs) in that they have not been completely reprogrammed. In certain embodiments, the T cell derived adherent cell colonies are loosely attached to the culture vessel surface. T cell derived adherent cells as described herein retain lineage stability e.g., the T cell derived adherent cells of the present disclosure retain the ability to return to the T cell lineage following culture in T cell activation/stimulation conditions (e.g., with T cell culture medium in the presence of activating and/or immunomodulating molecules, such as anti-CD3, anti-CD28, anti-CD27 antibodies and cytokines such as IL2, IL7, IL15, and the like). In certain embodiments, the T cell derived adherent cell is not multipotent. In certain embodiments, a T cell derived adherent cell is larger than a non-partially reprogrammed T cell or an activated T cell. In certain embodiments, T cell derived adherent cells are larger and have a more complex structure as measured by FACS analysis. In certain embodiments, the T cell derived adherent cell is SSEA4+CD3+. In another embodiment, the T cell derived adherent cells express one more of the following cell surface markers as determined using flow cytometry or transcriptome analysis: CD50, CD352, CD31, Integrin β7, CD49e, CD122, CD314, HLA-DR, CD134, CD245, CD105 (Endoglin), CD366, CD39, Integrin α6β1, Integrin β5, CD71, CD164, CD10, CD63, XCR1, CD298, CD201, CD151, CD325, CD324, CD147, SSEA-3, TRA-1-81, TRA-2-54, Podoplanin, CD9, CD340, CD24, CD90, CD326, SSEA-5, SSEA4, TRA-1-60-R.

Figures 3A, 3B:
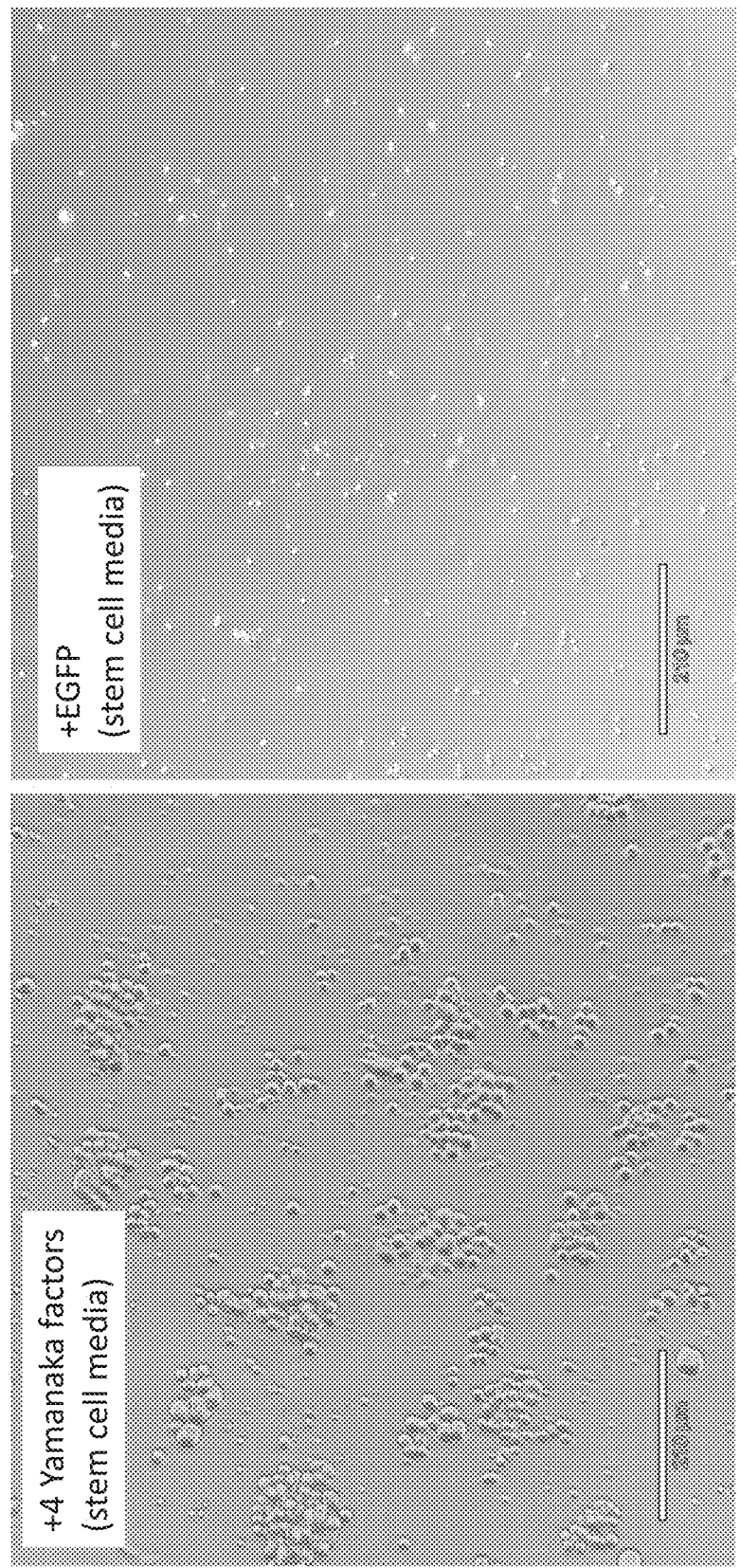
FIGS. 3A-3F show the difference in morphology of T cells cultured in different conditions as described in Example 1.
Figure 3D:
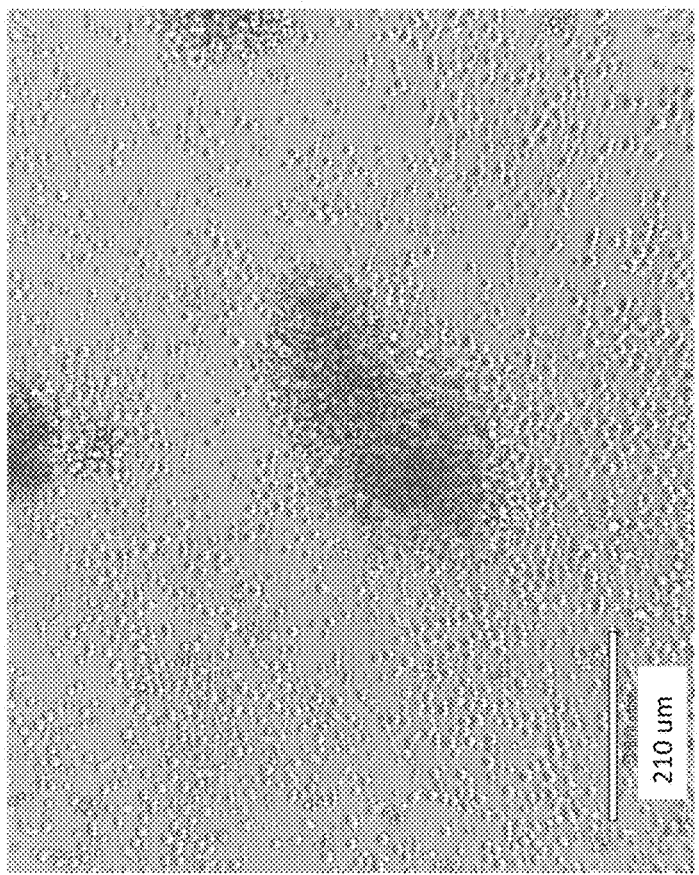
Figure 3C:
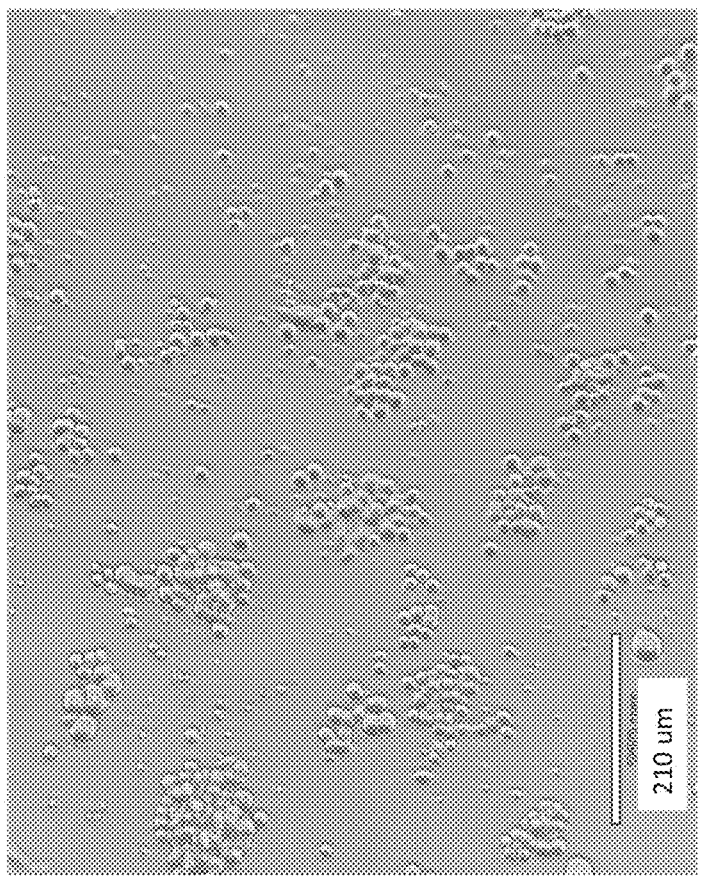
Figure 3F:
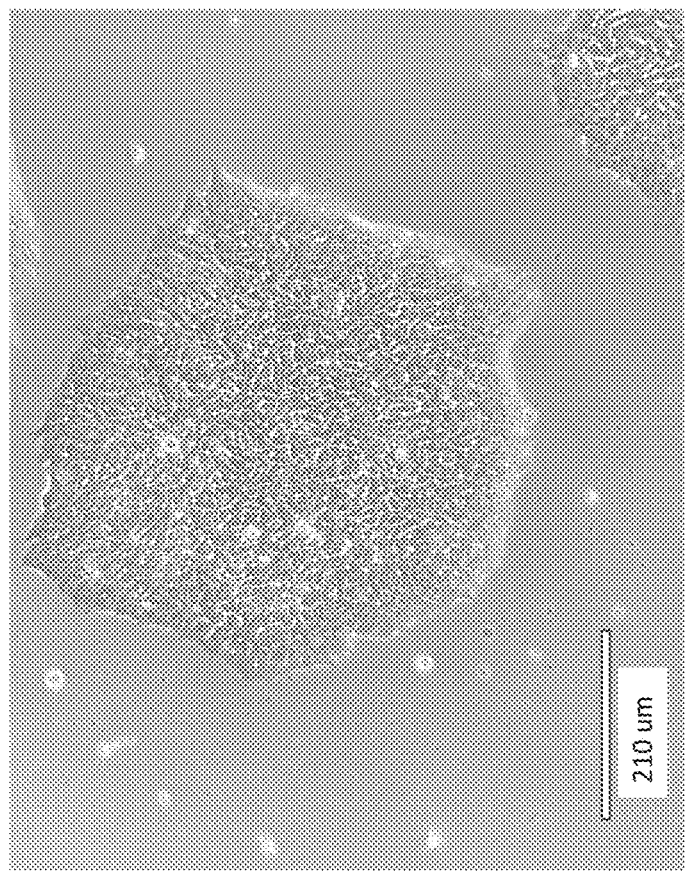
Figure 3E:
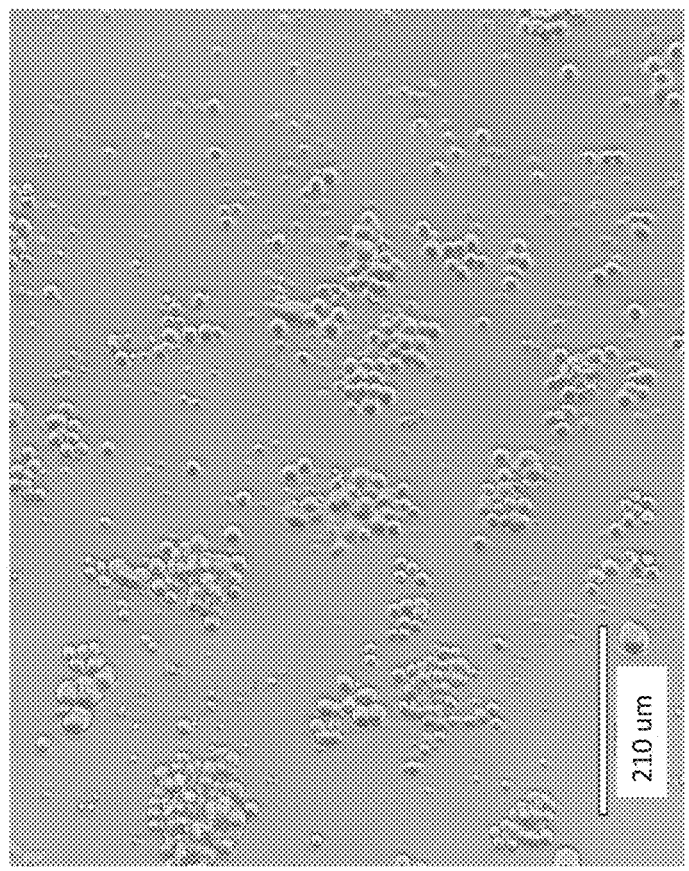

As would be readily appreciated by the person of ordinary skill in the art, iPS cells can be distinguished from T cell derived adherent cells by morphology. In particular, as shown in FIG. 3F, iPS cell colonies are much larger and have a more defined colony structure. iPS cells are well known in the art and are described for example in, Nishimura 2013, Cell Stem Cell 12, 114-126; Vizcardo et al., 2013, Cell Stem Cell 12, 31-36).

In certain embodiments, at least 10% of the T cell derived adherent cells express one or more of the following cell surface markers as determined using flow cytometry or transcriptome analysis: CD50, CD352, CD31, Integrin α6β1, Integrin β7, CD49e, CD122, CD314, HLA-DR, CD134, CD245, CD105 (Endoglin), CD366, CD39, Integrin β5, CD71, CD164, CD10, CD63, XCR1, CD298, CD201, CD151, CD325, CD324, CD147, SSEA-3, TRA-1-81, TRA-2-54, Podoplanin, CD9, CD340, CD24, CD90, CD326, SSEA-5, SSEA4, TRA-1-60-R.

In certain embodiments, at least about 10% to about 80% of the T cell derived adherent cells express one or more of the following cell surface markers as determined using flow cytometry or transcriptome analysis: CD50, CD352, CD31, Integrin α6β1, Integrin β7, CD49e, CD122, CD314, HLA-DR, CD134, CD245, CD105 (Endoglin), CD366, CD39, Integrin β5, CD71, CD164, CD10, CD63, XCR1, CD298, CD201, CD151, CD325, CD324, CD147, SSEA-3, TRA-1-81, TRA-2-54, Podoplanin, CD9, CD340, CD24, CD90, CD326, SSEA-5, SSEA4, TRA-1-60-R. In another embodiment, at least about 15% to about 80%, at least about 20% to about 75%, at least about 25% to about 75%, at least about 30% to about 50%, at least about 10%, 15%, 20%, 25%, 30%, 40%, 50%, 60%, 70%, 75%, or about 80% of the T cell derived adherent cells express one or more of the aforementioned cell surface markers as determined using assays known in the art, such as flow cytometry, gene expression or transcriptome analysis. The expression level of these markers and the % of positive cells will vary depending on the number of days of partial reprogramming.

In certain embodiments, partial reprogramming may result in partial loss of certain markers of immune cell (e.g., a T cell) identity. For example, in certain embodiments, partial reprogramming of T cells may result in a loss or reduction of expression of any one or more of CD3, CD4, CD8 (e.g., CD8αα, and/or CD8αβ). In certain embodiments, reduction of expression may mean from about 10% to about 95% reduction in expression of the marker as measured by flow cytometry. In certain embodiments, the reduction in expression is a reduction in mean fluorescence intensity (MFI) of about 0.25, 0.5, 0.75, 1, 1.25, 1.5, 1.75, or 2 logs, in at least a portion of the T cell derived adherent cells.

In certain embodiments, the T cells are transiently contacted with one or more reprogramming factors for a period of time sufficient for T cell derived adherent cells to form. In certain embodiments, the T cells are transiently contacted with one or more reprogramming factors for a period of time sufficient for attached cell colonies to form wherein at least a portion of the attached cells express one or more of the following cell surface markers: CD50, CD352, CD31, Integrin α6β1, Integrin β7, CD49e, CD122, CD314, HLA-DR, CD134, CD245, CD105 (Endoglin), CD366, CD39, Integrin β5, CD71, CD164, CD10, CD63, XCR1, CD298, CD201, CD151, CD325, CD324, CD147, SSEA-3, TRA-1-81, TRA-2-54, Podoplanin, CD9, CD340, CD24, CD90, CD326, SSEA-5, SSEA4, TRA-1-60-R. Expression of such markers may be determined using flow cytometry, gene expression analysis, RNAseq or other techniques known in the art.

In certain embodiments, the T cells are transiently contacted with one or more reprogramming factors for a period of time sufficient for attached cell colonies to form wherein at least a portion of the attached cells express Integrin α6β1, CD9, CD90, and/or SSEA4.

In certain embodiments, at least a portion of the T cell adherent cells express Integrin α6β1, CD9, CD90, or SSEA4, or any combination thereof. In certain embodiments, at least a portion of the T cell adherent cells expresses Integrin α6β1; at least a portion of the T cell adherent cells expresses integrin α6β1 and SSEA4, at least a portion of the T cell adherent cells express integrin α6β1, SSEA4 and CD9; or at least a portion of the T cell adherent cells express integrin α6β1, SSEA4, CD9, and CD90. In certain embodiments, at least a portion of the T cell adherent cells express SSEA4; SSEA4 and CD9; or SSEA4, CD9 and CD90.

In certain embodiments, at least a portion of the T cell derived adherent cells express CD9 and/or CD90 which are early markers for the partial reprogramming process. CD9 is also known as tetraspanin-29 and has four transmembrane domains. It is involved in cell adhesion, signal transduction and cellular differentiation. CD90 is also known as THY-1. It is an immunoglobulin superfamily surface glycoprotein and is a marker associated with mesenchymal stem cells. It is also involved in cell adhesion and communication. While Thy-1 is expressed commonly in murine T cells, T cell Thy-1 expression in human T cell lineage is limited to specialized populations in the thymic cortex and subsets of CD4 Th17 T cells.

In certain embodiments, at least 5%, 10%, 15%, 20%, 25%, 30%, 35%, 40%, 45%, 50%, 55%, 60%, 65%, 70%, 75% or more of the T cell derived adherent cells express CD9 and/or CD90.

In certain embodiments, the T cell derived adherent cells express one or more of Integrin α6β1, CD164, CD9, CD63, CD90, CD71, CD326, TRA-1-81 and TRA-1-60-R, in certain embodiments as compared to stimulated and unstimulated T cells. In another embodiment, the T cell derived adherent cells have decreased expression of CD352 and CD31 as compared to stimulated or unstimulated T cells.

In certain embodiments, at least 5%, 10%, 15%, 20%, 25%, 30%, 35%, 40%, 45%, 50%, 55%, 60%, 65%, 70%, 75% or more of the T cell derived adherent cells express one or more of CD164, CD9, CD63, CD90, CD71, CD326, TRA-1-81 and TRA-1-60-R.

In certain embodiments, the disclosure provides a population of T cell derived adherent cells whose epigenetic age is at least 5% younger than the chronological age of relevant control T cells or the starting isolated T cell population. In another embodiment, the present disclosure provides a population of T cell derived adherent cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than the chronological age of the source isolated T cells (i.e., the isolated T cells that were contacted with the reprogramming factors).

In certain embodiments, when the T cell derived adherent cells are contacted with a T cell activating agent (e.g., anti-CD3, anti-CD28, one or more cytokines such as IL2, IL7, IL15), the cells exhibit increased expansion potential as compared to control T cells. In certain embodiments, the partially reprogrammed T cells expand at least 2, 3, 4, 5, 6, 7, 8, 9, 10, 11, 12, 13, 14, 15, 16, 17, 18, 19, 20, 25, 30, 35, 40, 45, 50, 100, 500, 100, 1500, or 2000-fold more than control T cells that have not been partially reprogrammed. In certain embodiments, the partially reprogrammed T cells expand at least about 50-2000 fold, at least about 50-1000 fold, at least 50-900-fold, at least 50-800-fold, at least 50-700-fold, at least 50-600-fold, at least 50 to 500-fold, at least 100 to 400-fold, at least 150 to 500-fold, at least 200 to 500-fold, or at least 300 to 500-fold more than control T cells that have not been partially reprogrammed. In certain embodiments, the partially reprogrammed T cells expand more quickly than T cells that have not been partially reprogrammed. In particular embodiments of the disclosure the partial reprogramming methods are carried out under conditions appropriate for maintenance of the isolated T cells and/or the partially reprogrammed T cells (T cell derived adherent cells). Conditions appropriate for the maintenance and proliferation of particular cell types will be apparent to the skilled artisan. Specialized culture medium may be obtained from commercial sources, or factors necessary or desirable for enhancing the proliferation may be added to standard culture medium. Additional factors and agents may also be added to culture medium, for example, to induce expression of inducible elements in said cells or to inhibit growth of cells which are sensitive to particular agents.

In certain embodiments, the isolated T cells are cultured in T cell culture medium (TCM) comprising commercially available media optimized for culture of T cells, such as TexMACS medium or OpTmizer Basal Medium, with the addition of one or more supplements such as OpTmizer Cell Supplement, in certain embodiments with the addition of Immune Cell Serum Replacement (e.g., a T cell serum replacement) and/or other supplements such as L-Glutamine; GlutaMAX; and/or cytokines such as IL-2, IL-7, and/or IL-15.

In certain embodiments, the partial reprogramming phase of the methods herein are carried out using media optimized for cell reprogramming, such as but not limited to STEMFIT media (Amsbio, Abington, UK), mTESR2 (Stem Cell Technologies), and ESSENTIAL 6 or 8 (Life Technologies); STEMPRO hESC SFM (Gibco); TESR, clone-R, dMEM F12, KSR.

In another embodiment, the partial reprogramming is carried out in a media comprised of 50% T cell media and 50% stem cell media (e.g., STEMFIT or Essential 8, mTESR, TESR, clone-R, dMEM F12, KSR), optionally with the addition of one or more cytokines, such as IL2, IL7 and/or IL15. In certain embodiments, the partial reprogramming is carried out for a first period of time in a first media and then for a second period of time in a second media. For example, in certain embodiments, the first media is 50/50 media as noted, optionally with the addition or one or more cytokines, for a period of 1, 2, 3, 4, 5, 6, days or more followed by culturing the cells in a second media which is a stem cell media (e.g., STEMFIT of Essential 8) media for 1, 2, 3, 4, 5, 6, 7, 8, 9, or more days. In certain embodiments, the first media is 50/50 and is used for 1, 2, or 3 days and the second media is a stem cell media (e.g., STEMFIT or Essential 8) and is used starting at day 2, 3, or 4 until formation of T cell derived adherent cells and reactivation as described further herein. In certain embodiments of the partial reprogramming methods, the T cells are cultured for a first period of time in a first media and then cultured for a second period of time in a second media. In certain embodiments of the partial reprogramming phase of the methods herein the T cells contacted with the one or more reprogramming factors (e.g., one or more of KLF4, OCT3/4, SOX2, C-MYC and SV40) are cultured in appropriate media in a culture vessel coated with recombinant human Laminin511-E8 fragment, such as iMatrix.

3. Reactivation of Partially Reprogrammed T Cell Derived Adherent Cells

In various embodiments, the partially reprogrammed, T cell derived adherent cells are reactivated in an activation media that enables the reprogrammed immune cell (e.g., a T cell) to regain T cell identity and functionality.

In various embodiments of the present disclosure, the T cell derived adherent cells are reactivated immediately following partial reprogramming using one or more T cell stimulation or activation agents and/or costimulatory agents in an appropriate T cell culture media.

In certain embodiments of the present disclosure, the T cell derived adherent cells are reactivated immediately following partial reprogramming in a T cell culture media supplemented with one or more cytokines, such as IL2, IL7, IL15, IL21, with or without one or more T cell activating agents and/or one or more costimulatory agents.

In certain embodiments, the T cell derived adherent cells are reactivated with one or more T cell activating and/or costimulatory and/or immunomodulatory agents as described elsewhere herein in an appropriate medium for T cell culture, such as T cell culture medium (TCM) comprising commercially available media optimized for culture of T cells, such as TexMACS medium or OpTmizer Basal Medium, with the addition of one or more supplements such as OpTmizer Cell Supplement, in certain embodiments with the addition of Immune Cell Serum Replacement (e.g., T cell serum replacement) and other supplements such as L-Glutamine; GlutaMAX; cytokines such as IL-2, IL7, and/or IL15.

In some embodiments, the stimulating or activating conditions or agents used herein may be used for preactivation, reactivation, and/or expansion phases of the methods herein. T cells can be activated and expanded generally using methods as described, for example, in U.S. Pat. Nos. 5,858,358; 5,883,223; 6,352,694; 6,534,055; 6,797,514; 6,867,041; 6,692,964; 6,887,466; 6,905,680; 6,905,681; 6,905,874; 7,067,318; 7,144,575; 7,172,869; 7,175,843; 7,232,566; 7,572,631; and 10,786,533. In certain embodiments, the T cells are contacted with a T cell activating agent, and/or a costimulatory agent, that provides a primary activation signal and an agent that provides a costimulatory signal. Agents that provide a primary activation signal are known in the art and include for example antibodies or antigen-binding fragments thereof or ligands, or target binding fragments thereof, that bind to the CD3 cell surface receptor (e.g., an anti-CD3 antibody) expressed on T cells. Agents that provide a costimulatory signal are known in the art and include, but are not limited to, antibodies or ligands that bind to CD28, OX-40, 4-1BB/CD137, CD2, CD7, CD27, CD30, CD40, etc. In certain embodiments, the activating agents include one or more agents, e.g., ligand, which is capable of activating an intracellular signaling domain of a TCR complex. In some aspects, the agent turns on or initiates a primary TCR/CD3 intracellular signaling cascade in a T cell, such as agents suitable to deliver a primary signal, e.g., to initiate activation of an ITAM-induced signal, such as those specific for a TCR component. In another embodiment, the activating agent is provided in combination with or at the same time as an agent that promotes a costimulatory signal. Suitable agents that promote a costimulatory signal are known in the art and include antibodies or ligands that promote signaling of CD28, OX-40, 4-1BB/CD137, CD2, CD7, CD27, CD30, CD40, inducible T cell costimulator (ICOS), lymphocyte function-associated antigen-1 (LFA-1 (CD11a/CD18), CD247, CD276 (B7-H3), Ig alpha (CD79a), DAP-10, Fc gamma receptor or any combination thereof. In certain embodiments, the stimulatory and costimulatory agents for the activation steps of the methods here comprise an anti-CD3, anti-CD28, anti-41-BB, or anti-CD27 antibody for example, bound to solid support such as a bead, and/or one or more cytokines. In certain embodiments, the agents comprise a ligand for an activating receptor or a costimulatory receptor, e.g., a peptide/MHC complex and/or the CD27 ligand (e.g., CD70 or trimerized versions thereof), CD80, CD86 and the like. Among the stimulating and costimulatory agents are anti-CD3/anti-CD28 beads (e.g., DYNABEADS M-450 CD3/CD28 T Cell Expander, and/or ExpACT beads). Optionally, the stimulation and/or activation may comprise adding anti-CD3 and/or anti CD28 antibody to the culture medium. In some embodiments, the stimulating agents include IL-2, IL-7 and/or IL-15.

In various embodiments, the activating agent is a tumor antigen, in particular a tumor antigen as disclosed herein.

In some embodiments, the activating and/or costimulatory agents herein may be coated or adsorbed onto one or more surfaces. Such surfaces include, for example, solid surfaces, porous surfaces, semi-porous surfaces, spherical surfaces, non-spherical surfaces, rod-like surfaces, and polymeric surfaces.

In certain embodiments, the T cells are activated (e.g., in the preactivation, reactivation or expansion phases of the methods herein) using commercially available reagents such as TRANSACT (Miltenyi Biotec). In various embodiments, the partially reprogrammed T cells are activated using TRANSACT at a ratio that allows the T cell derived adherent cells to regain its T cell identity. In various embodiments, the partially reprogrammed T cells are activated with TRANSACT at 1:10, 1:50 1:100, 1:150, 1:200, 1:250, 1:300, 1:350, 1:400, 1:450, 1:500, 1:550, 1:600, 1:650, 1:700, 1:750, 1:800, 1:850, 1:900, 1:1,000, 1:2000, 1:3000, 1:4000 or 1:10,000. In various embodiments, the T cell derived adherent cells are activated in an appropriate T cell activation media and cultured for sufficient time that allows the T cell derived adherent cell to regain its identity. In various embodiments, the partially reprogrammed cells are activated and cultured in a T cell activation media for a period of about 1, 2, 3, 4, 5, 6, or 7 or more days. In certain embodiments, the partially reprogrammed cells are activated and cultured for about 1-20 days, for about 2-20 days, for about 3-20 days for about 4-20 days for about 5-20 days for about 6-20 days for about 7-20 days, 8-20 days, for about 9-20 days, or for about 10-20 days. In certain embodiments, the partially reprogrammed cells are activated and then cultured for about 1-15 days, for about 2-15 days, for about 3-15 days, for about 4-15 days, for about 5-15 days, for about 6-15 days, for about 7-15 days, for about 8-15 days, for about 9-15 days or for about 10-15 days.

In certain embodiments, the T cell derived adherent cells are redirected or reactivated with antigen or antigen expressing cells, such as tumor antigen expressing autologous cells or tumor antigen. In certain embodiments, the T cell derived adherent cells are reactivated with by co-culture with APC expressing tandem minigenes (i.e., tumor can be sequenced the fragments re-expressed from tandem minigenes expressed and presented by the APC). Any tumor antigens known to be associated with a cancer is contemplated for use herein. Non-limiting examples of antigens include: AFP (alpha-fetoprotein), αvβ6 or another integrin, BCMA, BRAF, B7-H3, B7-H6, CA9 (carbonic anhydrase 9), (carcinoembryonic antigen), Claudin 18.2, Claudin 6, c-MET, DLL3 (delta-like protein 3), DLL4, ENPP3 (ectonucleotide pyrophosphatase/phosphodiesterase family member 3), EpCAM, EPG-2 (epithelial glycoprotein 2), EPG-40, ephrinB2, EPHa2 (ephrine receptor A2), ERBB dimers, estrogen receptor, ETBR (endothelin B receptor), FAP-α (fibroblast activation protein α), fetal AchR (fetal acetylcholine receptor), FBP (a folate binding protein), FCRL5, FR-α (folate receptor alpha), GCC (guanyl cyclase C), GD2, GD3, GPC2 (glypican-2), GPC3, gp100 (glycoprotein 100), GPNMB (glycoprotein NMB), GPRC5D (G Protein Coupled Receptor 5D), HER2, HER3, HER4, hepatitis B surface antigen, melanoma-associated antigen (MAGE)-A1, MAGE-A3, MAGE-A6, MART-1 (melan A), mesothelin, mucin 1 (MUC1), MUC16, MHC/peptide complexes (e.g., HLA-A complexed with peptides derived from AFP, KRAS, NY-ESO, MAGE-A, and WT1), NCAM (neural cell adhesion molecule), Nectin-4, NY-ESO, oncofetal antigen, PRAME (preferentially expressed antigen of melanoma), progesterone receptor, PSA (prostate specific antigen), PSCA (prostate stem cell antigen), PSMA (prostate specific membrane antigen), ROR1, ROR2, SIRPα (signal-regulatory protein alpha), SLIT, SLITRK6 (NTRK-like protein 6), survivin, TAG72 (tumor-associated glycoprotein 72), TPBG (trophoblast glycoprotein), Trop-2, VEGFR1 (vascular endothelial growth factor receptor 1), p53, p53 mutant, prostein, survivin, telomerase, PCTA-1/Galectin 8, MelanA/MART1, Ras mutant, hTERT, sarcoma translocation breakpoints, ML-IAP, ERG (TMPRSS2 ETS fusion gene), NA17, PAX3, androgen receptor, cyclin B1, MYCN, RhoC, TRP-2, CYP1B1, BORIS, SART3, PAX5, OY-TES1, LCK, AKAP-4, SSX2, RAGE-1, human telomerase reverse transcriptase, RU1, RU2, intestinal carboxyl esterase, mut hsp70-2, CD79a, CD79b, CD72, LAIR1, FCAR, LILRA2, CD300LF, CLEC12A, BST2, EMR2, LY75, GPC3, FCRL5, IGLL1, CD2, CD3c, CD4, CD5, CD7, the extracellular portion of the APRIL protein, neoantigen, or any combinations thereof.

In various embodiments, the activation media for the reactivation of the T cell derived adherent cells may further comprise an immunomodulatory molecule such as a cytokine. Examples of immunomodulatory molecules are lymphokines, monokines, and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor (HGF); fibroblast growth factor (FGF); prolactin; placental lactogen; mullerian-inhibiting substance; mouse gonadotropin-associated peptide; inhibin; activin; vascular endothelial growth factor; integrin; thrombopoietin (TPO); nerve growth factors (NGFs) such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs)

such as IL-1, IL-1 alpha, IL-2, IL-3, IL-4, IL-5, IL-6, IL-7, IL-8, IL-9, IL-10, IL-11, IL-12, IL-15; a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

In certain embodiments, the partially reprogrammed and reactivated T cells herein may be further stimulated and expanded using the same methods for reactivation as described herein. Such methods for activating and expanding T cells are known in the art.

In various embodiments, the methods herein comprising the partial reprogramming followed by reactivation and optionally, further expansion, will be sufficient for the rejuvenated T cells to acquire any one or more of the following characteristics:

In certain embodiments, the rejuvenated T cells have one or more stemness properties including high epigenetic plasticity. Other advantageous phenotypic markers that the rejuvenated cells may acquire include expression of L-selectin (CD62L), IL-7Ra, CD132, CCR7, CD45RA, CD45RO, CD27, CD28, CD95, CXCR3, TCF7 and LFA-1. In certain embodiments, the rejuvenated T cells acquire T memory stem cell expression markers, e.g., are memory T cells that express CD95, CD45RA, CCR7, and CD62L and are endowed with the stem cell-like ability to self-renew and the multipotent capacity to reconstitute the entire spectrum of memory and effector T cell subsets. In certain embodiments, the rejuvenated T cells are "central memory T cells" or "TCM cells" which are memory T cells that express CD45RO, CCR7, and CD62L. In another embodiment, rejuvenated T cells have effector memory T cell markers such as expression of CD45RO but lack of expression of CCR7 and CD62L. In certain embodiments, the rejuvenated T cells herein have a stem-like phenotype and have an improved capacity for proliferation.

In certain embodiments, the rejuvenated T cells have characteristics of a naïve T cell, "TN cells," which are T cells that express CD45RA, CCR7, and CD62L, but which do not express CD95.

In certain embodiments, the rejuvenated T cells may exhibit biological and phenotypic characteristics of younger T cells in terms of epigenetic signature, telomere length and functionality.

In various embodiments, partial reprogramming and reactivation as described herein results in T cells that are rejuvenated as can be measured by assessing the methylation status of various CpG sites in a cell's DNA. Such techniques are known in the art. See, e.g., Horvath and Raj, 2018, Nature Reviews Genetics, 19:371-375. Various groups have established models or "epigenetic clocks" that use the methylation status of a cell to provide an estimate of that cell or tissues "biological age" using a mathematical algorithm that uses values assigned to the methylation state of a specific CpGs in the genome. In various embodiments, the methylation status of various CpGs cites is used to determine whether partial reprogramming has occurred. In various embodiments, the methylation status of various CpG cites is used to predict the counts of exhausted CD8 T cells. In various embodiments, the methylation status of various CpG cites is used to determine whether a population of immune cell (e.g., a T cell) is suitable for administration to a patient.

In various embodiments the "Horvath Clock" as described in Horvath and Raj (2018, Nature Reviews Genetics, 19:371-375) is used to determine the epigenetic age of the cells described herein including the rejuvenated immune cell (e.g., a T cell). In various embodiments the Horvath Clock is used to determine whether partial reprogramming has occurred. In various embodiments, the Horvath Clock is used to predict the counts of exhausted CD8 T cells. In various embodiments, the Horvath clock is used to determine whether a population of imm immune cell (e.g., a T cell) is suitable for administration of patient. In various embodiments other epigenetic clocks or algorithms (for example, the Hannum Clock or the Levine Clock) are used. See, e.g., Hannum et al., 2013, Mol. Cell., 49:359-369; Levine et al., 2018, Aging, 10(4):573-591.

In certain embodiments, rejuvenated T cells (partially reprogrammed and reactivated T cells as described herein) exhibit a reduced epigenetic age (eAge) as compared to control T cells (e.g., T cells that have been cultured without contact with one or more reprogramming factors). eAge may be determined using a known epigenetic clock determination method, such as the Horvath clock as described elsewhere herein. In certain embodiments, the eAge of a rejuvenated T cell as described herein is reduced by about 5%-75%, 10%-75%, 10%-50%, 15%-75%, 15%-50%, 20%-75%, or 20%-50% as compared to the eAge of an appropriate control T cell (e.g., T cell from the original donor sample prior to partial reprogramming and reactivation or chronologically age-matched T cells). In certain embodiments, the eAge of a rejuvenated T cell as described herein is reduced by at least 5%, 6%, 7%, 8%, 9%, 10%, 15%, 20%, 25%, 30%, 35%, 40%, 45%, 50%, 55%, 60%, 65%, 70%, 75% or more as compared to an appropriate control T cell (e.g., T cell from the original donor sample prior to partial reprogramming or chronologically age-matched T cells).

In certain embodiments, the present disclosure provides a population of T cells whose epigenetic age is at least 5% younger than its chronological age. In another embodiment, the present disclosure provides a population of T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than its chronological age. In certain embodiments, the disclosure provides a population of T cells whose epigenetic age is at least 2, 3, 4, 5, 6, 7, 8, 9, 10, 11, 12, 13, 14, 15, 16, 17, 18, 19, 20, or more years younger that its chronological age. In this regard, epigenetic age can be measured using methods known in the art, such as by measuring the Horvath epigenetic clock.

In certain embodiments, rejuvenated T cells (partially reprogrammed and reactivated T cells as described herein) exhibit an epigenetic age (eAge) that is around 7-16 years of age. In certain embodiments, rejuvenated T cells exhibit an epigenetic age (eAge) that is reduced to around the equivalent age of puberty as compared to control T cells (e.g., T cells that have been cultured without contact to one or more reprogramming factors; e.g., compared to the chronological age of the starting cells). In certain embodiments, the rejuvenated T cells have increased telomere length as compared to control T cells. Telomere length can be measured using methods known in the art (see e.g., Rosenberg et al., 2011, Clin Cancer Res 17, 4550-4557) and commercially available kits (e.g., TELOTAGGG, Sigma-Aldrich). In certain embodiments, the telomere length is elongated by between about 0.1-3 kb. In certain embodiments, the telomere length is elongated by about 0.1, 0.2, 0.3, 0.4, 0.5, 0.6, 0.7, 0.8, 0.9, or about 1 kb. In another embodiment, the telomere is elongated by about 1.1, 1.2, 1.3, 1.4, 1.5, 1.6, 1.7, 1.8, 1.9, or 2 kb.

In certain embodiments, the rejuvenated T cells exhibit increased expansion potential. In certain embodiments, the rejuvenated T cells expand 2, 3, 4, 5, 6, 7, 8, 9, 10, 11, 12, 13, 14, 15, 16, 17, 18, 19, 20, 25, 30, 35, 40, 45, 50-fold more than control T cells that have not been partially reprogrammed or that are chronologically age-matched T cells. In certain embodiments, the rejuvenated T cells expand from 25-1000 fold more than chronologically age-matched control T cells or control T cells that have not been partially reprogrammed. In certain embodiments, the rejuvenated T cells expand from 25, 30, 40, 50, 60, 70, 80, 90, 100, 125, 150, 175, 200, 225, 250, 275, 300, 350, 400, 450, 500 fold more than chronologically age-matched control T cells or control T cells that have not been partially reprogrammed. In certain embodiments, the rejuvenated T cells expand more quickly than T cells that have not been partially reprogrammed.

In certain embodiments, the present disclosure provides a population of T cells whose epigenetic age is at least 5% younger than its chronological age wherein the T cells do not express aberrant NK, T or B cell markers.

In another embodiment, the present disclosure provides a population of T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than the chronological age of the source T cells or appropriate control T cells, and wherein the T cells do not express aberrant NK, T or B cell markers.

In another embodiment, the present disclosure provides a population of T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than the chronological age of the source T cells or appropriate control T cells, and wherein the T cells have a stem-like phenotype.

In another embodiment, the present disclosure provides a population of T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than the chronological age of the source T cells or appropriate control T cells, and wherein the T cells express CCR7, CD62L, and TCF7.

In another embodiment, the present disclosure provides a population of T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than the chronological age of the source T cells or appropriate control T cells, and wherein the T cells express CCR7, CD62L, and TCF7; and have an increased killing capacity as compared to appropriate control T cells. Killing capacity can be measured using assays known in the art such as those described in the Examples herein.

In certain embodiments, the present disclosure provides a population of T cells whose epigenetic age is at least 5% younger than the chronological age of the source T cells wherein the T cells do not express NCAM1, NCR2, FCGR3A, KIR2DL4 or KIR2DS4.

In certain embodiments, the present disclosure provides a population of T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than its chronological age and wherein the T cells do not express NCAM1, NCR2, FCGR3A, KIR2DL4, or KIR2DS4.

In certain embodiments, the present disclosure provides a T cell whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than its chronological age (or an appropriate control T cell) and wherein the T cell is enriched for oxidative phosphorylation, fatty acid metabolism, glycolysis and hypoxia gene sets as determined by transcriptome analysis.

In certain embodiments, the present disclosure provides a T cell or a population of such T cells, whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than its chronological age (or an appropriate control T cell) and wherein the T cells is enriched for both oxidative phosphorylation and glycolysis gene sets as compared to control T cells as determined by transcriptome analysis.

In certain embodiments, the present disclosure provides T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than the chronological age of an appropriate control T cell and wherein the T cells have increased TCR repertoire diversity as compared to control T cells.

In various embodiments, the present disclosure provides a population of T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than its chronological age and wherein the T cells comprise an incomplete set of V, D, and J segments of T cell receptor genes.

In certain embodiments, the present disclosure provides a population of T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than the chronological age of the source T cells; wherein the T cells do not express NCAM1, NCR2, FCGR3A, KIR2DL4, or KIR2DS4; and wherein the T cells are enriched for oxidative phosphorylation, fatty acid metabolism, glycolysis and hypoxia gene sets as determined by transcriptome analysis.

In certain embodiments, the present disclosure provides a population of T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than the chronological age of the source T cells; wherein the T cells do not express NCAM1, NCR2, FCGR3A, KIR2DL4, or KIR2DS4; and wherein the T cells are enriched for both oxidative phosphorylation and glycolysis gene sets as compared to control T cells as determined by transcriptome analysis.

In certain embodiments, the present disclosure provides a population of T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than the chronological age of the source T cells; wherein the T cells do not express NCAM1, NCR2, FCGR3A, KIR2DL4, or KIR2DS4; wherein the T cells are enriched for both oxidative phosphorylation and glycolysis gene sets as compared to control T cells as determined by transcriptome analysis; and wherein the T cells have increased TCR repertoire diversity as compared to control T cells.

In certain embodiments, the present disclosure provides a population of T cells whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than the chronological age of the source T cells; wherein the T cells do not express NCAM1, NCR2, FCGR3A, KIR2DL4, or KIR2DS4; wherein the T cells are enriched for both oxidative phosphorylation and glycolysis gene sets as compared to control T cells as determined by transcriptome analysis; wherein the T cells have increased TCR repertoire diversity as compared to control T cells; and wherein the T cells comprise an incomplete set of V, D, and J segments of T cell receptor genes.

As would be recognized by the person of skill in the art, T cell receptor V, D, and J gene segments rearrange during T cell development to form complete variable domain exons. These gene rearrangements take place in the thymus. The rejuvenated T cells produced herein are produced from isolated T cells that have a rearranged TCR locus and express a TCR. Thus, in certain embodiments, the rejuvenated T cells produced herein are epigenetically younger than the source isolated T cells yet have a functional TCR (i.e., an incomplete set of V, D, and J segment of T cell receptor genes), which distinguishes them from the isolated T cells.

In certain embodiments, the metabolic state of rejuvenated T cells is improved (see e.g., Cell Metabolism 14, 264-271). In certain embodiments, metabolic gene sets corresponding to oxidative phosphorylation, fatty acid metabolism, glycolysis and hypoxia are enriched in the rejuvenated T cells described herein as compared to appropriate controls (see e.g., Nishimura 2019 Int. J. Mol. Sci. 20:2254). In certain embodiments, the rejuvenated T cells described herein have upregulated glycolytic enzymes and downregulated electron transport chain subunits. In certain embodiments, the rejuvenated T cells herein demonstrate one or more of the following characteristics: a metabolic switch converting somatic oxidative metabolism into a glycolytic flux-dependent, mitochondria independent state; downregulated expression of age-related stress response genes in the p53 tumor suppressor pathway, including p16INK4a, p21CIP1, Atf3, and Gadd45B; downregulation of the senescence-associated metalloprotease MMP13 and interleukin-6; reduced senescence-associated β-galactosidase activity; reduced production of mitochondrial reactive oxygen species (ROS); restored levels of H3K9me3 and H4K20me3 (epigenetic modifications involved in the maintenance of heterochromatin) (see e.g., Ocampo, Cell. 2016, 167(7): 1719-1733; Benayoun B A, Nat Rev Mol Cell Biol. 2015; 16:593-610; Liu B, Nat Commun. 2013, 4:1868; Database, Volume 2016, baw100; doi.org/10.1093/database/baw100).

In certain embodiments, the rejuvenated T cells herein are enriched for stemness gene signatures as compared to non-rejuvenated control T cells (see, e.g., Gattinoni et al., 2011 Nature Medicine 17(10):1290-1297).

II. Methods of Treatment

In various embodiments, the disclosure provides a method of treating a patient in need thereof with a population of rejuvenated T cells produced by the partial reprogramming and reactivation methods disclosed herein. Methods are provided for treating diseases or disorders, including cancer by administering a composition comprising the rejuvenated T cells described herein. In various embodiments, the disclosure relates to a method of treating a patient in need thereof with a population of T cells produced by a method comprising (a) transiently contacting T cells with at least one reprogramming factor selected from the group consisting of KLF4, OCT3/4, SOX2 and C-MYC and optionally SV40, for a time sufficient for T cell derived adherent cell colonies form; and (c) contacting said T cell derived adherent cells with a culture medium comprising a T cell activating and/or costimulatory agent, such as anti-CD3, anti-CD28, and or one or more cytokines such as IL-2. In some embodiments, the T cells are engineered to express a cell surface receptor that recognizes a specific antigenic moiety on the surface of a target cell. In various embodiments of the disclosure, the target cell is a cancer cell.

In certain embodiments, the disclosure relates to a method of treating a patient in need thereof with a population of rejuvenated T cells as described herein.

In various embodiments, the disclosure relates to a method of treating a patient in need thereof with a population of rejuvenated immune cell (e.g., a T cell) produced by the methods disclosed herein. Methods are provided for treating diseases or disorders, including cancer, infectious disease, or autoimmune disease. In various embodiments, the disclosure relates to a method of treating a patient in need thereof with a population of immune cell (e.g., a T cell) produced by a method comprising (a) isolating a plurality of immune cells (e.g., T cells) from a source; (b) transiently contacting said plurality of immune cells (e.g., T cells) with at least one reprogramming factor selected from the group consisting of KLF4, OCT3/4, SOX2 and C-MYC; and (c) contacting said immune cells (e.g., T cells) with a culture medium comprising IL-2, wherein said immune cells (e.g., T cells) are contacted with at least one reprogramming factor for a period of at least about four days. In some embodiments, the plurality of immune cells (e.g., T cells) are engineered to express a cell surface receptor that recognizes a specific antigen on the surface of a target cell. In various embodiments of the disclosure, the target cell is a cancer cell.

In various embodiments, the disclosure comprises a pharmaceutical composition comprising a plurality of rejuvenated T cells produced by the methods herein. In certain embodiments, the pharmaceutical composition comprises rejuvenated T cells produced by a method comprising (a) transiently contacting a plurality of T cells with at least one reprogramming factor selected from the group consisting of KLF4, OCT3/4, SOX2 and C-MYC; for a period time sufficient for the partially reprogrammed cells to attach to the culture vessel surface; and (b) contacting said attached reprogrammed T cells with a culture medium comprising a T cell activating agent. In some embodiments, the pharmaceutical composition further comprises an additional active agent.

In some aspects, the disclosure comprises a pharmaceutical composition comprising at least one rejuvenated T cell as described herein and a pharmaceutically acceptable excipient. In some embodiments, the pharmaceutical composition further comprises an additional active agent.

It will be appreciated that target doses for rejuvenated T cells can range from about $1 \times 10^6$ to about $2 \times 10^{10}$ cells/kg, preferably $2 \times 10^6$ cells/kg. It will be appreciated that doses above and below this range may be appropriate for certain subjects, and appropriate dose levels can be determined by the healthcare provider as needed. In various embodiments the target dose is $1 \times 10^5$. In various embodiments the target dose is $1 \times 10^6$. In various embodiments the target dose is $1 \times 10^7$. In various embodiments the target dose is $1 \times 10^8$. In various embodiments the target dose is $1 \times 10^9$. In various embodiments the target dose is $1 \times 10^{10}$. In various embodiments the target dose is $2 \times 10^{10}$. Additionally, multiple doses of cells can be provided in accordance with the disclosure. In various embodiments at least 1, 2, 3, 4, 5, 6, 7, 8, 9 or 10 doses of cells are administered to the patient in need thereof.

Also provided are methods for reducing the size of a tumor in a subject, comprising administering to the subject a rejuvenated T cell of the present disclosure. In some embodiments, the subject has a solid tumor, or a blood malignancy such as lymphoma or leukemia. In some embodiments, the rejuvenated immune cell (e.g., a T cell) is delivered to a tumor bed. In some embodiments, the cancer is present in the bone marrow of the subject.

As used herein, the term "subject" or "patient" means an individual. In some aspects, a subject is a mammal such as a human. In some aspects, a subject can be a non-human primate. Non-human primates include marmosets, monkeys, chimpanzees, gorillas, orangutans, and gibbons, to name a few. The term "subject" also includes domesticated animals, such as cats, dogs, etc., livestock (e.g., llama, horses, cows), wild animals (e.g., deer, elk, moose, etc.), laboratory animals (e.g., mouse, rabbit, rat, gerbil, guinea pig, etc.) and avian species (e.g., chickens, turkeys, ducks, etc.). Preferably, the subject is a human subject. More preferably, the subject is a human patient.

The methods can further comprise administering one or more chemotherapeutic agents. In certain embodiments, the chemotherapeutic agent is a lymphodepleting (preconditioning) chemotherapeutic. Beneficial preconditioning treatment regimens, along with correlative beneficial biomarkers are described in U.S. Provisional Patent Applications 62/262,143 and 62/167,750. These describe, e.g., methods of conditioning a patient in need of a T cell therapy comprising administering to the patient specified beneficial doses of cyclophosphamide (between 200 mg/m2/day and 2000 mg/m2/day) and specified doses of fludarabine (between 20 mg/m2/day and 900 mg/m2/day). A preferred dose regimen involves treating a patient comprising administering daily to the patient about 500 mg/m2/day of cyclophosphamide and about 60 mg/m2/day of fludarabine for three days prior to administration of a therapeutically effective amount of rejuvenated T cells to the patient.

In other embodiments, the rejuvenated T cells and the chemotherapeutic agent are administered each in an amount effective to treat the disease or condition in the subject.

In certain embodiments, compositions comprising rejuvenated immune cell (e.g., T cells) disclosed herein may be administered in conjunction with any number of chemotherapeutic agents. Examples of chemotherapeutic agents include alkylating agents such as thiotepa and cyclophosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine resume; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofiran; spirogermanium; tenuazonic acid; triaziquone; 2, 2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (Taxol®, Bristol-Myers Squibb) and doxetaxel (Taxotere®, Rhone-Poulenc Rorer); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS2000; difluoromethylomithine (DMFO); retinoic acid derivatives such as Targretin™ (bexarotene), Panretin™, (alitretinoin); Ontak™ (denileukin diftitox); esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and anti-androgens such as flutamide, nilutamide, bicalutamide, leuprolide, and goserelin; and pharmaceutically acceptable salts, acids or derivatives of any of the above. Combinations of chemotherapeutic agents are also administered where appropriate, including, but not limited to CHOP, i.e., Cyclophosphamide (Cytoxan®) Doxorubicin (hydroxydoxorubicin), Fludarabine, Vincristine (Oncovin®), and Prednisone.

In some embodiments, the chemotherapeutic agent is administered at the same time or within one week after the administration of the engineered cell or nucleic acid. In other embodiments, the chemotherapeutic agent is administered from 1 to 4 weeks or from 1 week to 1 month, 1 week to 2 months, 1 week to 3 months, 1 week to 6 months, 1 week to 9 months, or 1 week to 12 months after the administration of the engineered cell or nucleic acid. In other embodiments, the chemotherapeutic agent is administered at least 1 month before administering the cell or nucleic acid. In some embodiments, the methods further comprise administering two or more chemotherapeutic agents.

A variety of additional therapeutic agents may be used in conjunction with the compositions described herein. For example, potentially useful additional therapeutic agents include PD-1 (or PD-L1) inhibitors such as nivolumab (Opdivo®), pembrolizumab (Keytruda®), pembrolizumab, pidilizumab, and atezolizumab (Tecentriq®).

Additional therapeutic agents suitable for use in combination with the disclosure include, but are not limited to, ibrutinib (Imbruvica®), ofatumumab (Arzerra®), rituximab (Rituxan®), bevacizumab (Avastin®), trastuzumab (Herceptin®), trastuzumab emtansine (KADCYLA®), imatinib (Gleevec®), cetuximab (Erbitux®), panitumumab (Vectibix®), catumaxomab, ibritumomab, ofatumumab, tositumomab, brentuximab, alemtuzumab, gemtuzumab, erlotinib, gefitinib, vandetanib, afatinib, lapatinib, neratinib, axitinib, masitinib, pazopanib, sunitinib, sorafenib, toceranib, lestaurtinib, axitinib, cediranib, lenvatinib, nintedanib, pazopanib, regorafenib, semaxanib, sorafenib, sunitinib, tivozanib, toceranib, vandetanib, entrectinib, cabozantinib, imatinib, dasatinib, nilotinib, ponatinib, radotinib, bosutinib, lestaurtinib, ruxolitinib, pacritinib, cobimetinib, selumetinib, trametinib, binimetinib, alectinib, ceritinib, crizotinib, aflibercept, adipotide, denileukin diftitox, mTOR inhibitors such as Everolimus and Temsirolimus, hedgehog inhibitors such as sonidegib and vismodegib, CDK inhibitors such as CDK inhibitor (palbociclib).

In additional embodiments, the composition comprising a rejuvenated T cell can be administered with an anti-inflammatory agent. Anti-inflammatory agents or drugs include, but are not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate. Exemplary NSAIDs include ibuprofen, naproxen, naproxen sodium, Cox-2 inhibitors, and sialylates. Exemplary analgesics include acetaminophen, oxycodone, tramadol of proporxyphene hydrochloride. Exemplary glucocorticoids include cortisone, dexamethasone, hydrocortisone, methylprednisolone, prednisolone, or prednisone. Exemplary biological response modifiers include molecules directed against cell surface markers (e.g., CD4, CD5, etc.), cytokine inhibitors, such as the TNF antagonists, (e.g., etanercept (ENBREL®), adalimumab (HUMIRA®) and infliximab (REMICADE®)), chemokine inhibitors and adhesion molecule inhibitors. The biological response modifiers include monoclonal antibodies as well as recombinant forms of molecules. Exemplary DMARDs include azathioprine, cyclophosphamide, cyclosporine, methotrexate, penicillamine, leflunomide, sulfasalazine, hydroxychloroquine, Gold (oral (auranofin) and intramuscular) and minocycline.

In certain embodiments, the compositions described herein are administered in conjunction with a cytokine. In some embodiments, a cytokine may comprise a protein from natural sources or from recombinant cell culture, and biologically active equivalents of the native sequence cytokines.

III. Formulations and Pharmaceutical Preparations

A variety of known techniques can be utilized in making the polynucleotides, polypeptides, vectors, antigen-binding molecules, immune cells (e.g., T cells), compositions, and the like according to the disclosure.

The isolated T cells can be genetically modified following isolation using known methods, or the T cells can be partially reprogrammed, activated and expanded in vitro prior to being genetically modified. In another embodiment, the T cells are genetically modified with a recombinant TCR or CAR and then are rejuvenated using the partial reprogramming and reactivation methods described herein. In certain embodiments, the rejuvenated cells described herein are further activated and/or expanded in vitro. Methods for activating and expanding immune cells (e.g., T cells) are known in the art and are described, for example, in U.S. Pat. Nos. 6,905,874; 6,867,041; 6,797,514; and WO2012/079000. Generally, such methods include contacting the T cells with a stimulatory (e.g., activating) agent (in certain embodiments, referred to as a T cell activating compound) (e.g., an agent that stimulates a CD3/TCR complex (for example, an anti-CD3 antibody or a CD3 agonist) and a costimulatory agent (an agent such as an antibody or ligand that stimulates CD28, ICOS, CD27, HVEM, LIGHT, CD40, 4-1BB, OX40, DR3, GITR, CD30, TIM1, CD2, CD226 or any combination thereof). In certain embodiments, the stimulatory agent and the costimulatory agent are attached to a bead or other surface, in a culture medium with appropriate cytokines, such as IL-2.

In other embodiments, the rejuvenated T cell may be activated and stimulated to proliferate with feeder cells and appropriate antibodies and cytokines using methods such as those described in U.S. Pat. Nos. 6,040,177; 5,827,642; and WO/2012129514.

Certain methods for making the constructs and engineered T cells of the disclosure are described in PCT application PCT/US2015/14520.

In certain embodiments, the disclosure provides a method of storing the rejuvenated T cells described herein. This involves cryopreserving the T cells such that the cells remain viable upon thawing. A fraction of the T cells can be cryopreserved by methods known in the art to provide a permanent source of such cells for the future treatment of patients afflicted with a malignancy. When needed, the cryopreserved T cells can be thawed, grown and expanded for more such cells.

As used herein, "cryopreserve" refers to the preservation of cells by cooling to sub-zero temperatures, such as (typically) 77 Kelvin or 196° C. (the boiling point of liquid nitrogen). Cryoprotective agents are often used at sub-zero temperatures to prevent the cells being preserved from damage due to freezing at low temperatures or warming to room temperature. Cryopreservative agents and optimal cooling rates can protect against cell injury. Cryoprotective agents which can be used in accordance with the disclosure include but are not limited to: dimethyl sulfoxide (DMSO) (Lovelock & Bishop, Nature, 1959, 183, 1394-1395; Ashwood-Smith, Nature, 1961, 190, 1204-1205), glycerol, polyvinylpyrrolidine (Rinfret, Ann. N.Y. Acad. Sci., 1960, 85, 576), and polyethylene glycol (Sloviter & Ravdin, Nature, 1962, 196, 48). The preferred cooling rate is 1°–3° C./minute.

The term, "substantially pure," is used to indicate that a given component is present at a high level. The component is desirably the predominant component present in a composition. Preferably it is present at a level of more than 30%, of more than 50%, of more than 75%, of more than 90%, or even of more than 95%, said level being determined on a dry weight/dry weight basis with respect to the total composition under consideration. At very high levels (e.g. at levels of more than 90%, of more than 95% or of more than 99%) the component can be regarded as being in "pure form." Biologically active substances of the present disclosure (including polypeptides, nucleic acid molecules, antigen-binding molecules, moieties) can be provided in a form that is substantially free of one or more contaminants with which the substance might otherwise be associated. When a composition is substantially free of a given contaminant, the contaminant will be at a low level (e.g., at a level of less than 10%, less than 5%, or less than 1% on the dry weight/dry weight basis set out above).

In some embodiments, the cells herein are formulated by first harvesting them from their culture medium, and then washing and concentrating the cells in a medium and container system suitable for administration (a "pharmaceutically acceptable" carrier) in a treatment-effective amount. Suitable infusion media can be any isotonic medium formulation, typically normal saline, Normosol™ R (Abbott) or Plasma-Lyte™ A (Baxter), but also 5% dextrose in water or Ringer's lactate can be utilized. The infusion medium can be supplemented with human serum albumin.

Desired treatment amounts of cells in the composition is generally at least 2 cells or is more typically greater than 102 cells, and up to 106, up to and including 108 or 109 cells and can be more than 1010 cells. The number of cells will depend upon the desired use for which the composition is intended, and the type of cells included therein. The density of the desired cells is typically greater than 106 cells/ml and generally is greater than 107 cells/ml, generally 108 cells/ml or greater. The clinically relevant number of immune cells (e.g., T cells) can be apportioned into multiple infusions that cumulatively equal or exceed 105, 106, 107, 108, 109, 1010, 1011, or 1012 cells. In some aspects of the present disclosure, particularly since all the infused cells will be redirected to a particular target antigen, lower numbers of cells, in the range of 106/kilogram (106-1011 per patient) may be administered. Rejuvenated T cell treatments may be administered multiple times at dosages within these ranges. The cells may be autologous, allogeneic, or heterologous to the patient undergoing therapy.

The rejuvenated T cells of the present disclosure may be administered either alone, or as a pharmaceutical composition in combination with diluents and/or with other components such as IL-2 or other cytokines or cell populations. Pharmaceutical compositions of the present disclosure may comprise a rejuvenated T cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration. Treatment may also include one or more corticosteroid treatment, such as dexamethasone and/or methylprednisolone.

The compositions of the present application can comprise, consist essentially of, or consist of, the components disclosed.

The pharmaceutical compositions of the disclosure (solutions, suspensions or the like), may include one or more of the following: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylene-diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

It will be appreciated that adverse events may be minimized by transducing the immune cells (e.g., T cells) with a suicide gene. Suitable "kill switches" are described for example in WO2021/189008. It may also be desired to incorporate an inducible "on" or "accelerator" switch into the immune cells (e.g., T cells). These techniques may employ the use of dimerization domains and optional activators of such domain dimerization. These techniques include, e.g., those described by Wu et al., Science 2014, 350(6258) utilizing FKBP/Rapalog dimerization systems in certain cells. Additional dimerization technology is described in, e.g., Fegan et al. Chem. Rev. 2010, 110, 3315-3336 as well as U.S. Pat. Nos. 5,830,462; 5,834,266; 5,869,337; and 6,165,787. Additional dimerization pairs may include cyclosporine-A/cyclophilin, receptor, estrogen/ estrogen receptor (optionally using tamoxifen), glucocorticoids/glucocorticoid receptor, tetracycline/tetracycline receptor, vitamin D/vitamin D receptor. Further examples of dimerization technology can be found in e.g., WO 2014/ 127261, WO 2015/090229, US 2014/0286987, US 2015/ 0266973, US 2016/0046700, U.S. Pat. No. 8,486,693, US 2014/0171649, and US 2012/0130076.

Suitable techniques for genetic modification of the rejuvenated cells herein include use of inducible caspase-9 (U.S. Appl. Pub. No. 2011/0286980) or a thymidine kinase, before, after or at the same time, as the cells are genetically modified to express a CAR or other engineered TCR. Additional methods for introducing suicide genes and/or "on" switches include CRISPR, TALENS, MEGATALEN, zinc fingers, RNAi, siRNA, shRNA, antisense technology, and other techniques known in the art.

IV. Kits

Also included within the scope of the present disclosure are kits, e.g., pharmaceutical kits, comprising at least one reprogramming factor for contacting one or more T cells in vitro. Kits typically include a label indicating the intended use of the contents of the kit and instructions for use. The term "label" includes any writing, or recorded material supplied on or with the kit, or which otherwise accompanies the kit.

In various, the disclosure provides a kit for preparing one or more T cells for a T cell therapy for a subject in need thereof, the kit comprising at least one reprogramming factor selected from the group consisting of KLF4, OCT3/4, SOX2 and C-MYC, and optionally, SV40. In various embodiments, the disclosure provides for a kit for preparing one or more T cells for a T cell therapy for a subject in need thereof, the kit comprising at least one expression vector capable of expression at least one reprogramming factor selected from the group consisting of KLF4, OCT3/4, SOX2 and C-MYC. In various embodiments, the disclosure provides for a kit for preparing one or more T cells for a T cell therapy for a subject in need thereof, the kit comprising at least one Sendai virus vector capable of expression at least one reprogramming factor selected from the group consisting of KLF4, OCT3/4, SOX2 and C-MYC. In various embodiments, the kit further comprises a Sendai virus vector capable of expressing SV40.

In various embodiments, the disclosure provides a kit for preparing one or more T cell vectors for a T cell therapy for a subject in need thereof, the kit comprising:

An expression vector encoding KLF4, OCT3/4 and SOX2;
An expression vector encoding KLF4;
An expression vector encoding C-MYC; and
An expression vector encoding SV40.

In various embodiments, the disclosure provides a kit for preparing one or more T cell vectors for a T cell therapy for a subject in need thereof, the kit comprising:

A Sendai Virus encoding KLF4, OCT3/4 and SOX2;
A Sendai virus encoding KLF4;
A Sendai virus encoding C-MYC; and
A Sendai virus encoding SV40.

In various embodiments, the disclosure provides a kit for preparing one or more T cell vectors for a T cell therapy for a subject in need thereof, the kit comprising a multicistronic Sendai virus vector encoding KLF4, OCT3/4, SOX2, C-MYC and optionally SV40.

In various embodiments, the kit may further comprise a T-cell activating compound or agent. In various embodiments the T cell activating compound or agent is an anti-CD3 antibody. In various embodiments the kit comprises a costimulatory agent, such as an anti-CD28 antibody. In various embodiments, the kit comprises both an anti-CD3 antibody and an anti-CD28 antibody. In various embodiments, the kit may further comprise one or more appropriate culture media for culturing and/or partially reprogramming T cells. In various embodiments, the kit may further comprise one or more cytokines. Such cytokines include but are not limited to IL-2, IL-7, IL-15 and IL-12.

V. Further Embodiments

The present invention may be characterized by one or more of the following clauses defining various embodiments as described herein.

In a first embodiment, the present invention relates to [1]:

[1] An in vitro method of producing at least one rejuvenated T cell comprises (a) contacting a population of T cells with at least one reprogramming factor selected from the group consisting of KLF4, OCT3/4, SOX2, C-MYC, and SV40, for a period of time sufficient for T cell derived adherent cells to form; wherein said T cells are not transformed into iPS or totipotent cells; and (b) contacting the T cell derived adherent cells with at least one T cell activating compound.

In a second embodiment, the present invention relates to [2]:

[2] An in vitro method of producing at least one T cell, comprising (a) contacting a population of T cells in a first culture medium in a culture vessel with at least one reprogramming factor selected from the group consisting of KLF4, OCT3/4, SOX2, C-MYC, and SV40, for a period of time sufficient for the T cells to form at least one colony attached to the culture vessel surface; wherein said T cells are not transformed into iPS cells or totipotent cells; and (b) contacting the at least one attached colony with at least one T cell activating compound.

In a third embodiment, the present invention relates to [3]:

[3] An in vitro method of producing at least one T cell, comprising (a) contacting a population of T cells in a first culture medium with at least one reprogramming factor selected from the group consisting of KLF4, OCT3/4, SOX2, C-MYC, and SV40, for a period of at least about 5 days and no more than about 10 days; wherein said T cells are not transformed into iPS cells or totipotent cells; and (b) contacting the T cells with at least one T cell activating compound.

In a fourth embodiment, the present invention relates to [4]:

[4] An in vitro method of producing at least one T cell, comprising (a) contacting a population of T cells with at least one reprogramming factor selected from the group consisting of KLF4, OCT3/4, SOX2, C-MYC, and SV40 for a period of time sufficient for the T cells to express at least one marker selected from the group consisting of integrin α6β1, SSEA4, CD9, and CD90; wherein said T cells are not transformed into iPS cells or totipotent cells; and (b) contacting the T cells with at least one T cell activating compound.

In further embodiments, the present invention relates to:

[5] The method of any one of [1] to [4] wherein the T cells are contacted with the at least one reprogramming factor for a period of time sufficient for at least a portion of the T cells to express CD3 and at least one marker selected from the group consisting of integrin a6131, SSEA4, CD9, and CD90, preferably SSEA4 and CD3, more preferably CD3, CD9 and CD90, even more preferably CD3, SSEA4, CD9 and CD90.

[6] The method of any one of [1] to [5] wherein prior to contacting said T cells with the at least one reprogramming factor, the T cells are contacted with IL-2 and/or at least one agent capable of activating said T cells, preferably the agent capable of activating said T cells is a tumor antigen.

[7] The method of any one of [1] to [6] wherein the T cell is a TCRα+ TCRβ+ cell; a TCRg(Gamma)+ TCRd(Delta) cell; a CD4+CD8αβ+ double positive cell, CD4+ single positive cell (such as Th1, Th2, Th17, Treg), a naïve T cell, a central memory T cell, or effector memory T cell, or wherein the T cell expresses an activation marker after co-culture with autologous tumor cells, wherein the activation marker is 4-1BB (CD137), PD1, LAG3, CD45, CD39, TIGIT, TIM3, CD69, OX40, CD28, CD25, CD49d, and CTLA4.

[8] The method of any one of [1] to [7] wherein said T cells are isolated from a mammal, preferably a human.

[9] The method of any one of [1] to [8] wherein the T cells are contacted with KLF4, OCT3/4, SOX2 and C-MYC.

[10] The method of any one of [1] to [9] wherein, the T cells are contacted with the at least one reprogramming factor, preferably KLF4, OCT3/4, SOX2 and C-MYC, for at least about 4 to 10 days, preferably for at least about 4 to 7 days, more preferably for about 5 days.

[11] The method of any one of [1] to [10] wherein the at least one reprogramming factor is expressed in the T cell, preferably the least one reprogramming factor is expressed using a non-integrating viral vector or a nucleic acid delivered to the cell with a nanoparticle, more preferably the vector is a Sendai virus, even more preferably the at least one reprogramming factor is KLF4, OCT3/4, SOX2 and C-MYC.

[11a] The method of any one of [1] to [11] wherein the at least one reprogramming factor is expressed in the T cell for: a) a period of time sufficient for T cell derived adherent cells to form and wherein said isolated T cells are not transformed into iPS or totipotent cells; b) about 4 days to about 10 days; c) about 4 days to about 11 days; d) about 4 days to about 12 days; e) about 4 days to about 13 days; or f) about 4 days to about 14 days.

[12] The method of any one of [1] to [11a] wherein the at least one reprogramming factor is constitutively expressed, wherein expression is later inhibited by the addition of a T cell activating agent, or a compound that inhibits expression of the at least one reprogramming factor, preferably said compound is a small molecule inhibitor that specifically inhibits the expression the at least one reprogramming factor, more preferably said compound is an siRNA or shRNA molecule that specifically inhibits the expression the at least one reprogramming factor, even more preferably the at least one reprogramming factor is KLF4, OCT3/4, SOX2 and C-MYC.

[13] The method of any one of [1] to [12], further comprising contacting the T cells with at least one cytokine selected from the group consisting of IL-2, IL-7, IL-15, and IL-12.

[14] The method of any one of [1] to [13] wherein said at least one T cell activating compound comprises an antibody that binds CD3 or an antibody that binds CD28 or both; and/or wherein the at least one T cell activating compound is a tumor antigen.

[15] The method of any one of [1] to [14], further comprising engineering the T cell to express a cell surface receptor, wherein said T cell is engineered prior to or after contacting said T cell with said at least one reprogramming factor, preferably said cell surface receptor is either a chimeric antigen receptor or a T cell receptor or a hybrid receptor thereof, more preferably said cell surface receptor recognizes a specific antigenic moiety on the surface of a target cell.

[16] The method of [15], wherein the antigenic moiety is MHC class I dependent or MHC class I independent.

[17] The method of any one of [1] to [16] wherein the resulting T cells comprise an incomplete set of V, D, and J segments of T cell receptor genes and/or further comprising measuring the epigenetic age of the resulting T cells, preferably the epigenetic age of the resulting T cells is at least 5% younger than the population of T cells prior to reprogramming. The method of any one of [1] to [16] wherein the resulting T cells comprise an incomplete set of V, D, and J segments of T cell receptor genes and/or further comprising measuring the epigenetic age of the resulting T cells, preferably the epigenetic age of the resulting T cells is at least 5% younger than the population of T cells prior to reprogramming and the T cells do not express NCAM1, NCR2, FCGR3A, KIR2DL4, or KIR2DS4.

[18] The method of any one of [1] to [17] wherein the partially reprogrammed T cells are capable of expanding at least 25-fold greater than T cells before contacting with the at least one reprogramming factor.

[19] The method of any one of [1] to [18] wherein contacting said isolated T cells with the at least one reprogramming factor results in a reduction in CD3 and CD8 expression.

In a further embodiment, the present invention relates to [20]:

[20] An in vitro method of producing a T cell, comprising culturing T cells in a first medium comprising IL-2 and activating said T cells with at least one antibody specific for CD3 or for CD28, or both; contacting said activated T cells with KLF4, OCT3/4, SOX2 and C-MYC, for a period of about five days to about 10 days; in a second culture medium that does not comprise IL-2, or antibody specific for CD3 or CD28; wherein said T cells are not completely reprogrammed into iPSC cells; replacing said second culture medium with a third culture medium comprising IL-2 and at least one antibody specific for CD3 and/or CD28; wherein the T cells are cultured in said third culture medium for at least about 5 days.

In further embodiments, the present invention relates to one or more of:

[21] The method according to [20], further comprising expanding the T cells.

[22] The method according to [20] or [21], wherein said T cell is a TCRα+ TCRβ+ cell; a TCRg(Gamma)+ TCRd (Delta) cell; a CD4+CD8αβ+ double positive cell, CD4+ single positive cell (Th1, Th2, Th17, Treg), a naïve T cell, a central memory T cell, or effector memory T cell.

[23] The method according to any one of [20] to [22], wherein said contacting further comprises contacting the activated T cells with SV40.

[24] The method of any one of [20] to [23], wherein the T cell expresses an activation marker after co-culture with autologous tumor cells, wherein the activation marker is 4-1BB (CD137), PD1, LAG3, CD45, CD39, TIGIT, TIM3, CD69, OX40, CD28, CD25, CD49d, and CTLA4.

[25] The method of any one of [1] to [24], wherein the T cell is a tumor infiltrating lymphocyte (TIL) that has been obtained from a tumor.

In a further embodiment, the present invention relates to [26]:

[26] A population of T cells whose epigenetic age is at least 5% younger than its chronological age, preferably at least 25% younger than its chronological age.

In a further embodiment, the present invention relates to [27]:

[27] A population of T cell derived adherent cells, wherein at least 70% of the cells express both CD3 and SSEA4.

In a further embodiment, the present invention relates to:

[28] The population of [27], wherein at least 30% of the cells express CD9 and/or wherein at least 30% of the cells express CD90, preferably at least 30% of the cells express both CD9 and CD90.

[29] A population of T cells produced by any one of the methods according to [1] to [25].

[30] The population of T cells of any one of [26] to [29], wherein contacting said T cells with at least one factor selected from the group consisting of KLF4, OCT3/4, SOX2, C MYC and SV40 results in a reduction in CD3 and CD8 expression.

[31] The population of any one of [26] to [30], wherein the T cells are TILs, wherein at least 50% of the TILs express both CCR7 and CD62L, or wherein at least 50% of the TILs express both CCR7 and TCF7.

[32] The population of any one of [26] to [31], wherein the T cells are rejuvenated TILs.

[33] A population of T cells according to any one of [26] to [32] for use in therapy.

[34] A population of T cells according to any one of [26] to [32], for use in a method for treating a cancer, a viral condition or an autoimmune disorder.

[35] The population of T cells for use according to [34], wherein the cancer is acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, head and neck cancers (e.g., cancer of the nose, nasal cavity, or middle ear, cancer of the oral cavity), cancer of the vulva, chronic lymphocytic leukemia, chronic myeloid cancer, colon cancer, esophageal cancer, cervical cancer, gastrointestinal carcinoid tumor, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer (e.g., renal cell carcinoma (RCC)), small intestine cancer, soft tissue cancer, stomach cancer, testicular cancer, thyroid cancer, ureter cancer, or urinary bladder cancer.

In a further embodiment, the present invention relates to:

[37] A method of producing rejuvenated T cells, comprising contacting a population of T cells (i) at least one reprogramming factor selected from the group consisting of KLF4, OCT3/4, SOX2 and C-MYC, and (ii) optionally SV40, for at least a period of time sufficient for at least 20% of the contacted T cells to express α6β1 integrin and wherein said contacted T cells are not transformed into iPS cells; isolating said at least 20% of the contacted T cells with a binding molecule that specifically binds to α6β1 integrin;

contacting the isolated cells of (b) with a T cell activating and/or a T cell costimulatory agent; thereby producing rejuvenated T cells.

In a further embodiment, the present invention relates to:

[38] A method of producing at least one rejuvenated T cell, comprising transiently contacting the population of T cells with (i) at least one reprogramming factor selected from the group consisting of KLF4, OCT3/4, SOX2 AND C-MYC, and (ii) optionally SV40, for a period of time sufficient for T cell derived adherent cells to form; wherein said T cells are not transformed into iPS or totipotent cells; isolating a subpopulation of T cell derived adherent cells that express either a6 (CD49f) or b1 (CD29) integrin or both; and contacting the isolated subpopulation with at least one T cell activating compound.

In a further embodiment, the present invention relates to:

[39] A population of rejuvenated T cells produced by a method comprising contacting the population of T cells with (i) at least one reprogramming factor selected from the group consisting of KLF4, OCT3/4, SOX2 AND C-MYC, and (ii) SV40, for a period of time sufficient for T cell derived adherent cells to form; wherein said T cells are not transformed into iPS or totipotent cells; isolating a subpopulation of T cell derived adherent cells that express either a6 integrin, b1 integrin or both; and contacting the subpopulation of T cell derived adherent cells with at least one T cell activating compound.

In a further embodiment, the present invention relates to:

[40] A population of T cell derived adherent cells, wherein at least 70% of the cells express integrin α6 or integrin β1, or

[41] A population of T cell derived adherent cells, wherein at least 50% of the cells express both integrin α6 and integrin β1.

In a further embodiment, the present invention relates to:

[42] A population of T cell derived adherent cells, wherein at least 70% of the cells express both integrin α6 and integrin β1.

In a further embodiment, the present invention relates to:

[43] a T cell whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than its chronological age (or an appropriate control T cell) and wherein the T cell is enriched for oxidative phosphorylation, fatty acid metabolism, glycolysis and hypoxia gene sets as determined by transcriptome analysis.

[44] a T cell whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than its chronological age (or an appropriate control T cell) and wherein the T cell is enriched for both oxidative phosphorylation and glycolysis gene sets as compared to control T cells, as determined by transcriptome analysis.

[45] a T cell whose epigenetic age is at least 5%, 6%, 7%, 8%, 9%, 10%, 15%, 20%, 25%, 30%, 35%, 40%, 45%, 50%, 55%, 60%, 65%, 70%, 75%, or at least 80% younger than its chronological age (or an appropriate control T cell) and wherein the T cell does not express unconventional, NK, T or B cell markers (e.g., NCAM1, NCR2, FCGR3A, KIR2DL4, or KIR2DS4).

In a further embodiment, the present invention relates to

[46] a method of producing rejuvenated T cells, comprising: a) contacting a population of T cells (i) at least one reprogramming factor selected from the group consisting of KLF4, OCT3/4, SOX2 and C-MYC, and (ii) optionally SV40, for a period of time sufficient for at least 20% of the contacted T cells to express α6β1 integrin and wherein said contacted T cells are not transformed into iPS cells; b)isolating said at least 20% of the contacted T cells with a binding molecule that specifically binds to α6β1 integrin; c) contacting the cells of (b) with a T cell activating and/or a T cell costimulatory agent; thereby producing rejuvenated T cells; [47] wherein the binding molecule that specifically binds to an α6β1 integrin is selected from Laminin-511, Laminin-511E8, an anti-CD29 antibody, and an anti-Cd49f antibody.

In a further embodiment, the present disclosure relates to

[48] A method of producing a rejuvenated T cell, comprising a) transiently contacting a population of T cells with (i) at least one reprogramming factor selected from the group consisting of KLF4, OCT3/4, SOX2 AND C-MYC, and (ii) optionally SV40, for a period of time sufficient for T cell derived adherent cells to form; wherein said T cells are not transformed into iPS or totipotent cells; b) isolating a subpopulation of T cell derived adherent cells that express either a6 (CD49f) or b1 (CD29) integrin or both; and c) contacting the subpopulation with at least one T cell activating compound.

In a further embodiment, the present disclosure relates to

[48] A population of rejuvenated T cells produced by a method comprising: a) contacting the population of T cells with (i) at least one reprogramming factor selected from the group consisting of KLF4, OCT3/4, SOX2 AND C-MYC, and (ii) SV40, for a period of time sufficient for T cell derived adherent cells to form; wherein said T cells are not transformed into iPS or totipotent cells; b) isolating a subpopulation of T cell derived adherent cells that express either a6 integrin, b1 integrin or both; and c) contacting the subpopulation of T cell derived adherent cells with at least one T cell activating compound.

[49] A population of rejuvenated T cells of any one of [46]-[48] wherein, in a subpopulation, at least 20% of the cells express integrin α6 or integrin β1; or [50] wherein in the subpopulation, at least 50% of the cells express integrin α6 or integrin β1; or [51] wherein, in the subpopulation, at least 20% of the cells express both integrin α6 and integrin β1; or [52] wherein in the subpopulation, at least 50% of the cells express both integrin α6 and integrin β1.

[50] A population of T cell derived adherent cells, wherein at least 70% of the cells express integrin α6 or integrin β1; or [51] wherein at least 50% of the cells express both integrin α6 and integrin β1; or [52] wherein at least 70% of the cells express both integrin α6 and integrin β1.

[53] A method of treating a patient in need thereof with a population of T cells of any one of embodiments of [1]-[52].

EXAMPLES

The following examples are not meant to be limiting, but are presented to provide further information and support for the present invention. The Examples below demonstrate that the transient exposure of T cells to cell reprogramming conditions (in this case using a Sendai virus carrying four Yamanaka factors) results in partially reprogrammed T cells with reduced epigenetic age that have high proliferative capacity and retain antigen specificity. The treated T cells begin to de-differentiate, express markers more typically seen in stem cells (e.g., SSEA4) and attach to the culture vessel surface to form epithelial-type colonies. At the same time, the treated cells begin to lose T cell identity (loss of CD3 and CD8 expression). Subsequent activation can guide these "T cell derived adherent cells" to recover their T cell identity and exhibit a surprisingly increased potential for expansion (250-fold in 6 days).

Example 1: Partial Reprogramming Conditions for T Cells

In this experiment the reprogramming conditions for rejuvenating and improving T cell biological properties was explored. CD8 positive T cells, isolated with MACS magnetic beads (Miltenyi Biotec) from the PBMC of a 21-year-old male (Donor 11360; cell purchased from Allcells, Alameda, CA), were stimulated with soluble CD3 (Cat. No. 317325, BioLegend) and CD28 for 3 days in T cell culture medium (TCM) with 60 IU/ml IL2 (TCM: OpTmizer Basal Medium (1000 mL bottle); OpTmizer Cell Supplement (Supplement #02); Immune Cell Serum Replacement (CTS SR); L-Glutamine 200 mM (100×); GlutaMAX 200 mM (100×); IL-2 (1 ug=2.1×10e4 IU)RS 50 ug in 105 ul; (1 ug=4.5×10e5 IU)RS 25 ug in 1125 ul). All the T cell culture medium described in this experiment contains 60 IU/ml of IL2. This activation process was done in order to increase the efficiency of transduction of the Sendai virus. The Sendai virus (Cytotune iPS 2.0 Sendai Reprogramming Kit, ThermoFisher) was composed of three vectors: 1) encoding KLF4-OCT3/4-SOX2 (KOS), 2) encoding KLF4; 3) encoding C-MYC. Collectively, these are known as the "Yamanaka factors" and are depicted as the "4Factors" or "4F" in the figures. Additionally, a Sendai virus vector encoding SV40 was used to increase reprogramming efficiency.

Figure 1:
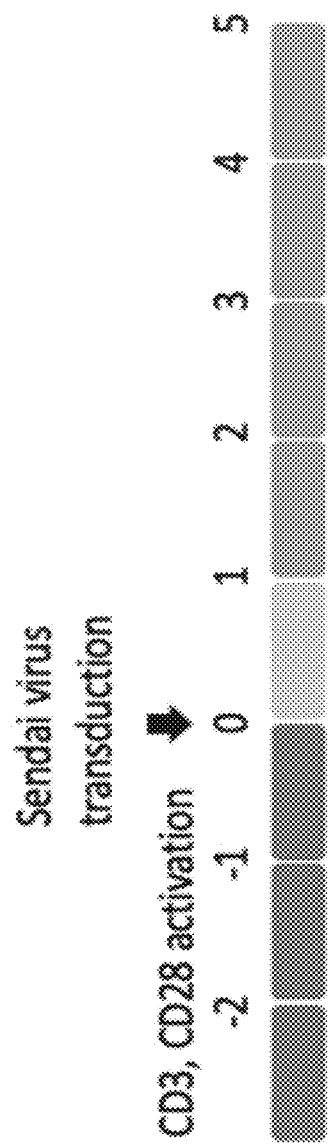
FIG. 1 shows the experimental design for partial reprogramming using Sendai virus transduction. After isolation from peripheral blood mononuclear cells (PBMC), T cells were activated for three days with a CD3, CD28 activation culture media comprising IL2 (Day −2 to Day 0). On Day 0, cells were either (i) left undisturbed (Group #1); (ii) placed in a stem cell culture medium without IL2 (Group #2); (iii) placed in a stem cell culture media without IL2 and transduced with two Sendai viruses-one expressing EmGFP; and one expressing SV40 (Group #3); or (iv) placed in a stem cell culture media without IL2 and transduced with four Sendai viruses-expressing KOS (KLF4, OCT3/4, SOX2), KLF4, cMyc and SV40 (Group #4). Expression continued for five days.

The activated CD8 T cells were divided into four groups. Group #1 is a control group in which the T cells were cultured in the T cell culture medium during the entire process. Group #2 was not transduced with Sendai virus either and was cultured in stem cell medium (SCM) (StemFit Basic02 with bFGF, Ajinomoto) without IL2 from day 1. Cells for Groups #1 and #2 were seeded 50,000 cells per well of 96-well plate in triplicate. Group #3 was transduced with 23 multiplicity of infection (MOI) of EmGFP Sendai virus (Cytotune EmGFP Sendai Fluorescence reporter, Thermo), and 5 MOI of SV40 Sendai virus. Group #3 cells were plated at a density of 50,000 per well in a 24 well plate which was coated with recombinant human Laminin511-E8 fragment (iMatrix-511, Cat. No. T304, Takara) in triplicate according to the manufacturer protocol. Group #4 was transduced with 10 MOI KOS Sendai vector, 10 MOI of KLF4 vector, 3 MOI of cMyc vector, and 5 MOI of SV40 vector. Cells were cultured in SCM without IL2 from day 1 and plated at a density of 80,000 cells per well in a 24-well plate coated with iMatrix-511 in quadruplicate. See FIG. 1 and Table 2 for the complete experimental design.

TABLE 2

T cell rejuvenation experimental conditions

| Condition | Sendai virus transduction | Culture medium from day 1 |
|---|---|---|
| #1 | No | T cell culture medium with 60 IU/ml IL2 |
| #2 | No | Stem cell culture medium without IL2 |
| #3 | 23 MOI EmGFP, 5 MOI SV40 | Stem cell culture medium without IL2 |
| #4 | 10 MOI KOS, 10 MOI KLF4, 3 MOI cMyc, 5 MOI SV40 | Stem cell culture medium without IL2 |

Figure 2:
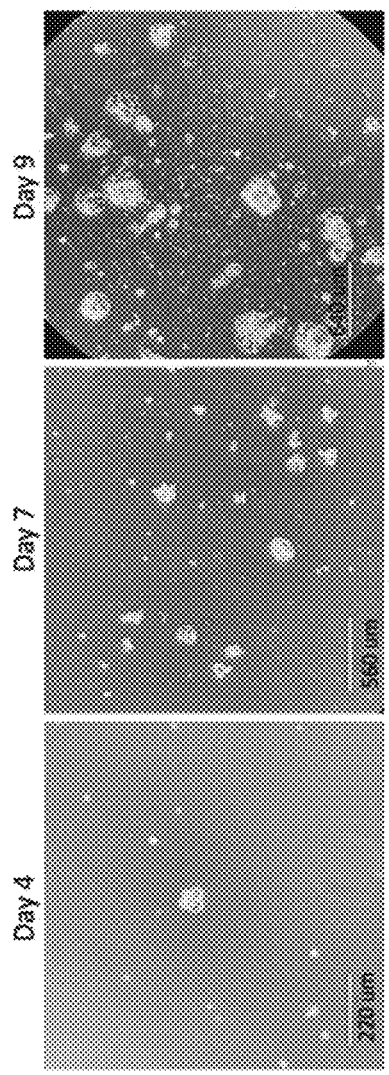
FIG. 2 shows the formation of colonies in Group #4 starting at Day 4 to Day 9 after transduction with Sendai virus expressing OSKM+SV40.
Figure 4:
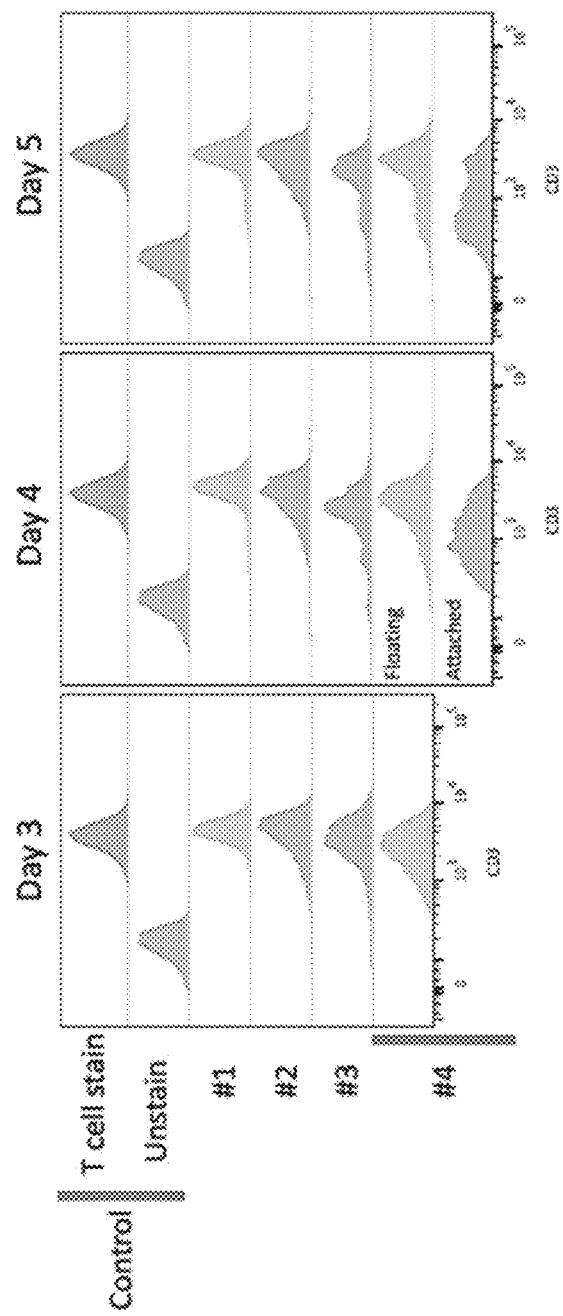
FIG. 4 shows CD3 expression on days 3, 4 and 5 of partial reprogramming Notably, the reprogrammed cells in Group #4 demonstrated a loss of CD3 over the course of partial reprogramming.

The T cells in Group #4 started colony formation from day 3 or day 4. See, FIG. 2. Cells attached to the bottom of the coated plate forming colonies is not seen in normal T cell culture. The T cells in the other conditions did not show any colony formation and did not attach to the bottom of the culture plate. FIG. 3 compares the attached cells from Group #4 (which expressed the four Yamanaka factors) with the appearance of the T cells from Group #3 (which did not express the Yamanaka factors; and instead expressed GFP). The attached cells showed colony formation and were bigger than the T cells in Group #3. This suggests that the T cell derived adherent cells were losing T cell identity. The T cell derived adherent cells from Group #4 are also bigger than standard activated T cells (FIG. 3D). FIGS. 3A-3F panels show T cells cultured under the various conditions as follows: 3A, 3C, 3E: attached colonies from Group #4; 3B: cells from Group #3; 3D: T cells cultured under standard T cell activation conditions; 3F: standard iPS cell colonies. As is evident from FIG. 3, the partially reprogrammed cells show a distinct morphology. Moreover, flow cytometry analysis showed decreased CD3 marker expression in Groups #2, #3, and #4 cells all of which were in stem cell medium without IL2 from day 1. See, e.g., FIG. 4. CD3 is an important marker of T cell identity among lymphocytes. The reduction was conspicuous in the T cell derived adherent cells of Group #4. This also suggests that the attached cells in Group #4 were losing T cell identity. Notably, this diverges from the work of other groups that have shown transient expression of the Yamanaka factors does not disturb cell fate but can still reverse aging and enhance efficacy of certain cell types. See, e.g., Sarkar et al., 2020, Nat Commun 11, 1545. Sarkar and colleagues demonstrated that "transient reprogramming does not disturb the myogenic fate but can enhance the myogenic potential" based on the result that Myogenic marker, MyoD, expression did not change after the transient reprogramming Here, T cell identity was at least partially transformed. Additionally, the attached cells of Group #4 were slightly bigger with a more complex structure as indicated by FSC/SSC FACS analysis (see FIG. 5 and FIG. 6).

Example 2: Reactivation of Partially Reprogrammed T Cells

Figure 5:
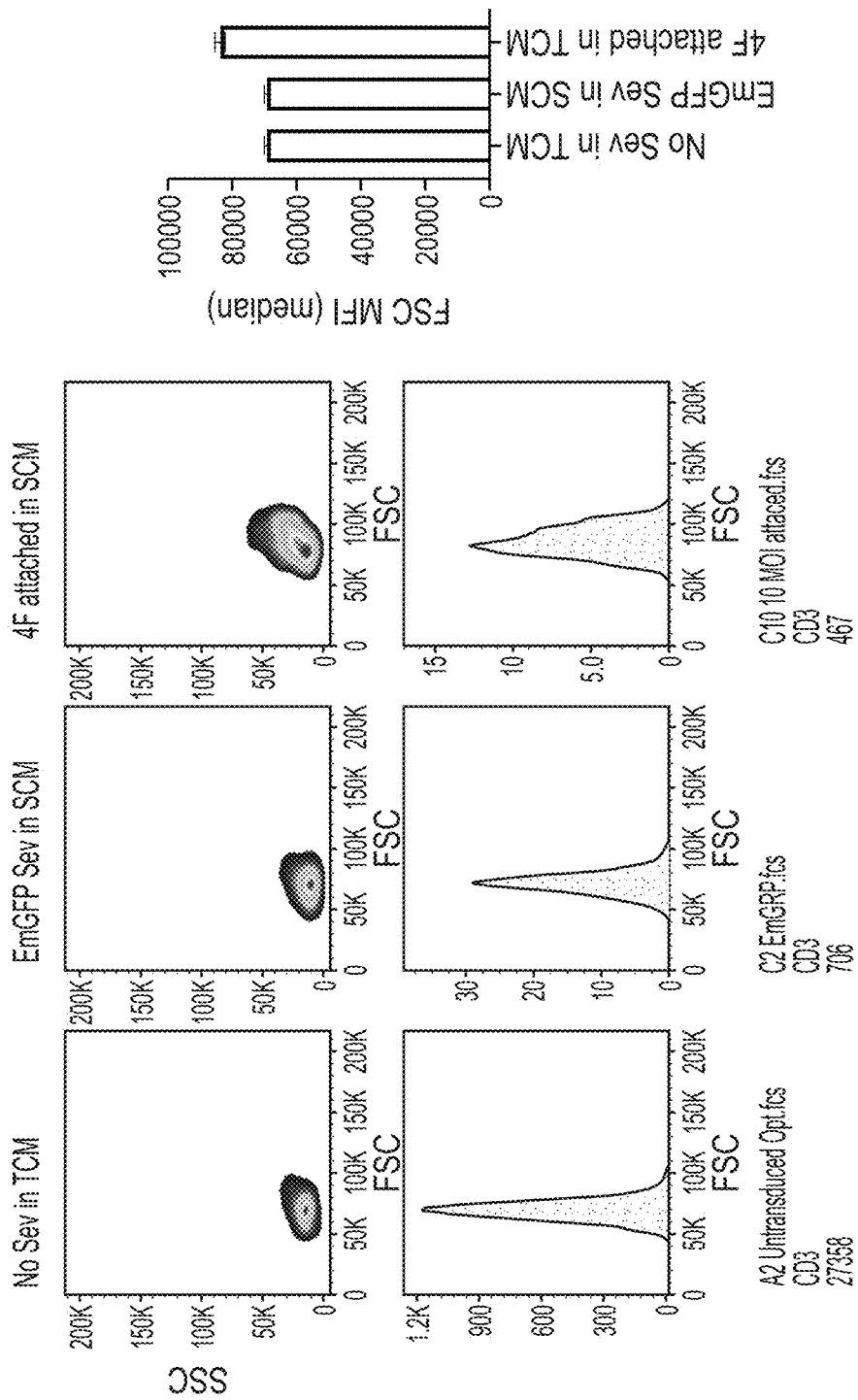
FIG. 5 shows a side scatter/forward scatter (SSC/FSC) FACS plot of the attached cells in Group #4 indicating that the attached cells are larger and have a more complex structure as compared to cells in Groups 1 and 3.
Figure 7:
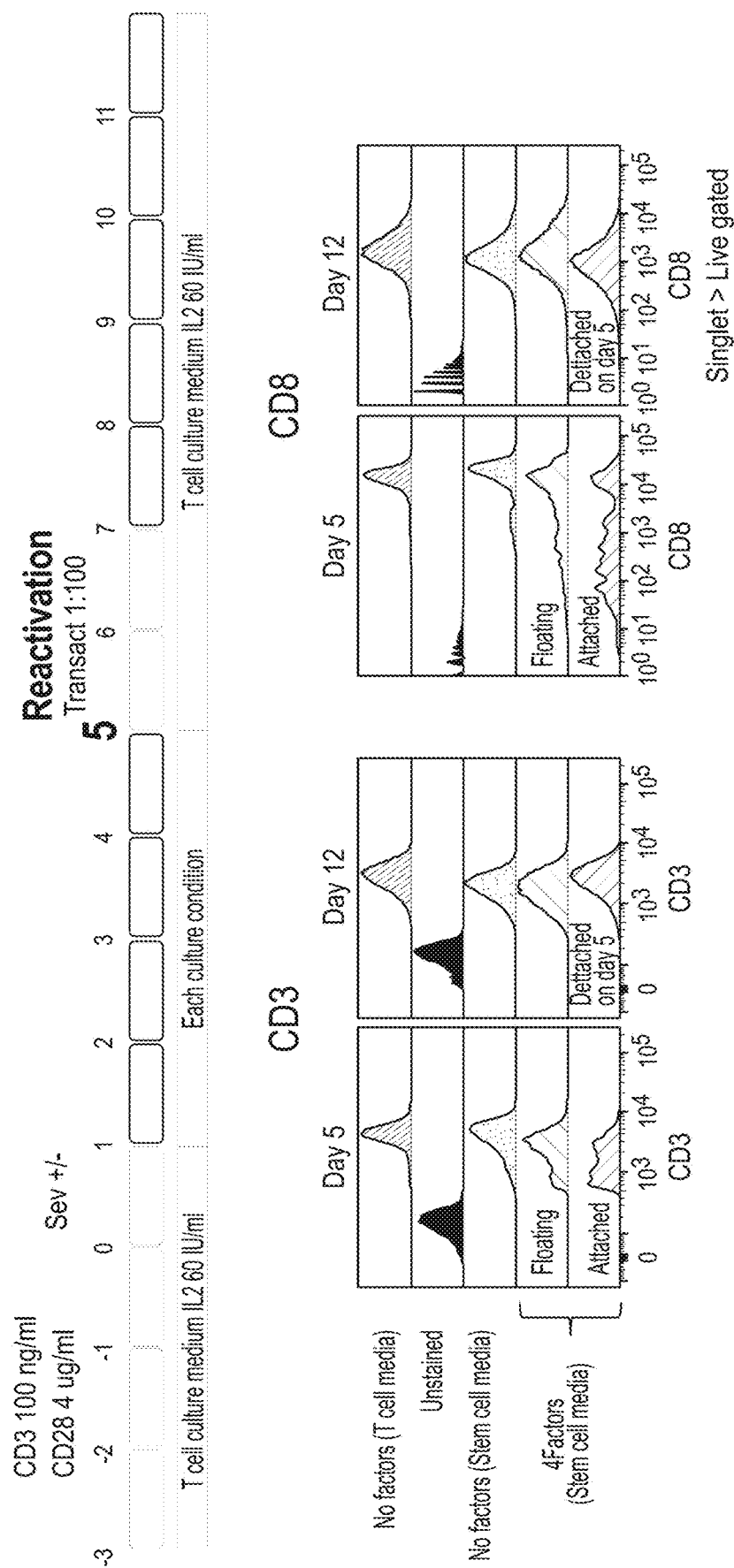
FIG. 7 shows that the attached cells in Group #4 regain CD3 and CD8 expression after T cell activation for two days followed by culture in T cell culture medium for five more days. T cells were activated at day 5 using one to one hundred diluted (1:100) T cell TRANSACT™ (Miltenyi Biotec) in T cell culture medium for 2 days in a 96 well plate. Cells in the Group #4 condition were divided into 2 wells at day 5, floating cells and attached cells which were harvested by pipetting. All the cells were cultured in T cell culture medium for 5 more days after activation.

Next, the partially reprogrammed T cells were reactivated on day five using one to one-hundred diluted T cell TRANS-ACT™ (Miltenyi Biotec) in T cell culture medium for 2 days in a 96 well plate. Cells in the Group #4 condition were divided into two wells at day 5—the floating cells were transferred to one well and the cells that were attached after being exposed to the reprogramming conditions were detached from the vessel surface, washed and transferred to another well. A large number of the cells from Group #3 died, likely due to the toxicity of Sendai virus. It is hypothesized that the Yamanaka factors expressed in Group #4 were able to rescue the cells from Sendai virus toxicity. All cells were cultured in T cell culture medium for an additional five days after activation. As shown in FIG. 5, cells which were losing CD3 and CD8 expression at day 5 of reprogramming regained expression of these genes at day 12. See, e.g., FIG. 7.

Figure 8:
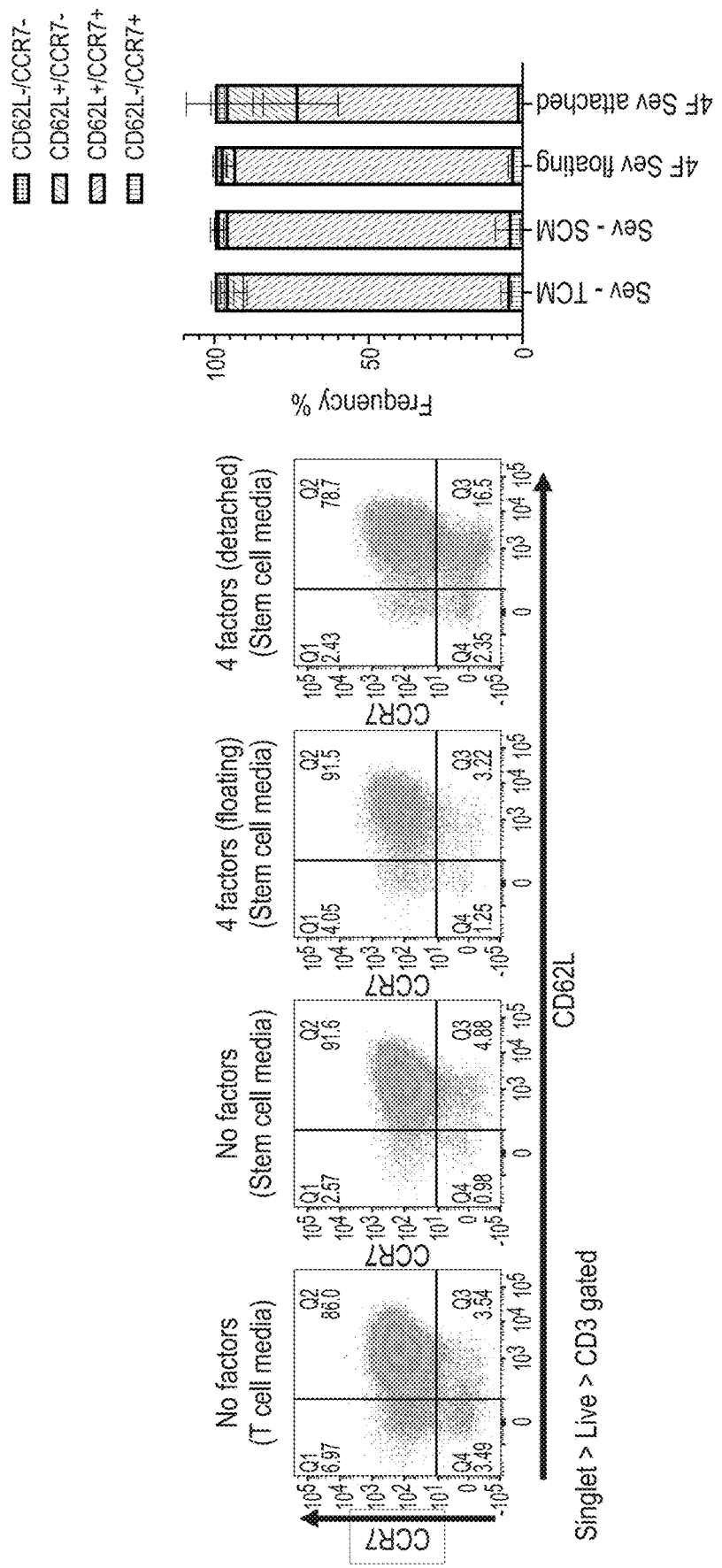
FIG. 8 shows the phenotype of CD3 positive cells at day 12. CCR7 and CD62L are markers to detect certain T cell types, such as naïve, memory stem cells, and central memory T cells. The cells regained CD3 expression at day 12 indicating a return to T cell phenotype.

In addition to regaining CD3 expression at Day 12, reactivated T cells demonstrated expression of CCR7 and CD62L, T cell homing markers which suggest a naïve T cell population. See, e.g., FIG. 8.

Figure 9:
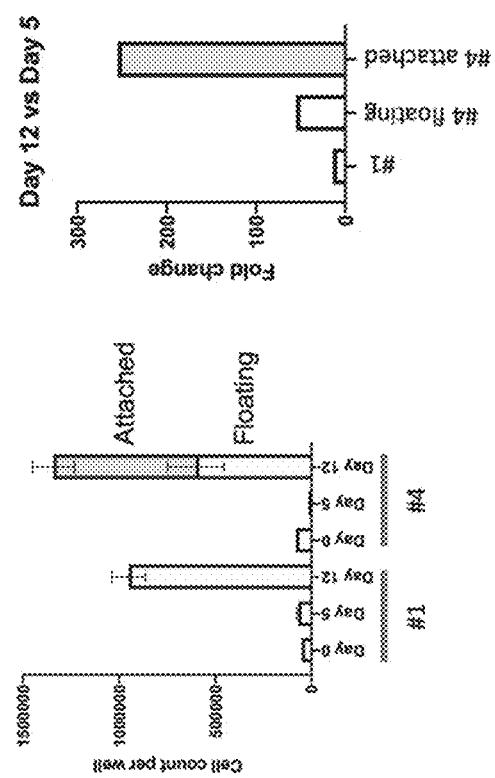
FIG. 9 is a bar graph that depicts cell expansion at Day 0, Day 5 and Day 12. Cell expansion was measured by counting beads (123 count eBeads Counting beads, Thermo) using flow cytometry. Though attached cells in group #4 showed aberrant appearance and reduced CD3 expression at day 5, after activation from day 5, they responded to the activation and expanded. The fold change of day 12 versus day 5 indicated increased expansion of #4 compared to #1 especially for attached cells. This indicates that the partial rejuvenation method used herein increases T cell expansion potential especially in the attached cells.

To assess T cell expansion, cells were counted on Days 0, 5 and 12 by counting beads (123count eBeads Counting beads, Thermo) using flow cytometry. Although attached cells in Group #4 showed aberrant appearance and reduced CD3 expression at day 5, following activation, they showed robust cell expansion. As shown in FIG. 9 the fold change in cell numbers on day 12 versus day 5 demonstrated increased expansion of the cells from Group #4 as compared to Group #1. This indicates that the partial reprogramming methods described herein increase T cell expansion potential, especially in the attached cells.

Figure 10:
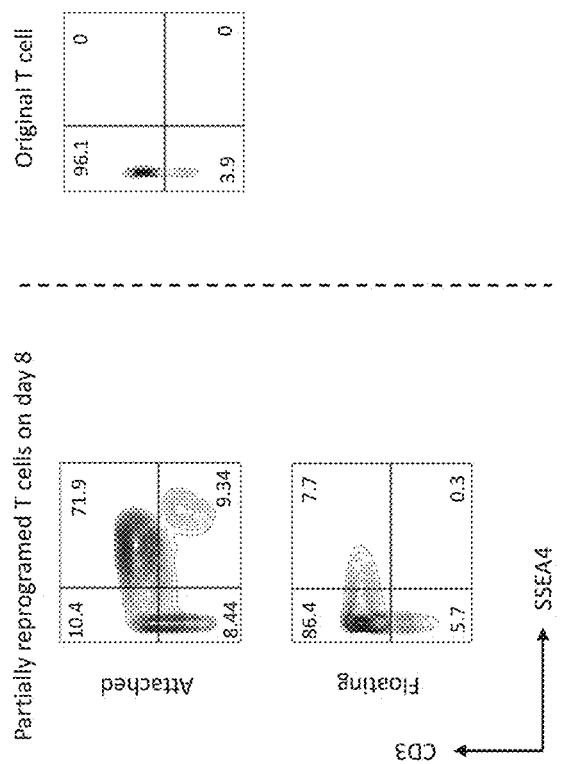
FIG. 10 is a FACS contour plot analysis of SSEA4 and CD3 expression in partially reprogrammed T cells. Sendai virus infected T cells as described in Example 2 were transferred onto iMatrix coated dishes on day 1 and were cultured in iPS cell media+60 IU/ml IL2 for 3 days and then changed to iPS cell media without IL2 from day 4. FACS analysis was performed on day 8 of reprogramming. The figure shows that partially reprogrammed T cells express the hiPS cell marker SSEA4 and lose expression of the CD3 T cell marker.

In a similar experiment, PBMC derived CD8 T cells were stimulated with TRANSACT for 1 day as described above. The next day, reprogramming factors (Yamanaka factors+ SV40) were introduced into the T cells by Sendai virus transduction also as described above. The infected T cells were transferred onto iMatrix coated dishes on day 1 and were cultured in (a) T cell media+60 IU/ml IL2 or (b) in iPS cell media 60 IU/ml IL2 for 3 days and then changed to iPS cell media without IL2 from day 4. On day 8, the floating and attached cells were harvested for flow cytometry analysis. In particular, to monitor T cell reprogramming more precisely, SSEA4 and CD3 expression were analyzed. SSEA4 is a carbohydrate epitope considered a wide-ranging stem cell marker expressed from partially reprogrammed somatic cells all the way to pluripotent stem cells. Remarkably, no attached colonies were detected in condition (a), suggesting that the culture conditions can have an impact on T cell reprogramming. As shown in FIG. 10, at day 8, the FACS analysis showed that 71.9% of the attached cells were CD3 and SSEA4 positive indicating that the attached cells express both T cell lineage markers as well as stem cell markers. A population of cells was observed that were SSEA4 high and CD3-negative. Compared with attached cells, very few floating cells in condition (b) expressed SSEA4, and no SSEA4 high CD3− population was observed. As expected, no SSEA4+ cells were found after culture condition (a) (standard T cell culture conditions). This data strongly suggests that the partially reprogrammed T cells that form attached colonies (the T cell derived adherent cells) are de-differentiated (i.e., partially de differentiated) and express SSEA4. Our observation was consistent with previous reports using fibroblasts for reprogramming to iPS cell (see e.g., Biol Open. 2017 Jan. 15; 6(1): 100-108).

Example 3: Measurement of Epigenetic Age

Horvath and colleagues have demonstrated that a cell's "epigenetic age" (eAge) can be estimated using a method that analyzes the methylation status at various DNA CpG cites in the cell genome. (Horvath et al., Aging, 10(7):1758-1775). In this example, the eAge of the T cells before and after partial reprogramming was calculated using the techniques described by Horvath and colleagues. Before partial reprogramming, the eAge for all experimental groups as described in Examples 1 and 2 and outlined in Table 1 was estimated at 21.5 years which is compatible with the actual (chronological) age of the donor. After reprogramming and subsequent T cell activation, Group #1 cells had a calculated eAge of 20.8 years, while the attached cells from Group #4 had a calculated eAge of 10.0 years old (note that cells that attach to the vessel surface during the partial reprogramming process detach from the surface upon or soon after activation. Such cells are referred to as "detached" cells to distinguish them from floating cells). This indicates that the partial reprogramming process resulted in rejuvenation of the cells from a measured eAge of 21.5 years to about 10 years. Floating cells in Group #4 had a calculated eAge of 14.5 years, and the T cells in Group #2 also had a calculated eAge of 14.6 years despite not being transduced with the four Yamanaka factors. This suggests that the stem cell culture medium itself (StemFit, Ajinomoto) contains components that provide some potential to rejuvenate cells although its contents are not publicly known. The results are summarized below in Table 3.

TABLE 3

Epigenetic age of partially reprogrammed T cells

| Condition | Horvath Epigenetic Age | Predicted counts of exhausted CD8 T cells |
| --- | --- | --- |
| Original cells | 21.2 | 6.5 |
| #1 | 20.8 | 10.4 |
| #2 | 14.6 | 7.9 |
| #3 floating | 14.5 | −1.6 |
| #3 attached>detached | 10.0 | −2.8 |

Figure 11:
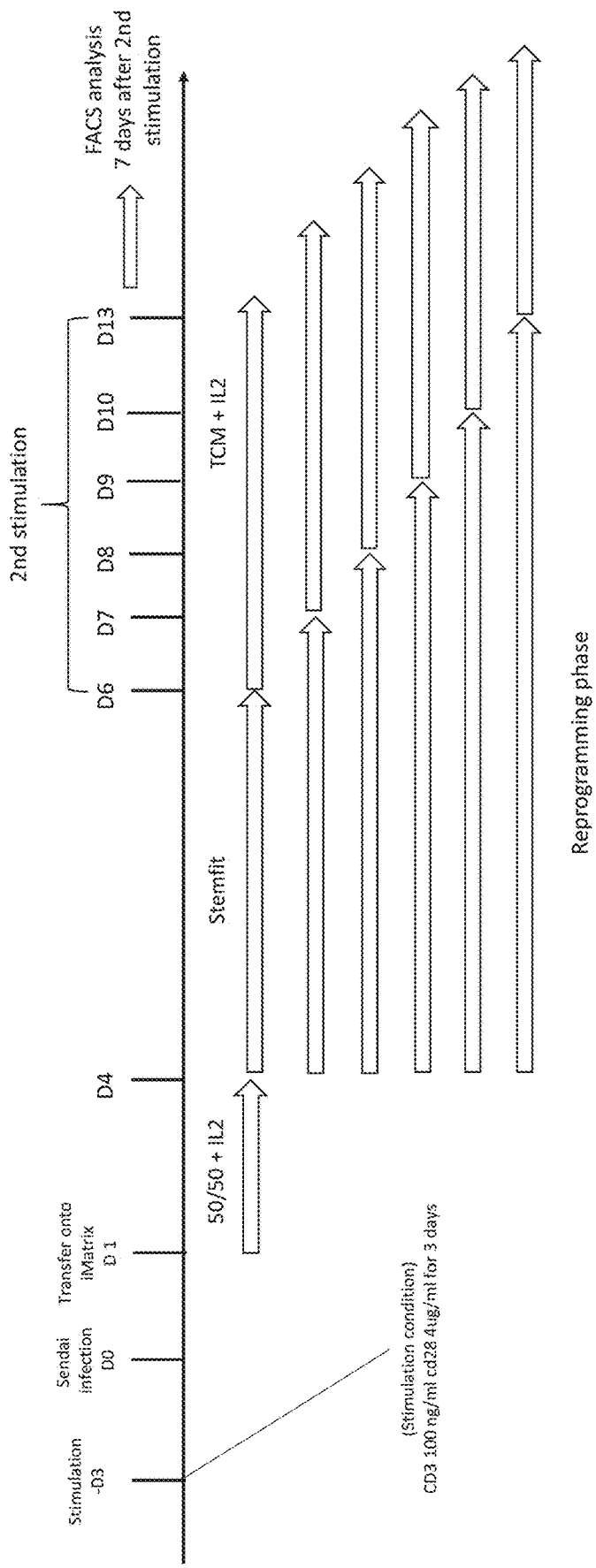
FIG. 11 is a schematic outlining the partial reprogramming of PBMC-derived CD8 T cells (See Example 4, Table 4).

Example 4: Partial Reprogramming Beyond Day 10 Resulted in Generation of Unconventional T Cells In this Example, a range of time points for the second stimulation (reactivation) was investigated. The experiment is outlined in Table 4 below. Sendai virus transductions were as follows: KOS 10MOI, KLF4 10MOI, cMyc 3MOI, SV40 5MOI and were carried out in TCM with 60 IU/ml IL2. The reprogramming culture conditions were 50/50 TCM/iPS media (Stemfit) with 60IU/ml IL2 for 3 days followed by culture in Stemfit w/o IL2 until the second activation. After reprogramming for the time periods indicated, the floating cells and the attached cells were harvested. Cells were then activated with TRANSACT at 1:100 in TCM+60 IU/ml IL2. Cells were then analyzed 7 days after the second stimulation by flow cytometry for expression of the following markers: CD3, CD4, CD8a, CD8β. FIG. 11 is a schematic summarizing the process for PBMC-derived CD8 T cells (see also Table 4).

TABLE 4

| xpt. No. | Pre-Sendai activation conditions | T cells | Timing for 2$^{nd}$ activation |
| --- | --- | --- | --- |
| | CD3 100 ng/ml CD28 4 ug/ml for 3 days | CD8+ T cells from PBMC | Day 6-Day 10 and Day 13 |

Generally, conventional cytotoxic T cells express CD8α-CD8β heterodimer. Non-conventional T cells, for instance intraepithelial lymphocyte (IEL) and gamma deltT cells express CD8αα homodimer. As such, in this experiment, FACS was used to determine whether the T cells generated using the partial rejuvenation process were able to express the canonical CD8 T cell markers. Lack of CD8αβ expression post-stimulation could indicate that the partially rejuvenated T cells are not conventional cytotoxic T cells.

Figures 12A, 12B:
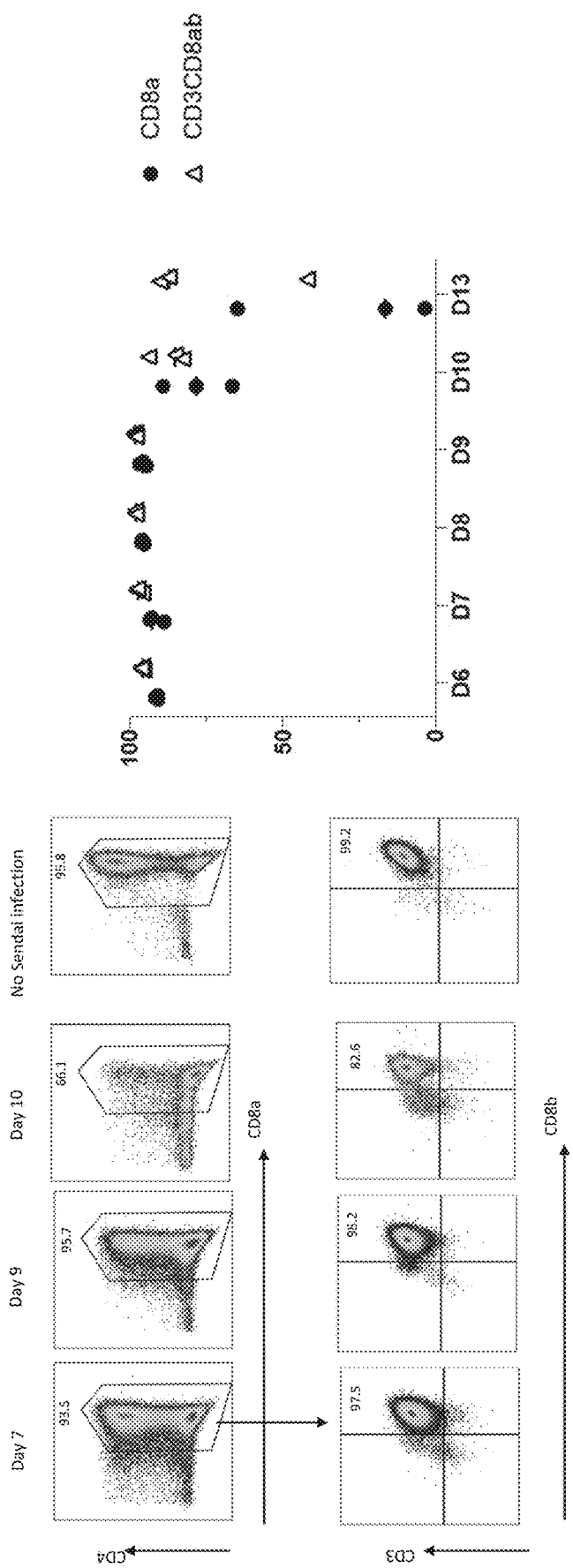
FIGS. 12A-12B show results from flow cytometry measuring CD8a, CD8b, CD3 in cells that have been partially reprogrammed for the indicated number of days prior to reactivation.

As shown in FIG. 12A and FIG. 12B, T cell derived adherent cell colonies reactivated with TCM from days 6-10 express CD8α and CD8β indicative of a return to a normal CD8 T cell phenotype. Delay of reactivation past day 10 of the current reprogramming method to return the de-differentiated T cells to the T cell phenotype resulted in an increase of CD4-CD8− population (see FIG. 12A, upper and lower panels at day 10 where the CD8α expression is shifting to the left side (lower MFI). As noted above, CD8α negative cells are not matured T cells. After day 10, when gating on the CD8α positive population, more CD8β negative cells (CD8αα+ non-conventional T cells) were observed (see FIG. 12B day 13 FACS plots).

Example 5: Cytokine Production Assay and Degranulation Assay of Rejuvenated NY-ESO-1 TCR Transduced T Cells Demonstrate T Cell Functionality To test whether partially reprogrammed T cells retain antigen-specificity, CD8+ T cells genetically modified to express an NY-ESO-1-specific TCR were partially reprogrammed, stimulated with T cell activation molecules and the response to target cells pulsed with NY-ESO-1 peptide was measured.

Peripheral blood-derived CD8+ T cells from a 42-year old male were purchased from Allcells (Alameda, CA). Cells were thawed and stimulated with TRANSACT (1/100) in TCM with IL-2 (60 IU/ml) as described in Example 4. The next day, T cells were transduced with NY-ESO-1 TCR by lentivirus vector transduction as follows:

For lentiviral transduction, the T cells were stimulated with a 1:100 dilution of T cell TRANSACT (Miltenyi) for 30 hours. Virus was then added to the T cells for 24 hours. Stimulation and viral infection were then terminated by addition of 7 volumes of fresh media without TRANSACT, and cells were cultured for 7 additional days in Grex-24 plates (Wilson Wolf) prior to cryopreservation in CryoStor CS10 (STEMCELL Technologies) at 3×10$^7$ cells/ml (see also Robbins 2008 J Immunol, 180(9) 6116-6131). Control T cells were not transduced and stimulated similarly.

Figure 13:
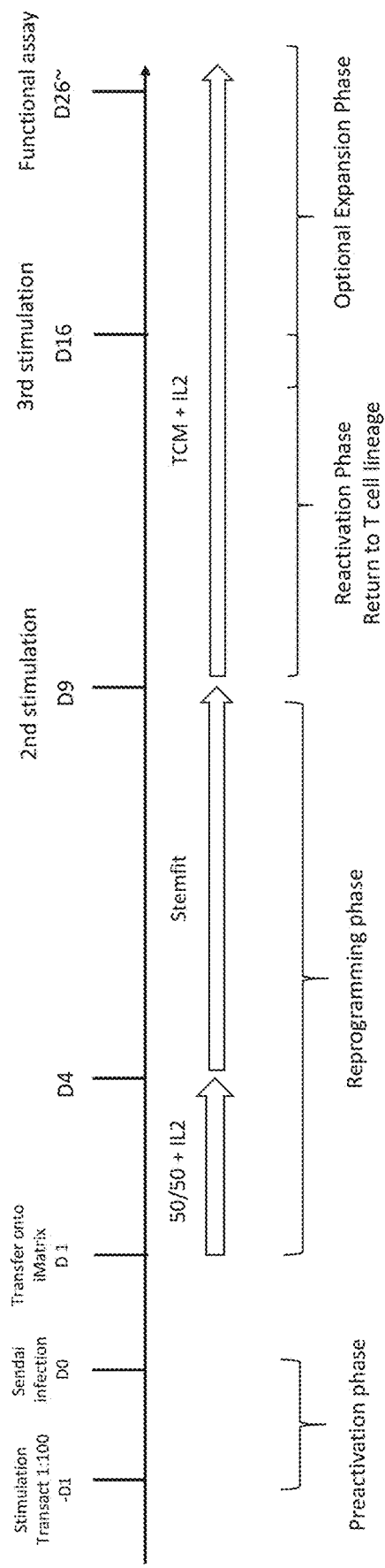
FIG. 13 is a schematic outlining the partial reprogramming and reactivation of NY-ESO-1+ T cells. The different phases of the full process are labeled for clarity.

For partial reprogramming and reactivation, NY-ESO-1 specific T cells were thawed and stimulated with TRANSACT (1/100) in TCM with IL-2 (60 IU/ml). On day 2, T cells were infected with Sendai virus containing four Yamanaka factors (KOSM MOI=10) and SV40 large T antigen (MOI=3). The cells were then stimulated on day 9 with TRANSACT to obtain the rejuvenated NY-ESO-1 specific T cells (second stimulation) as described above. For the functional assay, the rejuvenated NY-ESO-1-specific T cells were re-stimulated with TRANSACT again at day 16 (3rd stimulation) to expand them (see FIG. 13).

Cytokine production and degranulation assays were carried out on day 26 as follows. Control non-transduced T cells and NY-ESO-1 specific TCR transduced T cells were thawed and stimulated with TRANSACT (1/500) in TCM with IL-2 (60 IU/ml) one week in order to expand. Non transduced T cells, NY-ESO-1 specific TCR transduced T cells and rejuvenated NY-ESO-1 specific TCR T cells were compared to effector cells. Target cells, T2 were cultured in T2 media (RPMI, 20% FCS and P/SM). T2 cells were pre-cultured with or without NY-ESO-1 peptide (SLLMWITQC) (10 nM) for one hour, washed and counted. One well contained 5×10$^4$ effector cells and 1×10$^5$ target cells (E:T ratio of 2:1). As positive control, PMA/Ionomycin (Cell Activation Cocktail by Biolegend) were added according to manufacturer instruction. GolgiPlug and GolgiStop (BD Biosciences) were added according to manufacturer instructions. Also, anti-CD107a Ab-BV421 were added in culture media (1 ul/well). Cells were cultured for six hours in TCM without cytokines. The co-cultured cells were then stained for surface antigens (PE-NY-ESO-1 tetramer, BUV395-CD8, BUV496-CD4, and BUV805-CD3). Live/dead eFluor 780 was also added to exclude dead cells. After 20 minutes cells were washed. Cells were fixed and permeabilized by BD cytofix/cytoperm kit according to manufacturer instruction.

The cells were then stained for intracellular cytokine expression (FITC-IFNg, APC-IL-2, and BV785-TNFa). After a 30-minute incubation, cells were washed twice and analyzed by flow cytometry using a ZE5 instrument. The FACS results were analyzed by FlowJo software. Single cells>Live cells>CD3+>CD8+CD4–>NY-ESO-1 tetramer+ cells were gated for NY-ESO-1 Tg T cells and Single cells>Live cells>CD3+CD8+CD4–>NY-ESO-1 tetramer– cells were gated for mock control T cells. The frequency of IFNg+, TNFa+, IL-2+, and CD107a+ were calculated as shown in FIG. 14. The results showed that the rejuvenated NY-ESO-1+ transduced T cells retain functionality and are antigen-specific.

Example 6: Surface Protein Profiling of T Cells, iPS and Partially Reprogrammed T Cells In this Example, cell surface proteins were profiled in activated T cells, unstimulated T cells, iPS cells and day 5 attached partially reprogrammed T cells (T cell derived adherent cells). The purpose of the screen was to identify markers expressed in partially reprogrammed cells that can be used to identify intermediate cells and to characterize the partial reprogramming process and cells produced using the method.

T cell culture media (TCM) was prepared as previously described. For the initial screen, CD4+ and CD8+ T cells (cell ID 3046087I&K from Allcells) were thawed. T cells were stimulated with 100 ng/ml anti-CD3 and 2 ug/ml anti-CD28 (anti-human CD3 OKT3 and CD28 CD28.2 antibodies from BioLegend, San Diego, CA), plus 60IU IL-2 for three days. The cord blood-derived iPS cell line, NLSGFP, and tumor infiltrating lymphocyte (TIL) derived iPS cell line, hi4095 #8, were cultured in Stemfit and harvested. T cells and iPS cells were stained with BioLegend LEGENDScreen (BioLegend, San Diego, CA) plus anti-CD8, CD4, CD3, SSEA4, Live/Dead and expression level of 371 markers was determined using flow cytometry.

Figure 15:
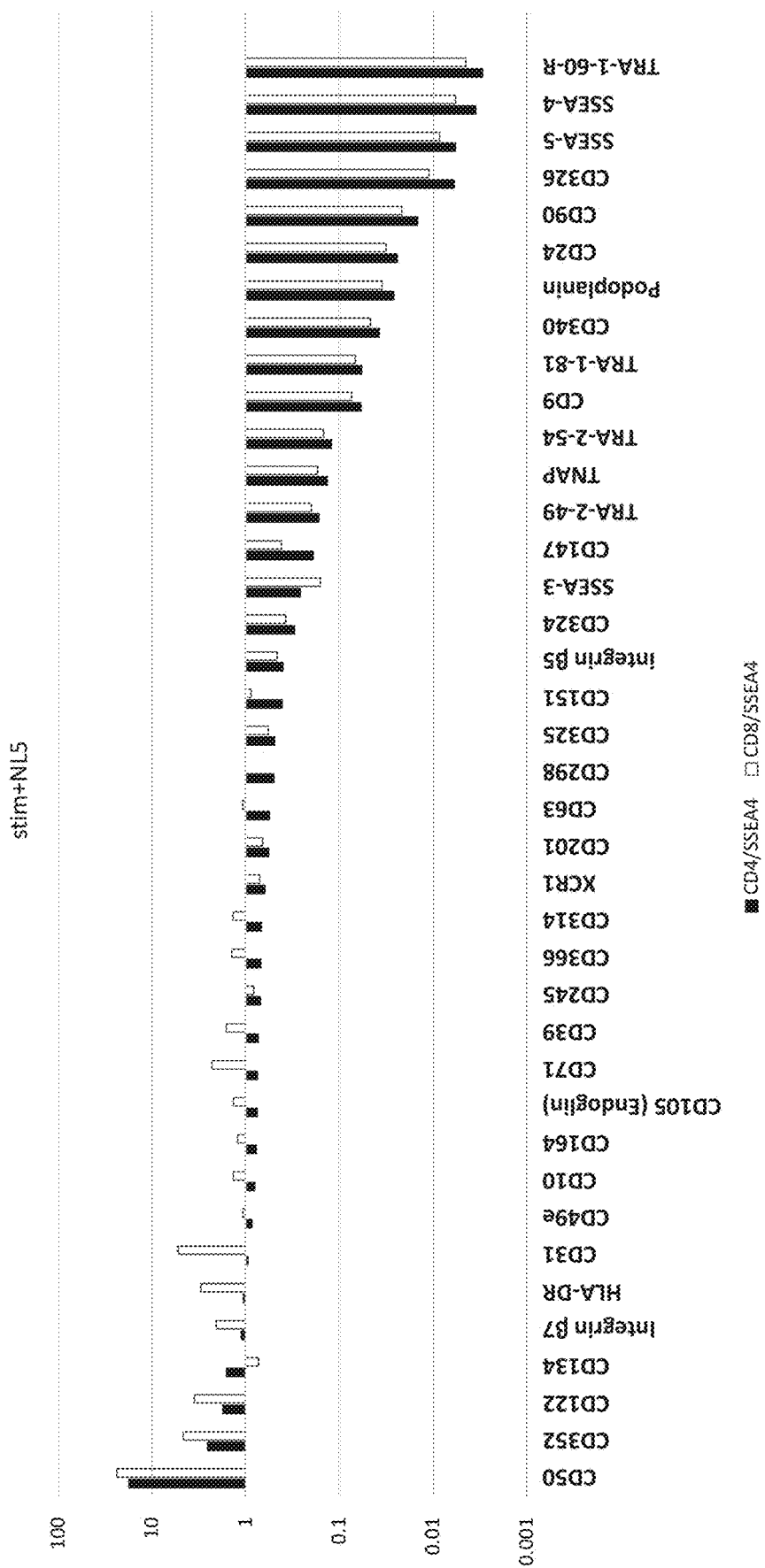
FIG. 15 is a waterfall plot of the ratio of the level of cell surface marker expression in stimulated T cells versus T cell derived iPS cell (see also Table 5).
Figure 16:
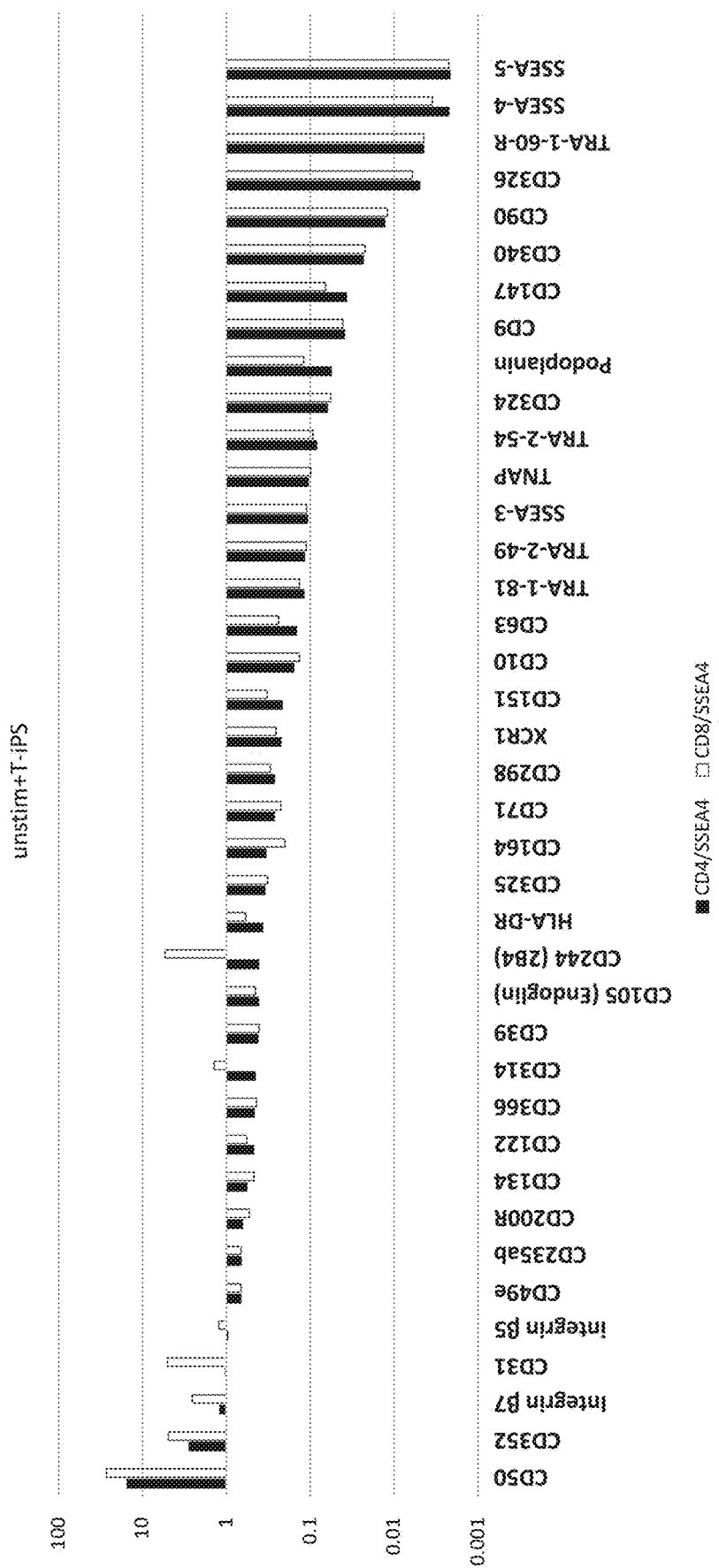
FIG. 16 is a waterfall plot of the ratio of the level of cell surface marker expression in unstimulated T cells versus T cell derived iPS cells (see also Table 5).

The results of the initial screen identified 39 candidate markers as listed below, chosen based on their expression level in T cells and iPS cells. Markers were selected that showed significantly higher level in stimulated or unstimulated T cells versus iPS cells or that showed a different expression pattern between iPS cells and T-iPS cells. These markers and the ranking of their relative expression levels in stimulated or unstimulated T cells versus iPS cells are summarized in Table 5 below. The data are also shown graphically in a waterfall plot in FIG. 15 (stimulated T cells versus NLSiPS cells) and FIG. 16 (unstimulated T cells versus T-iPS cells).

TABLE 5

Candidate Cell Surface Markers in Partially Reprogrammed T cells

| | | Ranking from high to low expression in T cells versus iPS | | | | |
|---|---|---|---|---|---|---|
| | | Stimulated T Cells | | Unstimulated T Cells | | |
| Name | CD | CD4/ iPS | CD8/ iPS | CD4/ T-iPS | CD8/ T-iPS | AVERAGE |
| ICAM-3 | CD50 | 10 | 11 | 8 | 7 | 9 |
| | CD352 | 32 | 29 | 28 | 28 | 29.25 |
| | CD31 | 65 | 27 | 45 | 26 | 40.75 |
| | Integrin β7 | 53 | 47 | 43 | 36 | 44.75 |

TABLE 5-continued

Candidate Cell Surface Markers in Partially Reprogrammed T cells

| | | Ranking from high to low expression in T cells versus iPS | | | | |
|---|---|---|---|---|---|---|
| | | Stimulated T Cells | | Unstimulated T Cells | | |
| Name | CD | CD4/ iPS | CD8/ iPS | CD4/ T-iPS | CD8/ T-iPS | AVERAGE |
| Integrin a5 | CD49e | 72 | 85 | 90 | 101 | 87 |
| | CD122 | 43 | 35 | 272 | 136 | 121.5 |
| NKG2D | CD314 | 122 | 63 | 283 | 50 | 129.5 |
| | HLA-DR | 55 | 38 | 320 | 130 | 135.75 |
| | CD134 | 45 | 167 | 148 | 246 | 151.5 |
| | CD245 | 110 | 123 | 259 | 238 | 182.5 |
| Endoglin | CD105 | 96 | 65 | 310 | 264 | 183.75 |
| Tim-3 | CD366 | 114 | 62 | 280 | 281 | 184.25 |
| | CD39 | 101 | 57 | 303 | 297 | 189.5 |
| | integrin β5 | 336 | 332 | 54 | 54 | 194 |
| | CD71 | 97 | 43 | 335 | 343 | 204.5 |
| | CD164 | 88 | 74 | 326 | 349 | 209.25 |
| | CD10 | 81 | 64 | 352 | 355 | 213 |
| | CD63 | 219 | 84 | 353 | 340 | 249 |
| | XCR1 | 150 | 178 | 344 | 339 | 252.75 |
| | CD298 | 293 | 94 | 336 | 326 | 262.25 |
| | CD201 | 206 | 226 | 343 | 330 | 276.25 |
| | CD151 | 334 | 110 | 347 | 321 | 278 |
| N-Cadherin | CD325 | 304 | 309 | 325 | 323 | 315.25 |
| E-Cadherin | CD324 | 347 | 348 | 361 | 364 | 355 |
| | CD147 | 356 | 343 | 364 | 363 | 356.5 |
| | SSEA-3 | 353 | 359 | 357 | 359 | 357 |
| | TRA-2-49 | 358 | 357 | 356 | 358 | 357.25 |
| | TNAP | 359 | 358 | 358 | 360 | 358.75 |
| | TRA-1-81 | 364 | 364 | 355 | 356 | 359.75 |
| | TRA-2-54 | 360 | 360 | 359 | 361 | 360 |
| | Podoplanin | 367 | 367 | 362 | 357 | 363.25 |
| | CD9 | 363 | 363 | 363 | 365 | 363.5 |
| | CD340 | 365 | 365 | 366 | 366 | 365.5 |
| | CD24 | 368 | 368 | 367 | 367 | 367.5 |
| | CD90 | 369 | 369 | 368 | 368 | 368.5 |
| EpCAM | CD326 | 370 | 370 | 369 | 369 | 369.5 |
| | SSEA-5 | 371 | 371 | 372 | 372 | 371.5 |
| | SSEA-4 | 372 | 372 | 371 | 371 | 371.5 |
| | TRA-1-60-R | 373 | 373 | 370 | 370 | 371.5 |

In a second screen, CD4+ and CD8+ T cells (cell ID 3046087I&K from Allcells) were thawed and stimulated with 100 ng/ml anti-CD3 and 2 ug/ml anti-CD28, plus 60IU IL-2. After three days, T cells were transduced with 10 MOI KOS Sendai vector, 10 MOI of KLF4 vector, 3 MOI of cMyc vector, and 5 MOI of SV40 vector as described in previous examples. After 5 days, attached cells were harvested and screened as described above for surface expression of the markers identified in the first screen. Unstimulated T cells, stimulated T cells, NL5 iPS cells and hi4095 iPS cells were used as controls.

Figure 17:
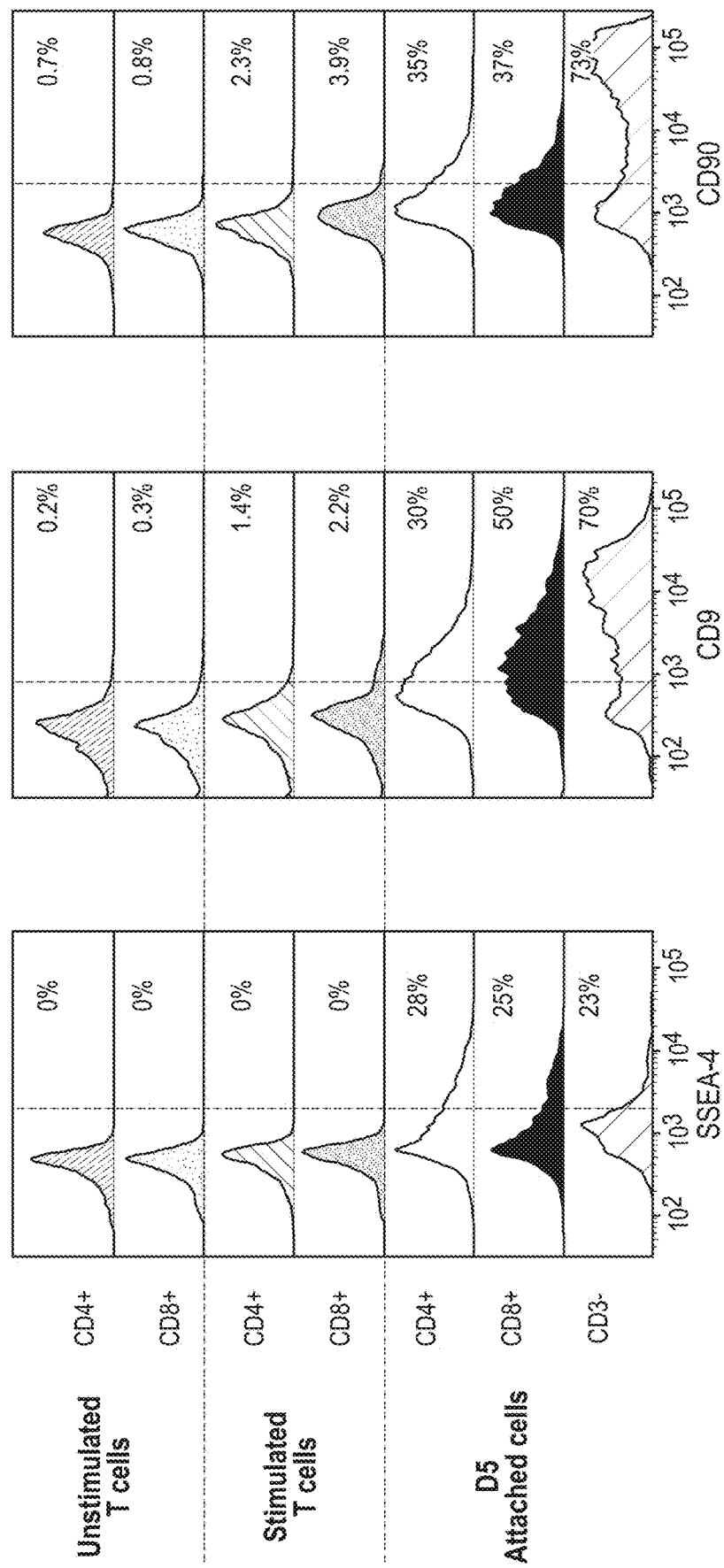
FIG. 17 shows that CD9 and CD90 are potential cell surface marker indicators of the early phase of partial reprogrammed T cells. The figure shows the flow cytometry analysis of the expression of CD9 and CD90 in stimulated T cells, unstimulated T cells and day 5 attached partially reprogrammed T cells (T cell derived adherent cells). Expression of the early iPS cell surface marker SSEA4 is not significantly changed at day 5 in T cell derived adherent cells, in contrast to expression of CD9 and CD90.

Expression of CD164, CD9, CD63, CD90, CD71, CD326, TRA-1-81 and TRA-1-60-R expression were found to be increased in Day 5 partially reprogrammed attached cells as compared to stimulated and unstimulated T cells, while CD352 and CD31 were downregulated. As shown in FIG. 17, this second screen identified CD9 and CD90 as potential indicators of the early transition during partial reprogramming while at day 5, expression levels of known iPS cell markers SSEA3 and SSEA4 were not significantly changed. CD9 is also known as tetraspanin-29 and has four transmembrane domains. It is involved in cell adhesion, signal transduction and cellular differentiation. CD90 is also known as THY-1. It is an immunoglobulin superfamily surface glycoprotein and is a marker associated with mesenchymal stem cells. It is also involved in cell adhesion and communication. Thus, the expression of these two markers may explain the attachment properties gained in the dedifferentiated T cells. The expression of these two markers also suggests that the partially reprogrammed T cells are dedifferentiating to an unknown type of cell that, to the best of the inventors' knowledge, has not been identified as a differentiational cell stage corresponding to the T cell lineage hierarchy.

Example 7: Stimulation Signaling is Critical for Rejuvenated T Cells to Survive and Proliferate To determine whether stimulation signaling was critical to the enhanced survival and proliferation, T cell adherent cells were subject to TRANSACT™ (Miltenyi Biotec) activation at varying concentrations.

First, T cells were partially reprogrammed using the methods described in Example 1. Briefly, CD8 positive T cells were stimulated with soluble CD3 and CD28 TRANSACT™ (Miltenyi Biotec) for 3 days in T cell culture medium with 60 IU/ml IL2. After 3 days, T cells were transduced with 10 MOI KOS Sendai vector, 10 MOI of KLF4 vector, 3 MOI of cMyc vector, and 5 MOI of SV40 vector. Cells were cultured in SCM without IL2 from day 1 and plated at a density of 80,000 cells per well in a 24-well plate coated with iMatrix-511 in quadruplicate.

1 On day 7, the adherent cells were detached from the vessel surface, washed and transferred to another well. The T cell derived adherent cells were then either reactivated with diluted T cell TRANSACT™ (Miltenyi Biotec) at a concentration of 1:500 or 1:1000, or incubated in no stimulation media at all. All cells were cultured in T cell culture medium (TCM plus IL2 at 60 IU/ml) for an additional nine days after activation. As shown in FIG. 18A, T cell derived adherent cells had largely lost expression of CD3 and CD8a. However, by day 22, 93%-94% of cells activated with either concentration of TRANSACT had reacquired expression of conventional T cell markers, CD3 and CD8a, while only 8.4% of cells cultured in only TCM without TRANSACT were expressing CD3 and CD8a. In addition, as shown in FIGS. 18C and 18D, the activated T cells showed significantly greater ability to survive and proliferate, when compared to partially reprogrammed T cells that were cultured in T cell media without TRANSACT™.

Example 8: Rejuvenated T Cells Show Effector Phenotype After Long Term Expansion in the Presence of IL-2

In this example, the ability of rejuvenated T cells from different donors to survive and proliferate over time was examined Peripheral blood-derived CD8+ T cells from three donors (a 42-year-old male, a 37-year-old female, and a 52-year-old male) where purchased from Allcells, Alameda, CA Cells were thawed and stimulated with TRANSACT™ (Miltenyi Biotec) at a concentration of 1:500 in TCM with IL-2 (60 IU/ml).

Figure 20A:
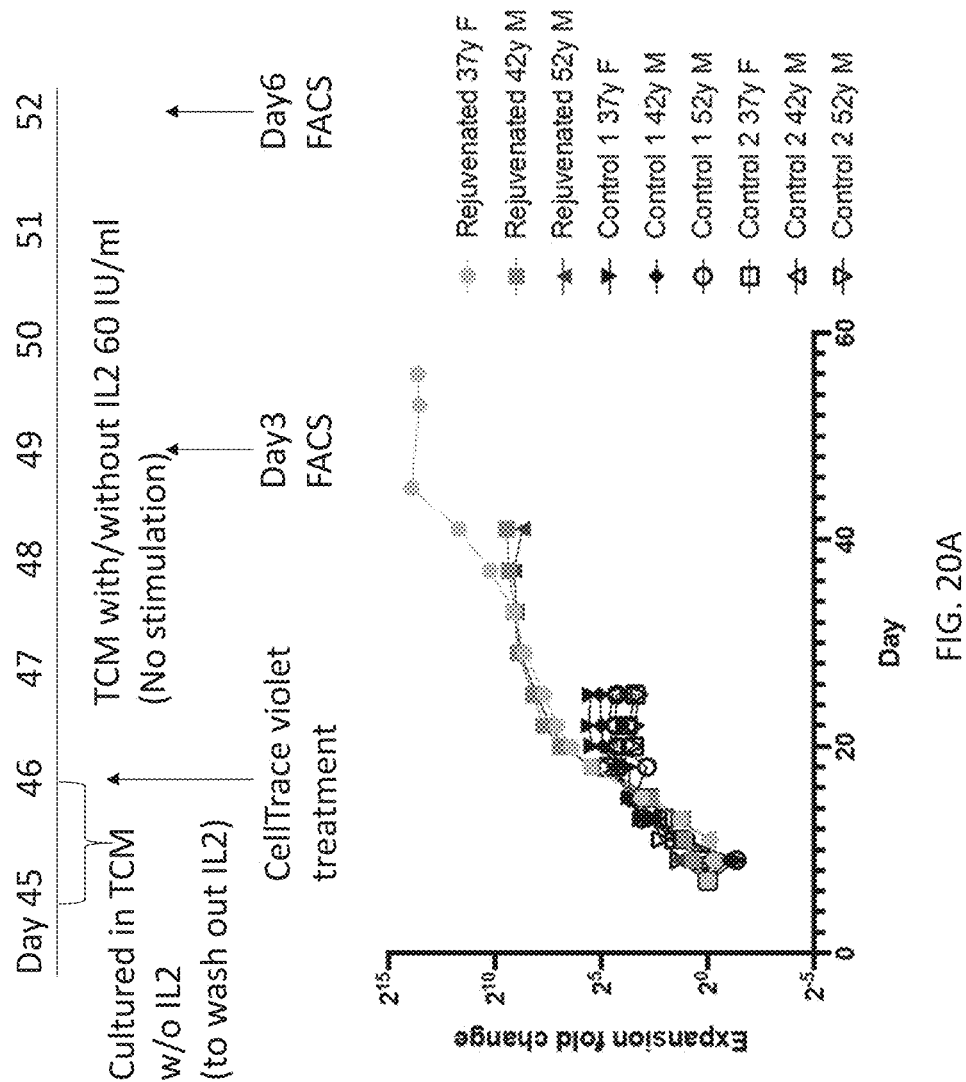
FIGS. 20A-20C show the effect of IL-2 on rejuvenated T cells. On day 45 after rejuvenation, the rejuvenated T cells were co-cultured in TCM without IL-2. The FACS results were analyzed by FlowJo software. Single cells>Live cells>CD3+ cells were gated for all cell groups. As can be seen from FIG. 20B and FIG. 20C, cells co-cultured without IL-2 died within six days.
Figure 20B:
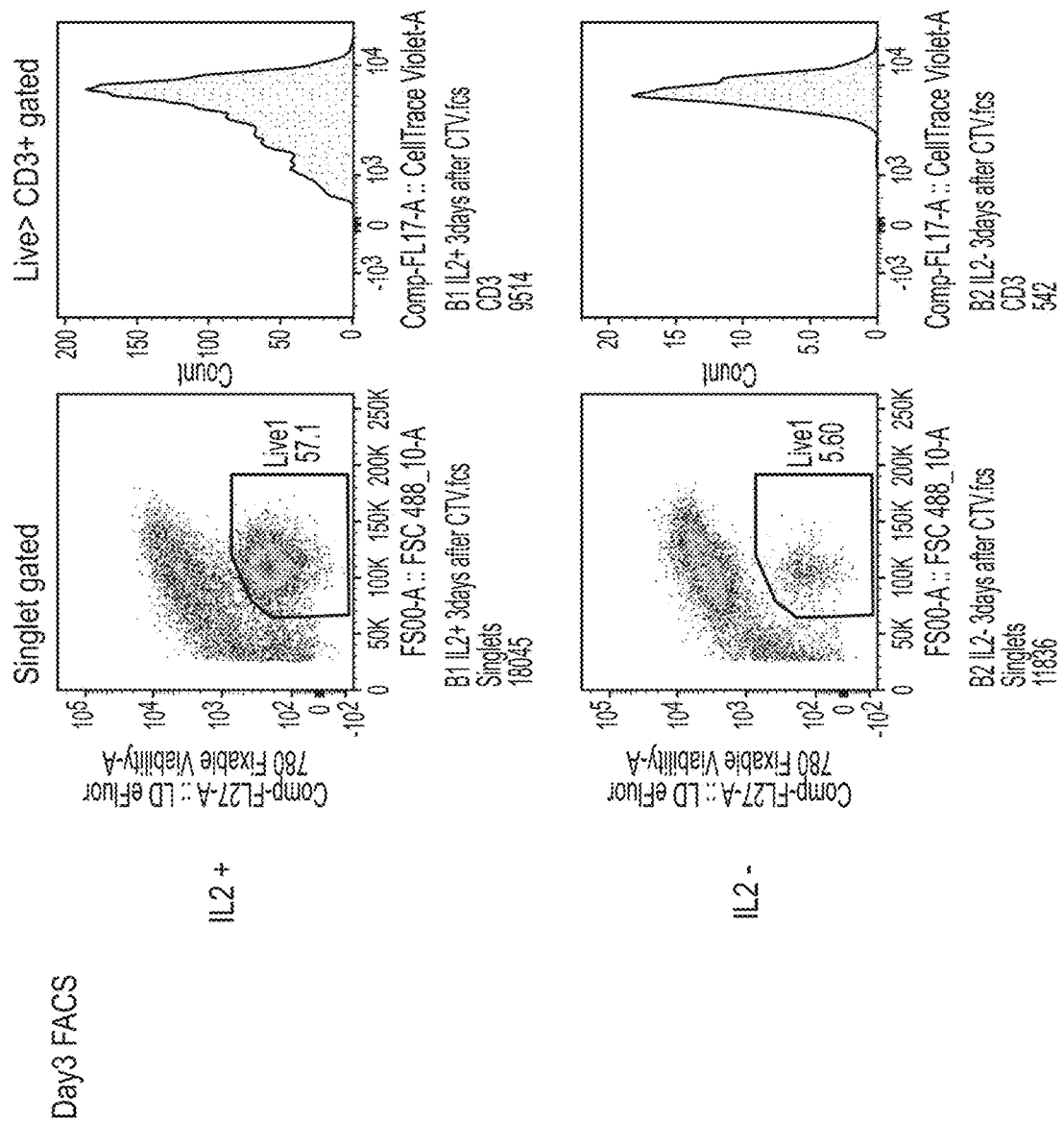
Figure 20C:
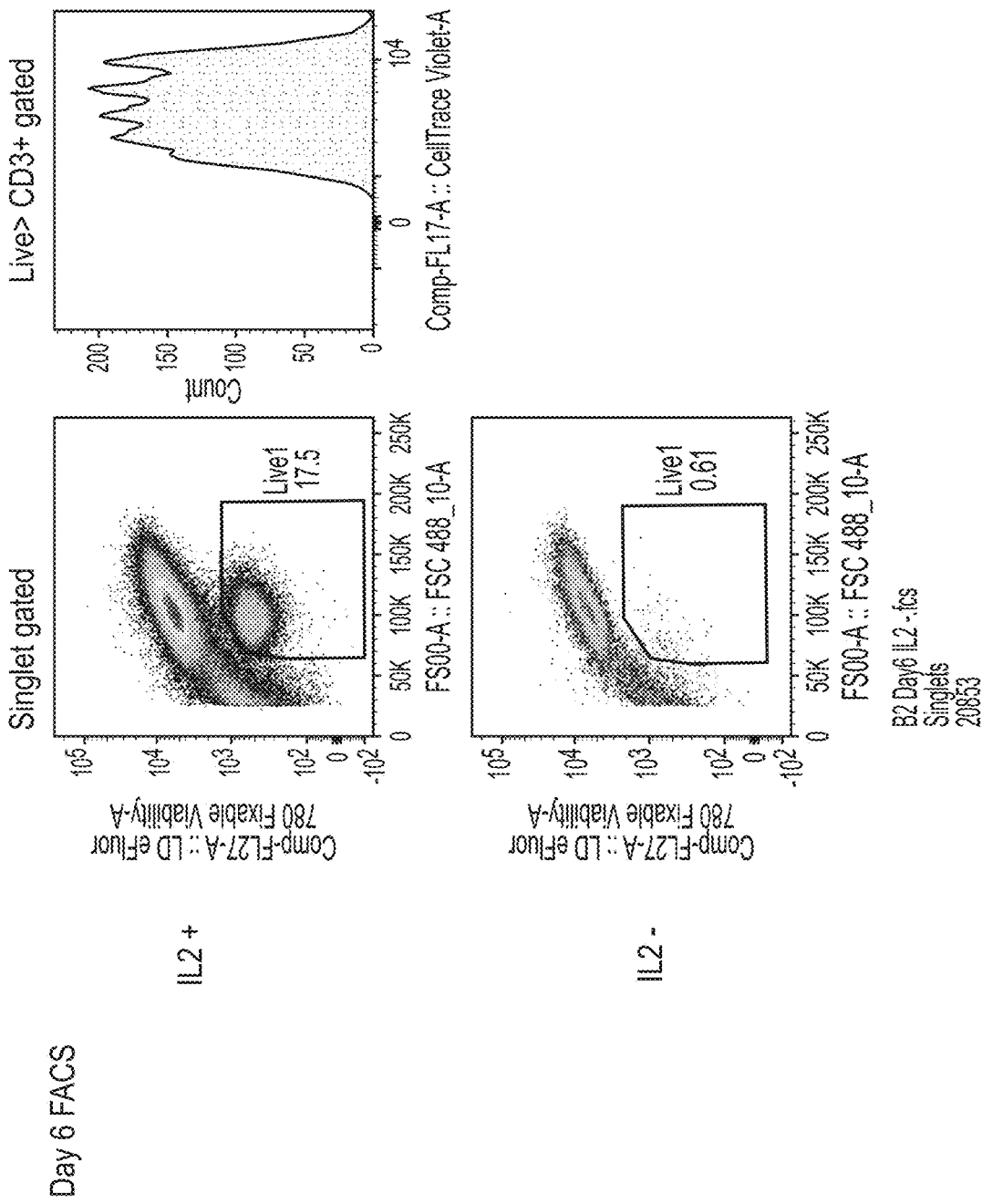

On day 2, T cells were infected with Sendai virus containing four Yamanaka factors (KOSM MOI=10) and SV40 large T antigen (MOI=3). The cells were then stimulated on day 9 with TRANSACT™ (1:500). An additional aliquot of CD8+ T cells from each donor were thawed and stimulated with TRANSACT™ (1:500) in TCM with IL-2 (60 IU/mL) on day 9 ("Control 1") or thawed and stimulated with TRANSACT™ (1:500) in TCM with IL-2 (60 IU/mL) on Day 0, and cultured in TCM with IL-2 (60 IU/mL) ("Control 2"). On day 9, Control 2 cells were stimulated with TRANSACT™ (1:500). Rejuvenated T cells were allowed to proliferate in vitro for 42 days. Expansion of non-rejuvenated T cells plateaued after approximately 3 weeks of expansion in vitro. See FIG. 19A. Rejuvenated T cells continued to show significant expansion for up to 42 days in culture. See FIG. 19B. This expansion is cytokine dependent, and rejuvenated T cells began to die within 6 days of IL-2 withdrawal. See FIGS. 20B and 20C.

Figure 21:
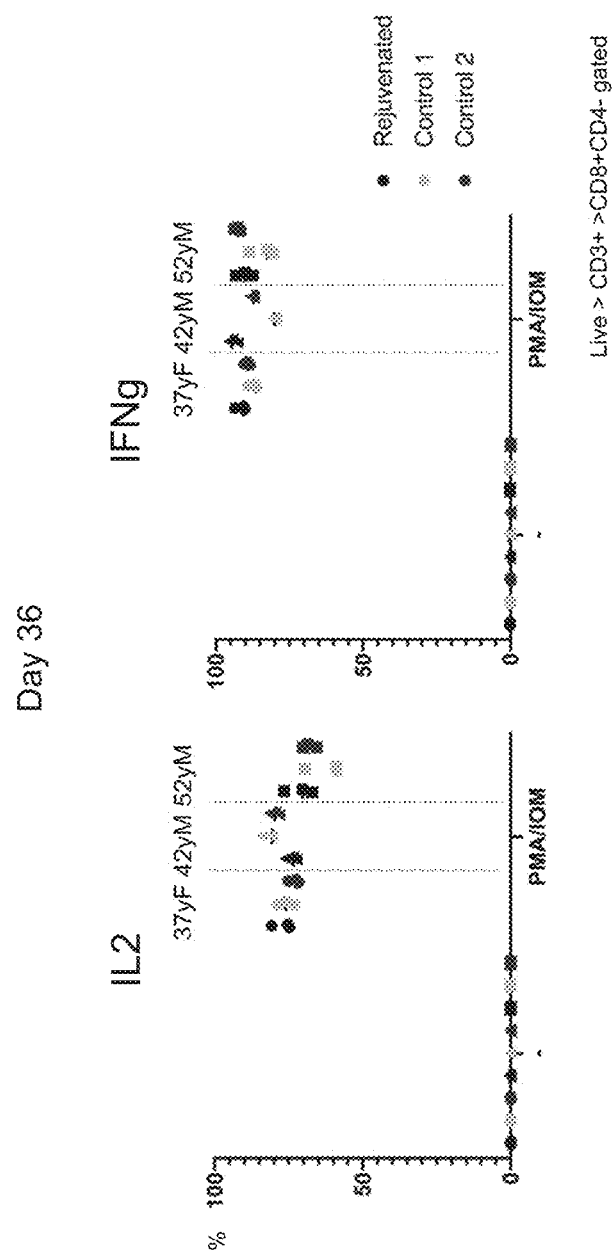
FIG. 21 shows the results from cytokine production assays of rejuvenated 37yF, 42yM and 52yM T cells. The FACS results were analyzed by FlowJo software. Single cells>Live cells>CD3+>CD8+CD4– cells were gated for all cell groups. The frequency of IL2+ and IFNg+ were calculated and plotted as shown.

Cytokine production and degranulation assays were carried out on day 36 as follows. Cells were cultured in TCM without cytokines with or without PMA/Ionomycin (Cell Activation Cocktail by Biolegend). GolgiPlug and GolgiStop (BD Biosciences) was also added according to manufacturer instructions. The co-cultured cells were then stained for surface antigens (BUV395-CD8, BUV496-CD4, and BUV805-CD3). Live/dead eFluor 780 was also added to exclude dead cells. After 20 minutes cells were washed. Cells were fixed and permeabilized by BD cytofix/cytoperm kit according to manufacturer instruction. The cells were then stained for intracellular cytokine expression (FITC-IFNg, and APC-IL-2). After a 30-minute incubation, cells were washed twice and analyzed by flow cytometry using a ZE5 instrument. The FACS results were analyzed by FlowJo software. Single cells>Live cells>CD3+>CD8+CD4− cells were gated for all cells. The frequency of IFNg+ and IL-2+ were calculated as shown in FIG. 21. The results showed that the rejuvenated T cells retain functionality. Usually, effector T cells express IFNg but do not express high amounts of IL2. Thus, these results suggest that the rejuvenated cells after 36 days of culture have still not reached full effector phenotype.

Figures 22A, 22B, 22C:
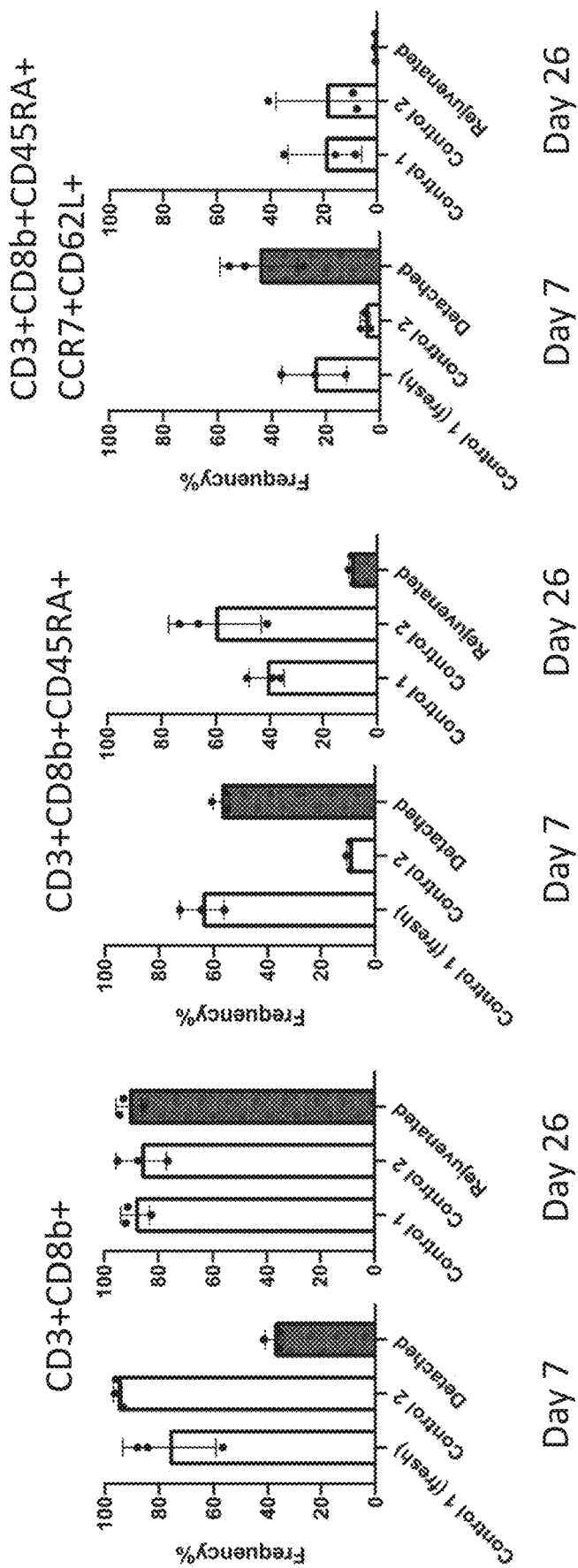
FIGS. 22A-22C show that rejuvenated T cells show effector phenotype after long term expansion. Sendai virus infected T cells were transferred onto iMatrix coated dishes on day 1 and were cultured in T cell media+60 IU/ml IL2 or in iPS cell media+60 IU/ml IL2 for 3 days and then changed to iPS cell media without IL2 from day 4. FACS analysis was performed on day 7 and day 26 after reprogramming.

Cell surface expression of CD3, CD8b, CD45RA, CCR7 and CD62L was measured by flow cytometry at day 7 and day 26. See FIGS. 22 and 23. Detached T cells that have undergone reprogramming demonstrate decreased CD3+CD8b+ expression, but elevated levels of CD45RA and CCR7+CD62L+ expression. By day 26, rejuvenated T cells show normal levels of CD3+CD8b+ expression, and reduced levels of CD45RA+ cells and CCR7+CD62L+ cells. See FIGS. 22 and 23.

Taken together, these data suggest that (FIGS. 19-23) after long term in vitro culture, the rejuvenated cells have high proliferative capacity and are polyfunctional. The rejuvenated cells continue to express IL2, an indication of stemness, but have an effector phenotype as shown by cell surface markers. Thus, despite long term culture and expansion, the rejuvenated cells still appear to have stemness properties.

Example 9: Rejuvenated NY-ESO-1 TCR Transduced T Cells Recognize NY-ESO-1 Expressing Tumor Cells To test whether rejuvenated T cells retain antigen-specificity to a tumor cell, CD8+ T cells genetically modified to express an NY-ESO-1-specific TCR were partially reprogrammed, stimulated with T cell activation molecules and the response to target cells pulsed with NY-ESO-1 peptide was measured.

Peripheral blood-derived CD8+ T cells two different donors (#3 42-year old male and #4 37-year old female) were purchased from Allcells (Alameda, CA). 2×106 cells were thawed and stimulated with TRANSACT™ (1:100) in TCM with IL-2 (60 IU/mL) in 1 well of a 24 well plate for each donor, as described in Example 4. The next day, T cells were transduced with NY-ESO-1 TCR by lentivirus vector transduction, as follows: First, the T cells were stimulated with a 1:100 dilution of T cell TRANSACT (Miltenyi) for 30 hours. Virus (MOI: 5) and LentiBOOST™ A & B (Sirion Biotech) was then added to the T cells for 24 hours. Stimulation and viral infection were then terminated by addition of 7 mls TCM with IL-2 (60 IU/L). On day 2, T cells were infected with Sendai virus containing four Yamanaka factors (KOS 10MOI, KLF 10 MOI, cMyc 3MOI, SV40 5MOI) and SV40 large T antigen (MOI=3). Control cells were kept culturing in TCM with IL-2 (60 IU/mL).

After 16 hours, the infected T cells were washed and transferred onto iMatrix coated dishes on day 1 and the medium was changed to Stemfit w/o IL-2 (2 mL/well). Sample #3 density was 2.6×105 cells/well and #4 density was 1.76×105 cells/well, in triplicate. On day 3, Stemfit was added (2 mL/well, total 4 mL).

On day 5, the floating cells were removed and the attached cells were harvested according to the following protocol. The medium was aspirated and washed twice with 2 mL PBS per well. 1 mL EDTA was added and the mixture was incubated at 37° C. for 5 minutes. Cells were collected by P1000 pipetting, with a final density of 6.1×105 in 3 wells for #3, and 1.9×106 in 1 well for #4. This resulted in about 2×105 cells/well in a 96-well U-shaped-bottom microplate. Cells were then activated with TRANSACT at 1:500 in TCM with IL-2 (60 IU/mL). The control non-Sendai infected NY-ESO-1 Tg cells were re-stimulated in the same way.

Figure 24:
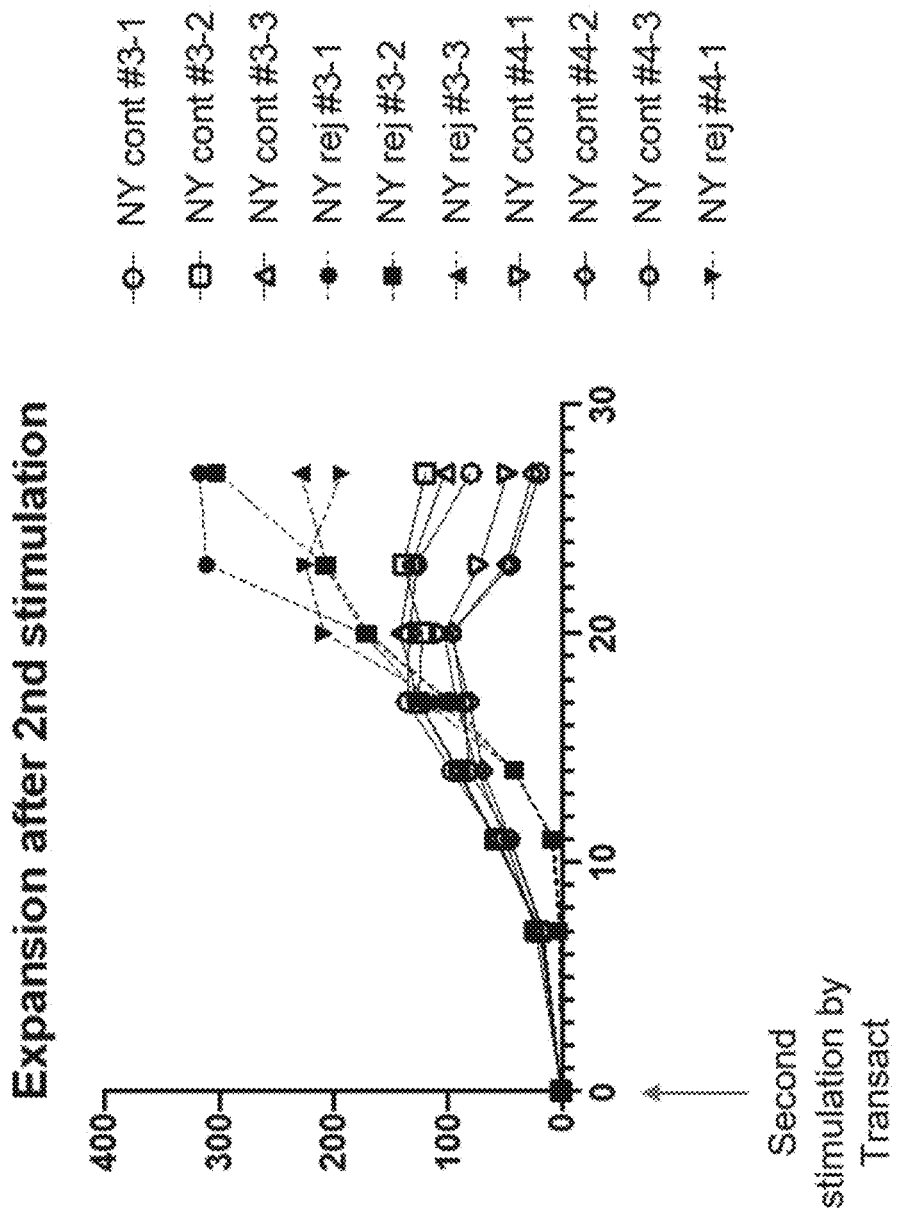
FIG. 24 shows the fold expansion of NY-ESO-1 rejuvenated or control cells from two different donors (#3 and #4) after stimulation with TRANSACT. Rejuvenated T cells proliferated longer than control and exceed controls around 2-3 weeks of culture.

On day 6, cell density was too high, so they were split into two wells in the 96-well microplate. TCM with IL-2 (60 IU/mL) was added. On day 8, the cells in two wells of the 96-well microplate were combined into one well of a 48-well plate and TCM with IL-2 (60 IU/mL) was added. On day 12, the cells were transferred to a 24-well plate so that the cell density was 2×106 cells/well. TCM with IL-2 (60 IU/mL) was added to each well. Every three to four days, cells were counted and fold changes were calculated. See FIG. 24. Cell numbers were adjusted to 2×106 cells/well and TCM with IL-2 (60 IU/mL) was added so that the volume was 2 mL/well.

Figure 25:
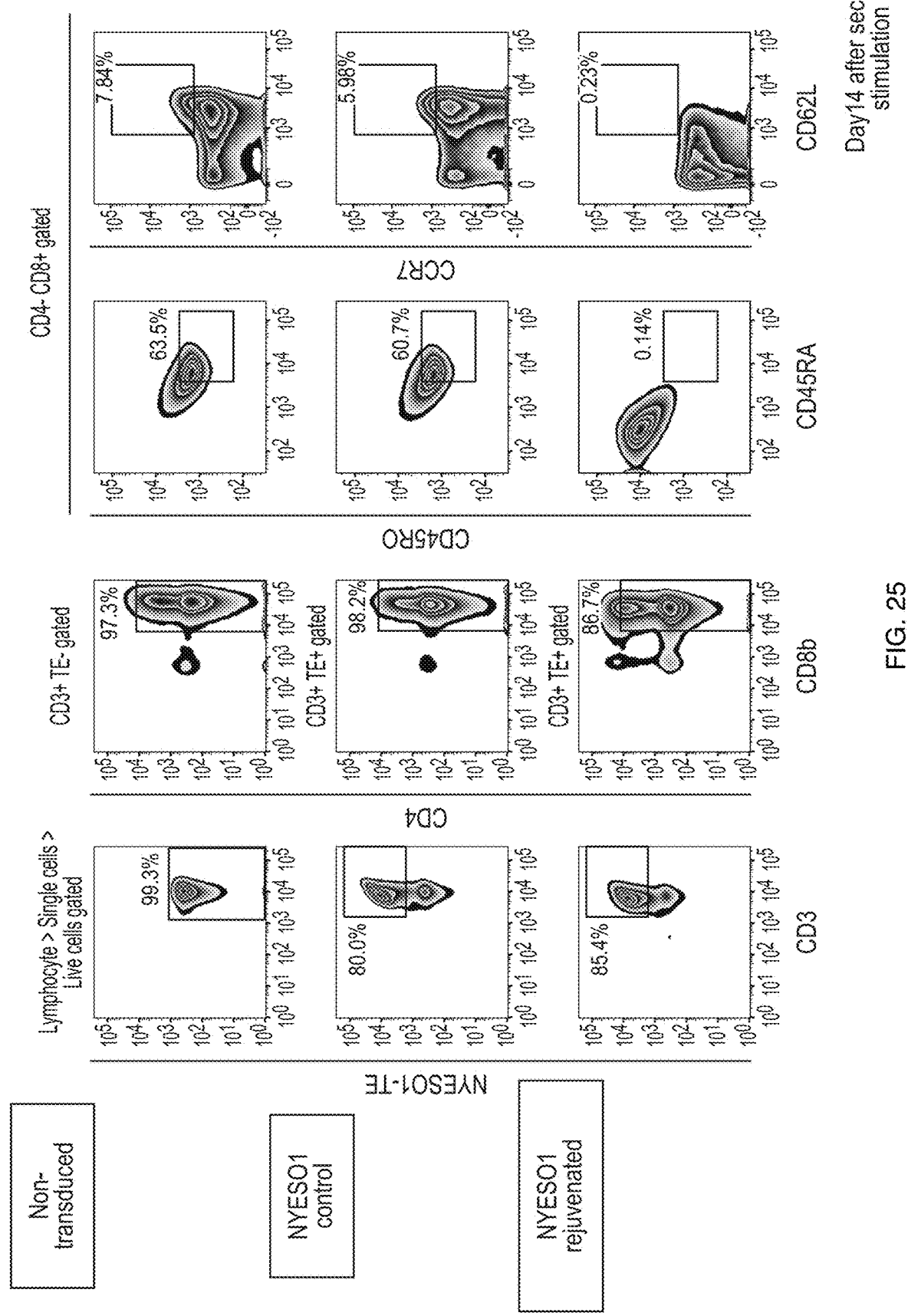
FIG. 25 is a FACS contour plot analysis of NY-ESO-1-CD3, CD4-CD8b, CCR7-CD62L and CD45RO-CD45RA expression in partially reprogrammed NY-ESO-1 T cells.
Figure 26B:
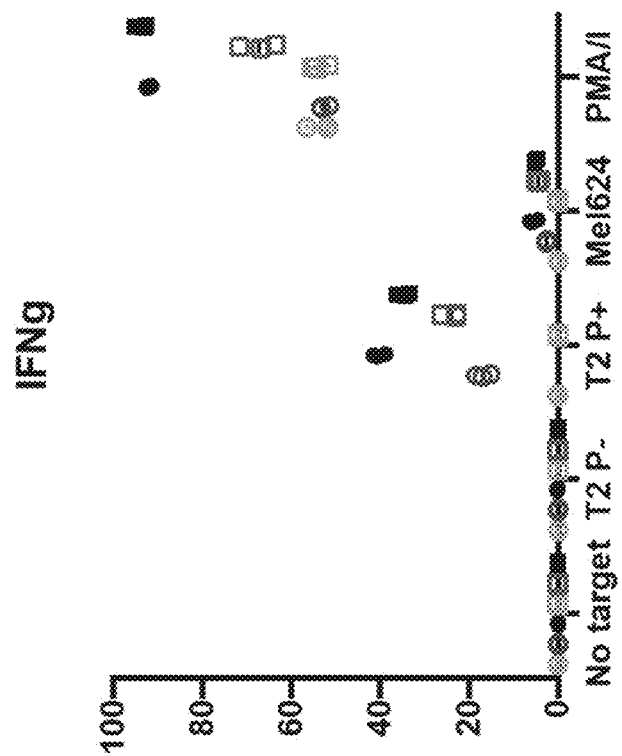
FIGS. 26A-26D are graphs showing the results from cytokine production and degranulation assays of rejuvenated NY-ESO-1 TCR transduced T cells. The FACS results were analyzed by FlowJo software. Single cells>Live cells>CD3+>CD8+CD4–>NY-ESO-1 tetramer+ cells were gated for NY-ESO-1 Tg T cells and Single cells>Live cells>CD3+>CD8+CD4–>NY-ESO-1 tetramer– cells were gated for mock control T cells. The frequency of IFNg+(A), TNFa+(B), IL-2+(C), and CD107a+(D) were calculated and plotted as shown. No target (control); T2P–: T2 target cells without peptide (–control); T2P+: T2 target cells pulsed with NYESO1 peptide; Me1624: HLA-A2+ tumor cells expressing endogenous NYESO1; PMA/I: cells activated with PMA/Ionomycin (+control).
Figure 26A:
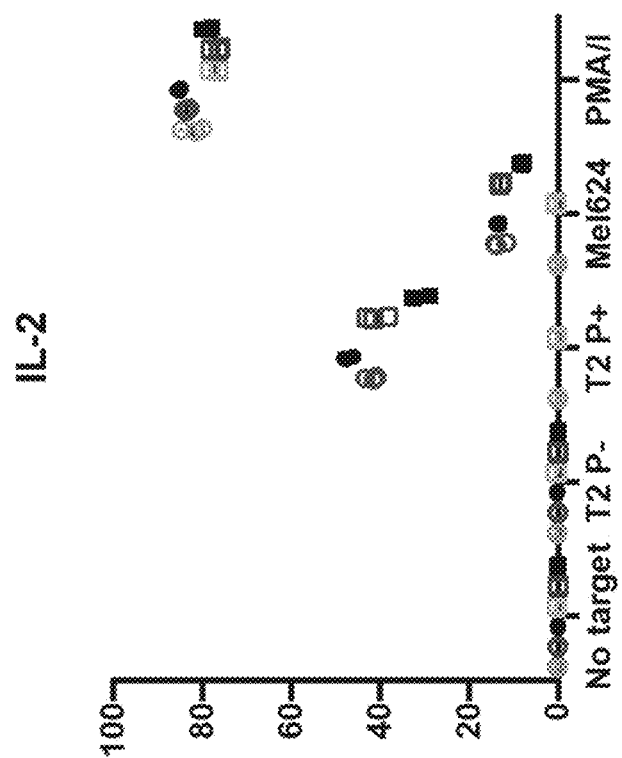
Figures 26C, 26D:
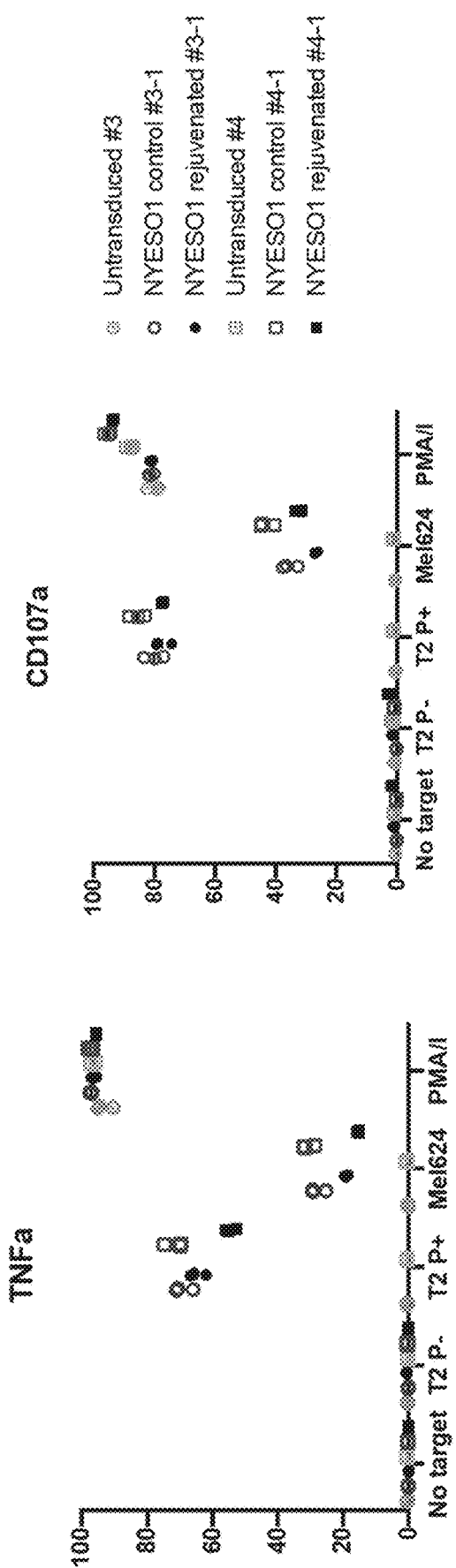

On day 19 (Day 14 after second stimulation), target cells, T2 and Me1624 HLA-A*02:01 positive tumor cells expressing endogenous NYESO1, were cultured in T2 media (RPMI, 20% FCS and P/SM). T2 cells were pre-cultured with or without NY-ESO-1 peptide (SLLMWITOC) (10 nM) for one hour, washed, and counted. One well contained 5×104 effector cells and 1×105 target cells (E:T ratio of 1:2). As positive control, PMA/Ionomycin (Cell Activation Cocktail by Biolegend) were added according to manufacturer instructions. GolgiPlug and GolgiStop (BD Biosciences) were added according to manufacturer instructions. Also, anti-CD107a Ab-BV421 were added in culture media (1 μL/well). Cells were cultured for six hours in TCM without cytokines. The co-cultured cells were then stained for surface antigens (PE-NY-ESO-1 tetramer, BUV395-CD8, BUV496-CD4, and BUV805-CD3). Live/dead eFluor 780 was also added to exclude dead cells. After 20 minutes, cells were washed. Cells were fixed and permeabilized by BD cytofix/cytoperm kit according to manufacturer instructions. The cells were then stained for intracellular cytokine expression (FITC-IFNg, APC-IL-2, and BV785-TNFa). After a 30-minute incubation, cells were washed twice and analyzed for cell surface marker expression of CD45RA, CD45RO, CCR7 and CD62L by flow cytometry using a ZE5 instrument. The FACS results were analyzed by FlowJo software. Single cells>Live cells>CD3+>CD8+CD4−>NY-ESO-1 tetramer+ cells were gated for NY-ESO-1 Tg T cells and Single cells>Live cells>CD3+>CD8+CD4-NY-ESO-1 tetramer− cells were gated for mock control T cells FIG. 25. The frequency of IFNg+, TNFa+, IL-2+, and CD107a+ were calculated as shown in FIGS. 26A-26D. This experiment confirms that the rejuvenated NYESO1 T cells are antigen-specific and recognize NYESO1 positive T2 and Me1624 target cells (FIGS. 24-26) (see also FIG. 14). These data also confirm that the rejuvenated cells continue to express IL2, an indication of stemness, but have an effector phenotype as shown by cell surface markers.

Example 10: NY-ESO-1 TCR Transduced T Cells are Rejuvenated with Antigen-Specific Stimulation To test whether antigen specific T cells are capable of being rejuvenated using antigen-specific stimulation, CD8+ T cells are isolated from one or more donors genetically modified to express an NY-ESO-1-specific TCR. The donor cells are thawed and stimulated with TRANSACT™ in TCM with IL-2 (60 IU/mL) in 1 well of a 24 well plate for each donor. One day later, T cells are transduced with a lentivirus expressing an NY-ESO-1 T cell receptor. The NY-ESO-1-specific T cells are then co-cultured with T2 cells that have been pulsed with NY-ESO-1 peptide (T2+NY-ESO-1 cells). Next, the cells are either enriched for NY-ESO-1 specific T cells (Group 1) or maintained as a heterogeneous mix of NY-ESO-1-specific T cells and untransduced T cells (Group 2). Cells are again co-cultured with T2+NY-ESO-1 cells for the duration of reprogramming Cells are next infected with Sendai virus containing four Yamanaka factors (KOS 10MOI, KLF 10 MOI, cMyc 3M01, SV40 SMOI) and SV40 large T antigen (MOI=3). Control cells are kept culturing in TCM with IL-2 (60 IU/mL) in co-culture with T2+NY-ESO-1 cells.

NY-ESO-1 specific T cells are capable of forming T cell derived adherent cells in the presence of T2+NY-ESO-1 cells, in the absence of any further stimulation. Attached cells are harvested according to the protocol described in Example 9, and then activated again by co-culture with T2+NY-ESO-1 cells.

Figure 27B:
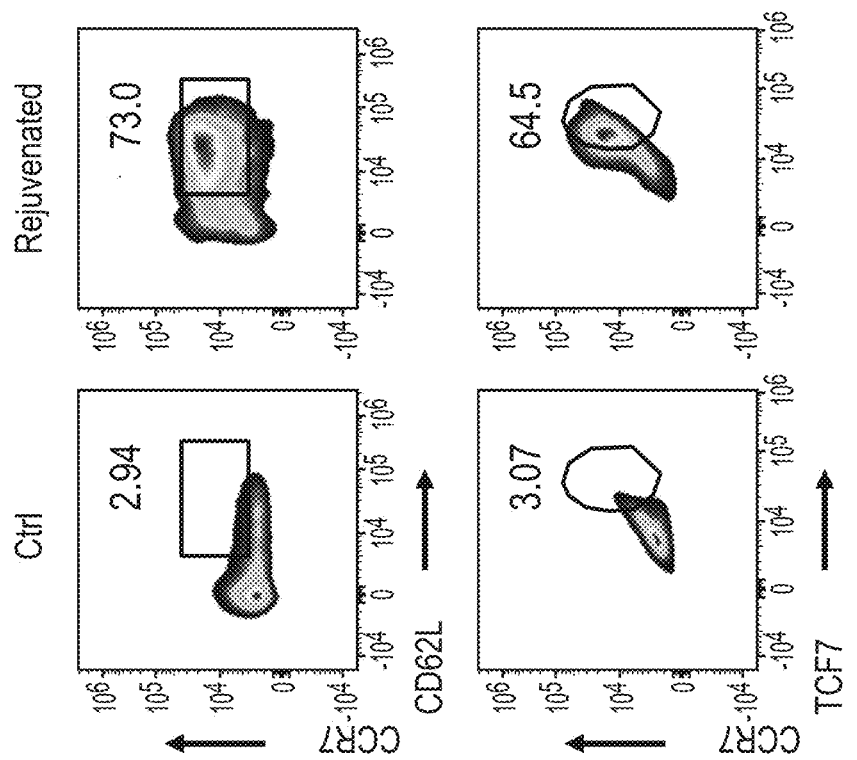
FIGS. 27A-27B show that rejuvenation of tumor infiltrating lymphocytes (TIL) augmented proliferation and resulted in more stem cell-like product.
Figure 27A:
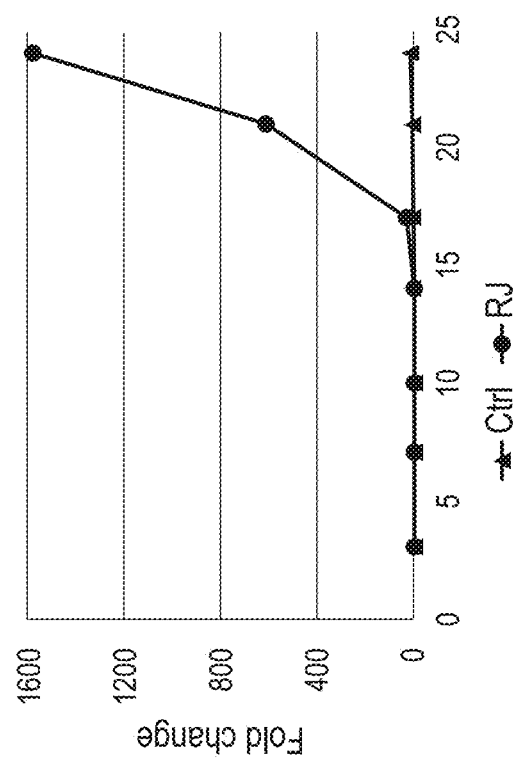

Example 11: Rejuvenation Enhanced T Cell Stemness Properties in Tumor Infiltrating Lymphocytes In this example, Tumor Infiltrating Lymphocytes (TILs) were isolated from a 66-year-old donor and rejuvenated as follows. TILs were enriched by culturing tumor fragments in T cell culture media for 2 weeks. T cells were activated through overnight co-culture with autologous antigen presenting cells derived from the tumor. The T cells were then FACS sorted and CD137 (4-1BB) positive cells were isolated. One day later (Day 0), cells were either left undisturbed, or transduced with four Sendai viruses expressing KOS (KLF4, OCT3/4, SOX2), KLF4, cMyc and SV40 as previously described. Cells were then transferred to stem cell media (StemFit) and cultured for seven days. T cell derived adherent cells were harvested on Day 7 and reactivated with TransAct (1:500) in T cell culture media for two additional days. From Day 9, cells were cultured in normal T cell culture media. On Day 21, the rejuvenated or control cells (which had undergone the same procedure except that the cells were not transduced with the four Sendai viruses) were assessed for expression of CD62L, CCR7 and TCF7 using flow cytometry. Rejuvenated TILs exhibited enhanced proliferation (FIG. 27A) and an enhanced expression of stemness phenotypic markers (FIG. 27B) relative to un-rejuvenated controls. In this experiment, 73.0% of rejuvenated TILs co-expressed CCR7 and CD62L and 64.5% of rejuvenated TILs co-expressed CCR7 and TCF7, which is significantly higher than the un-rejuvenated TIL populations, which only showed 2.94% co-expression of CCR7 and CD62L and 3.07% co-expression of CCR7 and TCF7. These data suggest that TILs, which are typically characterized by low proliferative capacity and phenotypic markers of exhaustion, can successfully be rejuvenated to allow for enhanced proliferation and sternness.

Example 12: Dynamic Analysis of Epigenetic Clock During T Cell Rejuvenation

In this example, CD8+ T cells from a 53-year-old male, a 55-year-old male, and a 50-year-old male were stimulated with T cell TransAct®, human (Miltenyi Biotec) at 1:500 dilution in T cell culture medium (TCM) with 60 IU/ml of IL-2 at a cell density of 1 million cells/ml in 48-well plate. All the TCM described hereinafter contains 60 IU/ml IL-2. After 26.5 h activation, the cells were divided into two groups. One group underwent the rejuvenation protocol; the other group was used as control without any viral manipulation and cultured in TCM during the whole process.

The Yamanaka factors and SV40 containing Sendai viruses (SeV) were transduced to the rejuvenation sample at a 10 MOI of KLF4-OCT3/4-SOX2, 10 MOI of KLF4, 3 MOI of cMyc and 5 MOI of SV40 (Day 0), then cultured at 37 degrees Celsius. After 16.5 hours, cells were washed and suspended with stem cell medium. The cells were plated on iMatrix-511 coated 24-well plate at 50,000 cells/well (corresponding to day 0 count of 50,000) and cultured at 37 degrees Celsius (Day 1). 500 ul of SCM was added on days 3 and 5.

On day 7, to detach the adherent cells, 1 ml of TrypLE Express (Thermo cat #12604013) was added and the cells were incubated in 37 degrees Celsius for 10 min. The detached cells were then harvested by pipetting. Floating cells in the supernatant were also kept and mixed with the detached cells. One part of the cells was saved for DNA to determine the eAge. 0.5 million cells of both control and rejuvenated samples were activated with 1:500 diluted T cell TransAct, human in 500 ul of TCM at a density of 1 million cells/ml in a 48-well plate. On day 9, cells were transferred to a 12-well plate and 1 ml of TCM was added to each well. On day 11, cells were transferred to a 6-well plate. The cells were then cultured in a 6-well plate.

Cell samples were collected before the preactivation step for the SeV transduction, and on days 7, 13, and 18 for epigenetic clock analysis. The cells from each time point were pelleted and kept at −20 degrees Celsius until DNA extraction. DNA was extracted from the frozen cell pellets using PureLink Genomic DNA mini kit (Invitrogen, K182002). Each extracted DNA was split into 3 tubes for technical replicates of methylome analysis. Due to the lack of enough DNA the control conditions of Donor 1 at day 18, and of Donor 3 at day 7 and 18 consist only in 2 technical replicates. Samples were prepared for epigenetic analysis by Illumina Infinium array. The CpG methylation status data was analyzed using the Horvath method as described in (Horvath et al., 2018, Aging 10, 1758-1775; Horvath and Raj, 2018, Nature Reviews Genetics, 19:371-375) to get skin and blood clock values.

Cells were stained with fluorescent conjugated antibodies and viability dye and cell phenotypes were acquired by flow cytometry in a Cytek Aurora.

Figure 28:
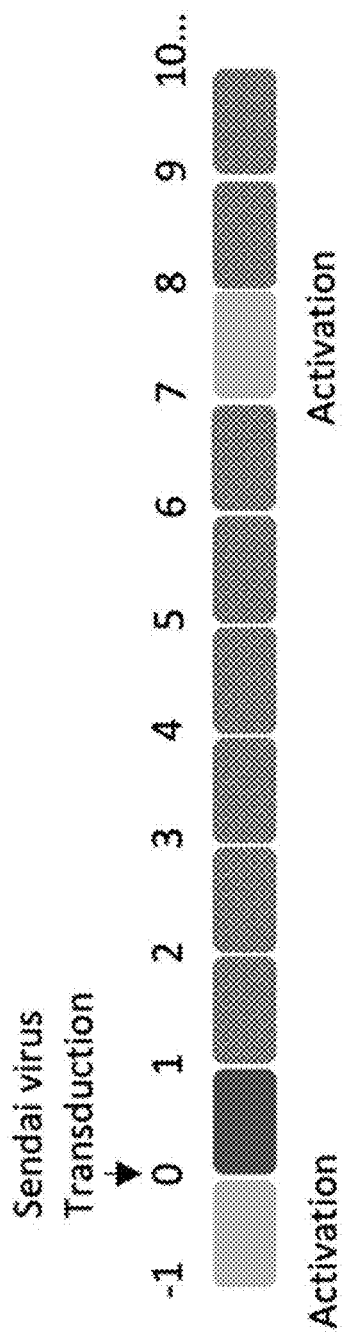
FIG. 28 depicts an exemplary, non-limiting scheme of the rejuvenation protocol employed in Example 12 described below.
Figures 29A, 29B:
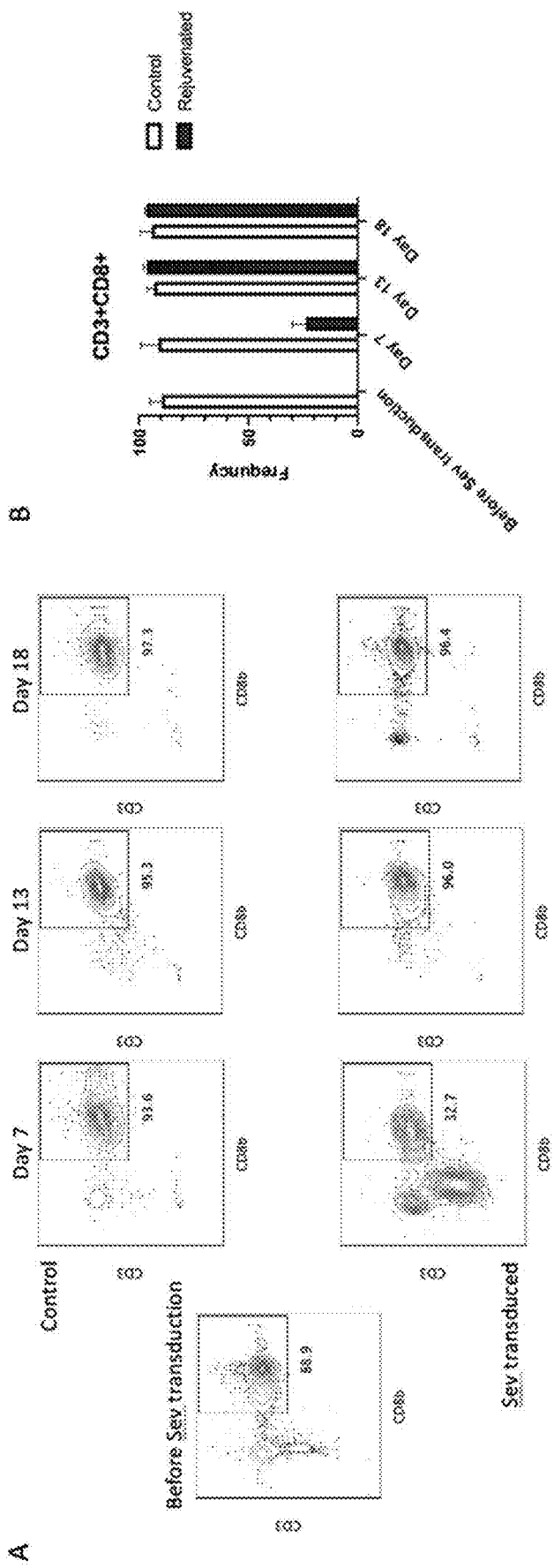
FIGS. 29A and 29B show phenotypic analysis conducted in connection with the rejuvenation protocol of Example 12.

CD8 positive T cells from the three male donors (aged 53, 55, and 50 years), were transduced with Yamanaka factors and SV40 according to the rejuvenation protocol depicted in FIG. 28, and compared with controls which were in non-transduced condition at each time point. The rejuvenated cells showed reduced CD3 and CD8b expression on day 7. After detaching and stimulating them, the T cell conventional marker expression was fully recovered in the rejuvenated cells on day 13 and 18 (FIGS. 29A and 29B). Thus, partially reprogrammed cells reacquired expression of conventional T cell markers in only 6 days following reactivation.

Skin and blood epigenetic clock (a highly accurate age estimator) was performed and analyzed in the DNA samples of the 3 male donors to check Epigenetic age (eAGE) at 4 time points of the rejuvenation protocol (FIGS. 30A-30C).

The eAge of Donor 1, whose chronological age was 53 years old (y/o), showed 45.1 y/o before the activation for Sev transduction. While the eAge in the un-rejuvenated control cells after the TransAct activation did not show variation, [ranging from 43.3 to 45.7 y/o (2.4 years variation)], the eAge of the Sendai virus transduced cells (rejuvenated cells) on day 7 showed the youngest age, 30.9 y/o, which gradually increased and reached 46.2 y/o on day 18. The difference between control and rejuvenated eAGEs on day 7 was 12.9 y/o. This is about a 24.3% reduction in age as measured by the Horvath clock analysis.

The eAge in control cells of Donor 2, whose chronological age was 55 y/o, ranged from 43.8 to 50.0 y/o (6.2 years variation). Again, the youngest age was achieved by rejuvenation on day 7, 34.4 y/o (12.9 years younger than control eAGE on day 7). Consistent with Donor 1's results, the eAge gradually increased.

The chronological age of Donor 3 was 50 y/o. The eAge in the non-rejuvenated control cells varied from 46.0 to 51.4 (5.4 years variation), while the youngest age was 31.5 y/o in rejuvenated cells on day 7 which was 19.9 years younger than control eAge on day 7. In summary, in all three donors the rejuvenated cells showed the youngest eAge on day 7, then the eAge gradually increased. eAge of Donor 1 rejuvenated cells reached control level on day 18, while in the case of the other two donors, rejuvenated cells continued to be younger than control.

As evidenced by the above-described results, the partially reprogrammed T cells lose common T cell markers, (e.g., CD3 and CD8b) as measured on the detachment day (i.e., day 7). After re-stimulation on day 7 and culturing in T cell medium, however, the T cell adherent cells fully reacquired the T cell markers by or on day 13. The epigenetic clock showed the youngest epigenetic age on day 7 in the three donors tested (50, 53 and 55 years old, respectively). The results of this example demonstrate that, although a gradual eAge increase was observed after day 7, rejuvenated cells remain younger than control on day 13 when the rejuvenated cells showed full T cell phenotype.

Example 13: Rejuvenation of NY-ESO-1 Transduced T Cells

This example demonstrates that T cells can be genetically engineered to express a TCR specific for a desired target (e.g., NYESO1) and rejuvenated using the methods herein.

Healthy donor CD4/CD8 T cell activation: On day 1, healthy human donor CD4 and CD8 T cells from two male donors (age 24 and 35) were thawed, washed once and resuspended in pre-warmed Complete TCM+IL-2 (60 IU/ml) (day-3). Cells were diluted to 2e6 cells/ml. Transact was added 10 ul/ml (1/100 dilution) to stimulate CD4 and CD8 T cells (see FIG. 31). On day 2, stimulated CD8+ and CD4+ T cells were counted and 7.5e+5 cells were suspended in 0.75 ml of TCM+IL-2. Lentiviral vector encoding the NYESO1-specific TCR were made using standard protocols. NYESO1-encoding lentivirus supernatant (7.5 ul, MOI; 10) and LentiBoost A&B (7.5 ul each) were added. The next day, 5.25 ml of new TCM+IL-2 was added (total 6 ml).

Reprogramming of NY-ESO-1 Transgenic (Tg) T cells and collection thereof: On day 0, 4e+5 cells were collected, re-suspended in TCM+IL-2 in a 48-well plate. The Cytotune® Sendai reprogramming kit was used for reprogramming (KOS: MOI=10, KLF4: MOI=10, C MYC: MOI=3, and SV40: MOI=5). The next day (i.e., day 1), cells were collected, re suspended in stem cell culture medium and seeded in an iMatrix-coated 6-well plate (two wells per condition). On day 3, new stem cell culture medium was added and on day 5 half of the medium was refreshed with new stem cell culture medium. Control cells were kept in culture in TCM+IL-2. On day 7, floating cells were collected, wells were washed with PBS, TrypLE was added, and attached cells were detached. Cell number of all the collected cells (i.e., floating cells+detached cells) was counted. Detached cells were re-stimulated with Transact (1/500 dilution) in 500 ul of TCM+1L2 (in a 48-well plate). On day 11 cells were collected, resuspended in 1 ml of new TCM+IL-2 and transferred to 6-well plate. Cell counting and medium change were performed every 3-4 days. On day 13, 1/20 of the cells were stained for surface expression with antibodies for CD3, CD62L, CD45RO, HLA-A02:01 NYESO1 MHC Tetramer, Cd197, CD4, CD8a, CD45RA, and intracellular staining for TCF1, fixed & permed using Foxp3 staining kit as described according to manufacturer's protocol, stained with Tcf7 antibody and analyzed by FACS. See, e.g., FIGS. 32A and 32B. Genomic DNA were extracted from 1e+6 cells per condition using PureLink Genomic DNA Mini Kit as per instructions. DNA were treated with RNAse and evaluated for epigenetic age analysis as previously described.

A stock vial of T2 cells were thawed and washed once and cultured in complete RP10 medium for one week. 5e+6 cells were resuspended in complete RP10 with or without 10 nM NY-ESO1 peptide for 2 hours in 5% CO2 incubator. After 2 hours, cells were washed and resuspended in TCM.

On day 19 control and rejuvenated NY-ESO-1 TCR Tg T cells were analyzed for their ability to generate cytokines upon co-culture with target cells. 5e+4 T cells were co-cultured with 1e+5 T2 cells with or without NY-ESO-1 peptide. Wells without target cells and wells with PMA/Ionomycin (Cell Activation Cocktail) were added as negative and positive control respectively. CD107a antibody was added to the culture medium. After 6 hours co-culture cells were stained with surface Abs mix, fixed and permeabilized by BD kit as described in the manufacturer's protocol, stained with intra-cellular Abs mix and analyzed by FACS (Cytek Aurora). The data were analyzed with Flowjo software. The gating strategy was as follows: Lymphocyte>Single cells>Live/Dead–>CD3+NY-ESO-1 tetramer+.

On day 19 control and rejuvenated NY-ESO-1 TCR Tg T cells were analyzed for their ability to kill target cells using sequential stimulation. Specifically, control and rejuvenated T cells were counted. 50,000 NY-ESO-1 tetramer+ T cells were co-cultured with 20,0000 NY-ESO-1+HLA A02:01+ target cells (A375-Nuclight Red (NLR) or H1703-NLR) at 1:4 E:T in 24-well plates. Every 3-4 days, 25% of the culture was transferred into a new plate with fresh target cells plated at the initial seeding density. Target clearance was quantified using Incucyte.

The results showed that the rejuvenated NY-ESO-1 TCR Tg T cells had a less differentiated phenotype. In particular, on day 13 rejuvenated NY-ESO-1 TCR transduced T cells—which were detected by the binding of NY-ESO-1 tetramer—contained a higher percentage of CCR7+CD62L+ population and Tcf1+ population, indicating a less differentiated phenotype. See, e.g., FIGS. 32A and 32B. Control and rejuvenated NY-ESO-1 TCR Tg T cells were kept in culture in TCM+IL-2 for a prolonged time. Medium was changed every 3-4 days and cells were kept in the concentration of 1-2e+6/ml. Rejuvenated NY-ESO-1 TCR Tg T cells required a longer time to start proliferation which could be due to recovery from the reprogramming process. However, over time they proliferated more than 100 fold more than control non-rejuvenated cells. See, e.g., FIG. 33. Epigenetic age of the control and rejuvenated NY-ESO-1 TCR Tg T cells were analyzed as depicted in FIG. 34. Compared to control T cells rejuvenated cells on day 19 showed about 8-18 years younger phenotype. More specifically, for the first donor (FIG. 34A), the epigenetic age of the rejuvenated CD4 T cells at day 7 (the T cell derived adherent cells) showed a 68% reduction in age as compared to the eAge of the control cells (eAge at day 19). At day 19, the rejuvenated CD4+ T cells showed a 33% reduction in age as compared to the control cells. The epigenetic age of the rejuvenated CD8 T cells at day 7 showed a 70% reduction in age as compared to the control cells. At day 19, the rejuvenated CD8 T cells showed a 45% reduction in age as compared to the control cells. In the second donor (FIG. 34B), the epigenetic age of the rejuvenated CD4 T cells at day 7 (the T cell derived adherent cells) showed a 62% reduction in age as compared to the control cells. At day 19, the rejuvenated CD4+ T cells showed a 27% reduction in age as compared to the control cells. The epigenetic age of the rejuvenated CD8 T cells at day 7 (the T cell derived adherent cells) showed a 68% reduction in age as compared to the control cells. At day 19, the rejuvenated CD8 T cells showed a 67% reduction in age as compared to the control cells.

Figure 35:
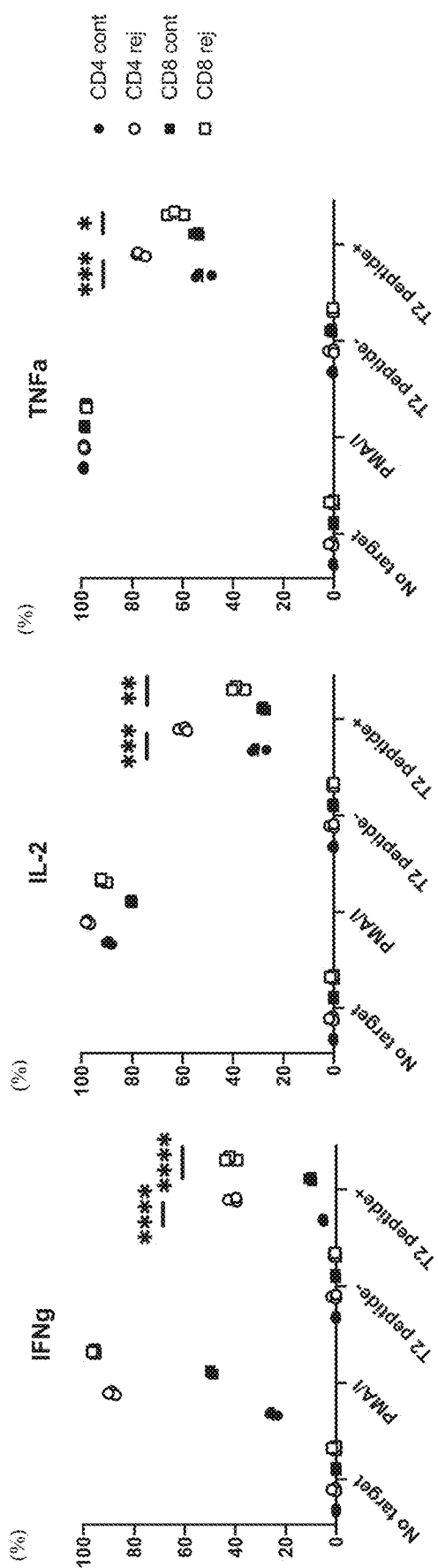
FIG. 35 depicts bar graphs showing intracellular cytokine staining from rejuvenated and control NY-ESO-1 cells. The graph shows that rejuvenated NY-ESO-1 Tg CD4 and CD8

Additionally, it was observed that rejuvenated NY-ESO-1 TCR Tg T cells produced more cytokines (IL-2, IFNg and TNFa) upon co-culture with target cells with NY-ESO-1 peptide (FIG. 35). Production of cytokines (IL-2, TNFa, IFNg) of control and rejuvenated NY-ESO-1 TCR Tg T cells were analyzed by co-culturing them with T2 cells (HLA A02:01+) with or without NY-ESO-1 peptide as described above. Both, control and rejuvenated NY-ESO-1 TCR Tg T cells did not produce cytokines upon co-culture with T2 cells without peptide. A higher percentage of the rejuvenated NY-ESO-1 TCR Tg T cells did produce IL-2, IFNg and TNFa upon co-culture with T2 cells with NY-ESO-1 peptide. See, e.g., FIG. 35.

Figure 31:
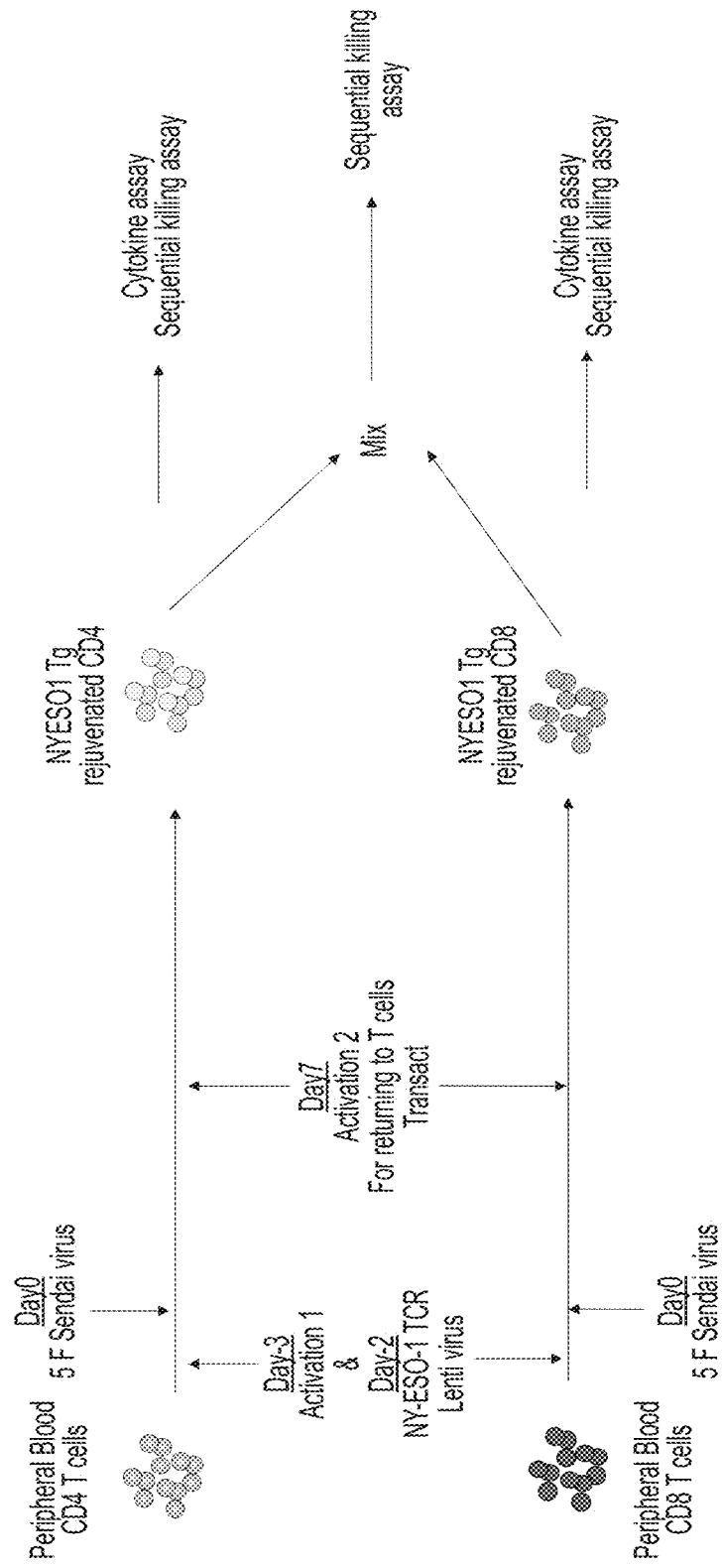
FIG. 31 illustrates the results of rejuvenation of NY-ESO-1 Tg CD4 and CD8 T cells. CD4 or CD8 T cells were stimulated by Transact and transduced with NY-ESO-1 TCR before reprogramming.

See, generally, FIGS. 31-37. FIG. 31 is a diagram of the experiment for rejuvenation of NY-ESO-1 Tg CD4 and CD8 T cells. CD4 or CD8 T cells were stimulated by Transact and transduced with NY-ESO-1 TCR before reprogramming. Cells were cultured in iPS cell culture condition from day 1 to day 7. On day 7 cells were collected, counted, re-stimulated by Transact and kept in culture in TCM+IL-2. On day 19, control and rejuvenated cells were analyzed for cytokine production and cytotoxic activity. In a condition of sequential killing assay rejuvenated CD4 and CD8 T cells were mixed to check their synergistic effect.

Figure 32A:
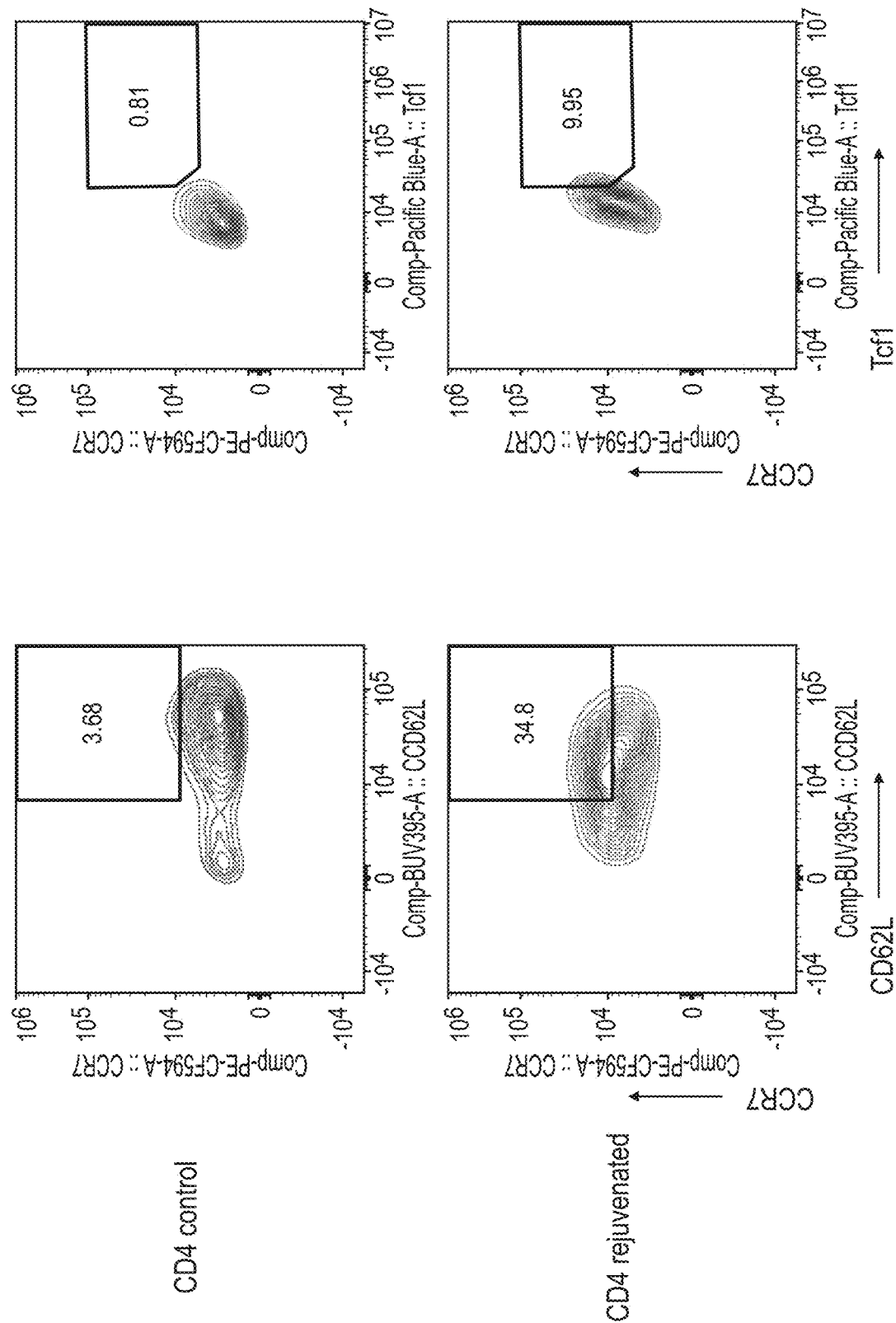
FIGS. 32A and 32B illustrate the results of rejuvenation NY-ESO-1 Tg CD4 and CD8 T cells showed less differentiated phenotype.
Figure 32B:
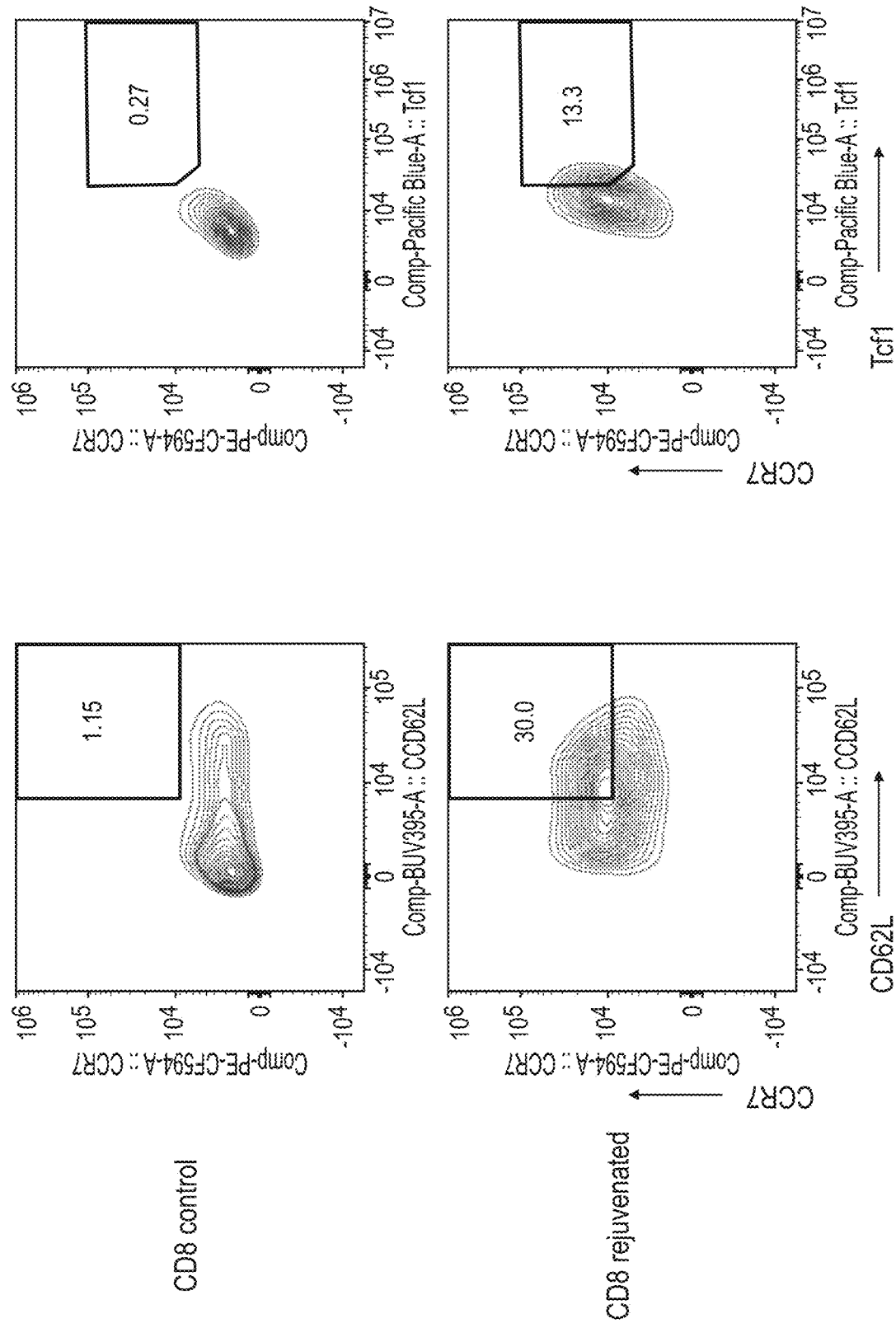

FIGS. 32A and 32B illustrate that rejuvenated NY-ESO-1 Tg CD4 (FIG. 32A) and CD8 T cells (FIG. 32B) showed a less differentiated phenotype. On day 13 control and rejuvenated NY-ESO-1 Tg CD4 and CD8 T cells were analyzed for surface markers and Tcf1 intracellular expression by FACS. Cells were gated as Lymphocytes>Single cells>Live/Dead−>NY-ESO-1 tetramer+, and plotted as CD4×CD8a, CCR7×CD62L and CCR7×Tcf1.

Figure 33:
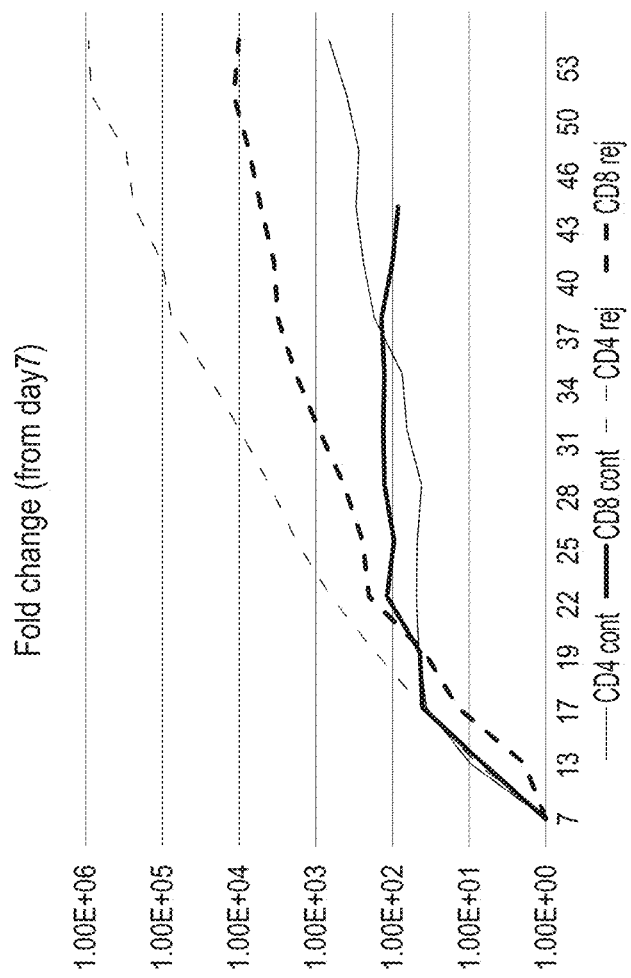
FIG. 33 illustrates the results of rejuvenation NY-ESO-1 Tg CD4 and CD8 T cells proliferated more than control NY-ESO-1 Tg CD4 and CD8 T cells.
Figure 34:
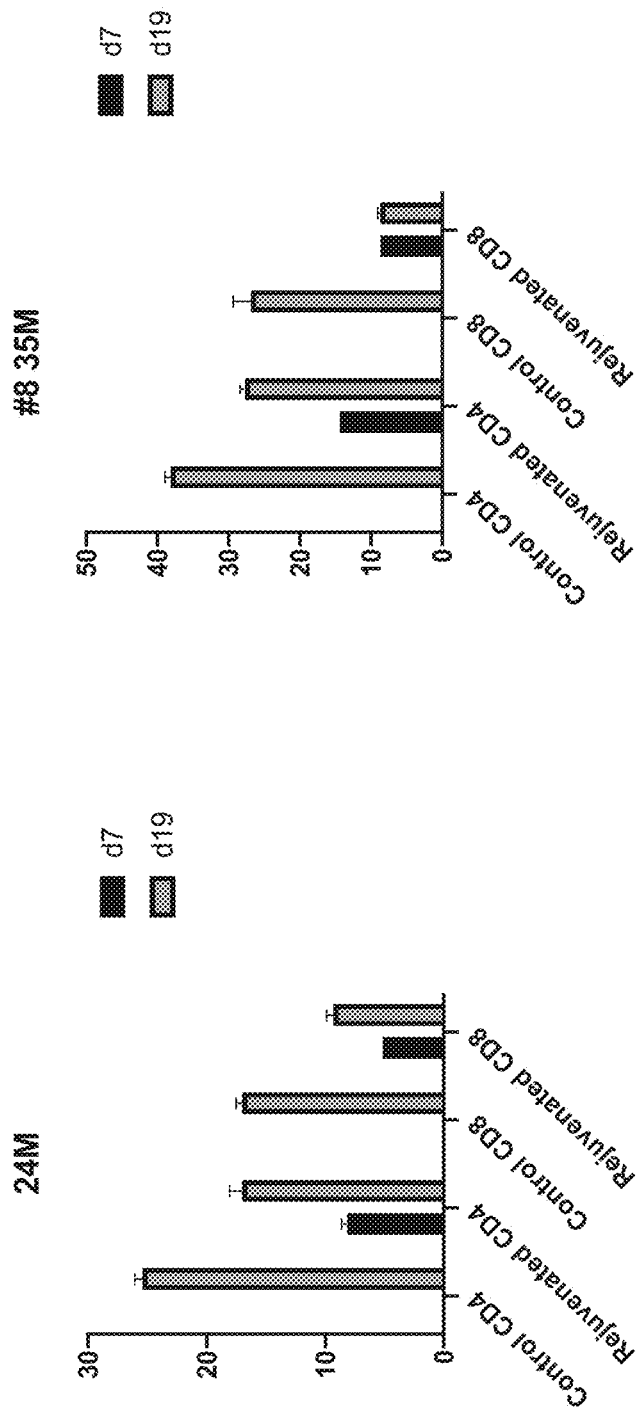
FIGS. 34A and 34B are bar graphs showing eAge values from two donors: a 24-year old male (A) and a 35-year old male (B). The figure illustrates that rejuvenated NY-ESO-1 Tg CD4 and CD8 T cells showed younger phenotype by epigenetic age analysis than control NY-ESO-1 Tg CD4 and CD8 T cells and chronological age of the donors. Graphs show the mean and S.D. of the values of age analyzed from methylation status of certain CpG sites.

FIG. 33 illustrates that rejuvenation NY-ESO-1 Tg CD4 and CD8 T cells proliferated more than control NY-ESO-1 Tg CD4 and CD8 T cells. NY-ESO-1 Tg CD4 and CD8 T cells were rejuvenated and cultured as described and cell number was counted every 3-4 days. Graph depicts the fold changes compared to day 7 after transduction of the Reprogramming factors and their corresponding control cells over time. Representative data of four different donors.

FIG. 34 illustrates that rejuvenated NY-ESO-1 Tg CD4 and CD8 T cells showed younger phenotype by epigenetic age analysis than control NY-ESO-1 Tg CD4 and CD8 T cells and the chronological age of the donors. Graphs show the mean and S.D. of the values of age analyzed from the methylation status of certain CpG sites.

FIG. 35 illustrates that rejuvenation NY-ESO-1 Tg CD4 and CD8 T cells produced more cytokines (IFNg, IL-2 and TNFa) upon co-culture with T2 cells with NY-ESO-1 peptide. On day 19 control or rejuvenated NY-ESO-1 Tg CD4 and CD8 T cells were cultured alone, or with PMA/Ionomycin, T2 cells with or without NY-ESO-1 peptide in the presence of Golgi transporter inhibitors. After staining surface antigens, cells were fixed, permeabilized and stained by intracellular Abs. Frequency of each cytokine positive NY-ESO-1 tetramer+ cells were depicted.

FIG. 36 illustrates that rejuvenated NY-ESO-1 Tg CD8 T cells persisted and retained their cytotoxic activity longer than control cells upon repeated co-culture with NY-ESO-1 expressing target cells (A375-NLR). Control or rejuvenated NY-ESO-1 Tg CD8 T cells were co-cultured with A375-NLR cell line. Every 3-4 days, 25% of the previous culture was transferred into a new plate with fresh targets. Growth of the target was monitored using the Incucyte® live-cell analysis system and analyzed with the Base Software Analysis Module. Graphs show the numbers of A375-NLR/image of each condition. Representative data of two different donors. NLR: Nuclight Red FIG. 37 describes the enhanced cytotoxicity of rejuvenated NY-ESO-1 Tg CD8 T cells resulting from addition of rejuvenated NY-ESO-1 Tg CD4 T cells. Rejuvenated NY-ESO-1 Tg CD4 and CD8 T cells were co-cultured with A375-NLR cell line in E:T=1:4. In one condition exogenous IL-2 (10IU/ml) was added. In another condition, rejuvenated CD4 and CD8 T cells were mixed in 1:1 ratio and co-cultured with A375-NLR cell line in E:T=1:2. Every 3-4 days, 25% of the previous culture was transferred into a new plate with fresh targets. Growth of the target cells was monitored using the Incucyte® live-cell analysis system and analyzed with the Base Software Analysis Module. The graphs show the numbers of A375-NLR/image of each condition. Representative data is from two different donors.

From this example, it can be concluded that rejuvenated NY-ESO-1 TCR Tg T cells showed a less differentiated phenotype and proliferated more than control NY-ESO-1 TCR Tg T cells. Additionally, the epigenetic age of rejuvenated NY-ESO-1 TCR Tg T cells was lower than that of the control NY-ESO-1 TCR Tg T cells. Rejuvenated NY-ESO-1 TCR Tg T cells also produced more cytokines (IL-2, IFNg and TNFa) upon coculture with target cells pulsed with the relevant NYESO1 peptide. Further, rejuvenated NYESO1

TCR+ cells retained cytotoxic activity over a longer period of time after repeated exposure to target antigen cells than non-rejuvenated control cells. Furthermore, rejuvenated NY-ESO-1 TCR Tg CD8 T cell activity was enhanced by addition of IL-2 or Rejuvenated NY-ESO-1 TCR Tg CD4 T cells.

Example 14: Cytokine Identification

This example was carried out to assess cytokine production of rejuvenated T cells.

Rejuvenation of PBMC. On Day −2, 1×106 donor cells were thawed and incubated in 1 mL TCM+IL-2 (60 IU/ml) per well in 24-well-plate for 24 hours. The next day (i.e., Day −1) cells were counted and T cells were activated with T Cell TransAct.Human (Miltenyi) REA107 1:500, and subsequently incubated for 24 hours. On Day 0, Sendai vector transduction (MOI: KOS 10, KLF4 10, c-MYC 3, SV40 5) was performed, and a matrix-coated (iMatrix 511) plate was prepared by diluting iMatrix 511 (57.6 ul iMatrix+9 ml PBS). 500 ul of the diluted iMatrix were added per well of a 24-well plate and kept at 37° C. for >1 h. On Day 1, cells were pelleted and dispensed into the iMatrix coated plate with 500 uL stem cell culture medium+bFGF per well. On Day 3, 500 ul fresh stem cell culture medium and bFGF were added to each well in 24-well plate. On Day 7, all floating cells were harvested without suspension, and 1 mLTrypLE Express added to detach cells. The cells were incubated at 37° C. for 10 min, and then 500 ul PBS was added to each well to dilute. Cells were harvested, to which 1 ml PBS was added. The cells were suspended and harvested, and floating cells were combined with detached cells. Cells were counted, pelleted and resuspended with TCM+IL-2 (60 IU/ml) and reactivated with T Cell TransAct.Human (Miltenyi) (1:500). Supernatant was harvested and frozen. On Day 11, 14 and 18, cells were pelleted, harvested, and resuspended with fresh TCM+IL-2 (60 IU/ml).

Quantitative analysis of adaptive immune related cytokines. Supernatant from both control and rejuvenated cells on Days 7, 11, 14 and 18 were analyzed by Isoplexis Codeplex adaptive immune secretome chips. The results are depicted in FIGS. 38A and 38B. In both donors, the D7 T cell derived adherent cells showed relatively lower expression levels of GM-CSF, IFN-g, IL-5, IL-13, MIP-1a and MIP-1b. Expression of these cytokines gradually increased to a level comparable to control cells at D18. The pattern of expression of IL-6, IL-8 and TNF-b in the T cell derived adherent cells (D7 cells) is distinct from control cells. These results indicated that the T cell derived adherent cells are a different cell type from control cells.

Quantitative analysis of innate immune related cytokines. Supernatant from both control and rejuvenated cells at Day 7, 11, 14 and 18 were analyzed by Isoplexis Codeplex innate immune secretome chips. The results are depicted in FIGS. 39A and 39B. In both donors, the T cell derived adherent cells (D7 cells) showed relatively lower expression levels of IFN-g, MIP-1a.

Example 15: Selective Rejuvenation of Antigen-Specific T Cells

This example was carried out to investigate if antigen stimulation of specific T cells results in selective rejuvenation of those cells.

Establishment of autologous LCL. Healthy human donor CD4 and CD8 depleted PBMCs were thawed, washed once and resuspended in pre-warmed Complete RP10 media. 1e+6 cells were cultured in 1 ml of complete RP10 medium in 24 well plates. The supernatant of Human gamma herpesvirus 4 (HHV-4)(ATCC) was thawed and 250 ul was added to the culture. After 4 days, 500 ul of old medium was aspirated and new complete RP10 (500 ul) was added. Medium was changed every three or four days until cells started to proliferate. After three weeks, cells started proliferating and were transferred to a culture flask. 2e+6 LCLs were frozen per vial.

Step A: Healthy donor CD8 T cell activation. Healthy human donor CD8 T cells were thawed, washed once and resuspended in pre-warmed Complete TCM+IL-2 (60 IU/ml). Cells were diluted to 2e6 cells/ml. Transact was added 10 ul/ml (1/100 dilution) to stimulate CD8 T cells.

Step B: Transduction of NY-ESO-1 TCRs. The following day, stimulated CD8 T cells were counted and 1e+6 cells were suspended in 1 ml of TCM+IL-2. Supernatant from lentivirus vector encoding NYESO1-TCR (10 ul, MOI; 9.7) and LentiBoost A&B (12.5 ul each) were added to the suspended cells. The next day, transduction efficiency was determined by FACS. In particular, 7 ml of TCM+IL-2 was added to dilute the virus. On day 7, cells were stained using the antibody mix described in Table 6 below, and the cells were analyzed for expression of NY-ESO-1 TCRs. See FIG. 40.

TABLE 6

Antibody mix staining for NY-ESO-1 TCR transduced rejuvenated T cells

| Material | uL/test |
| --- | --- |
| CD3-BUV805 (SK7) | 0.5 |
| CD4-PECy7 (RPA-T4) | 0.5 |
| CD8b-BV421 (2ST8.5H7) | 0.5 |
| PE-iTAg MHC Tetramer HLA-A02:01 NY-ESO-1 | 1 |
| Fixable Viability Dye eFluor 780 | |
| BD Horizon Brilliant Stain Buffer Plus | 5 |

Step C: Reprogramming.

Mitomycin C (MMC) treatment of autologous LCL and pulsing with NY-ESO-1 peptide. Autologous LCLs were thawed, washed once and cultured in complete RP10 medium for one week. 1e+7 cells were resuspended in 2 ml of pre-warmed complete RP10 medium with added MMC (final concentration 50 ug/ml) and cultured for 1 hour in a 5% CO2 incubator. After one hour, cells were collected in a conical tube to which 10 ml of PBS were added. The cells were spun down and the supernatant was aspirated. The cells were then suspended in complete RP10. Cells were cultured in complete RP10 with or without 10 nM NY-ESO1 peptide for 2 hours in a 5% CO2 incubator. After 2 hours, the cells were washed and resuspended in TCM+IL-2.

Activation of NY-ESO-1 TCR transduced T cells by Transact or autologous LCL pulsed with or without NY-ESO-1 peptide. On day-2 NY-ESO-1 TCR Tg CD8 T cells from Step B (Transduction of NY-ESO-1 TCRs) were counted, resuspended in TCM+IL-2 and 5e+5 cells/well were seeded to 24 well plate. Four different conditions were tested; no stimulation, Transact (1/500 dilution), autologous LCL (1e+6 cells (T cell:LCL=1:2)) without NY-ESO-1 peptide, and autologous LCL (1e+6 cells (T cell:LCL=1:2)) pulsed with NY-ESO-1 peptide. The next day (day-1) T cells with Transact activation were collected, washed with 10 ml PBS, resuspended in 1 ml of TCM+IL-2, and kept in culture. T cells co-cultured with autologous LCLs were collected and T cells were enriched by EasySep™ Human T Cell Isolation Kit, resuspended in TCM+IL-2 and kept in culture. See FIG. 41.

Reprogramming of NY-ESO-1 TCR Tg T cells with Cytotune reprogramming kit. On day 0, 2.4e+5 cells were collected from each condition, re-suspended in TCM+IL-2 in 96 U-bottom plate. Cytotune Sendai reprogramming kit was used for reprogramming (KOS: MOI=10, KLF4: MOI=10, c-myc: MOI=3, and SV40: MOI=5). The following day (Day 1), cells were collected, re-suspended in stem cell culture media and seeded in an iMatrix coated 6 well plate (2 wells per condition). On Day 3, new stem cell culture media was added and on day 5 half of the medium was changed to new stem cell media (FIG. 3A).

Step D: Detachment and Re-Stimulation of Partially Reprogrammed NY-ESO-1 TCR Tg T Cells.

Collection of partially reprogrammed cells. On day 7, floating cells were collected, wells were washed with PBS, TrypLE was added, and attached cells were detached. Cell number of all the collected cells (floating cells+detached cells) were counted. All cells were then used for reactivation.

Re-stimulation of partially reprogrammed cells. Cells previously stimulated with Transact or autologous LCL with NY-ESO-1 peptide were re-stimulated with Transact or autologous LCLs with NY-ESO-1 peptide. Autologous LCLs were treated with MMC and pulsed with NY_ESO-1 peptide as previously described. 1e+5 cells/well restimulation by no stimulation/Transact(1/500)/LCL P−/LCL P+(E:T=1:1) in 200 ul of TCM+1L2 (96 U bottom plate). On day 10, half of the medium was refreshed with new TCM+IL-2. On day 14, cells were collected, resuspended in 1 ml of new TCM+IL-2 and transferred to 24 well plates. Cell counting and medium change were performed on days 18 and 21.

Surface phenotype analysis of rejuvenated T cells. On day 14, 1/20 of the cells were stained with the antibodies described in Table 6, and then analyzed by FACS for frequency of NY-ESO-1 TCR tetramer positive (TE+) cells.

The results showed that TCR stimulation by autologous LCL+NY-ESO-1 peptide prior to reprogramming resulted in more partially reprogrammed cells on day 7. NY-ESO-1 TCR transduced CD8 T cells which contain about 60% NY-ESO-1 TCR positive cells (as shown in FIG. 40) were stimulated by either Transact or autologous LCLs with or without NY-ESO-1 peptide as described above. On day 7, cells were collected (both floating and attached cells) and counted (see FIGS. 41 and 42). Compared to the number of the cells on day 0 (the day of Sendai virus infection) Transact and autologous LCLs with NY-ESO-1 peptide stimulated conditions showed an increase in cell number of 5.5 fold and 8.7 fold respectively, while, in no-stimulation and autologous LCLs without peptide conditions, the observed fold change was of 0.62 and 1.6 respectively. Autologous LCLs express EB virus antigens, therefore EB virus-specific T cells may receive TCR stimulation when co-cultured with autologous LCLs without peptide.

Re-stimulation of Partially Reprogrammed NY-ESO-1 Tg T Cells Resulted in Preferential Rejuvenation of NY-ESO-1 TCR+ Cells. On day 7, partially reprogrammed cells including attached and floating cells were collected and re-stimulated with either Transact® or autologous LCLs with or without NY-ESO-1 peptide as described. On day 14, 1/20 of the cells were harvested and analyzed for expression of NY-ESO-1 TCRs using NY-ESO-1 tetramer as described above.

Compared to cells non-specifically stimulated with TRANSACT at both the preactivation and reactivation steps (i.e., at day −2 and day 7), T cells that were stimulated with antigen (LCL+NYESO1 peptide) at either step had a higher frequency of NY-ESO-1 tetramer+ cells (see FIG. 43 and FIG. 44, 78.6% versus 97% or 97.1%) regardless of whether the primary stimulation was nonspecific (with TRANSACT) or antigen-specific (with LCL+peptide) (see FIG. 43).

Rejuvenated NY-ESO-1 Tg T Cells Proliferate. Partially reprogrammed T cells re-stimulated by Transact or autologous LCLs with peptide (first stimulation by Transact) were cultured as described until day 21. The proliferation curve is shown in FIG. 45. Rejuvenated T cells re-stimulated with autologous LCL with NY-ESO-1 peptide proliferated as well as those re-stimulated with Transact.

Example 16: Rejuvenation of CD19-CAR T Cells

This Example CD19 CAR-T cells were produced and subjected to the partial reprogramming process and then proliferation and cytotoxicity was assessed. Rejuvenated CD19 CAR T cells showed higher proliferation compared to control, as had been shown previously with NY-ESO-1 Tg CD8 T cells. Cytotoxicity of rejuvenated CD19 CART cells was tested by repeated co-culture with target cells expressing CD19 (Nalm6). After repeated co-culture, rejuvenated CAR T cells showed higher persistence and cytotoxicity.

Materials and Methods

Step A: Healthy donor CD8 T cell activation. Healthy human donor CD8 T cells were thawed, washed once and resuspended in pre-warmed Complete TCM+IL-2 (60 IU/ml) (day-3). Cells were diluted to 2e6 cells/ml. Transact was added 10 ul/ml (1/100 dilution) to stimulate CD8 T cells.

Step B: Transduction of CD19-CAR: The day after simulation with TRANSACT (day-2), stimulated CD8 T cells were counted and 3e+5 cells were suspended in 1 ml of TCM+IL-2. Lentiviral vector encoding a CD19 CAR and a truncated EGFR was produced using conventional methods. Virus supernatant (6 ul, MOI) and LentiBoost A&B (10 ul each) were added to the activated cells. The following day, 0.7 ml of the media containing virus was removed and 1.8 mls new TCM+IL-2 was added. On day 5 after CAR transduction, cells were stained using the antibody mix in Table 7 below, and analyzed for the expression of CAR by idiotype antibody and EGFR antibody. (FIG. 46)

TABLE 7

| Antibody Mix Surface Staining for CD19 CAR Transduced Rejuvenated T Cells | |
|---|---|
| Material | ul/test |
| CD62L-BUV395 (DREG-56) | 0.5 |
| CD3-BUV805 (SK7) | 0.5 |
| CD45RO-BV785 (UCHL1) | 0.5 |
| CD8a-PE (HIT8a) | 0.5 |
| CD197 (CCR7)-PE-CF594 (150503) | 0.5 |
| CD4-PECy7 (RPA-T4) | 0.5 |
| Idiotype-AF647 ( ) | 1 |
| CD45RA-AF700 (HI100) | 0.5 |
| Fixable Viability Dye eFluor 780 | |
| BD Horizon Brilliant Stain Buffer Plus | 5 |

Reprogramming of CD19 CAR Tg T cells with Cytotune reprogramming kit. On day 0 3e+5 cells (Donor #1) or 4e+5 cells (Donor #2) were collected, re-suspended in TCM+IL-2 in 48 well plates. The Cytotune Sendai reprogramming kit was used for reprogramming (KOS: MOI=10, KLF4:

MOI=10, c-myc: MOI=3, and SV40: MOI=5). Cells were collected the next day, re-suspended in stem cell media (StemFit) and seeded on iMatrix coated 6 well plate (2 wells/condition). On day 3 fresh stem cell media was added and on day 5 half of the medium was refreshed. Control cells were kept in culture in TCM+IL-2.

Step D: Re-stimulation of partially reprogrammed CD19 CAR Tg T cells. On day 7 floating cells were collected, wells were washed with PBS, TrypLE enzyme was added, and attached cells were detached. The collected cells (floating cells+detached cells) were counted. See FIG. 47. 5e+5 cells were preserved in −80° C. for DNA age examination. Harvested cells (1.7e+6 and 2.3e+6 for Donors #1 and #2 respectively) were re-stimulated with Transact (1/500 dilution) in TCM+IL-2. 1e+6 of control cells were stimulated in the same way. On day 10, half of the medium was refreshed with new TCM+IL-2. On day 13 and after, cell counts and medium changes were performed every three or four days. Cells were cultured at the concentration of 1-2e+6 cells per ml.

FACS analysis of rejuvenated T cells. On day 13, 1/20 of the cells were stained with a surface antibody (TCF7-PB (C63D9), commercially available from Cell Signaling Technology), fixed and permed using Foxp3 staining kit as described in the manufacturer's protocol, stained with Tcf7 antibody and analyzed by FACS.

Intracellular Cytokine Production Assay of Rejuvenated CD19 CAR Tg T Cells. On day 20 control and rejuvenated CD19 CAR Tg T cells were analyzed for their ability to generate cytokines upon co-culture with CD19 antigen-specific target cells. 5e+4 T cells were co-cultured with 1e+5 Colo205 (CD19−) or Nalm6 (CD19+) cells at a 1:2 E:T ratio (See FIG. 49). Wells without target cells and wells with PMA/Ionomycin (Cell Activation Cocktail) were added as negative and positive controls respectively. After 5 hours co-culture cells were stained with surface antibodies, fixed & permeabilized using a BD kit as described in the manufacturer's protocol, stained with intracellular antibodies mix (Table 7) and analyzed by FACS (Cytek Aurora). The data were analyzed with Flowjo software. The gating strategy used is as follows. Lymphocyte>Single cells>Live/Dead−>CD3+EGFR+.

Step F: Assaying the Ability for CAR-T Cells to Repeatedly Clear Target Cells Using Sequential Stimulation.

Sequential killing assay of rejuvenated CD19 CAR Tg T cells. On day 20 control and rejuvenated CD19 CAR Tg T cells were analyzed for their ability to kill target cells using sequential stimulation. Control and rejuvenated T cells were counted. 50,000 EGFR+CAR T cells were co-cultured with 20,0000 CD19+ targets (Nalm6-NLR) at 1:4 E:T in 24-well plates coated with Poly-D-Lysin. Every 3-4 days, 25% (10% for 4th and 5th co-culture) of the previous culture was transferred into a new plate with fresh target cells plated at the initial seeding density. Target clearance was quantified using the Incucyte® live-cell analysis system and analyzed with the Base Software Analysis Module.

Results

Rejuvenated CD19 CAR T cells showed less differentiated phenotype. Healthy donor CD8+ T cells were activated and transduced with CD19 CAR as described above, reprogrammed for 7 days, detached and re-stimulated by Transact. On day 13 rejuvenated CD19 CAR transduced T cells, which were distinguished by the expression of EGFRt, had a higher percentage of CCR7+CD62L+ population and Tcf1+ population, indicating that the rejuvenated CAR-T cells had a less differentiated more stem-like phenotype. (see FIG. 47)

Rejuvenated CD19 CAR T cells proliferated more than control CD19 CAR T cells. Control and rejuvenated CD19 CAR Tg T cells were cultured in TCM+IL-2 and cell counts were monitored over time. Media was changed every 3-4 days, and the cell concentration was adjusted to stay at 1-2e+6/ml. Although rejuvenated CD19 CAR Tg T cells initially showed delayed proliferation rate, day 25 marked an inflexion point, after which by day 55 rejuvenated cells exhibited over 100 fold greater expansion compared to control. (see FIG. 48)

Rejuvenated CD19 CAR T cells produced comparable levels of cytokines upon co-culture with CD19 expressing target cells. Production of cytokines (IL-2, TNFa, IFNg) of control and rejuvenated CD19 CAR T cells were analyzed by co-culturing them with target cells expressing CD19 (Nalm6) or no CD19 (Colo205) as described above. Neither the control or rejuvenated CD19 CAR Tg T cells produced cytokines upon co-culture with control Colo205 cells. However, both groups produced cytokines upon co-culture with Nalm6 at comparable levels with the exception of IFNg. (see FIG. 49). Notably, IFNg production was higher in rejuvenated cells as compared to control.

Rejuvenated CD19 CAR T cells persisted and retained their ability to kill target cells longer than control cells upon repeated stimulation (co-culture) with CD19 expressing target cells. n both donors, rejuvenated and control CAR T cells effectively killed and cleared target cells up to the 4th or 5th round of co-culture. However, at restimulation rounds 6 and 7, rejuvenated cells maintained superior cytotoxicity and persistence while the control cells did not. (see FIGS. 50A and 50B) Collectively, these studies suggest that the rejuvenation process utilizing partial reprogramming results in CD19 CAR T cells that have a more stem-like phenotype, higher proliferative capacity, higher persistence and cytotoxicity as compared to control cells.

Example 17: mSev vs. Sev

In this example, a Sendai virus vector that was modified to express the four Yamanaka factors from a single multicistronic (i.e., "mSev") vector was used for rejuvenating T cells and compared to rejuvenation with the Cytotune kit as described in previous examples.

As described previously, the Cytotune-iPS 2.0 Sendai reprogramming kit (i.e., "Sev") contains 3 separate viral vectors: (KOS encoding Klf4, OCT4 and SOX2; cMyc; Klf4 for reprogramming Generally, an additional Sendai virus (Sev) expressing SV40 is also used to inhibit apoptosis and increase reprogramming efficiency. Using the cytotune kit, four separate vectors have to be transduced into T cells. As discussed in further detail below, it was found that transduction with four separate viruses results in uneven co-transduction, inefficient reprogramming, and can result in significant variation in later products.

Accordingly, T cells were subjected to the rejuvenation process described herein, using either (a) the multicistronic Sendai vector expressing the four Yamanaka factors (but not expressing SV40) or (b) the Cytotune Sev (+SV40).

Both experimental groups showed similar proliferation curves for 23 days after detachment. The multicistronic Sendai group showed slightly higher stemness T cell phenotype (TCF1+CCR7+). These data indicate that the multicistronic Sendai vector even without SV40, which increases reprogramming efficiency, can be used for partial reprogramming and rejuvenation of T cells.

Step A: T cell rejuvenation. CD8+ T cells from a 53-year-old male (Donor 1) and a 55 year-old male (Donor 2) were stimulated with T cell TransAct, human (Miltenyi Biotec, cat #130-111-160) at 1:500 dilution in T cell culture medium containing 60 IU/ml of IL-2 at a cell density of 1 million cells/mL in a 48-well plate. In this Example, the inventors found that 24 hours of activation resulted in the most efficient transduction using the multicistronic Sendai virus vector (mSev). After 26 hours of stimulation with TransAct, the cells were divided into two groups (i.e., on Day 0). One group of cells underwent the rejuvenation process using Sendai virus vectors from the CytoTune kit (Sev or "Comparative Example 17") whereas the other group was rejuvenated with multicistronic Sendai virus vector (mSev). The Sev rejuvenated group was transduced with 10 MOI of Klf4-Oct3/4-Sox2, 10 MOI of Klf4, 3 MOI of cMyc (Cytotune iPS 2.0 Sendai Reprogramming Kit, Thermo) and 5 MOI of SV40, while MSev group was transduced with 5 MOI of mSev expressing all four Yamanaka factors without SV40. Cells were then cultured at 37° C. After 16.5 h, cells were washed and suspended with stem cell medium (SCM; Stemfit Basic 04 with bFGF). The cells were plated on iMatrix-511 (PEPROTEC cat #RL511S) coated 24-well plate at 50,000 cells/well (corresponding to day 0 counts) and cultured at 37° C. (i.e., Day 1). 500 ul of SCM was added on days 3, 5, 7, 9. 1 ml of SCM was aspirated on day 7. For the restimulation, both groups were detached on day 7, 9 and 11 using 1 ml of TrypLE Express (Thermo cat #12604013) and incubated at 37° C. for 10 min. The detached cells were harvested by pipetting. 1×105 cells were activated with 1:500 diluted T cell TransAct human in 200 uL of T cell culture medium at a density of 5×105 cells/ml in 96-well round bottom plate. Two days after detachment, cells were transferred to a 12-well plate and 1 ml of T cell culture medium was added to each well. Four days after detachment, cells were transferred to a 6-well plate. Thereafter, the cells were cultured with T cell culture medium with IL2 60 IU/ml, in a six-well plate.

Step B: Flowcytometry analysis. Cells were stained with fluorescent conjugated antibodies and viability dye (see Table 8 below). Cell phenotypes were acquired by flow cytometry in a Cytek Aurora.

TABLE 8

Antibodies and Viability Dye for Staining

| | Fluorescent | Dilution factor | Vendor | Cat# |
|---|---|---|---|---|
| Fixable Viability Dye | eFluor 780 | 5:10000 | Thermo | 50-169-66 |
| CCR7 | PE CF594 | 3:100 | BD | 562381 |
| CD3 | BUV805 | 2.5:100 | Thermo | 612893 |
| CD45RA | Alexa 700 | 2.5:100 | BD | 560673 |
| CD45RO | BV786 | 1.25:100 | BD | 564290 |
| CD8b (CD8 beta) | BV421 | 1:100 | BD | 742390 |
| CD4 | BUV496 | 1:100 | BD | 612937 |
| CD62L | BUV395 | 0.3:100 | BD | 740301 |
| TCF1/7 | PE | 1:100 | Cell Signaling Technology | 14456 |

Step C: DNA Extraction and Epigenetic Analysis

DNA was extracted from the frozen cell pellets using PureLink Genomic DNA mini kit (Invitrogen, K182002). Each extracted DNA was split into 3 tubes for technical replicates of methylome analysis. Samples were sent to AKESOgen, Inc for epigenetic analysis by Illumina Infinium array. The CpG methylation status data was analyzed using the Horvath method as described in (AGING 2018, Vol. 10, No. 7, 1758-1774) for skin and blood clock values.

Step D: Analysis

CD8+ T cells from 2 male donors aged 53 and 55 were transduced with Sev or mSev, detached, and restimulated on day 7, 9 and 11 (see FIG. 51). After detaching and restimulating, conventional T cell markers CD3 and CD8b were fully recovered in both groups of rejuvenated cells 6 days after detachment and reactivation (see FIGS. 52A and 52B).

Cell were cultured for 23 days after detachment.

For cells detached on Day 7 (FIG. 53A) and Day 9 (FIG. 53B), both Sev and mSev transduced groups showed similar proliferation curves. For cells detached on Day 11 (FIG. 53C), the mSev group showed higher proliferation. It was observed that Sev reprogramming resulted in bigger colonies at detachment and resulted in cell yield that was 3-4 times higher than the yield measured in the mSev group. The mSev group had more colonies but the colonies were smaller. Without being bound to a single theory, it is believed that the difference in cell count between the Sev and mSev groups may be caused by the lower expression levels of the reprogramming factors from the mSev vector and the absence of SV40, which increases reprogramming efficiency. Overall, the proliferation curves for the Sev and mSev groups are similar, indicating that the mSev reprogrammed cells acquired a similarly rejuvenated capacity for proliferation.

The Sev and mSev appeared to have different reprogramming speeds. In particular, at the time of detachment on Day 11 (see FIGS. 52A and 52B), cells in the Sev group had lost more CD3 and CD8b cell surface expression than the mSev group (see FIG. 52A). This suggests that more cells in the Sev group were reprogrammed up to the point of no return than in the mSev group, resulting in fewer cells that respond to TranAct and proliferate in the Sev group. These data also suggest that reprogramming using the mSev vector is slower than reprogramming using Sev, and that mSev reprogramming requires more time for the formation of sufficient T-cell derived adherent cells and rejuvenation of the partially reprogrammed cells. Without wishing to be bound by a single theory, the observed difference might be caused by the expression level of the reprogramming factors in the multicistronic vector and/or the absence of SV40, as discussed above. Modifying the vector to increase expression of the reprogramming factors and/or the addition of SV40 could reduce the number of days required to reach desired reprogramming.

In terms of cell phenotype, mSev showed a higher TCF1+ CCR7+ and higher CCR7+CD62L+ population among CD3+CD8b+ population which suggests more stem-like population in the mSev group (see FIGS. 54A and 54BA).

The epigenetic age determination by Horvath clock analysis showed that the mSev transiently reprogrammed T cells had reduced epigenetic age as compared to control cells (see FIG. 55) on detachment Day 7, detachment Day 9, and detachment Day 11. The reduction in eAge for each group as graphed in FIG. 55 is summarized below in Table 9:

TABLE 9

% Reduction in eAge 6 days after detachment (see FIG. 55)

| Day of Detachment | % Reduction in eAge 53 year old donor | | % Reduction in eAge 55 year old donor | |
|---|---|---|---|---|
| | Sev | mSev | Sev | mSev |
| 7 | 9% | 0.89% | 014% | 9.7% |
| 9 | 17% | 7% | 26% | 7.79% |
| 11 | 13% | 6% | 25% | 8% |

As shown in Table 9, the reduction in eAge in the mSev group was lower than the reduction observed in the Sev group. Such a result is not surprising, given that the mSev vector required a longer time for reprogramming. As discussed above, modifying the vector to increase expression of the reprogramming factors could result in further reduction in eAge of transiently reprogrammed T cells.

Accordingly, this Example and the accompanying data suggest that the multicistronic Sendai vector can be used for rejuvenation of T cells.

Example 18: Transcriptome Characterization of Rejuvenated CD8+ T-Cells

In this Example high-dimensional transcriptional analysis of single cell and bulk RNAseq was used to characterize rejuvenated T cells as compared to control T cells. In summary, analysis of the clustered single cell RNA-seq data showed that, after seven days of reprogramming, the rejuvenated T-cells had a very different global phenotype than the control T cells. Most of the partially reprogrammed cells expressed the four Yamanaka factors on Day 7 but by Day 13, the expression of the transduced Yamanaka factors was at background levels. Expression of one of the Yamanaka factors—C-MYC—was observed on Day 13, but it was confirmed that this was endogenous (i.e., not transduced) C-MYC. By Day 13, the rejuvenated cells reverted to T cells expressing classic T cell markers but without expression of lymphocytic/myeloid lineage markers classically seen in iPSC-derived T cells (Maeda et al. 2016). The single-cell RNA-seq results were confirmed with bulk RNA-seq analysis. Enrichment of several metabolic gene sets was seen in rejuvenated cells at both Day 7 and Day 13. In summary, transcriptional analysis highlighted that at day 7 after Yamanaka factor transduction, the T cell adherent cells are very different from corresponding control T-cells. After D13, following reactivation, the rejuvenated cells are expressing T-cell markers and genes enriched in metabolic gene sets while losing Yamanaka factor expression.

T Cell Rejuvenation

In this Example, two independent experiments were done using four donors.

In the first experiment, CD8 positive T cells from a 54-year-old male donor (Donor No. 18698) were subjected to the rejuvenation process as described below. Cells were divided into two groups, one rejuvenated as described below and the other used as control.

In the second experiment, CD8 positive T cells from a 53-year-old male donor, 55-year-old male donor and 50-year-old male donor (Donor Nos. 11347, 12254 and 26221, respectively) were subjected to the same protocol.

For both of the experiments, CD8 positive T cells from each donor were stimulated with T cell TransAct, human (Miltenyi Biotec) at 1:500 dilution in T cell culture medium containing 60 IU/ml of IL-2 at a cell density of 1 million cells/mL in a 48-well plate. After 24 h activation with TransAct, cells from each donor were divided into 2 groups, one group was subjected to the rejuvenation process as described herein and the other was used as controls (no transduction with Sendai vectors) and cultured in T cell culture medium. Control groups were activated with TRANSACT at the preactivation step, cultured in TCM with IL2 and then were reactivated with TRANSACT at the same time the partially reprogrammed cells were reactivated (after detachment at Day 7).

In the rejuvenated groups, the four Yamanaka factors and SV40 containing Sendai viruses (SeV) were transduced at a 10 MOI of Klf4-Oct3/4-Sox2, 10 MOI of Klf4, 3 MOI of cMyc (Cytotune iPS 2.0 Sendai Reprogramming Kit, Thermo) and 5 MOI of SV40 (ID Pharma, Tsukuba, Japan) (i.e., on Day 0), then cultured at 37° C. After 16 hours, cells were washed and suspended with stem cell medium (Stemfit Basic 02 with bFGF, Ajinomoto Co., Tokyo, Japan). The cells were plated on iMatrix-511 (PEPROTEC) coated 24-well plate at 50,000 cells/well (corresponding to day 0 count of 50,000) and cultured at 37° C. (Day 1). On days 3 and 5, 500 ul of SCM was added to the cultures. On day 7, the T-cell derived adherent cells were incubated at 37° C. for 10 minutes with 0.5 ml of TrypLE Express (Thermo) to detach the cells from the culture dish. The detached cells were then harvested by pipetting. Floating cells in the supernatant were also harvested and mixed with the detached cells. Floating cells in the first experiment were abandoned due to insufficient cell numbers.

0.5 million cells of both control and rejuvenated samples were activated with 1:500 diluted T cell TransAct, human in 500 ul of T cell culture medium at a density of 1 million cells/ml in 48-well plate in the second experiment while the cell number in the first experiment was 364,050/well in 48-well plate due to low cell numbers. Both control and rejuvenated cells were seeded at the same density. Cells were cultured out to day 13 (from detachment at day 7) with samples acquired at 2 time points (day 7 and day 13) and subjected to dead cell removal as described below for transcriptome analysis. Cells were allowed to continue in culture to Day 17 for experiment 1 and out to Day 29 for experiment 2. Cells were counted on Days 7 and 13 for both the first and second experiments. Cells were also counted on Days 18, 21 and 29 for the second experiment.

Dead cells were removed using EasySep Dead Cell Removal (Annexin V) kit (STEMCELL technologies) according to manufacturer's instructions. The samples were processed twice with EasySep to increase viable cell purity.

Transcriptional Profiling of T Cells by Bulk RNA-Seq

Cells from both rejuvenated and control samples from the four male donors were also collected on Days 7 and 13 for bulk RNA-seq.

At each collection time point, cells were subjected to dead cell removal (as described above) and approximately 50,000 cells from each sample were collected in Lysis binding mix prepared according to the MagMAX mirVana Total RNA Isolation Kit protocol (Thermo Fisher Scientific) and stored at −80° C. until processing.

Total RNA was extracted from cells using the MagMAX mirVana RNA kit on the Kingfisher Flex system and stored at −80° C. RNA quality and quantity were assessed using the Agilent RNA 6000 Pico kit (Agilent) on the 2100 BioAnalyzer. Libraries for mRNA sequencing were prepared with 5 ng of total RNA for cDNA generation using the SMART-Seq v4 Ultra Low Input RNA kit (Takara Bio USA) using the manufacturer's protocol automated on the Biomek i7 workstation. cDNA assessment was performed using the High sensitivity DNA kit (Agilent) on the 2100 BioAnalyzer and 150 pg of full-length cDNA was used to prepare barcoded libraries for sequencing using the Nextera XT DNA Library Prep kit (Illumina) using the manufacturer's protocol automated on the Biomek i7 workstation. Quality assessment was performed using a DNA1000 ScreenTape Assay (Agilent) with a 4200 TapeStation System. Barcoded libraries across samples were then multiplexed in an equimolar pool, purified, and sequenced using a NovaSeq 6000 system.

Single Cell CITE-Seq Analysis

Single Cell CITE-Seq data was processed using the 10× Cell Ranger software version 5.0.1 (10× Genomics) with Genome Reference Consortium Human Build 38 (GRCh38) as reference genome and default parameters. The reference genome was supplemented with the transduced Yamanaka factor sequences and control sequences from the Sendai virus backbone. The cell-gene matrix was further processed using Seurat package (see Hao et al. 2021) in R. Cell level quality control and removal of outliers were performed by visually selecting thresholds for percent mitochondria, nCount_RNA, nFeature_RNA, nCount_ADT and hashtag doublets. Cells from both rejuvenated and control samples collected from the four male donors were merged for Day 7 and Day 13 single cell transcriptome analysis. The filtered cell-gene matrix was globally scaled with 'NormalizeData' function with scale.factor parameter set to default 10000. For each donor sample, the effects of cell cycle heterogeneity were corrected by calculating cell cycle phase scores (G2M.Score, S.Score) with 'CellCycleScoring' function in Seurat and then regressing out the cell cycle phase scores and percent mitochondrial reads in the function. Genes correlated with either of the two cell cycle phase scores (with Pearson correlation coefficient greater than 0.25) were excluded from selected features to further minimize the effects of cell cycle heterogeneity. Mitochondria, ribosome, TCR, and IG complex related genes were also excluded from the selected features.

To correct for possible batch effects and to account for donor heterogeneity, the datasets from each donor on Days 7 and 13 were combined with 'FindIntegrationAnchors' and 'IntegrateData' function calls using the first 30 canonical correlation analysis dimensions. Then, the integrated data was scaled, and the top 30 PCs were calculated by 'RunPCA' function using the filtered features. Afterward, uniform manifold approximation and projection (UMAP) by 'RunUMAP' function in Seurat was used to map cells to two-dimensional space for visualization with each dot representing a cell. Cells were subjected to cluster analysis using the 'FindClusters' function in Seurat. CITE-Seq analysis is also referred to as single cell RNA-Seq analysis in the report, since the analysis (UMAP, clustering) was done using RNA expression without protein expression in the CD8+ T-cells.

Single Cell Phenotype Assessment

After single cell clustering analysis, expression level of marker genes coding for Yamanaka factors was visualized with the 'FeaturePlots' function. The expression of conventional and unconventional T or B cell markers observed on human induced pluripotent stem cell-derived cells (Themeli et al. 2013, Maeda et al 2016) was assessed with heatmap visualization implemented in the pHeatmap package (pheatmap CRAN). Pseudo-bulk gene markers for rejuvenated cells were identified using 'FindMarkers' in Seurat. The cells positive for significant gene sets were visualized with the 'AddModuleScore' function in Seurat.

[0109] The single cell reads alignments were visualized with Integrative Genomics Browser (see, e.g., Thorvaldsdóttir et al. 2013).

Bulk RNA-Seq Analysis

Gene expression was generated from sequencing data using a standard processing pipeline. Trim galore (Krueger-Github) was used for adaptor trimming and STAR (see, e.g., Dobin et al. 2013) was used for alignment to a reference genome compiled with GRCh38 sequences supplemented with overexpressed Yamanaka factors sequences and control sequences from the Sendai virus backbone. Gene expression quantification was performed by RSEM (see, e.g., Li and Dewey. 2011) with default parameters. Differential analysis was performed using the DESeq2 (Love et al 2014) package, from which statistics such as log 2 fold change (log 2FC) in expression and adjusted p value (padj) were calculated.

Enrichment of metabolic gene sets (MSigDB version 7, Subramanian et al 2005) was performed with the 'enricher' function implemented in the clusterProfiler package (see, e.g., Yu et al. 2012).

Phenotypical Assessment of Rejuvenated Cells.

CD8 positive T cells from the four male donors were transduced with Yamanaka factors and SV40 (i.e., rejuvenated cells) according to the rejuvenation protocol and compared with corresponding controls which were in non-transduced condition at each time point. Cells were allowed to grow out to Days 17 and 29 in Experiments 1 and 2, respectively. As shown in FIG. 56 consistent with previous Examples, rejuvenated cells showed increased proliferation as compared to the control cells.

Single-cell RNA-seq analysis was performed on CD8+ T-cells from control and rejuvenated cells on Day 7 and Day 13 using cells from all four donors (Donor nos. 18698, 11347, 12254 and 26221). Bulk RNA-seq was performed from the same samples as used in the second experiment described above (i.e., the 53-year-old, 55-year-old, and 50-year-old males of the second experiment).

Cells at the end of seven-day partial reprogramming show a different phenotype than corresponding control T cells. Single cell RNA-seq UMAP plots showed that the rejuvenated cells cluster separately than the control cells (see FIG. 57A). There were two rejuvenated cell clusters on Day 7, one with most cells expressing Yamanaka factors (OCT4. SOX2, KLF4 and C-MYC) and another one negative for these factors (see FIG. 57A). The downregulation of exogenous reprogramming factors after Day 7 was observed in both single-cell (see FIG. 57B) and bulk (see FIG. 57C) RNA-seq data. Of note, there are some single cells that express cMYC on Day 13 after redirection to the T-cell state (see FIG. 57B, panel labeled Myc). We have confirmed that C-MYC expression after reprogramming to be predominantly endogenous and not from the transduced C-MYC (FIG. 57D). The main peak of alignment of single-cell RNA-seq reads from day 7 is to exon 1 (data range, 0-66547) while the peak of alignment at Day 13 is from the 5' UTR of C-MYC (data range 0-2596). The transduced C-MYC starts at exon 1 while endogenous cMYC is expected to start at the 5' UTR confirming that the C-MYC seen at Day 7 is transduced while that at Day 13 is endogenous. These data suggest that Rejuvenated T cells are still expressing the four Yamanaka Factors until the day of detachment, resuspension and activation (Day 7). Exogenous expression of these factors are not detected on Day 13. Although rejuvenated T cells are still expressing C-MYC, the expression origin is endogenous.

Expression of lineage-specific lymphoid/myeloid marker genes in the rejuvenated and control T cells was then assessed both in single-cell and bulk RNA-seq data (Themeli et al. 2013, Maeda et al 2016). The Day 7 detached rejuvenated cells (e.g., T cell adherent cells) showed reduced expression of CD3 and CD8b. After detaching and stimulating them, the T cell lineage markers were fully recovered in the rejuvenated cells on Day 13. Abnormal expression of unconventional, NK, T or B cell markers (e.g., NCAM1, NCR2, FCGR3A, KIR2DL4, KIR2DS4), like those observed on human iPSC-derived T cell products (Themeli et al. 2013, Maeda et al 2016) was not seen in rejuvenated T cells. Thus, rejuvenated T cells produced using the partial reprogramming methods described herein did not aberrantly express unconventional markers NCAM1, NCR2, FCGR3A, KIR2DL4, KIR2DS4.

Differentiation of human iPSC into conventional mature T cells has been challenging, involving the use of 3D organoid cultures to provide an appropriate environment for the orderly commitment and differentiation that is required for T cell differentiation (Montel-Hagen et al., 2019). Additionally, differentiation of T cells from iPSC results in T cells that express aberrant NK, T or B cell markers (Themeli et al. 2013, Maeda et al 2016). The data confirmed that the partial T cell reprogramming process not only avoids the time-consuming reprogramming to iPSC and the use of complex T cell redifferentiation systems, but surprisingly, after activation of the T cells, the process resulted in T cells that do not express aberrant markers, have reduced epigenetic age as compared to controls and starting T cells, and have increased proliferation capacity.

The rejuvenated cells were then assessed to determine whether they were metabolically different from the corresponding control T cells at both Day 7 and Day 13. Metabolic gene sets corresponding to oxidative phosphorylation, fatty acid metabolism, glycolysis and hypoxia were significantly enriched in the Day 7 and Day 13 rejuvenated cells (see FIG. 58A). Projection of these metabolic gene sets onto single-cell RNA-seq data indicated that, at Day 7, the rejuvenated cells were enriched for both glycolysis and oxidative phosphorylation. Surprisingly, while by Day 13 the rejuvenated cells shift to being either high in oxidative phosphorylation or high in glycolysis (see FIG. 58B), the cells were still significantly enriched for both these gene sets globally in comparison to control cells.

Additionally, naïve gene sets (Gattinoni et al., 2011 Nature Medicine 17(10):1290-1297) in the rejuvenated cells and corresponding control T cells were assessed at Day 13. Gene sets corresponding to naïve T cell phenotype were enriched in the Day 13 rejuvenated cells (see FIGS. 59A and 59B). Further, relative T cell receptor repertoire diversity was estimated by Simpson clonality (Wong et al. J. Immunology V: 197. Pp 1642-1649). T-cell repertoire diversity was estimated with Simpson Clonality metric, which ranges from 0 to 1, where 0 represents a completely uniform sample and 1 represents a monoclonal sample. Lower Simpson Clonality, indicating increased TCR repertoire diversity, was observed in rejuvenated samples at day 7 and day 13 as compared to control T-cells. (see FIG. 75).

Accordingly, the rejuvenated T cells of this Example were enriched for expression of genes associated with higher metabolic activity as compared with control cells. The data in this Example also suggests that rejuvenated T cells are more fit to use energy and synthesize nucleotides needed for proliferation and further explains the significantly increased proliferative capacity observed in the rejuvenated cells as compared to controls. The enrichment of both oxidative phosphorylation and glycolysis gene sets is associated with the metabolic shift during reprogramming of somatic cells to iPSCs (see, e.g., Nishimura 2019 Int. J. Mol. Sci. 20:2254; doi:10.3390/ijms20092254) and suggests that the rejuvenated cells may have acquired some stem cell-related qualities without reprogramming to a fully pluripotent iPSC stage. Moreover, rejuvenated T cells are enriched for gene sets corresponding to naive T cell phenotype and have increased polyclonality. Taken together, the data suggest that the rejuvenation process described herein results in T cells that have improved and advantageous properties for use in adoptive cell therapy treatments.

Example 19: Rejuvenation Enhanced T Cell Stemness Properties in Tumor Infiltrating Lymphocytes In this example, TILs were rejuvenated from numerous different tumor types (lung adenocarcinoma, colorectal, liver, melanoma, colorectal carcinoma metastasis to the liver), using the process as described in Example 11 with differences as noted below in Table 10.

Tumor samples were procured from the Cooperative Human Tissue Network (CHTN). TILs were freshly isolated and either 1) enriched by magnetic bead separation for CD45+ immune cells (e.g., T cells) and used directly; 2) enriched by magnetic bead separation for CD45+ immune cells (e.g., T cells) followed by activation with TransAct (1:500) for 1 or 2 days; or 3) isolated and expanded for between 5 and 17 days in media containing 6000 IU/ml IL-2. Because the tumor samples were small, enrichment and/or expansion was needed to generate enough cells for the rejuvenation process. For the pre-activation step, TILs were activated by one of the following as outlined in Table 10 below:

1) TransAct (1:500 dilution unless noted otherwise; in certain experiments, a dilution of 1:2000 was used. No significant difference was noted between the two dilutions);

2) co-culture with autologous tumor organoid prepared essentially as follows: tumor fragments were finely minced on ice, washed with PBS and embedded with Matrigel on ice, forming domes in 6 well plate with around 20 ul per dome. After solidifying at 37° C. for 20 minutes, the domes were overlayed with 2 mL IntestiCult™ Organoid Growth Medium (Human) (Stemcell Technologies). In the case where tumor fragments could not be finely minced, collagenase IV (200 IU/mL; (Worthington Biochemical Corporation) was used to digest the tissue in 37° C. for 30 minutes before washing and embedding. or autologous tumor cell line, followed by FACS sorting of 4-1BB+ cells.

TILs were then rejuvenated as follows: TILs from the pre-activation step were transduced with 10 MOI of Klf4-Oct3/4-Sox2, 10 MOI of Klf4, 3 MOI of cMyc (Cytotune iPS 2.0 Sendai Reprogramming Kit, Thermo) and 5 MOI of SV40. Cells were then cultured at 37° C. After about 16 hours, cells were washed and suspended with stem cell medium (SCM; Stemfit Basic 02 with bFGF). The cells were plated on iMatrix-511 (PEPROTEC) coated 24-well plate at around 50,000 cells/well (corresponding to day 0 cell counts) and cultured at 37° C. (Day 1). TILs were detached on day 7 with enzyme (1 ml of TryplE Express (Thermo)) and incubated at 37° C. for 10 min. The detached cells were harvested by pipetting. 1E5 cells were activated with 1:500 diluted T cell TransAct human in 200 ul of TCM supplemented with 60 IU/mL IL2 at a density of 5×105 cells/ml in 96-well round bottom plate. Cell counts were taken at various time points as noted in the associated figures (FIGS. 60, 62, 64 and 68) out as far as day 30. Expression of surface markers associated with stemness (CD62L, CCR7, TCF7) were measured by flow cytometry at the days noted in FIGS. 61, 63 and 65. Note that at earlier time points, there were often insufficient cell numbers to assess phenotype.

For experiment 6, epigenetic age determination was carried out as follows: DNA was extracted from the frozen cell pellets using PureLink Genomic DNA mini kit (Invitrogen, K182002). Each extracted DNA was split into 3 tubes for technical replicates of methylome analysis. Samples were sent to AKESOgen, Inc for epigenetic analysis by Illumina Infinium array. The CpG methylation status data was analyzed using the Horvath method as described in ((1) Horvath Genome Biology 2013, 14: R115; (2) doi:10.1371/journal-.pone.00148211 for skin and blood epigenetic clock values. (see FIG. 66 and FIG. 67)

As shown in FIGS. 60-68, the data from this Example confirm the results and conclusions outlined previously in Example 11 and shown in FIG. 27 that TIL can be rejuvenated using the methods herein and extend the data to several different tumor types including lung adenocarcinoma, colorectal cancer, liver cancer, melanoma, and colorectal carcinoma metastasis to the liver. The results show that rejuvenated TILs exhibited enhanced proliferative capacity, increased expression of phenotypic markers associated with stemness and reduced epigenetic age.

While the enhanced expression of stemness phenotypic markers declines and the epigenetic age increases gradually with expansion over time, TILs are generally exhausted, terminally differentiated and difficult to expand. The ability of TILs to acquire enhanced proliferative capacity, increased expression of phenotypic markers associated with stemness and reduced epigenetic age following the rejuvenation process suggests that the rejuvenation process can be used to improve the therapeutic potential of TILs in adoptive cell therapy applications.

TILs from 52- and 83-year-old female donors (Donors 6 and 8; see Table 10) were isolated from tumor sample by mechanical dissociation on ice followed by enzymatic digestion for between about 30 to about 90 minutes and either used directly (i.e., "bulk") or enriched by magnetic bead separation for CD45+ immune cells (e.g., T cells) followed by expansion with TransAct.

For donor 8 (83-year-old female), TILs were expanded by culturing in T cell culture medium with 6000 IU/ml of IL-2 and expanded for 1 month. For the pre-activation step prior to transduction, TIL were activated with T cell TransAct, human (Miltenyi Biotec) at 1:500 dilution for 1 day. The pre-activated TIL were then transduced with 5 MOI of mSev expressing 4 Yamanaka factors without SV40. Cells were then cultured at 37° C.

After about 16 hours, cells were washed and suspended with stem cell medium (Stemfit Basic 02 with bFGF) and

TABLE 10

Summary of rejuvenation of TILs from multiple tumor types

| Expt | Donor No. | Age/sex | Tumor Type | TILs isolation/expansion | Pre-Activation | Proliferation[a] | FIGS (if provided) |
|---|---|---|---|---|---|---|---|
| 1 | 1 | 66/M | Lung Adenocarc. | 6000 IU/mL IL2 | Trans Act | +++ | FIG. 61A |
|   |   |   |   |   | Coculture with tumor organoid; 4-1BB+ sort | ++ | FIG. 27 FIG. 61B[b] |
| 1 | 2 | 58/M | CRC met to Liver | 6000 IU/mL IL2 | Trans Act | – | FIG. 60B |
|   |   |   |   |   | Coculture with tumor organoid; 4-1BB+ sort | +++ | FIG. 61B[b] |
| 2 | 3 | 85/M | Colon | 6000 IU/mL IL2 | TransAct | +++ | FIG. 62 |
|   |   |   |   | Fresh isolated; CD45 enriched |   | +++ | FIG. 63[b] |
| 3 | 4 | 61/M | Melanoma | 6000 IU/mL IL2 | TransAct 1:500 (High) TransAct 1:2000 (Low) | + | FIG. 64 FIG. 65[b] |
| 4 | 1 | 66/M | Lung Adenocarc. | 6000 IU/mL IL2 | TransAct | + | Not shown |
| 4 | 2 | 58/M | CRC met to Liver | 6000 IU/mL IL2 | TransAct | + | Not shown |
| 4 | 5 | 71/M | Liver | 6000 IU/mL IL2 | TransAct | + | Not shown |
| 4 | 6 | 52/F | CRC met to Liver | Fresh isolated; CD45 enriched | TransAct | + | Not shown |
| 4 | 4 | 61/M | Melanoma | 6000 IU/mL IL2 | Coculture with tumor cell line; 4-1BB+ sort | + | Not shown |
| 5 | 7 | 61/M | CRC met to Liver | Fresh isolated; CD45 enriched | TransAct | +++ | Not shown |
| 5 | 3 | 85/M | Colon | 6000 IU/mL IL2 | TransAct | +++ | Not shown |
| 5 | 8 | 83/F | Colon | 6000 IU/mL IL2 | TransAct | ++ | Not shown |
| 6 | 7 | 61/M | CRC met to Liver | 6000 IU/mL IL2 | TransAct | + | FIG. 66[c] FIG 68 |
| 6 | 9 | 73/M | Colon | 6000 IU/mL IL2 | TransAct | + | FIG. 67[c] FIG. 68 |

[a]+++Significantly better than control;
++Better than control;
+comparable to control;
–Did not proliferate
[b]Stemness phenotype analysis;
[c]Horvath clock epigenetic age (eAge) analysis

Example 20: Rejuvenating Tumor Infiltrating Lymphocytes Using mSev

In this Example, the multicistronic Sendai vector (mSev) encoding the four Yamanaka factors (without SV40) as described in Example 17 was used to rejuvenate TILs.

plated on iMatrix-511 (PEPROTEC) coated 24-well plate at 50,000 cells/well (corresponding to Day 0 counts) and cultured at 37° C. (i.e., on Day 1).

On Day 11, the T cell derived adherent cells were detached using 1 mL of TryplE Express (Thermo) incubated at 37° C. for 10 min. The detached cells were then harvested by pipetting. 1×105 cells were activated with 1:500 diluted T cell TransAct human in 200 ul of T cell culture medium at a density of 5×105 cells/mL in 96-well round bottom plate. Two days after detachment, cells were transferred to a 12-well plate and 1 mL of T cell culture medium was added to each well. Four days after detachment, cells were transferred to a 6-well plate. Thereafter, the cells were cultured with T cell culture medium in a 6-well plate. On days 14 and 18, cells were stained with fluorescent conjugated antibodies and viability dye and cell phenotypes were acquired by flow cytometry in a Cytek Aurora.

On Days 14 and 18, the mSev rejuvenated cells showed a higher TCF7+CCR7+ population among CD3+ population which suggests a more stem-like population in the mSev group than controls (see FIGS. 69A and 69B).

Thus, this Example indicates that the mSev vector can be used for rejuvenation of TILs.

Example 21: Integrin α6 and Integrin β1 as a Marker of Rejuvenated T Cells

In this Example it was assessed whether integrin α6β1 could be a marker for T cell adherent cells which may contribute to cell adhesion and a less-differentiated phenotype(s).

Integrins are one of the most important proteins which are involved in cell adhesion. The heterodimer transmembrane proteins bind actin cytoskeleton to extracellular matrix thereby connecting cells with the extracellular matrix. They work as not only cell adhesion molecules but also as receptors which transmit intracellular signaling that regulate cell proliferation and survival. An important feature of the partial reprogramming of T cells described herein is cell attachment to a matrix-coated plate in the early phase, which suggests that the partially reprogrammed T cells express cell adhesion molecules, namely integrins (see, e.g., www(dot)ncbi(dot)nlm(dot)nih(dot)gov/books/NBK26867/). In iPS cells, the most dominant integrin complex is integrin α6β1 (see, e.g., Nishiuchi et al., Matrix Biology 2006, 25(3):189-197). Integrin α6β1 is known to bind to laminin-511, which was used in the instant Example as extracellular matrix and has been used for culture of human pluripotent stem cells (see e.g., Miyazaki T. et al. Nat Commun (2012) 3, 1236).

Materials and Methods

Step A: T Cell Rejuvenation

CD8 positive T cells from a 49-year-old female donor were stimulated with T cell TransAct, human (Miltenyi Biotec, cat #130-111-160) for 1 day in T cell culture medium (TCM) with 60 IU/ml of 1L2 as 1 million cells/1 ml in a 48-well plate. All TCM used in this Example contained 60 IU/ml IL2. After 24 h activation, transduction was carried out.

Sendai viruses were transduced at 10 MOI of Klf4-Oct3/4-Sox2, 10 MOI of Klf4, 3 MOI of cMyc, and 5 MOI of SV40 (Cytotune iPS 2.0 Sendai Reprogramming Kit, Thermo) for 17 hours, then washed and suspended in stem cell medium (SCM) (StemFit Basic02 with bFGF, Ajinomoto) without IL2.

The cells were plated on an iMatrix-511 (PEPROTEC cat #RL511S) coated 24-well plate as 0.05 million cells/well (corresponding to day 0 count of 0.05 million).

Step B: Partially Reprogrammed T Cell Detachment

On Day 10, the partially reprogrammed T cells were separated into 3 groups. After the SCM was removed, 1 ml of TCM was added and resuspended twice by P1000 pipet then harvested and referred to as weakly attached cells. The detached cells harvested by vigorous pipetting with 1 ml TCM were referred to as attached cells. Strongly attached cells were detached by incubating with a recombinant enzyme, TrypLE Express (Thermo cat #12604013) for 10 minutes at 37° C. Cells were stained for viability and with fluorescent conjugated antibodies for detection of CCR7, CD3, CD45RA, CD45RO, CD8b, CD4, CD62L, CD49f, CD29, TCF1/7. Integrin α6 and Integrin β1 was detected with CD49f antibody and CD29 antibody respectively. For intracellular staining of TCF1, cells were fixed and permed by Foxp3 stain buffer set (Thermo, 00-5523-00). Cell phenotypes were acquired by Cytek Aurora.

Analysis and Results

Integrin α6 and integrin β1 are expressed higher in rejuvenated cells than activated T cells (i.e., control). On Day 10, detached cells were compared with activated T cells which were activated on day −1 and cultured in TCM for 10 days. Integrin α6 and integrin b1 expression was higher in T cell derived adherent cells than in activated T cell control (FIG. 70). Among the detached cells, strongly attached cells showed a higher proportion of Integrin α6 (CD49f) and Integrin β1 (CD29) double positive cells than attached cells, and especially weakly attached cells, which suggested the integrin complex expression level correlates with the adhesion intensity.

After T cell activation on day 10 followed by culturing in TCM, Integrin expression level decreased toward the expression level in activated control cells (FIG. 71).

T cell phenotype and proliferation. CD3 is the most common marker of T cells, and CD8 is a marker for cytotoxic T cells. The CD3+CD8+ population decreased in weakly attached cells, attached cells, and strongly attached cells on day 10, but this population increased by day 17 (FIG. 72). Given that the strongly attached cells lost CD3+CD8+ expression almost completely on day 10, the day 17 result showing the reemergence of the CD3+CD8+ population confirmed that the CD3− or CD8− population (the T cell derived adherent cell population) regains T cell marker expression by T cell activation and growth in T cell culture condition. It is unclear from this experiment whether the CD3+CD8− population observed at day 10 (see FIG. 72) in the strongly attached cells corresponds to the population that regains CD8 expression. The weakly attached cells, attached cells, and strongly attached cells showed more proliferation after T cell activation on day 10 (FIG. 73). Strongly attached cells proliferated slowly directly after detachment, but eventually rebounded and expanded more than control cells.

Less differentiated phenotype. TCF1 and CCR7 are well known markers of less differentiated T cells. Strongly attached cells showed higher expression of TCF1 and CCR7 than activated controls at both day 10 and day 17, while attached cells and weakly attached cells showed comparable expression of TCF1 and higher expression of CCR7 than activated control at both time points (FIG. 74).

Summary: It was observed that detached T cell adherent (i.e., partially reprogrammed) cells on Day 10 showed higher expression of integrin α6 and integrin β1 than activated T cells. The expression level decreased after activation on Day 10 followed by culturing in T cell condition. The expression level was higher in strongly attached cells which needed enzyme digestion to be detached from the plate. Expression was lower in weakly attached cells which could be detached from plates by pipetting without enzyme. This suggested that the integrin expression level correlated with the cell adhesion intensity. All attached cell groups (weakly attached cells, attached cells, and strongly attached cells) exhibited high proliferation after Day 10 activation (see FIG. 73). The strongly attached cells proliferated slowly directly after detachment but eventually rebounded and demonstrated robust proliferation. The strongly attached cells also had high TCF1 and CCR7 expression on Days 10 and 17, indicating a stem-like phenotype. High integrin β1 expression could cause upregulation of β-catenin expression through the signaling (see, e.g., Yuzuriha et al., Stem Cell Res. 2021 May; 53:102287) which can potentially contribute less differentiated phenotype of rejuvenated T cells (see, e.g., Clin Cancer Res, 2010 Oct. 1; 16(19):4695-701).

CITED REFERENCES

Dobin et al. 2013 Bioinformatics Vol. 29 P: 15-21

Feng, B., Jiang, J., Kraus, P., Ng, J. H., Heng, J. C., Chan, Y. S., Yaw, L. P., Zhang, W., Loh, Y. H., Han, J., et al. (2009). Reprogramming of fibroblasts into induced pluripotent stem cells with orphan nuclear receptor Esrrb. NAT CELL BIOL 11, 197-203.

Gurusamy, D., Henning, A. N., Yamamoto, T. N., Yu, Z., Zacharakis, N., Krishna, S., Kishton, R. J., Vodnala, S. K., Eidizadeh, A., Jia, L., et al. (2020). Multi-phenotype CRISPR-Cas9 Screen Identifies p38 Kinase as a Target for Adoptive Immunotherapies. CANCER CELL 37, 818-833 e819.

Hannum, G., Guinney, J., Zhao, L., Zhang, L., Hughes, G., Sadda S., Klotzle, B. Bibikova, M., Fan, J., Gao, Y., Deconde, R., Chen, M., Rajapakse, I., Friend, S., Ideker, Tr., Zhang, K., 2013, Genome-wide methylation profiles reveal quantitative views of human aging rates. MOL. CELL. 49, 359-369.

Horvath S, Oshima J, Martin G M, Lu A T, Quach A, Cohen H, Felton S, Matsuyama M, Lowe D, Kabacik S, Wilson J G, Reiner A P, Maierhofer A, Flunkert J, Aviv A, Hou L, Baccarelli A A, Li Y, Stewart J D, Whitsel E A, Ferrucci L, Matsuyama S, Raj K. (2019) Epigenetic clock for skin and blood cells applied to Hutchinson Gilford Progeria Syndrome and ex vivo studies. AGING, 10(7):1758-1775.

Hao et al. 2021 Cell Vol. 184 P: 3573-3587

Haynes et al. 2012 Semin Immunol Vol. 24 P: 350-355

Hou, P., Li, Y., Zhang, X., Liu, C., Guan, J., Li, H., Zhao, T., Ye, J., Yang, W., Liu, K., et al. (2013). Pluripotent stem cells induced from mouse somatic cells by small-molecule compounds. SCIENCE 341, 651-654.

Im, S. J., Hashimoto, M., Gerner, M. Y., Lee, J., Kissick, H. T., Burger, M. C., Shan, Q., Hale, J. S., Lee, J., Nasti, T. H., et al. (2016). Defining CD8+ T cells that provide the proliferative burst after PD-1 therapy. NATURE 537, 417-421.

Jiang, Y., Li, Y., and Zhu, B. (2015). T-cell exhaustion in the tumor microenvironment. CELL DEATH DIS 6, e1792.

Kochenderfer, J. N., Wilson, W. H., Janik, J. E., Dudley, M. E., Stetler-Stevenson, M., Feldman, S. A., Maric, I., Raffeld, M., Nathan, D. A., Lanier, B. J., et al. (2010). Eradication of B-lineage cells and regression of lymphoma in a patient treated with autologous T cells genetically engineered to recognize CD19. BLOOD 116, 4099-4102.

Kruger et al. TrimGalore package obtained from github[dot]com/FelixKrueger/TrimGalore Levine M. E., Lu, A. T., Quach, A., Chen, B. H., Assimes, T. L., Bandinelli, S., Hou, L., Baccarelli, A. A., Stewart, J. D., Li, Y., Whitsel, E. A., Wilson, J. G., Reiner, A. P., Aviv, A., Lohman, K., Liu, Y., Ferrucci, L., Horvath, S., 2018, An epigenetic biomarker for aging for lifespan and healthspan. AGING, 10(4):573-591.

Li and Dewey 2011 BMC Bioinformatics Article No. 323

Love et al. 2014 Genome Biology Article No. 550

Maeda et al. 2016 Cancer Res Vol. 76 P: 6839-6850

Moffett, H. F., Coon, M. E., Radtke, S., Stephan, S. B., McKnight, L., Lambert, A., Stoddard, B. L., Kiem, H. P., and Stephan, M. T. (2017). Hit-and-run programming of therapeutic cytoreagents using mRNA nanocarriers. NAT COMMUN 8, 389.

Nikolich-Zugich 2008 Nat Rev Immunol Vol. 8 P: 512-22

Ocampo, A., Reddy, P., Martinez-Redondo, P., Platero-Luengo, A., Hatanaka, F., Hishida, T., Li, M., Lam, D., Kurita, M., Beyret, E., et al. (2016). In Vivo Amelioration of Age-Associated Hallmarks by Partial Reprogramming. CELL 167, 1719-1733 e1712.

Rosenberg, S. A., Yang, J. C., Sherry, R. M., Kammula, U. S., Hughes, M. S., Phan, G. Q., Citrin, D. E., Restifo, N. P., Robbins, P. F., Wunderlich, J. R., et al. (2011). Durable complete responses in heavily pretreated patients with metastatic melanoma using T-cell transfer immunotherapy. CLIN CANCER RES 17, 4550-4557.

Sarkar, T. J., Quarta, M., Mukherjee, S., Colville, A., Paine, P., Doan, L., Tran, C. M., Chu, C. R., Horvath, S., Qi, L. S., et al. (2020). Transient non-integrative expression of nuclear reprogramming factors promotes multifaceted amelioration of aging in human cells. NAT COMMUN 11, 1545.

Subramanian et al. 2005 PNAS Vol. 43 P: 15545-15550

Takahashi, K., Tanabe, K., Ohnuki, M., Narita, M., Ichisaka, T., Tomoda, K., and Yamanaka, S. (2007). Induction of pluripotent stem cells from adult human fibroblasts by defined factors. CELL 131, 861-872.

Themeli et al. 2013 Nat Biotech Vol. 31 P: 928-933

Thorvaldsdottir et al. 2013 Briefings in Bioinformaics Vol. 14 P: 178-192

Vizcardo, R., Masuda, K., Yamada, D., Ikawa, T., Shimizu, K., Fujii, S., Koseki, H., and Kawamoto, H. (2013). Regeneration of human tumor antigen-specific T cells from iPSCs derived from mature CD8(+) T cells. CELL STEM CELL 12, 31-36.

Vizcardo, R., Klemen, N. D., Islam, S. M. R., Gurusamy, D., Tamaoki, N., Yamada, D., Koseki, H., Kidder, B. L., Yu, Z., Jia, L., et al. (2018). Generation of Tumor Antigen-Specific iPSC-Derived Thymic Emigrants Using a 3D Thymic Culture System. CELL REP 22, 3175-3190.

Vodnala, S. K., Eil, R., Kishton, R. J., Sukumar, M., Yamamoto, T. N., Ha, N. H., Lee, P. H., Shin, M., Patel, S. J., Yu, Z., et al. (2019). T cell stemness and dysfunction in tumors are triggered by a common mechanism. SCIENCE 363(6434): eaau0135.

Yu et al. 2012 OMICS Vol: 16 P: 284-287

What is claimed:

1. A method of producing rejuvenated T cells, comprising:
   a) contacting a starting population of T cells with reprogramming factors comprising KLF4, OCT3/4, SOX2, and C-MYC for 6 to 13 days, thereby producing a population of partially reprogrammed cells, wherein the partially reprogrammed cells are not transformed into induced pluripotent stem (iPS) cells; and
   b) contacting the partially reprogrammed cells with at least one T cell activating compound, thereby producing a population of rejuvenated T cells.

2. The method of claim 1, wherein the starting population of T cells is contacted with the reprogramming factors for a period of time sufficient for at least a portion of the starting population of T cells to express CD3 and at least one marker selected from the group consisting of integrin α6β1, SSEA4, CD9, and CD90.

3. The method of claim 2, wherein the starting population of T cells is contacted with the reprogramming factors for a period of time sufficient for at least a portion of the contacted starting population of T cells to express CD3, SSEA4, CD9 and CD90.

4. The method of claim 1, wherein, prior to contacting the starting population of T cells with the reprogramming factors, the starting population of T cells is activated with IL-2 and at least one agent capable of activating the starting population of T cells.

5. The method of claim 4, wherein the activated T cells are enriched by selection for cells expressing CD137, PD1, or LAG3.

6. The method of claim 1, wherein the starting population of T cells is comprised of TCRαβ cells, TCRγδ cells, CD4+CD8αβ+ double positive cells, CD4+ single positive cells, naïve T cells, central memory T cells, effector memory T cells, or a combination thereof.

7. The method of claim 1, wherein the reprogramming factors are expressed in the partially reprogrammed cells.

8. The method of claim 7, wherein the reprogramming factors are expressed using a non-integrating viral vector.

9. The method of claim 8, wherein the reprogramming factors are expressed using a Sendai virus.

10. The method of claim 7, further comprising inhibiting expression of the reprogramming factors within the partially reprogrammed cells by adding a compound that inhibits expression of the reprogramming factors.

11. The method of claim 10, wherein the compound is a small molecule inhibitor that specifically inhibits the expression of one or more of KLF4, OCT3/4, SOX2 and C-MYC expression.

12. The method of claim 7, wherein expression of the reprogramming factors are inhibited by contacting the partially reprogrammed cells with an agent that activates T cells.

13. The method of claim 7, wherein the at least one reprogramming factors are delivered with a nanoparticle.

14. The method of claim 1, further comprising contacting the starting population of T cells with a cytokine.

15. The method of claim 1, wherein the at least one T cell activating compound comprises an antibody or an antigen binding fragment thereof that binds CD3 or an antibody or an antigen binding fragment thereof that binds CD28 or both; or wherein the at least one T cell activating compound is a tumor antigen.

16. The method of claim 1, further comprising engineering the starting population of T cells to express a chimeric antigen receptor (CAR), a T cell Receptor or a hybrid receptor thereof, wherein the starting population of T cells is engineered prior to contacting the starting population of T cells with the reprogramming factors, and wherein the cell surface receptor recognizes a specific antigen on the surface of a target cell.

17. The method of claim 1, further comprising engineering the partially reprogrammed cells to express a CAR, a T cell Receptor or a hybrid receptor thereof, wherein the partially reprogrammed cells are engineered after contacting the starting population of T cells with the reprogramming factors, and wherein the cell surface receptor recognizes a specific antigen on the surface of a target cell.

18. The method of claim 1, wherein the rejuvenated T cells comprise an incomplete set of V, D, and J segments of T cell receptor genes.

19. The method of claim 1, wherein the epigenetic age of the rejuvenated T cells is at least 5% younger than the starting population of T cells prior to reprogramming.

20. The method of claim 1, wherein the partially reprogrammed cells are capable of expanding at least 25-fold greater than control T cells.

21. The method of claim 1, wherein contacting the starting population of T cells with the reprogramming factors results in a reduction in CD3 and CD8 expression.

22. The method of claim 1, further comprising contacting the starting population of T cells with SV40, LIN28, NANOG, or a combination thereof.

23. The method of claim 1, wherein the starting population of T cells is contacted with the reprogramming factors of (a) for a period of about 7 days before (b) contacting the partially reprogrammed cells with the at least one T cell activating compound.

24. The method of claim 1, wherein the partially reprogrammed cells are contacted with the at least one T cell activating compound about 7 days after the starting population of T cells is contacted with the reprogramming factors.

25. The method of claim 1, wherein the starting population of T cells is contacted with the reprogramming factors of (a) for 6 days before (b) contacting the partially reprogrammed cells with the at least one T cell activating compound.

26. The method of claim 1, wherein the partially reprogrammed cells are contacted with the at least one T cell activating compound 6 days after the starting population of T cells is contacted with the reprogramming factors.

27. A method of producing T cells, comprising:
a) culturing a starting population of T cells in a first medium comprising IL-2 and activating the T cells with at least one antibody or an antigen binding fragment thereof specific for CD3 or for CD28, or both; or a tumor antigen, tumor organoid, or tumor cell line;
b) contacting the activated T cells with KLF4, OCT3/4, SOX2, and C-MYC for 6 to 13 days in a second culture medium that does not comprise IL-2, or an antibody or an antigen binding fragment thereof specific for CD3 or CD28; or tumor antigen, tumor organoid, or tumor cell line, thereby producing a population of partially reprogrammed cells, wherein the partially reprogrammed cells are not completely reprogrammed into iPS cells; and
c) replacing the second culture medium with a third culture medium comprising IL-2 and at least one antibody or an antigen binding fragment thereof specific for CD3 and/or CD28, wherein the contacted partially reprogrammed cells are cultured in the third culture medium for at least about 5 days.

28. The method of claim 27, further comprising expanding the contacted partially reprogrammed cells.

29. The method of claim 27, wherein the starting population of T cells is comprised of TCRαβ cells, TCRγδ cells, CD4+CD8αβ+ double positive cells, CD4+ single positive cells, naïve T cells, central memory T cells, effector memory T cells, or a combination thereof.

30. The method of claim 27, wherein the starting population of T cells is contacted with autologous tumor cells in step (a) and express an activation marker after coculture with the autologous tumor cells, wherein the activation marker is CD137, PD1, or LAG3.

31. The method of claim 27, wherein the activated T cells are contacted with KLF4, OCT3/4, SOX2 and C-MYC for a period of about 7 days before (c) replacing the second culture medium with a third culture medium comprising IL-2 and at least one antibody specific for CD3 and/or CD28.

32. The method of claim 27, wherein the activated T cells are contacted with KLF4, OCT3/4 SOX2 and C-MYC for 6 days before (c) replacing the second culture medium with a third culture medium comprising IL-2 and at least one antibody specific for CD3 and/or CD28;

contacting the first cultured cell population with a first culturing medium comprising IL-2 to obtain a second cultured cell population;

contacting the second cultured cell population with a second culturing medium comprising IL-2 and IL-12 to obtain a third cultured cell population; and contacting the third cultured cell population with a third culturing medium comprising IL-2, IL-12 and IL-18 after contacting with the second culturing medium to obtain a fourth cultured cell population that comprises the modified T cells;

wherein each of the inducing culturing medium, the first culturing medium, the second culturing medium, and the third culturing medium further comprises L-glutamine, streptomycin sulfate, gentamicin sulfate and human platelet lysate.

* * * * *